United States Patent
Palmer et al.

(10) Patent No.: US 11,235,020 B2
(45) Date of Patent: Feb. 1, 2022

(54) METHODS AND COMPOSITIONS FOR INHIBITING GLYOXALASE 1 (GLO1)

(71) Applicants: Abraham Palmer, La Jolla, CA (US); Margaret Distler, Los Angeles, CA (US); Katherine M. J. McMurray, Oxford, OH (US)

(72) Inventors: Abraham Palmer, La Jolla, CA (US); Margaret Distler, Los Angeles, CA (US); Katherine M. J. McMurray, Oxford, OH (US)

(*) Notice: Subject to any disclaimer, the term of this patent is extended or adjusted under 35 U.S.C. 154(b) by 49 days.

(21) Appl. No.: 14/774,886

(22) PCT Filed: Mar. 12, 2014

(86) PCT No.: PCT/US2014/024901
§ 371 (c)(1),
(2) Date: Feb. 1, 2016

(87) PCT Pub. No.: WO2014/159720
PCT Pub. Date: Oct. 2, 2014

(65) Prior Publication Data
US 2016/0038559 A1 Feb. 11, 2016

Related U.S. Application Data

(60) Provisional application No. 61/780,509, filed on Mar. 13, 2013.

(51) Int. Cl.
| | |
|---|---|
| *A61K 38/05* | (2006.01) |
| *A61B 5/00* | (2006.01) |
| *A61K 45/06* | (2006.01) |
| *A61K 31/223* | (2006.01) |
| *A61K 33/00* | (2006.01) |
| *A61K 38/00* | (2006.01) |
| *A61K 38/06* | (2006.01) |
| *A61B 5/16* | (2006.01) |

(52) U.S. Cl.
CPC ............. *A61K 38/05* (2013.01); *A61B 5/165* (2013.01); *A61B 5/4023* (2013.01); *A61B 5/4806* (2013.01); *A61B 5/4848* (2013.01); *A61K 31/223* (2013.01); *A61K 33/00* (2013.01); *A61K 38/005* (2013.01); *A61K 38/063* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,984,569 A | 10/1976 | Kalopissis et al. | 514/562 |
| 4,185,106 A | 1/1980 | Dittmar et al. | 514/336 |
| 4,552,754 A | 11/1985 | Muramatsu et al. | 424/70.11 |
| 4,711,775 A | 12/1987 | Dittmar et al. | 514/350 |
| 5,230,985 A | 7/1993 | Lohaus et al. | 430/280.1 |
| 5,299,254 A | 3/1994 | Dancer et al. | 378/163 |
| 5,616,563 A | 4/1997 | Creighton et al. | 514/19.2 |
| 5,969,174 A | 10/1999 | Creighton et al. | 558/232 |
| 6,060,471 A | 5/2000 | Ztyczynski et al. | 514/248 |
| 2006/0051786 A1* | 3/2006 | Akil | C12Q 1/6883 435/6.16 |

FOREIGN PATENT DOCUMENTS

| | | |
|---|---|---|
| EP | 0510440 | 10/1992 |
| EP | 0510443 | 10/1992 |
| WO | WO 1998/009986 | 3/1998 |
| WO | WO 1999/035128 | 7/1999 |
| WO | WO 1999/037277 | 7/1999 |

OTHER PUBLICATIONS

Distler et al. (Journal of Clinical Investigation, 122(6), 2306-2315, 2012) Glyoxalase 1 increases . . . .*
Taporoski et al. (PLoS One, 10(12), 1-10, 2015) Shared Genetic Factors of Anxiety and Depression Symptoms . . . .*
Benton et al. (Psychopharmacology, 221, 297-315, 2012, published online Nov. 24, 2011)Evaluating genetic markers and . . . .*
Fujimoto et al. (Neuroscience Letters, 438, 196-199, 2008) Reduced expression of glyoxalase-1 . . . .*
Hovatta et al. (Nature Letters, 438, 662-666, 2005), Glyoxalase 1 and glutathione . . . .*
Thornalley et al. (J. Med. Chem., 39(17), 3409-3411, 1996) Antitumor Activity of S-(p-Bromobenzyl)glutathione . . . .*
Ahmed & Thornalley, *Diabetes Obes Metabl.* 9:233-45, 2007.
Bair, et al., *Melanoma Res.* 20:85-96, 2010.
Barua, et al., *Autism Res.* 4:262-70, 2011.
Brodie, et al., *Epilepsy Behav.* 21 :331-341, 2011.
Brownlee, *Nature* 414:813-820, 2001.
Chen, et al., *Proc Natl Acad Sci US A* 101:7687-7692, 2004.
Creighton, *Biochem Soc Trans* 31:1378-1382,2003.
Curia, et al., *J Neurosci Methods.* 172:143-157, 2008.
Di Cristo, *Clin Genet* 72:1-8, 2007.
Distler & Palmer. *Front Genet.* 3:250. doi: 10.3389/fgene.2012.00250, 2012.
Egan, et al., *Nat Genet* 39:1384-1389, 2007.
Fisher, *Brain Res Brain Res Rev.* 14:245-278, 1989.
Fleming, et al., *Gerontology.* 57(5):435-43, 2011.
Junaid, et al., *Am J Med Genet A* 131:11-17, 2004.
Kalueff & Nutt, *Depress Anxiety* 24:495-517, 2007.
Kuhla, et al., *J Neurosci Res.* 83:1591-600, 2006.
Masterjohn 2011—Does he mean Masterjohn 2012 as cited in References?

(Continued)

*Primary Examiner* — Tigabu Kassa
(74) *Attorney, Agent, or Firm* — Norton Rose Fulbright US LLP

(57) ABSTRACT

Methods and compositions are provided for treating or preventing a neurological disease or disorder using an inhibitor of Glyoxalase 1 (GLO1). In some embodiments, the inhibitor is a small molecule. In certain embodiments, the disease or disorder is a sleep disorder, a mood disorder such as depression, epilepsy, an anxiety disorder, substance abuse, substance dependence or substance such as an alcohol withdrawal syndrome.

12 Claims, 38 Drawing Sheets

Specification includes a Sequence Listing.

(56) References Cited

OTHER PUBLICATIONS

Morcos, et al., *Aging Cell.* 7:260-269, 2008.
Perucca, et al., *Lancet Neurol.* 10:446-456, 2011.
Pollack, *J Clin Psychiatry.* 70 Suppl 2:32-38, 2009.
Rossetti & Lowenstein, *Lancet Neurol.* 10:922-930, 2011.
Rubenstein, *J Child Psycho Psychiatry.* 52:339-355, 2011.
Sacco, et at., *BMC Med Genet.* 8:11, 2007.
Shinohara, et al., *J Clin Invest.* 101:1142-7, 1998.
Thornalley, *Mol Aspects Med* 14, 287-371, 1993.
Thornalley, *Biochem Soc Trans.* 31:1343-1348. 2003.
Thornalley, *Biochem Soc Trans.* 31:1372-7, 2003.
Thornalley, et al., *Semin Cell Dev Biol.* 22:318-325, 2011.
Williams, et al., *PLoS One.* 4:e4649, 2009.
American Psychiatric Association, "Depressive Disorders" *Diagnostic and Statistical Manual of Mental Disorders (DSM-5)*, ProQuest Ebook, 2013, 155-188.
American Psychiatric Association, "Anxiety Disorders" *Diagnostic and Statistical Manual of Mental Disorders (DSM-5)*, ProQuest Ebook, 2013, 188-233.

\* cited by examiner

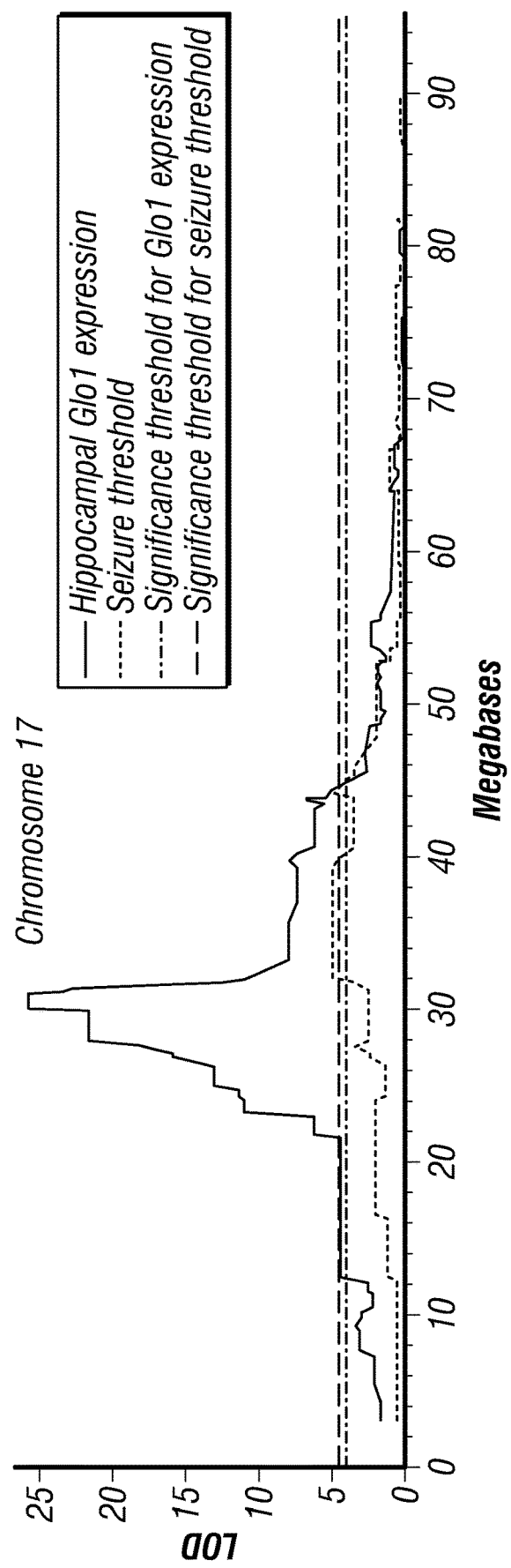
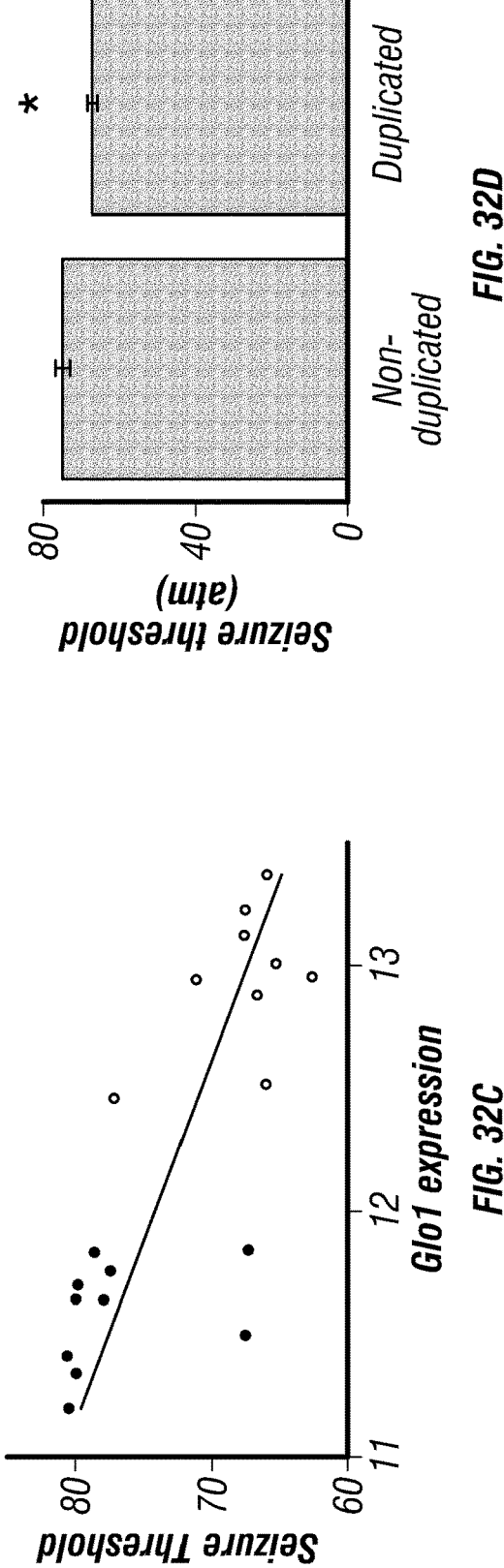
FIG. 32B
FIG. 32C
FIG. 32D

METHODS AND COMPOSITIONS FOR INHIBITING GLYOXALASE 1 (GLO1)

CROSS-REFERENCE TO RELATED APPLICATIONS

This application claims priority to U.S. Application No. 61/780,509 filed on Mar. 13, 2013, the entire contents of which is hereby incorporated by reference without disclaimer.

STATEMENT OF GOVERNMENT RIGHTS

This application is a national phase application under 35 U.S.C. § 371 of International Application No. PCT/US2014/024901 filed Mar. 12, 2014, which claims priority to U.S. Application No. 61/780,509 filed on Mar. 13, 2013. The entire contents of each of the above-referenced disclosures are specifically incorporated herein by reference without disclaimer.

BACKGROUND OF THE INVENTION

A. Field of the Invention

Embodiments are directed generally to neurology and medicine. In certain aspects, there is provided prevention or treatment of neurological diseases or disorders, such as sleep disorders, mood disorders, anxiety disorders, epilepsy, substance abuse or dependence, or alcohol withdrawal syndromes.

B. Background

Various diseases or disorders related to neural systems lack effective treatments. For example, recent estimates indicate that more than 19 million Americans over the age of 18 years experience a depressive illness each year. The American Psychiatric Association recognizes several types of clinical depression, including Mild Depression (Dysthymia), Major Depression, and Bipolar Disorder (Manic-Depression). Major Depression is defined by a constellation of chronic symptoms that include sleep problems, appetite problems, anhedonia or lack of energy, feelings of worthlessness or hopelessness, difficulty concentrating, and suicidal thoughts. Approximately 9.2 million Americans suffer from Major Depression, and approximately 15 percent of all people who suffer from Major Depression take their own lives. Bipolar Disorder involves major depressive episodes alternating with high-energy periods of rash behavior, poor judgment, and grand delusions. An estimated one percent of the American population experiences Bipolar Disorder annually.

Significant advances in the treatment of depression have been made in the past decade. Since the introduction of selective serotonin reuptake inhibitors (SSRIs), e.g., Prozac®, many patients have been effectively treated with anti-depressant medication. New medications to treat depression are introduced almost every year, and research in this area is ongoing. However, an estimated 10 to 30 percent of depressed patients taking an anti-depressant are partially or totally resistant to the treatment. Those who suffer from treatment-resistant depression have almost no alternatives. Thus, there is a need to develop alternative treatments for these patients as well as patients of other neurological diseases such as epilepsy, anxiety disorders, sleep disorders epilepsy or alcohol withdrawal syndromes.

SUMMARY OF THE INVENTION

Certain aspects are based in part on the finding that Glyoxalase 1 (GLO1) is involved in various diseases or disorders related to the neural system, such as psychiatric disorders, sleep disorders or epilepsy. For example, decreased GLO1 activity, such as by administration of GLO1 inhibitors, results in reduction of anxiety, epilepsy or depression-related symptoms.

There may be provided methods and compositions involving GLO1 inhibitors, or increasing methylglyoxal (MG) or MG precursor or prodrugs such as glyceraldehyde for preventing or treating neural system disorders or diseases.

In some embodiments, the GLO1 inhibitor may be an antibody, an inhibitory nucleic acid, or a small molecule. For example, the GLO1 inhibitor may have or may not have a glutathione structure. A particular example having a glutathione structure may be S-bromobenzylglutathione cyclopentyl diester (BrBzGCp2). In other aspects, the GLO1 inhibitor may be a 1-hydroxy-6,7-diphenylpyridin-2-one derivative (3d), a flavonoid, a curcumin, a benzothiazole derivative, a 4-(7-azaindole)-substituted 6-phenyl-N-hydroxypyridones, or 4,6-diphenyl-N-hydroxypyridon.

In some embodiments, the GLO1 inhibitor has half maximal inhibitory concentration (IC50) of about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200 nm, µM or mM (or any range derivable therein).

Certain embodiments are directed to methods of inhibiting a neurological disease or disorder in a patient comprising administering to the patient a composition comprising a GLO1 inhibitor, for example, a GLO1 inhibitor that comprises a glutathione structure. In particular embodiments, the patient is administered an amount of the composition that has been previously shown to be an effective amount. In other aspects, administration of MG or a related molecule may be also contemplated.

Additional embodiments concern methods for treating a neurological disease or disorder, such as psychiatric disorders, sleep disorders, substance abuse, substance dependence or substance withdrawal, or epilepsy in a subject comprising administering to the subject a GLO1 inhibitor, including one that comprises a glutathione structure.

In other embodiments there are methods for promoting GABA signaling in a subject comprising administering to the subject a GLO1 inhibitor, including one that comprises or does not comprise a glutathione structure.

In further embodiments there are methods of treating a subject having or at risk of developing a neurological disease or disorder, such as psychiatric disorders like anxiety disorders or mood disorders (e.g., depression or bipolar disorders), sleep disorders, alcohol withdrawal syndrome, substance abuse, substance dependence or substance withdrawal, or epilepsy, comprising administering an effective amount of a pharmaceutically acceptable composition comprising a GLO1 inhibitor. The GLO1 inhibitor may have a glutathione structure, including but not limited to S-bromobenzylglutathione cyclopentyl diester (BrBzGCp2), or may be a flavonoid, a curcumin, a benzothiazole derivative, a 4-(7-azaindole)-substituted 6-phenyl-N-hydroxypyridones, or 4,6-diphenyl-N-hydroxypyridon.

In some embodiments, methods related to a sleep disorder are provided. In further embodiments, the sleep disorder is rapid eye movement (REM) sleep behavior disorder (RBD), insomnia, insomnia related to another medical or psychiatric disorder, a circadian rhythm sleep disorder, dyssomnia NOS, parasomnias, or restless leg syndrome.

In further embodiments, methods related to a mood disorder are provided. Examples of mood disorders include, but are not limited to, a depressive disorder, bipolar disorder, phobia, obsessive-compulsive disorder, or post-traumatic stress disorder. In particular embodiments, methods related to a depressive disorder are provided.

In other embodiments, methods and compositions may apply to an anxiety disorder, such as a generalized anxiety disorder, panic disorder, phobia, obsessive compulsive disorder, posttraumatic stress disorder, acute stress disorder, or anxiety disorder due to another known or unknown medical disorder.

In certain embodiments, methods and compositions for preventing, treating or managing a substance abuse, substance dependence or substance withdrawal are provided. The substance can be any drug or addictive agent, including but not limited to, alcohol, caffeine, nicotine, *cannabis* (marijuana) and *cannabis* derivatives, opiates and other morphine-like opioid agonists such as heroin, phencyclidine and phencyclidine-like compounds, sedative hypnotics such as benzodiazepines and barbiturates and psychostimulants such as cocaine, amphetamines and amphetamine-related drugs such as dextroamphetamine and methylamphetamine. In one embodiment, the addictive agent is alcohol. In another embodiment, the addictive agent is nicotine. In a further embodiment, the addictive agent is an opioid or opiate, e.g., morphine, methadone, fentanyl, sufentanil, codeine, oxycodeine, and heroin. In a further embodiment, the addictive agent is a psychostimulant, e.g., cocaine, amphetamine or an amphetamine derivative. In another embodiment, the addictive agent is cocaine.

In further embodiments, methods and compositions may be used for treating or preventing epilepsy. The epilepsy may be benign Rolandic epilepsy, frontal lobe epilepsy, infantile spasms, juvenile myoclonic epilepsy, juvenile absence epilepsy, childhood absence epilepsy (pyknolepsy), hot water epilepsy, Lennox-Gastaut syndrome, Landau-Kleffner syndrome, Dravet syndrome, progressive myoclonus epilepsies, reflex epilepsy, Rasmussen's syndrome, temporal lobe epilepsy, limbic epilepsy, status epilepticus, abdominal epilepsy, massive bilateral myoclonus, catamenial epilepsy, Jacksonian seizure disorder, Lafora disease, or photosensitive epilepsy.

In some embodiments, methods concern a GLO1 inhibitor that increases methylglyoxal (MG) and administering a composition comprising a GLO1 inhibitor, or MG or its precursors or prodrugs. In further embodiments, the GLO1 inhibitor increases GABA-A signaling.

In additional embodiments, there are methods that further comprise administering a second neural treatment to be administered before, during or after the primary treatment comprising the use of a GLO1 inhibitor. The second neural treatment may be a second sleep disorder treatment, a second mood disorder treatment, a second epilepsy treatment, a second anxiety disorder treatment, a second substance abuse, substance dependence or substance withdrawal treatment such as a second alcohol withdrawal syndrome treatment.

Some aspects concern a second sleep disorder treatment that is a drug such as amitriptyline (Elavil and others), amoxapine (Asendin and others), bupropion (Wellbutrin), buspirone (BuSpar), carbidopa-levodopa (Sinemet and others), citalopram (Celexa), clonazepam (Klonopin and others), clorazepate (Tranxene and others), desipramine (Norpramin and others), desmopressin (DDAVP and others), dextroamphetamine (Dexedrine and others), diazepam (Valium and others), doxepin (Sinequan and others), estazolam (ProSom and others), fluoxetine (Prozac), flurazepam (Dalmane and others), fluvoxamine (Luvox), medroxyprogesterone (Provera and others), methylphenidate (Ritalin and others), mirtazapine (Remeron), modafinil (Provigil), nefazodone (Serzone), nortriptyline (Pamelor and others), paroxetine (Paxil), pemoline (Cylert), pergolide (Permax), phenelzine (Nardil), phenobarbital (Donnatal and others), pramipexole (Mirapex), protriptyline (Vivactil), ropinirole (Requip), selegiline (Eldepryl), sertraline (Zoloft), temazepam (Restoril and others), tranylcypromine (Parnate), trazodone (Desyrel and others), triazolam (Halcion and others), trimipramine (Surmontil), venlafaxine (Effexor), zaleplon (Sonata), or zolpidem (Ambien).

Further aspects concern a second mood disorder, depressive disorder, or anxiety treatment may be stimulating drugs such as medications, anesthetic agents, synthetic or natural peptides or hormones, neurotransmitters, cytokines and other intracellular and intercellular chemical signals and messengers, and the like. For example, second mood disorder treatment may include antipsychotics, mood stabilizers and/or lithium. The second depressive disorder or anxiety disorder treatment may be selective serotonin reuptake inhibitors (SSRIs), serotonin-norepinephrine reuptake inhibitors (SNRIs), benzodiazepines and/or tricyclic antidepressants.

There may also be provided a second epilepsy treatment that is a medication, surgery, a ketogenic diet, electrical stimulation, avoidance therapy, alternative or complementary medicine, including acupuncture, psychological interventions, vitamins and yoga. For example, medications approved by the Food and Drug Administration for the use of treatment of epileptic seizures in the U.S. include carbamazepine (common U.S. brand name Tegretol), clorazepate (Tranxene), clonazepam (Klonopin), ethosuximide (Zarontin), felbamate (Felbatol), fosphenytoin (Cerebyx), gabapentin (Neurontin), lacosamide (Vimpat), lamotrigine (Lamictal), levetiracetam (Keppra), oxcarbazepine (Trileptal), phenobarbital (Luminal), phenytoin (Dilantin), pregabalin (Lyrica), primidone (Mysoline), tiagabine (Gabitril), topiramate (Topamax), valproate semisodium (Depakote), valproic acid (Depakene), and zonisamide (Zonegran).

Additional treatments to be used in combination treatments for a substance abuse/dependence disorder may include any therapeutic agent that contributes to an aspect of the effective treatment or prevention of the abuse, dependence or addiction. For example, the additional therapeutic agent may be a drug used to treat a substance abuse/dependence/addiction or a drug used to alleviate side-effects associated with physiological withdrawal from an addictive agent. In addition, the additional therapeutic agent may be any drug that affects brain serotonin neurotransmission, such as selective serotonin reuptake inhibitors (SSRIs), and tricyclic and tetracyclic serotonin and norepinephrine reuptake inhibitors (SNRIs) as described below, and serotonin agonists such as sumatriptan, ergonovine, dihydroergotamine and buspirone. In certain embodiments, the additional therapeutic agent is an opioid antagonist, including mixed opioid partial agonist/antagonists, an antidepressant, an antiepileptic, an antiemetic, a dopaminergic agent such as a dopamine D1 receptor agonist, a corticotrophin-releasing factor-1 (CRF-1) receptor antagonist, a selective serotonin-3 (5-HT3) antagonist, a 5-HT2A/2C antagonist such as mianserin, mirtazapine and ketanserin, or a cannabinoid-1 (CB1) receptor antagonist, including but not limited to those therapeutic agents specifically described herein.

Additional treatments to be used in combination treatments for an alcohol withdrawal syndrome include, but are not limited to, benzodiazepines, such as diazepam or lorazepam, antipsychotic agents, such as haloperidol, anticonvulsants such as topiramate, carbamazepine and other anticonvulsants, baclofen, barbiturates, clomethiazole, clonidine, ethanol, flumazenil, trazodone, magnesium, nitrous oxide, and vitamins.

In a further aspect, a GLO1 inhibitor is administered orally, topically, nasally, intravenously, intravascularly, intrathecally, intratracheally, by inhalation, or by instillation. The Glo1 inhibitor can be administered to various organs or tissues including, but not limited to the subject's skin, respiratory tract (including the lungs) kidneys, central nervous system, reproductive organs, vagina, or eyes. The neurological disease or disorder to be treated may be a sleep disorder, mood disorder, epilepsy, anxiety disorder, substance abuse, substance dependence or substance withdrawal such as an alcohol withdrawal syndrome.

In additional methods, the patient has been determined to have a neurological disease or disorder, such as a sleep disorder, mood disorder, depressive disorder, epilepsy, anxiety disorder, or alcohol withdrawal syndrome. Methods may involve identifying the patient as having a neurological disease or disorder, such as a sleep disorder, mood disorder, depressive disorder, epilepsy, anxiety disorder, or alcohol withdrawal syndrome. They may also involve selecting the patient after the patient is diagnosed with a neurological disease or disorder, such as a sleep disorder, mood disorder, depressive disorder, epilepsy, anxiety disorder, or alcohol withdrawal syndrome. In some embodiments, there are methods in which the patient has been determined to have or be at risk of developing a neurological disease or disorder, such as a sleep disorder, mood disorder, depressive disorder, epilepsy, anxiety disorder, or alcohol withdrawal syndrome. Some embodiments include testing the patient for a neurological disease or disorder, such as a sleep disorder, mood disorder, depressive disorder, epilepsy, anxiety disorder, or alcohol withdrawal syndrome. For instance, some aspects further concern obtaining from the patient a biological sample for testing whether the patient has a neurological disease or disorder, such as a sleep disorder, mood disorder, depressive disorder, epilepsy, anxiety disorder, or alcohol withdrawal syndrome. In additional embodiments, the patient is tested for the type of a neurological disease or disorder, such as a sleep disorder, mood disorder, depressive disorder, epilepsy, anxiety disorder, or alcohol withdrawal syndrome.

In some methods the patient is at risk of a neurological disease or disorder, such as a sleep disorder, mood disorder, epilepsy, anxiety disorder, or alcohol withdrawal syndrome. In particular examples the patient is at risk for a sleep disorder or mood disorder. In particular situations, the patient has a disorder or condition of the central nervous system. In certain instances, the patient exhibits neurological symptoms.

In a further aspect the patient can be at risk for a neurological disease or disorder, such as a sleep disorder, mood disorder, epilepsy, anxiety disorder, or alcohol withdrawal syndrome. In another embodiment the patient can be at risk for a mood disorder or a sleep disorder. In additional embodiments the patient is at risk for an anxiety disorder. In still further aspects, the patient is at risk for epilepsy. In other aspects, the patient is at risk for alcohol withdrawal syndrome.

In some embodiments, there are methods that involve monitoring the patient for the neurological disease or disorder, such as a sleep disorder, mood disorder, or neurological symptoms within a week of first administering a therapeutic composition comprising a GLO1 inhibitor.

The methods can include treating a subject having or at risk of developing a neurological disease or disorder, such as a sleep disorder, mood disorder, comprising administering an effective amount of a GLO1 inhibitor to a subject having or at risk of developing such a neurological disease or disorder. The methods can also include inhibiting, attenuating, treating, or ameliorating neurologic symptoms and its related pathology. In certain embodiments, the subject has been evaluated and determined to have a neurological disease or disorder. This may or may not have occurred prior to administration of a GLO1 inhibitor.

A patient is a human patient in some embodiments. It is contemplated that any embodiment involving a patient may also be applied to a subject, which refers to any organism that suffers physiologically or psychologically as a result from a neurological disease or disorder. In certain embodiments, the subject is a mammal, which includes but is not limited to dogs, cats, cows, horses, pigs, monkeys, and sheep.

In certain aspects a patient is administered a GLO1 inhibitor within at least about, at most about, or about 1, 2, 3, 4, 5, 6, 7, 8, 9, or 10 hours, 12 hours, 1, 2, 3, 4, 5, 6, 7, 8, 9, or 10 days, or 1, 2, 3, 4, 5, 6, 7, 8, 9, or 10 weeks (or any range or value derived therefrom) of being determined to have a neurological disease or disorder, such as a sleep disorder, mood disorder, epilepsy or anxiety disorder or for a period of at least about, at most about, or about 1, 2, 3, 4, 5, 6, 7, 8, 9, or 10 hours, 12 hours, 1, 2, 3, 4, 5, 6, 7, 8, 9, or 10 days, or 1, 2, 3, 4, 5, 6, 7, 8, 9, or 10 weeks (or any range or value derived therein).

Methods may involve administering a composition containing about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 nanograms (ng), micrograms (mg), milligrams (mg), or grams of a GLO1 inhibitor or MG or its prodrug or precursor, or any range derivable therein.

Alternatively, embodiments may involve providing or administering to the patient or to cells or tissue of the patient about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 nM, μM, mM, or M of a GLO1 inhibitor or MG or its prodrug or precursor, or any range derivable therein, in one dose or collectively in multiple doses. In some embodiments, the composition comprises between about 0.1 ng and about 2.0 g of a GLO1 inhibitor.

Alternatively, the composition may have a concentration of GLO1 inhibitor or MG that is 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 μg/ml or mg/ml, or any range derivable therein.

If a liquid, gel, or semi-solid composition, the volume of the composition that is administered to the patient may be about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 microliters (μl) or milliliters (ml), or any range derivable therein. In certain embodiments, the patient is administered up to about 10 ml of the composition.

The amount of a GLO1 inhibitor or MG or its prodrug or precursor that is administered or taken by the patient may be based on the patient's weight (in kilograms). Therefore, in some embodiments, the patient is administered or takes a dose or multiple doses amounting to about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 µg/kilogram (kg) or mg/kg, or any range derivable therein.

The composition may be administered to (or taken by) the patient about, at least about, or at most about 1, 2, 3, 4, 5, 6, 7, 8, 9, 10, 11, 12, 13, 14, 15, 16, 17, 18, 19, 20 or more times, or any range derivable therein, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months, or any range derivable therein. It is specifically contemplated that the composition may be administered once daily, twice daily, three times daily, four times daily, five times daily, or six times daily (or any range derivable therein) and/or as needed to the patient. Alternatively, the composition may be administered every 2, 4, 6, 8, 12 or 24 hours (or any range derivable therein) to or by the patient. In some embodiments, the patient is administered the composition for a certain period of time or with a certain number of doses after experiencing symptoms of a neurological disease or disorder.

In additional embodiments, the composition may be administered to (or taken by) the patient about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 µl/min, µl/hour, µl/day, µl/week, µl/month, ml/min, ml/hour, ml/day, ml/week, ml/month, µg/min, µg/hour, µg/day, µg/week, µg/month, mg/min, mg/hour, mg/day, mg/week, mg/month or any range derivable therein.

Other embodiments are discussed throughout this application. Any embodiment discussed with respect to one aspect applies to other aspects as well and vice versa. The embodiments in the Example section are understood to be embodiments that are applicable to one or all aspects of the invention.

The terms "inhibiting," "reducing," or "preventing," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition, and vice versa. Furthermore, compositions and kits can be used to achieve methods in certain aspects.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. Certain aspects may be better understood by reference to one or more of these drawings in combination with the detailed description of specific embodiments presented herein.

FIG. 1A, Glo1 copy number was measured in the offspring of homozygous breeders for 2, 3, or 4 copies of Glo1; n=14 mice in the 2-copy group, 35 mice in the 3-copy group, and 54 mice in the 4-copy group. FIG. 1B, Allelic frequency of Glo1 copy numbers in A/J mice obtained from JAX. FIG. 1C, Glo1 mRNA expression was measured by qPCR in the brains of A/J mice with 2 and 3 copies of Glo1; n=6 per group. Data are mean±SEM. All values are relative to a control strain that does not carry the Glo1 duplication. *P=0.0002 by two-tailed t-test.

FIG. 2A, Mice with 3 copies of Glo1 spent less time in the center of the OF. FIG. 2B, Glo1 copy number did not affect total distance traveled. n=9 mice with 2-2.5 copies, 41 mice with 3 copies. Data are mean±SEM. *P<0.05 by two-tailed t-test.

Figures 3A, 3B:
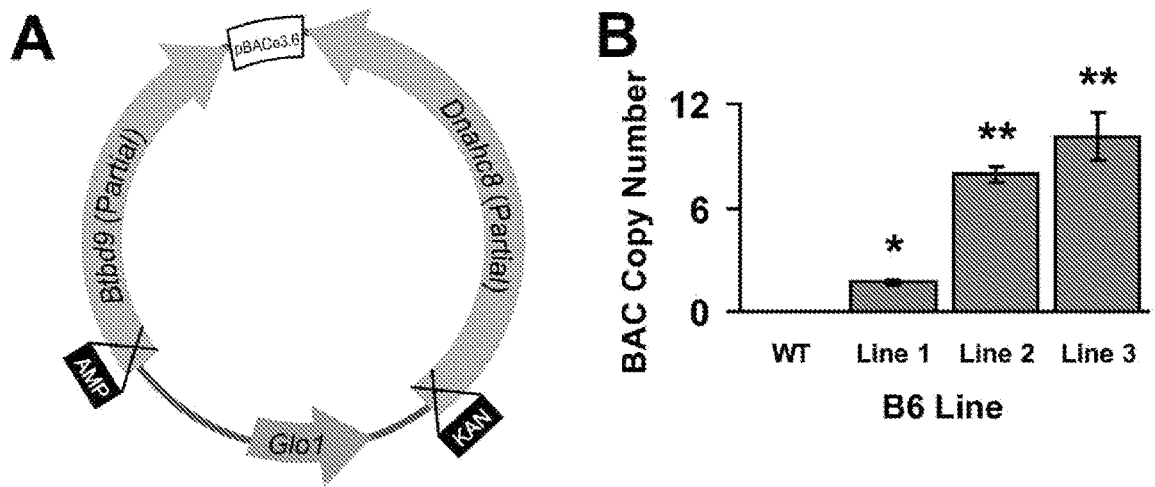

FIGS. 3A-3B: Generation of BAC transgenic mice. FIG. 3A, Map of the BAC used for generating transgenic mice. The BAC contained Glo1 and partial copies of Dnahc8 and Btbd9. The first exons of Dnahc8 and Btbd9 were ablated by replacing them with ampicillin (AMP) and kanamycin (KAN) cassettes, respectively. FIG. 3B, BAC copy number was estimated by qPCR on genomic DNA. Data are mean±SEM. $P<10^{-10}$ by one-way ANOVA; *P<0.05, **P<0.0001. n=8 WT, 3-5 Tg per line.

Figures 4A, 4B, 4C, 4D, 4E, 4F, 4G, 4H:
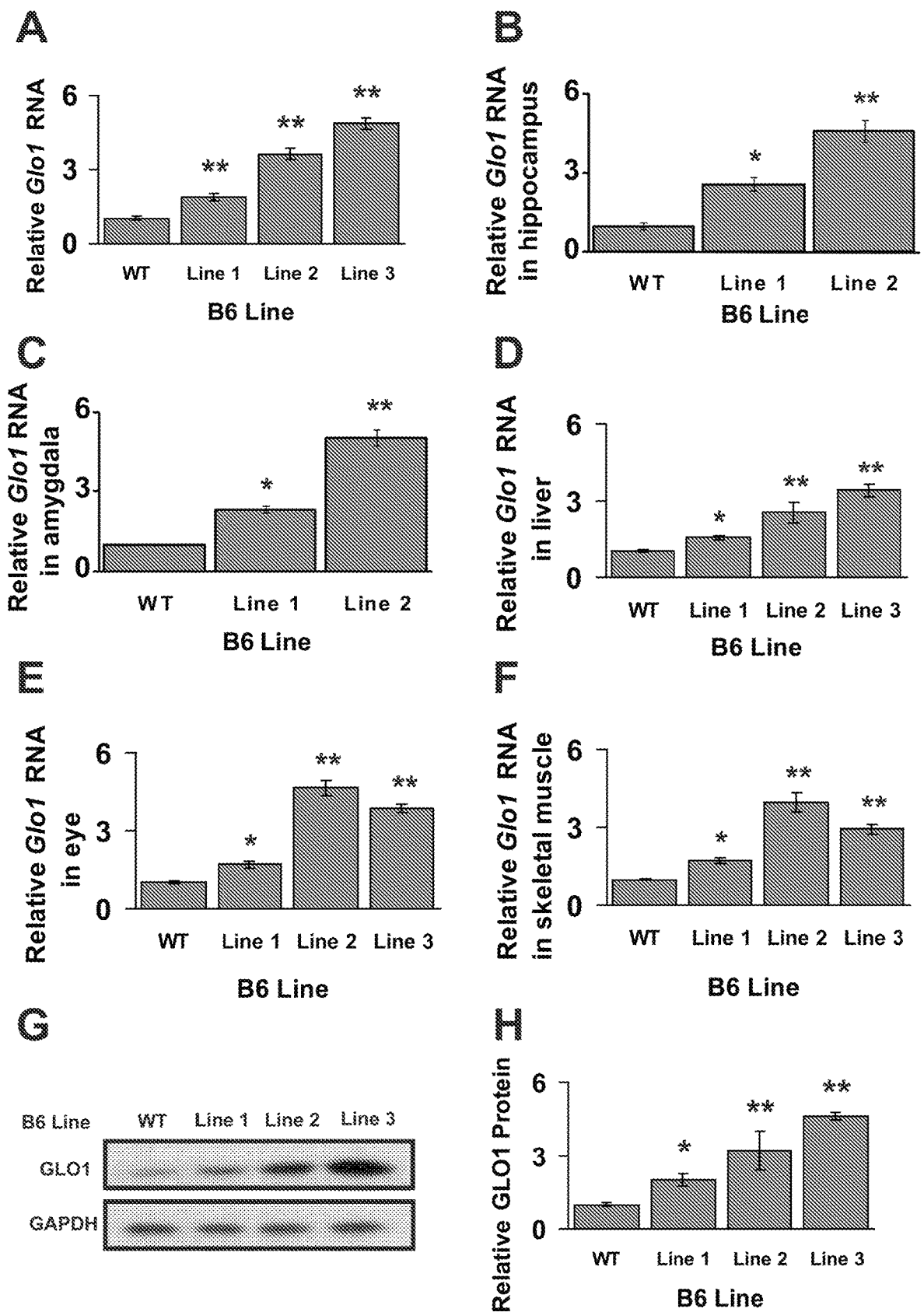

FIGS. 4A-4H: BAC transgenic mice overexpress Glo1 at the mRNA and protein levels. FIGS. 4A-4F, Glo1 mRNA was estimated in whole brain (FIG. 4A), hippocampus (FIG. 4B), amygdala (FIG. 4C), liver (FIG. 4D), eye (FIG. 4E), and skeletal muscle (FIG. 4F) by qPCR. One-way ANOVAs: $P<10^{-14}$ (brain), $P<10^{-5}$ (hippocampus), $P<10^{-5}$ (amygdala), $P<10^{-9}$ (liver), $P<10^{-15}$ (eye), $P<10^{-10}$ (skeletal muscle). For Brain, liver, eye, and skeletal muscle, n=10-12 WT, 3-7 Tg per line. For hippocampus and amygdala, n=3 WT, 4 Tg per line. FIGS. 4G-4H, GLO1 protein was estimated in whole brain by immunoblot. n=16 WT, 3-6 Tg per line; one-way ANOVA: $P<10^{-11}$. Data are mean±SEM. *P<0.05, **P<0.0001.

Figures 5A, 5B:
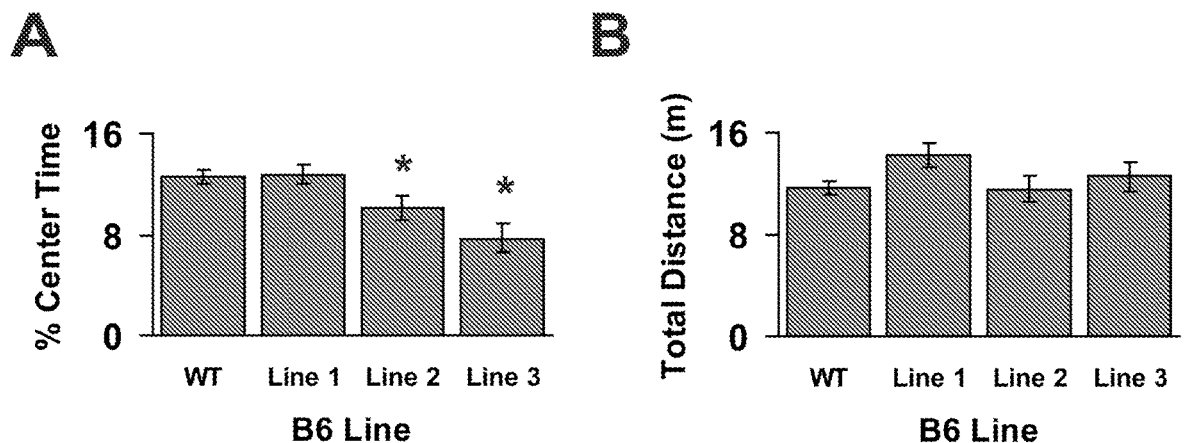

FIGS. 5A-5B: Glo1 overexpression increases anxiety-like behavior. WT and Tg littermates were tested in the OF. FIG. 5A, Center time; one-way ANOVA P<0.001. FIG. 5B, Total distance; one-way ANOVA P>0.1. Data are mean±SEM. Data were pooled from multiple individual experiments. n=74 WT (pooled across all lines), 14-21 Tg per line. *P<0.05.

Figures 6A, 6B, 6C, 6D:
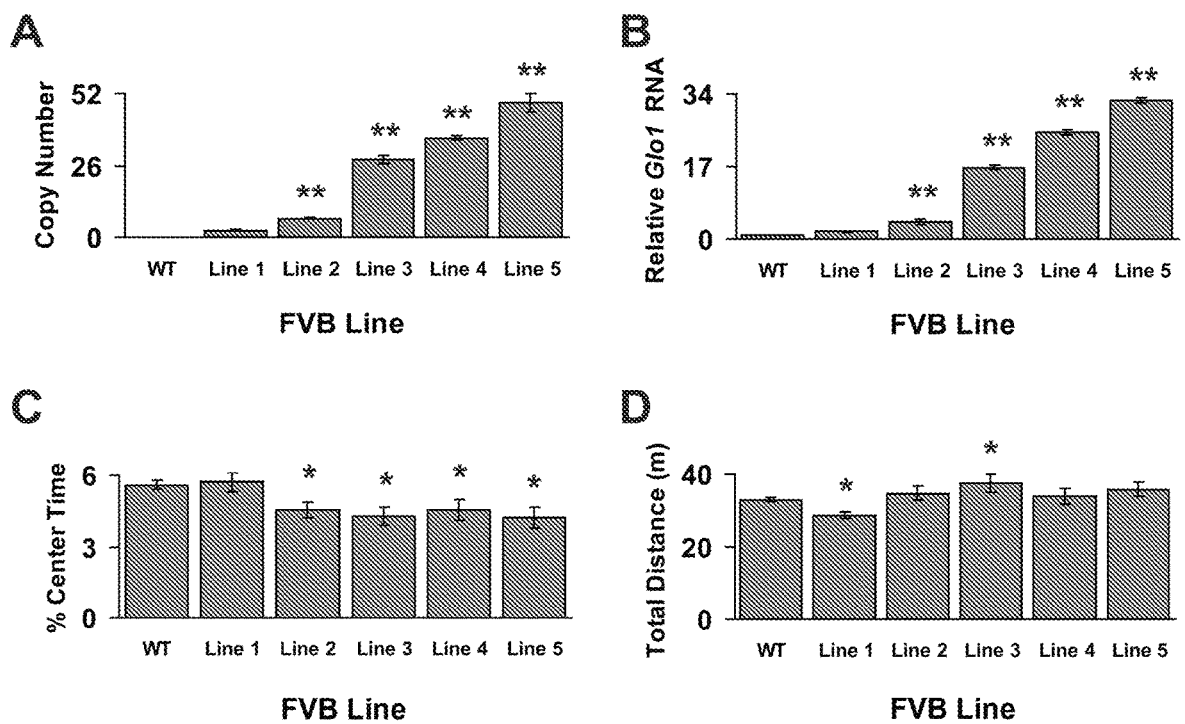

FIGS. 6A-6D: Glo1 copy number regulates Glo1 expression and anxiety-like behavior in FVB mice. FIG. 6A, BAC copy number was measured in each FVB line by qPCR on genomic DNA. n=33 WT, 4-14 Tg per line; one-way ANOVA $P<10^{-9}$. FIG. 6B, Glo1 mRNA was measured in whole brains of WT and Tg mice from each FVB line using qPCR. n=17 WT, 3-7 Tg per line; one-way ANOVA $P<10^{-15}$. FIG. 6C, Center time in the OF. n=111 WT, 14-22 Tg per line; one-way ANOVA P=0.0015. FIG. 6D, A one-way ANOVA was significant for the effect of genotype on locomotor activity (P=0.003). Data are mean±SEM. WT mice from each line were pooled into a common WT group. *P<0.05, **P<0.0001.

Figures 7A, 7B:
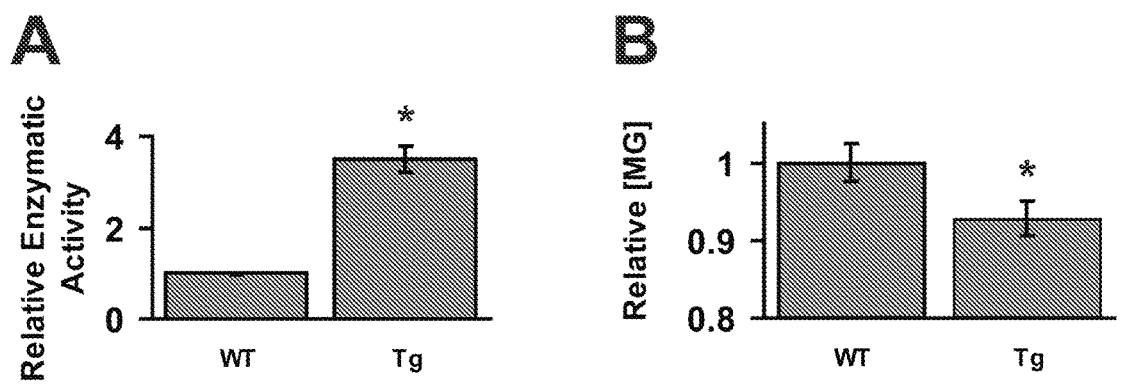

FIGS. 7A-7B: Glo1 overexpression increases GLO1 enzymatic activity and reduces methylglyoxal concentration. FIG. 7A, GLO1 enzymatic activity in whole brain. n=3 WT, 3Tg. FIG. 7B, HPLC measurement of MG concentration in whole brain. n=9 WT, 8 Tg. Data are mean±SEM. *P<0.05 by two-tailed t-tests.

Figures 8A, 8B, 8C:
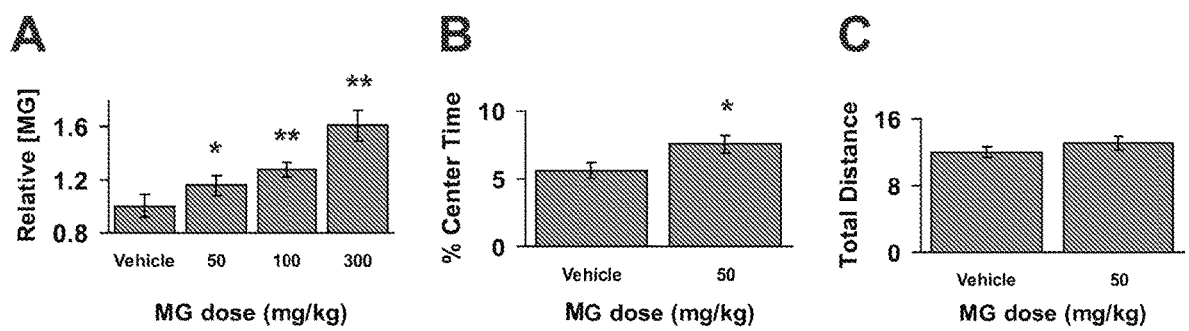

FIGS. 8A-8C: Methylglyoxal is acutely anxiolytic. FIG. 8A, HPLC measurement of MG concentration in whole brain after i.p. treatment with MG. Assay order had a significant effect on MG concentration and was used as a covariate in a one-way ANCOVA for the factor treatment, P=0.009; n=4-7 per group. FIGS. 8B-C, MG decreased anxiety-like behavior in the OF test. MG (50 mg/kg) increased time in the center of the OF (FIG. 8B) but did not change total distance traveled (FIG. 8C), n=18 per group. Data are mean±SEM. *P<0.05, **P<0.0005.

Figure 9:
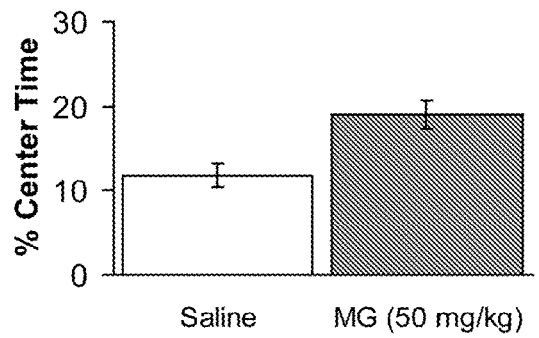
Figure 9:
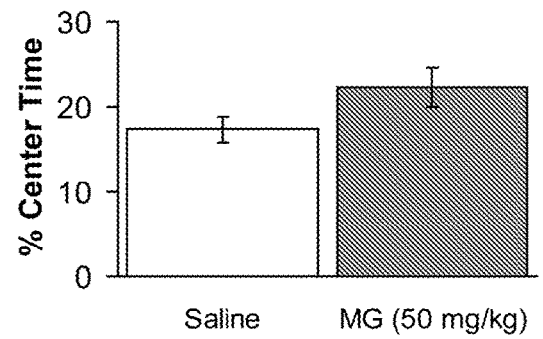
Figure 9:
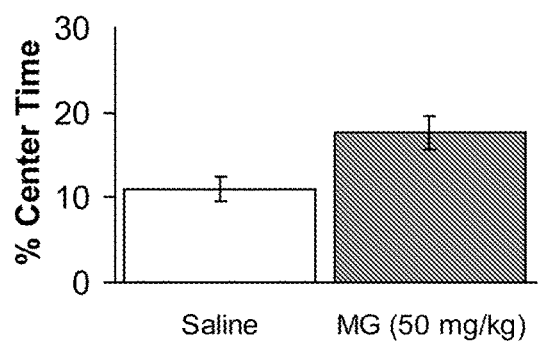
Figure 9:
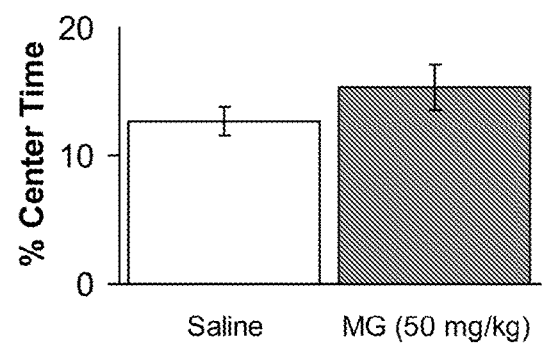
Figure 9:
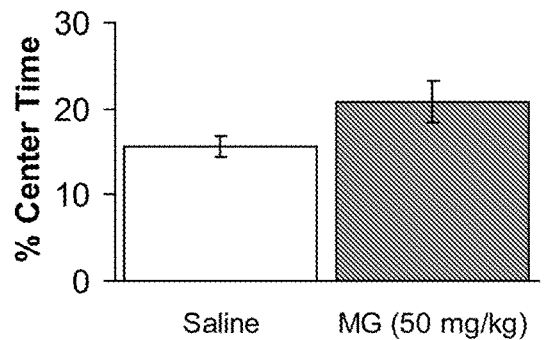
Figure 9:
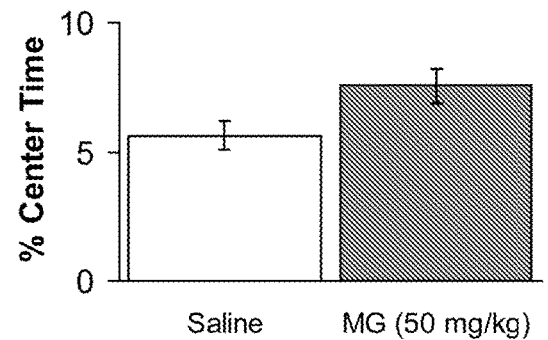

FIG. 9: Replicate experiments demonstrating methylglyoxal's anxiolytic effect in the open field test. Male B6 mice were treated with i.p. vehicle or MG (50 mg/kg). Ten or twenty minutes post-injection, mice were tested in the OF test for five or ten minutes. Each panel represents an independent replication experiment. Data are mean±SEM. Sample sizes ranged from 7-18 per group. A meta-analysis of the replication studies demonstrated that MG treatment had a large effect on anxiety-like behavior (Cohen's d=0.78; meta-analysis z-score=5.0) that was highly significant ($P<10^{-5}$) (FIG. 9 and Table 7).

Figures 10A, 10B:
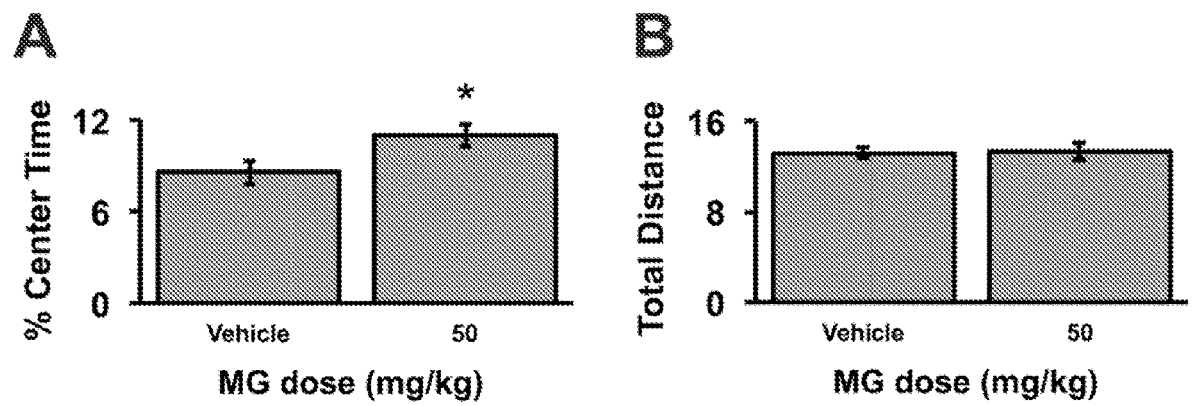

FIGS. 10A-10B: Methylglyoxal is anxiolytic in CD-1 mice. Male CD-1 mice were treated with i.p. vehicle or MG (50 mg/kg). Ten minutes post-injection, mice were tested in the OF test. n=27 vehicle, 28 MG. FIG. 10A, MG treatment increased time in the center of the open field. FIG. 10B, MG treatment did not change total distance traveled. Data are mean±SEM. *P<0.05 by two-tailed t-test.

Figures 11A, 11B:
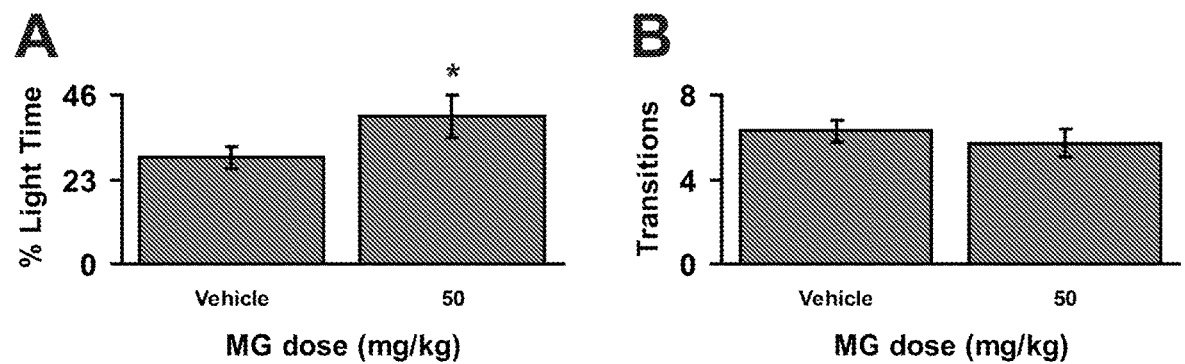

FIGS. 11A-11B: Methylglyoxal has anxiolytic effects in the light-dark box test. WT B6 mice were with treated i.p. with vehicle or MG (50 mg/kg). Ten minutes post-injection, mice tested in the LD box test. FIG. 11A, Mice treated with MG spent significantly more time in the light compartment. FIG. 11B, MG treatment did not significantly change number of transitions between the compartments. Data are mean±SEM. *P<0.05 by one-tailed t-test. n=16 per group.

Figure 12:
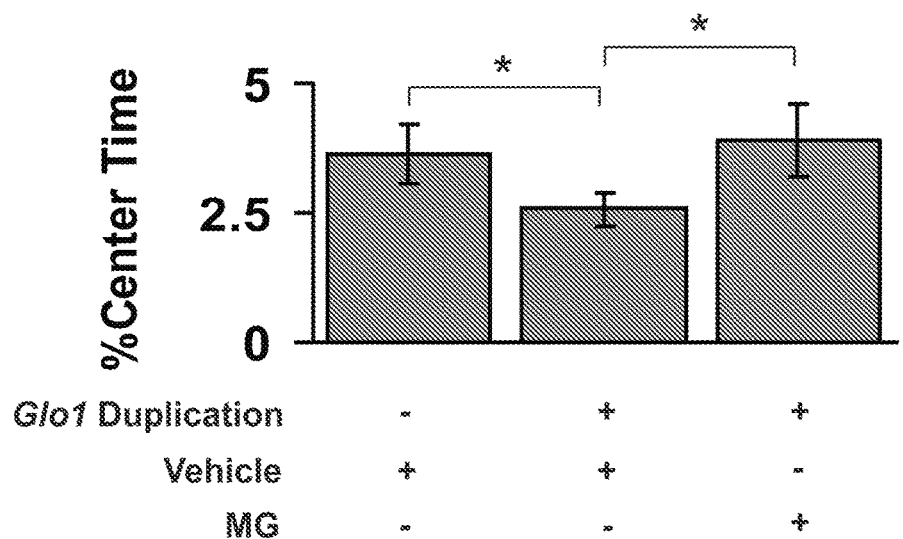

FIG. 12: Methylglyoxal administration reverse GLO1's anxiogenic effect. Male CD-1 mice were genotyped for the presence or absence of the Glo1 duplication. Mice were treated with vehicle or MG (50 mg/kg) by i.p. injection. Ten minutes post-injection, mice were tested in the OF. Mice with the Glo1 duplication spent less time in the center of the OF, and MG treatment reversed this effect. n=12 non-duplicated treated with vehicle, 15 duplicated treated with vehicle, 15 duplicated treated with MG. Data are mean±SEM. *P<0.05 by one-tailed t-tests.

Figures 13A, 13B:
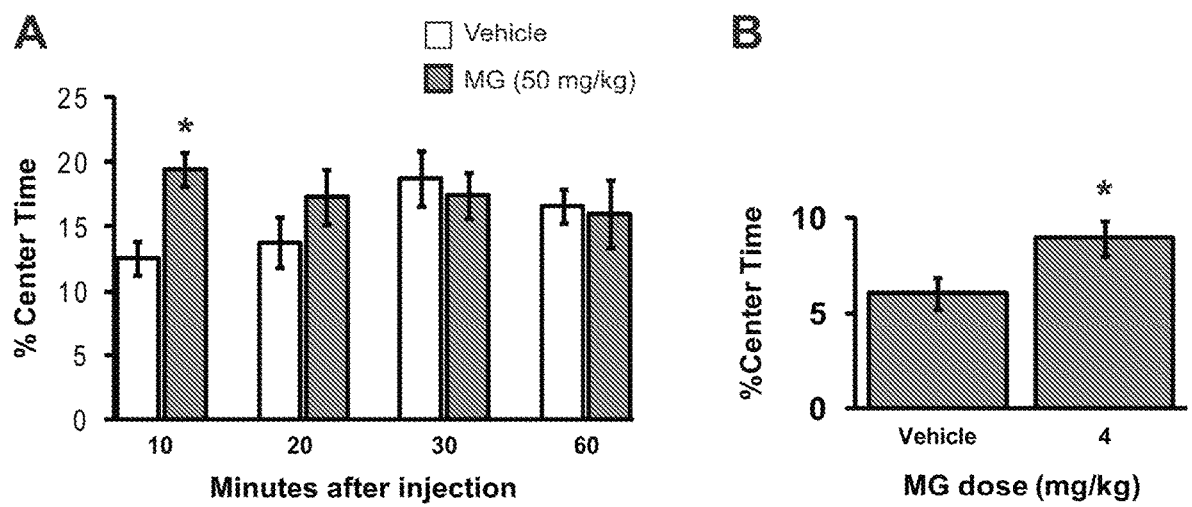

FIGS. 13A-13B: Methylglyoxal is anxiolytic when administered acutely and chronically. FIG. 13A, Separate cohorts of mice were injected with vehicle or MG (50 mg/kg) by i.p. injection. Mice were tested in the OF after the indicated interval. n=12 per group per cohort. FIG. 13B, Mice were treated twice daily for five days with MG (4 mg/kg) by i.p. injection. On the sixth day, mice were tested in the OF. n=9 vehicle, 5 MG. Data are mean±SEM. *P<0.05 by two-tailed t-test.

Figures 14A, 14B, 14C, 14D, 14E, 14F:
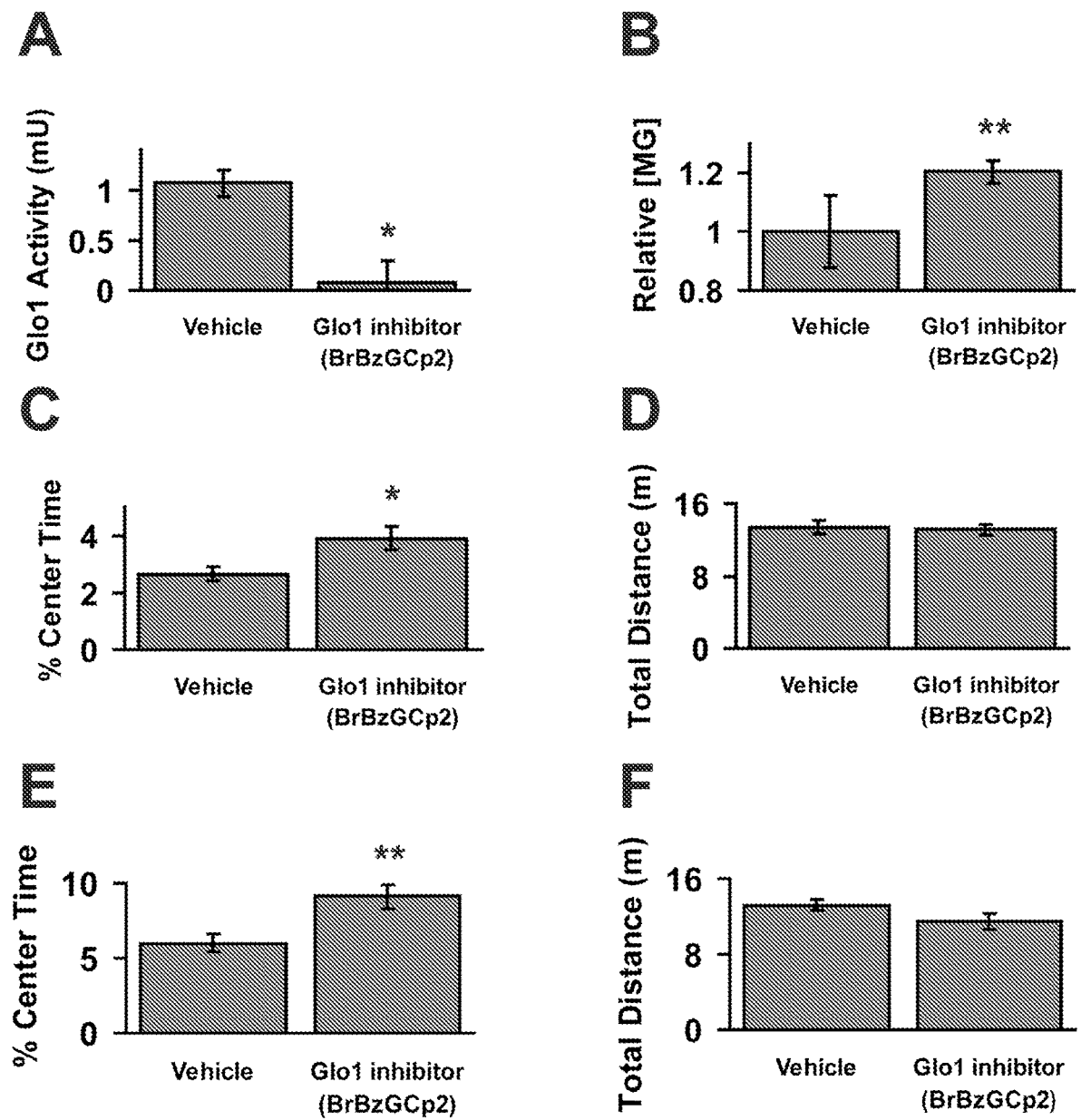

FIG. 14A-14F: GLO1 inhibition increases methylglyoxal concentration and reduces anxiety-like behavior in vivo. FIG. 14A, Enzymatic activity of 10 ng purified GLO1 protein treated with vehicle or 100 µM BrBzGCp2. n=3 vehicle, 4 BrBzGCp2. FIG. 14B, HPLC measurement of MG concentration in whole brain two hours after i.p. treatment with vehicle or BrBzGCp2. Assay order had a significant effect on MG concentration and was used as a covariate in a one-way ANCOVA for the factor treatment, P<0.0001; n=8 per group. FIGS. 14C-D, B6 mice were treated with i.p. vehicle or BrBzGCp2 (30 mg/kg) and then tested in the OF test two hours post-injection. n=25 vehicle, 24 BrBzGCp2. FIG. 14C, Center time. FIG. 14D, Total distance. FIGS. 14E-F, Male CD-1 mice were treated with i.p. vehicle or BrBzGCp2 (50 mg/kg). Two hours post-injection, mice were tested in the OF test. n=19 vehicle, 19 BrBzGCp2. FIG. 14E, Center time. FIG. 14F, Total distance traveled. Data are mean±SEM *P<0.05, **P<0.0005

Figure 15:
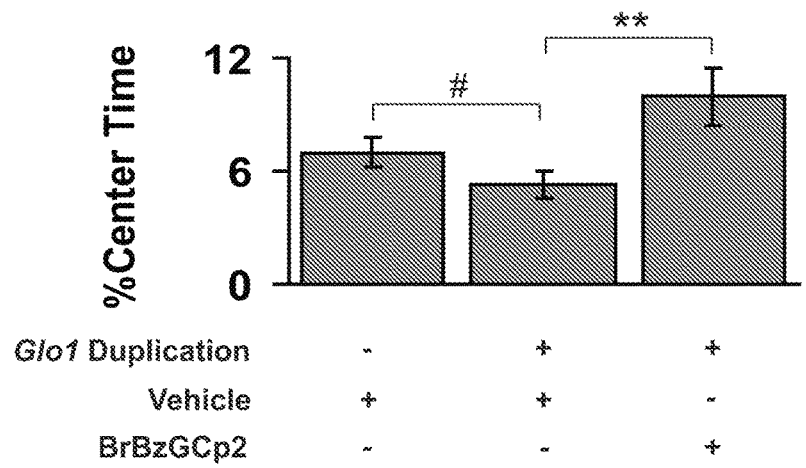

FIG. 15: GLO1 inhibition reverse GLO1's anxiogenic effect. Male CD-1 mice were genotyped for the presence or absence of the Glo1 duplication. Mice were treated with vehicle or BrBzGCp2 (50 mg/kg) by i.p. injection. Two hours after injection, mice were tested in the OF test. Mice with the Glo1 duplication spent less time in the center of the OF, and GLO1 inhibition reversed this effect. n=8 non-duplicated treated with vehicle, 11 duplicated treated with vehicle, 9 duplicated treated with BrBzGCp2. Data are mean±SEM. #P<0.08, **P<0.005 by one-tailed t-tests.

Figures 16A, 16B, 16C:
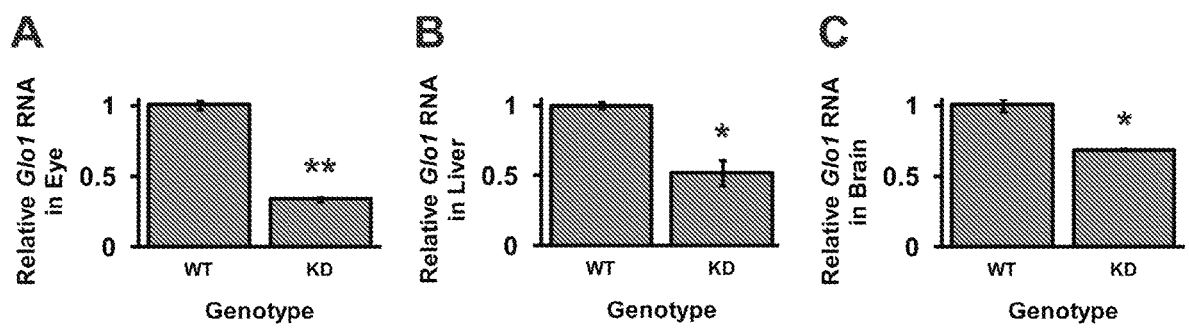

FIG. 16A-16C: Glo1 knockdown mice have reduced levels of Glo1 mRNA. Glo1 mRNA was estimated in eye (A), liver (B), and brain (C) by qPCR. n=4 per genotype. Data are mean±SEM. *P<0.01, **P<0.0001.

Figures 17A, 17B:
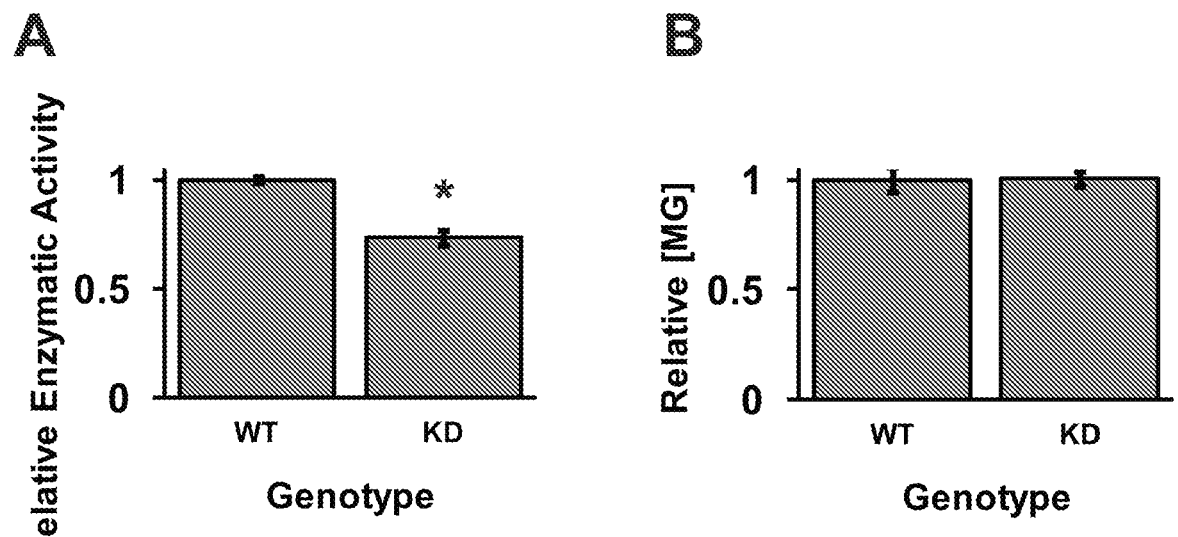

FIG. 17A-17B: Enzymatic activity and methylglyoxal concentration in Glo1 knockdown mice. FIG. 17A, GLO1 enzymatic activity in whole brain. n=3 per group. FIG. 17B, HPLC measurement of MG concentration in whole brain. n=5 WT, 6 KD. Data are mean±SEM. *P<0.002 by two-tailed t-test.

Figures 18A, 18B:
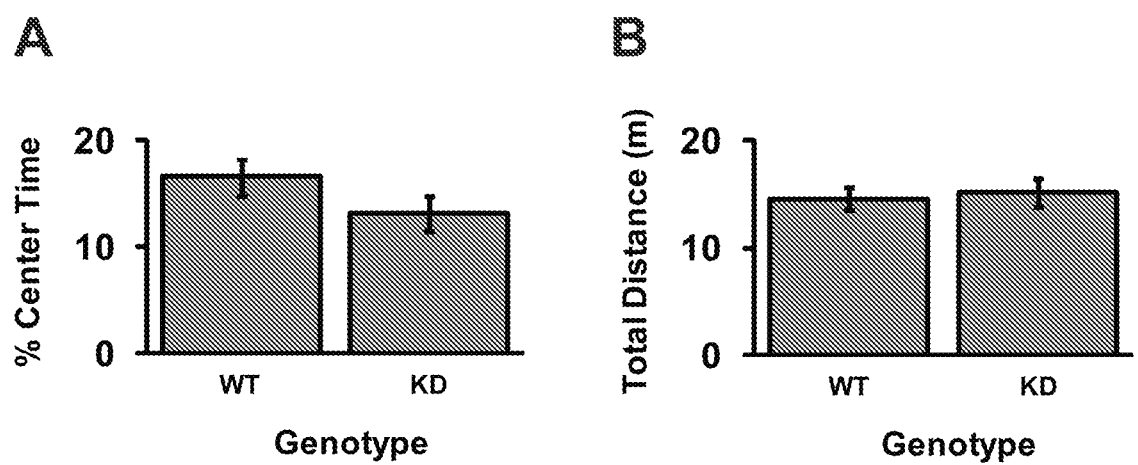

FIGS. 18A-18B: Glo1 knockdown mice do not differ from wild-type mice in anxiety-like behavior. WT and KD littermates were tested in the OF. FIG. 18A, Center time; two-tailed t-test, P=0.157. FIG. 18B, Total distance; two-tailed t-test, P=0.96. Data are mean±SEM. n=11 WT, 13 KD.

Figures 19A, 19B:
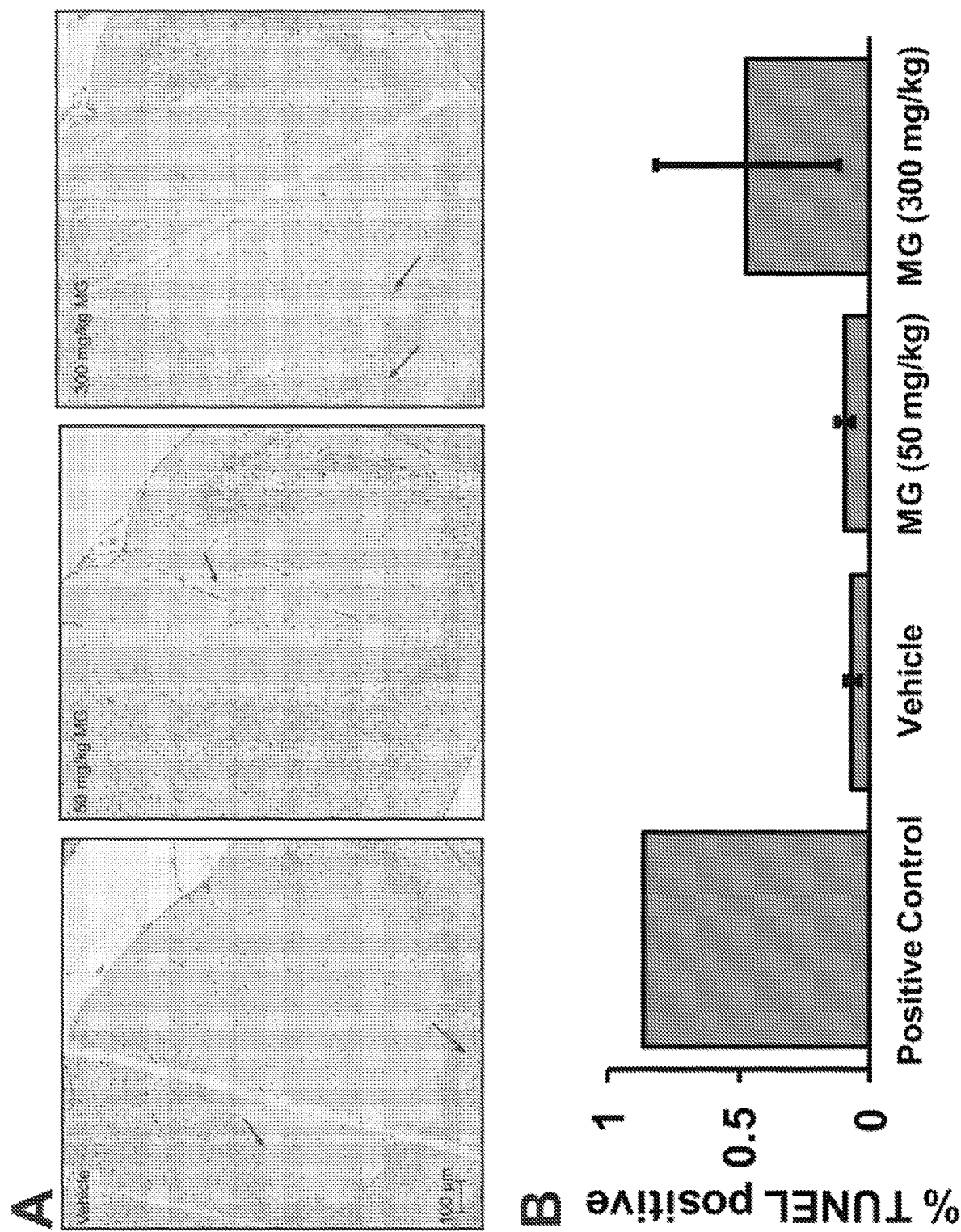

FIGS. 19A-19B: Methylglyoxal administration does not induce apoptosis in the brain. Mice were treated with i.p. vehicle or MG (50 or 300 mg/kg). Twenty-four hours after treatment, the brains were processed, and apoptotic cells were detected by in situ TUNEL staining A positive control (female rodent mammary gland 3-5 days post-weaning) was stained and analyzed in parallel. Neuropathological analysis of hematoxylin and eosin stained brain sections revealed no overt pathology in MG-treated mice. FIG. 19A, There was no discernible difference in TUNEL staining between vehicle- and MG-treated mice. Red arrows indicate TUNEL positive cells. FIG. 19B, Apoptotic cells were quantified in the hippocampus. MG treatment did not significantly change levels of apoptosis in the hippocampus compared to vehicle treatment; one-way ANOVA P>0.3. Data are mean±SEM. n=4 per group (3-4 sections per brain).

Figures 20A, 20B, 20C, 20D:
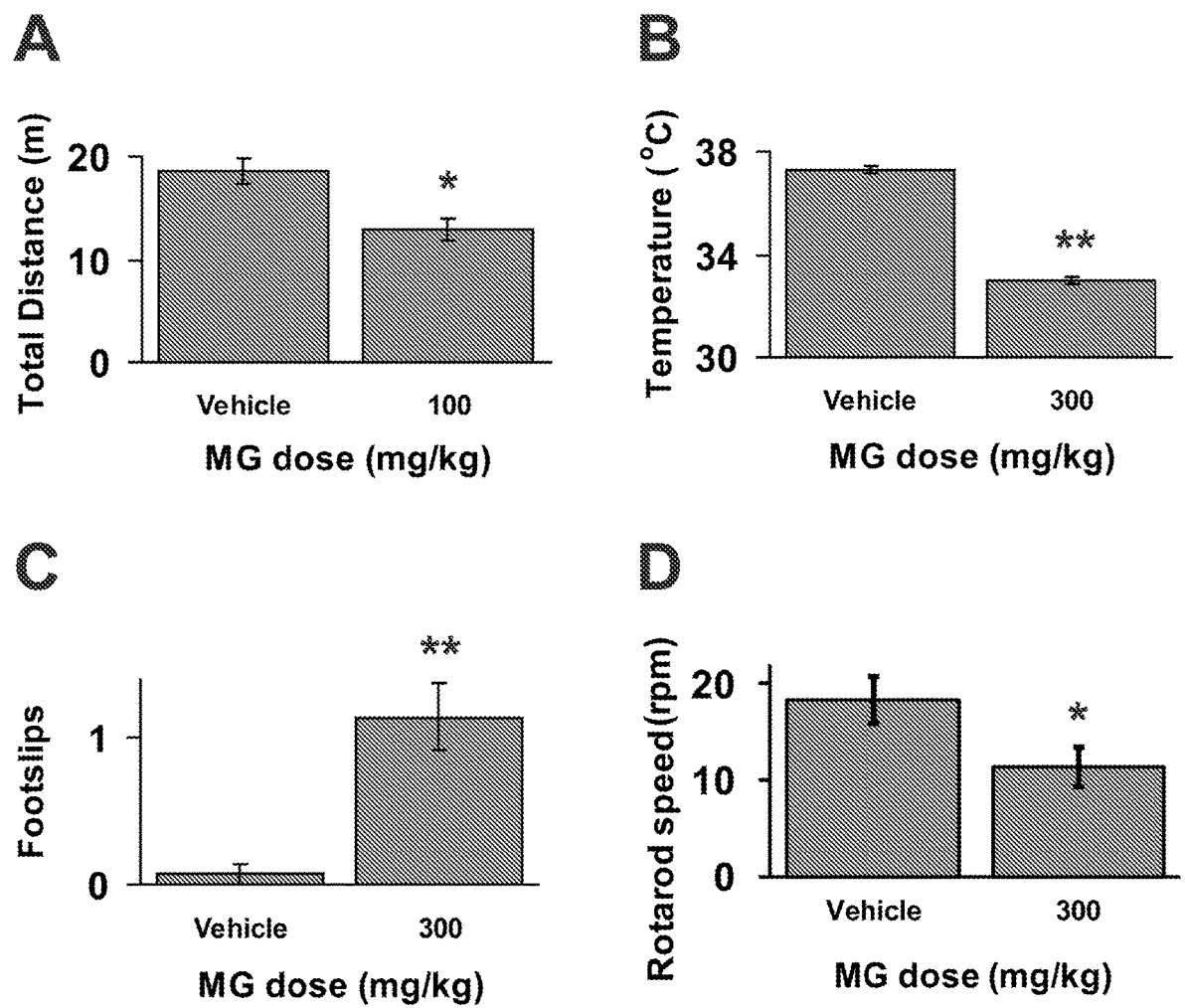

FIG. 20A-20D: Methylglyoxal has GABAergic properties in vivo. FIG. 20A, At 100 mg/kg, MG caused locomotor depression. n=8 per group. Two-tailed t-test. FIG. 20B, At 300 mg/kg, MG caused hypothermia. n=10 per group. Two-tailed t-test. FIG. 20C, At 300 mg/kg, MG increased footslips on the balance beam. n=14 per group. Mann-Whitney U test U=26, P=0.0002. FIG. 20D, At 300 mg/kg, MG reduced the average speed at which animals fell from an accelerating rotarod (rpm). n=10 vehicle, 5 MG. One-tailed t-test. All data are mean±SEM. *P<0.05, **P<0.0005.

Figures 21A, 21B, 21C, 21D:
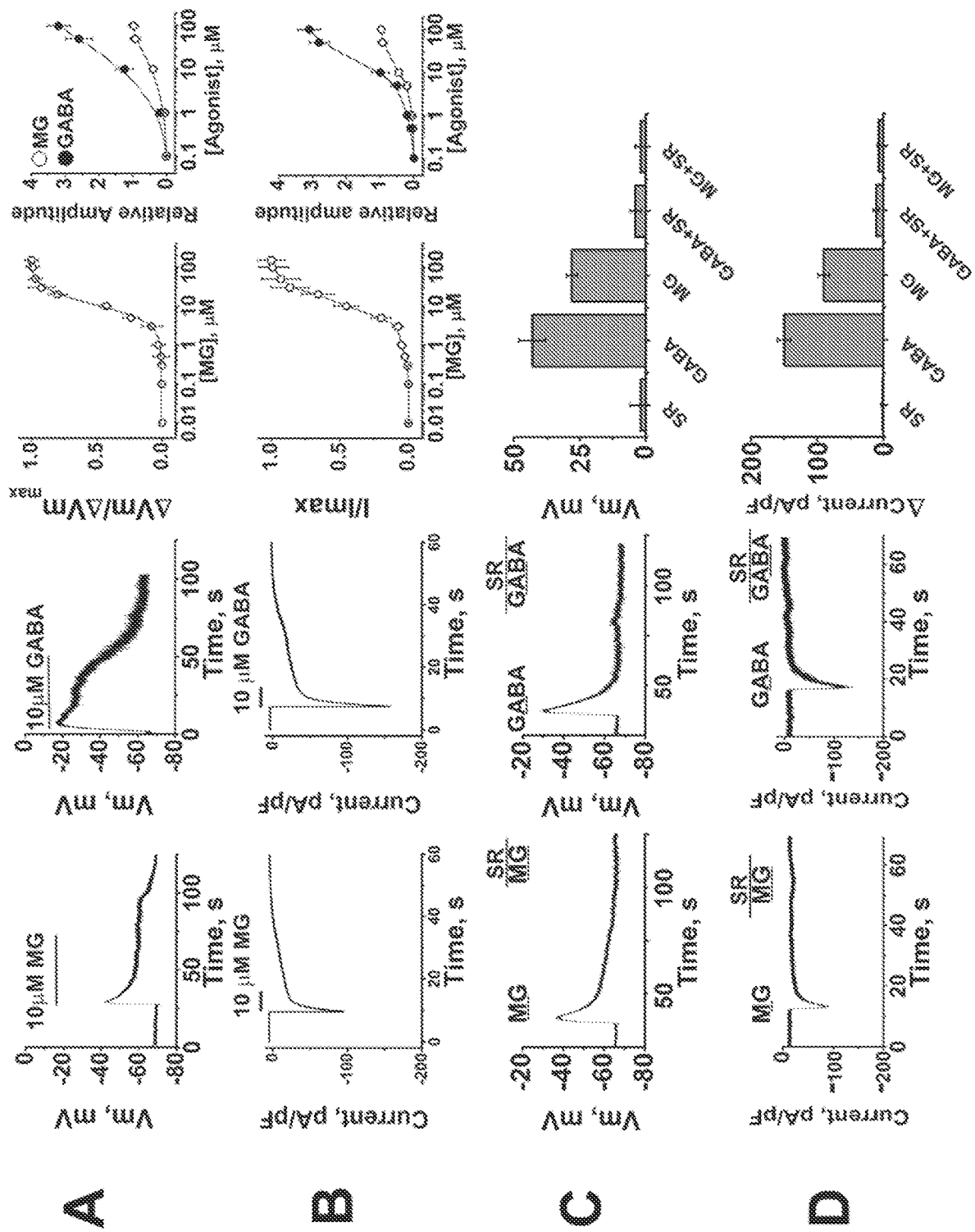

FIGS. 21A-21D: Methylglyoxal activates $GABA_A$ receptors in cerebellar granule neurons. FIG. 21A, CGN were depolarized by MG (○) or GABA (●) ($EC_{50}$: 10.5±0.5 µM MG, Hill co-efficient: 1.17). The relative amplitude of depolarization is shown normalized to the response of each cell to 100 µM MG. FIG. 21B, MG evoked inward currents in a concentration-dependent manner ($EC_{50}$: 12±0.7 µM, Hill co-efficient: 1.13). The amplitude of the currents is shown normalized to the peak response of each cell. FIG. 21C, Depolarization evoked by 10 µM MG (left) or GABA (middle) was blocked by 10 µM SR. Mean data are plotted as a histogram (right). FIG. 21D, Inward currents evoked by 10 µM MG (left) or GABA (middle) were also blocked by 10 µM SR. Mean data are plotted as a histogram (right).

Figures 22A, 22B, 22C, 22D, 22E, 22F, 22G, 22H, 22I:
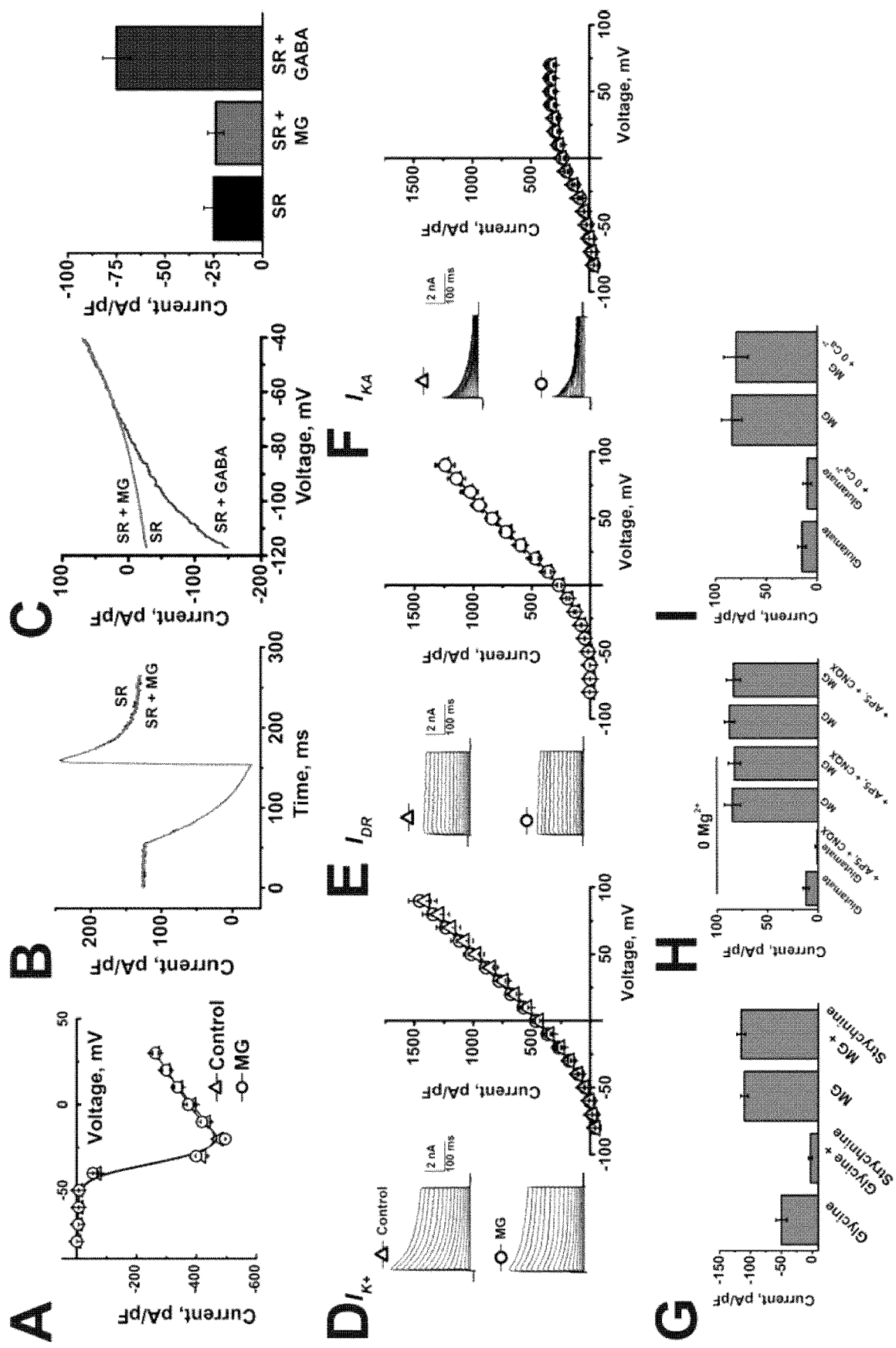

FIGS. 22A-22I: Methylglyoxal does not activate other conductances. FIG. 22A, Voltage-gated sodium currents, $I_{Na}$, were evoked by 100 ms step depolarizations between −80 and 30 mV. Mean current-density±SEM is plotted against test voltage for ten cells studied during perfusion of the bath solution without (A) and then with 10 µM MG (0).

FIG. 22B, The potassium leak current, $I_{Kso}$, was studied by voltage ramps from −20 mV to −120 mV at a rate of −1 mV/ms applied every 20 seconds. Currents were evoked in the presence of 10 µM SR.

FIG. 22C, $I_{KIR}$ Left, Representative current-density ramps from the protocol described in B replotted against voltage. In the presence of SR, or SR+MG, $I_{Kso}$ showed open rectification and had a reversal potentials close to $E_{K+}$ (−80 mV). In contrast, an inwardly rectifying, potassium-selective current was observed when 10 µM GABA is applied in the continued presence of SR (SR+GABA). Right, a histogram of mean current-density±SEM at −100 mV for 10 cells studied in each group.

FIG. 22D, $I_{K+}$ Left, Voltage-gated potassium currents ($I_{K+}$) were evoked by 250 ms voltage steps from −80 to 90 mV following a 250 ms prepulse to −140 mV to remove inactivation. $I_{K+}$ was studied during perfusion with control bath solution (upper, Δ) and then with the addition of 10 µM MG (lower, 0). Right, Mean peak current-density±SEM for 10 cells is plotted against test voltage for each condition.

FIG. 22E, $I_{DR}$ Left, The delayed rectifier current, $I_{DR}$, was studied in the same cells used to study $I_{K+}$ (panel D). $I_{DR}$ was evoked by the protocol described in D, with the prepulse voltage changed to −50 mV to promote inactivation. The effect of 10 µM MG (0) was tested for each cell, and the currents are plotted (right) as mean peak current-density±SEM against test voltage.

FIG. 22F, $I_{KA}$ The inactivating component of current, $I_{KA}$, calculated by subtraction of $I_{DR}$ (panel E) from $I_{K+}$ (panel D) for each cell, is shown as both current families (left) and as mean current density plots (right).

FIG. 22G, $I_{GLY}$ MG did not modulate currents evoked by the application of 100 µM glycine to CGNs voltage clamped at −50 mV. Glycinergic currents, but not currents activated by 10 µM MG, were blocked by 500 nM strychnine Bars represent the mean peak current density±SEM for 10 cells in each group.

FIG. 22H, $I_{Glu}$ MG did not modulate currents evoked by application of 10 µM glutamate to CGNs that were voltage clamped at −50 mV in the absence of 1 mM extracellular magnesium. Glutamatergic currents, but not currents activated by 10 µM MG, were blocked by co-application of the NMDA receptor antagonist, AP-5, and the AMPA and kainate receptor antagonist, CNQX. The magnitude of the MG-activated current was not dependent on extracellular magnesium. Bars represent the mean peak current density±SEM for ten cells in each group.

FIG. 22I, A histogram showing that the magnitude of the MG-activated current was not altered by the presence or absence of 1 mM extracellular calcium. Bars represent the mean peak current density±SEM for ten cells in each group.

Figures 23A, 23B, 23C, 23D, 23E:
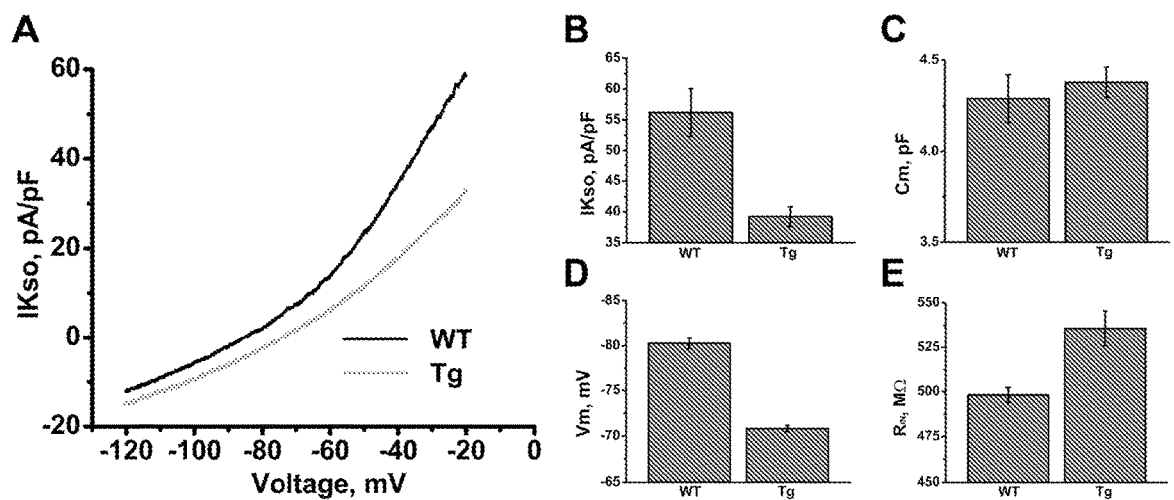

FIGS. 23A-23E: Neurons from transgenic mice are hyperexcitable. CGN were cultured from WT and Tg littermates from B6 Tg line 3. IKso, $V_m$, and cellular input resistance ($R_{in}$) were determined. FIG. 23A, Representative recordings demonstrate that IKso is smaller in Tg neurons compared WT neurons, indicating increased excitability. FIG. 23B, A histogram of mean IKso from each group at −20 mV normalized to capacitance. FIG. 23C, Mean cell capacitance was not difference between WT and Tg neurons. FIG. 23D, Tg neurons were depolarized compared with WT neurons. FIG. 23E, Mean $R_{in}$ was larger in Tg neurons, indicating increased excitability. Data are mean±SEM. n=18 WT, 58 Tg.

Figure 24:
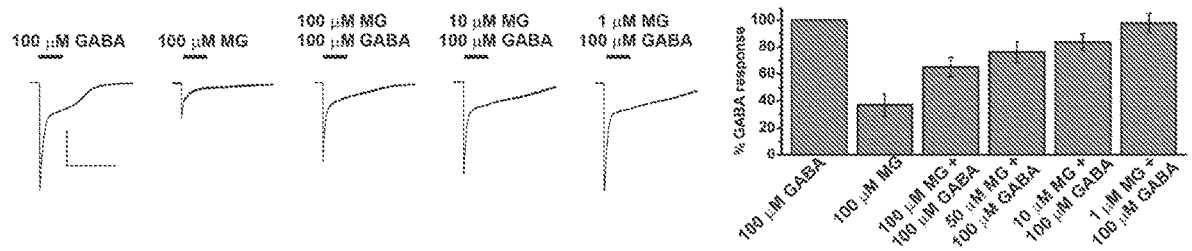

FIG. 24: Methylglyoxal acts competitively with GABA at $GABA_A$ receptors. Currents evoked by 100 µM GABA were reduced by co-application of MG. Scale bars represent 200 pA/pF and 25 s (left). Mean data are normalized to the current evoked by 100 µM GABA in each cell (right). Data are mean±SEM. n=6-12 cells per condition.

Figure 25:
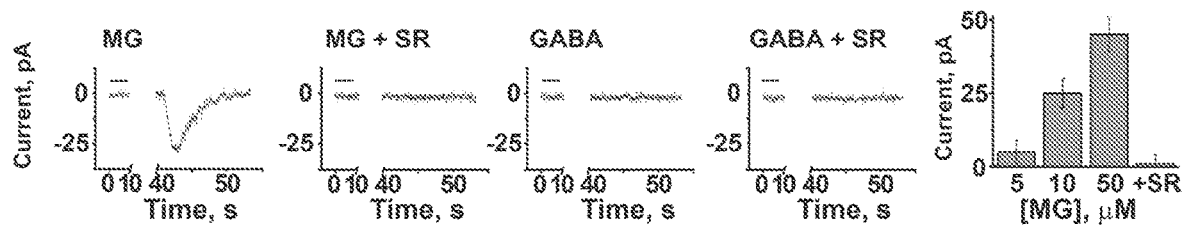

FIG. 25: Methylglyoxal crosses the plasma membrane to activate $GABA_A$ receptors. Currents were observed ~40 s after the application of 10 µM MG to the inside of macropatches excised from CGN and were blocked when 10 μM SR was included in the pipette. Application of 10 μM GABA to the inside of macropatches did not evoke a current. Mean data are plotted as a histogram. The bar above each trace shows the duration of drug application. Data are mean±SEM. n=6-12 macropatches per condition.

Figures 26A, 26B:
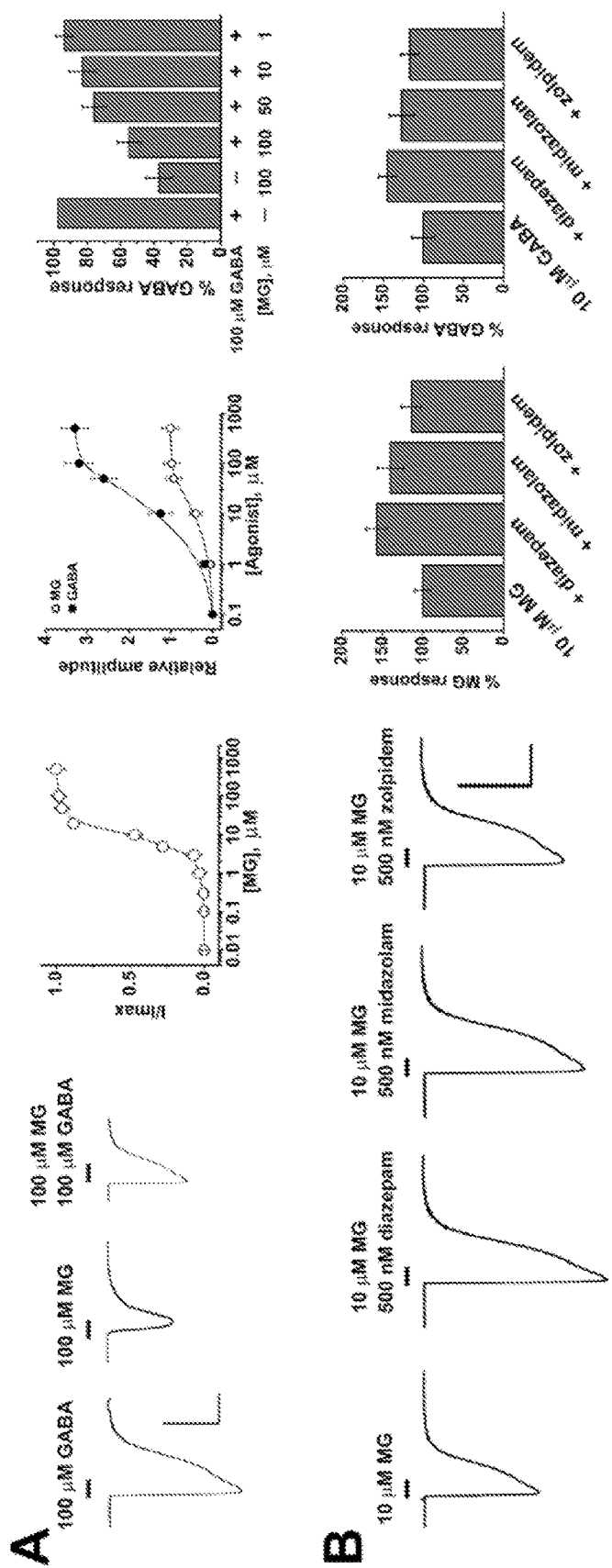

FIGS. 26A-26B: Methylglyoxal activates $GABA_A$ receptors in hippocampal neurons, and its effect is modulated by allosteric $GABA_A$ receptor agonists. FIG. 26A, Both GABA and MG evoked concentration-dependent inward currents in hippocampal neurons. The $EC_{50}$ of currents evoked by MG was 9.5±0.9 04 with a Hill co-efficient of 1.05. The relative amplitude of the currents was normalized to that cell's response to 100 μM MG. Currents evoked by 100 μM GABA were reduced by co-application of MG in a concentration-dependent manner. Scale bars represent 1 nA and 10 s. Mean data for competition experiments are shown normalized to the current evoked by 100 μM GABA in each cell. FIG. 26B, Currents evoked by 10 μM MG or GABA were augmented by co-application of 500 nM diazepam, midazolam, or zolpidem. Scale bars represent 1 nA and 10 s. Mean data are plotted as histograms. The bar above each trace shows the duration of drug application. Data are mean±SEM; n=8-10 cells per condition.

Figures 27A, 27B, 27C, 27D, 27E:
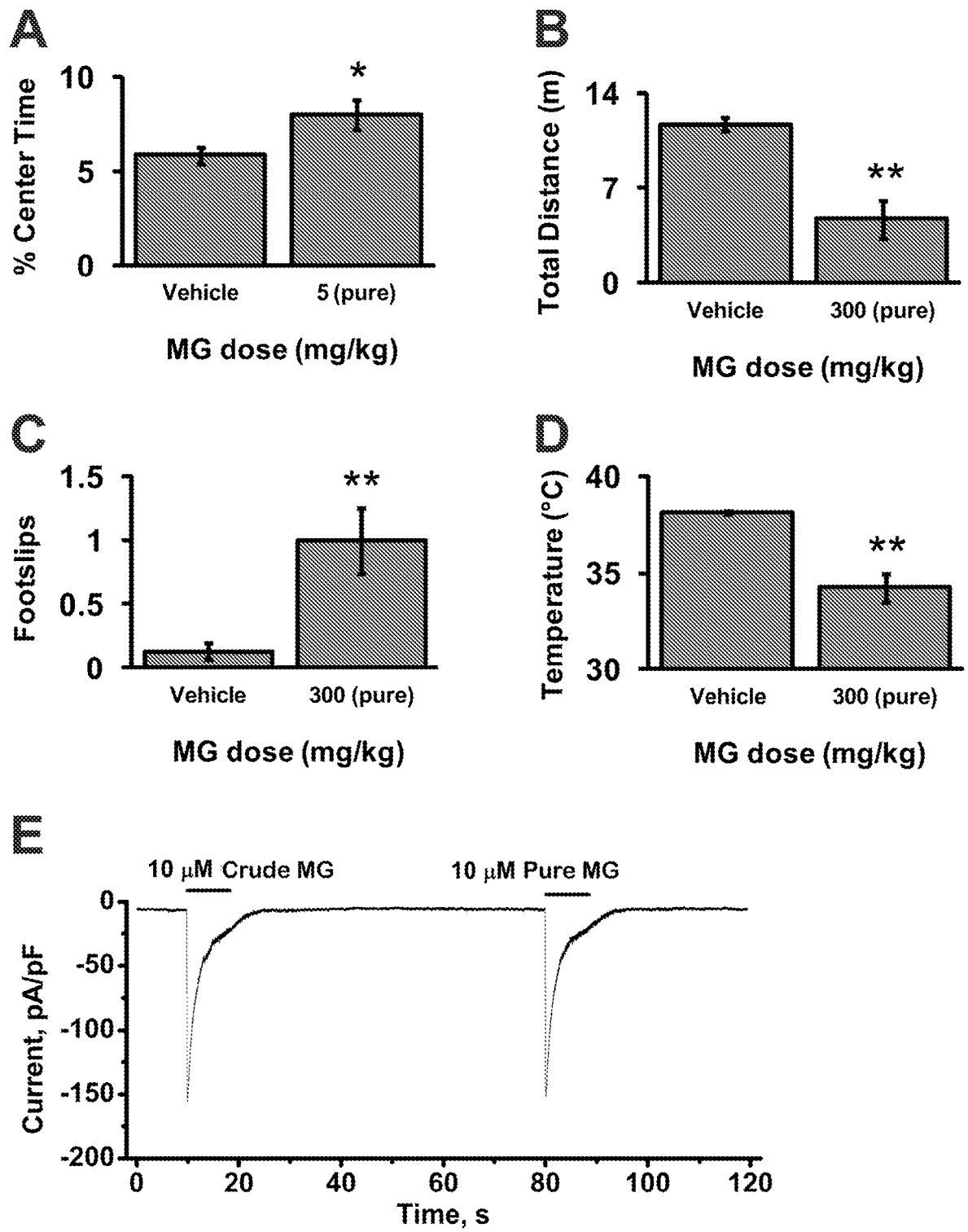

FIGS. 27A-27E: Pure methylglyoxal has GABAergic effects in vivo and in vitro. FIG. 27A, B6 mice were treated with vehicle or pure MG (5 mg/kg); ten minutes later, they were tested in the OF. Pure MG increased time in the center of the OF. n=30 vehicle, 18 MG (5 mg/kg). FIGS. 27B-D, B6 mice were treated with vehicle or pure MG (300 mg/kg). n=30 saline, 6 MG (300 mg/kg). Pure MG (300 mg/kg) reduced total distance traveled in the OF (FIG. 27B), increased footslips on the balance beam (FIG. 27C), and caused hypothermia (FIG. 27D). FIG. 27E, Both pure and crude MG (10 μM) evoked inward currents in CGN. Data are mean±SEM. A, C, and D were analyzed by two-tailed t-tests. B was analyzed by Mann-Whitney U test. *P<0.001, **P<0.0001

Figures 28A, 28B:
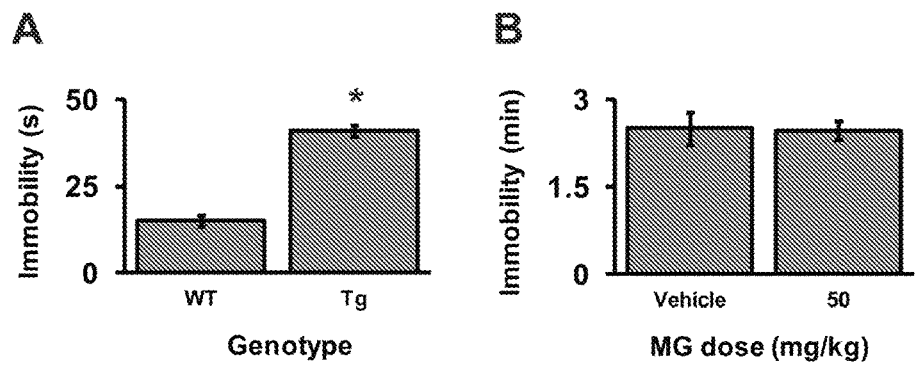

FIGS. 28A-28B: Effects of Glo1 overexpression and methylglyoxal administration in the tail suspension test. FIG. 28A, WT and Tg mice from FVB Tg Line 3 were tested in the TST. n=7 WT, 3 Tg. FIG. 28B, B6 mice were treated with vehicle or MG (50 mg/kg) by i.p. injection. Ten minutes post-injection, mice were tested in the TST. n=8 vehicle, 7 MG. Data are mean±SEM. *P=0.025.

Figures 29A, 29B, 29C:
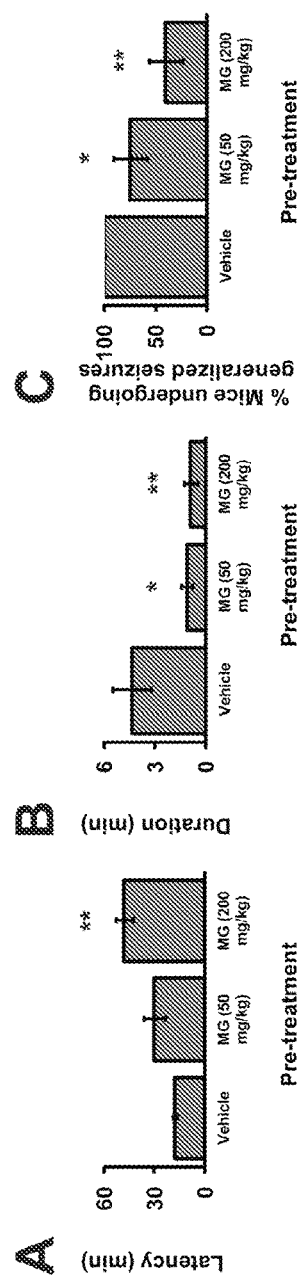

FIGS. 29A-29C: Methylglyoxal pre-treatment attenuates picrotoxin-induced seizures. Mice were pre-treated with vehicle or MG (50 and 200 mg/kg) prior to seizure induction with picrotoxin (5 mg/kg). FIG. 29A, MG pre-treatment increased the latency to first generalized convulsion. P=0.0002 by Kruskal-Wallis test. FIG. 29B, MG pre-treatment reduced the duration of generalized convulsions. P=0.0025 by Kruskal-Wallis test. FIG. 29C, MG pre-treatment reduced the percentage of mice undergoing generalized convulsions. P=0.0033 by Kruskal-Wallis test. Data are mean±SEM. n=16 vehicle, 8 MG (50 mg/kg), 10 MG (200 mg/kg). *P<0.05, **P<0.005 versus vehicle-treated group by Mann-Whitney U tests.

Figures 30A, 30B, 30C, 30D:
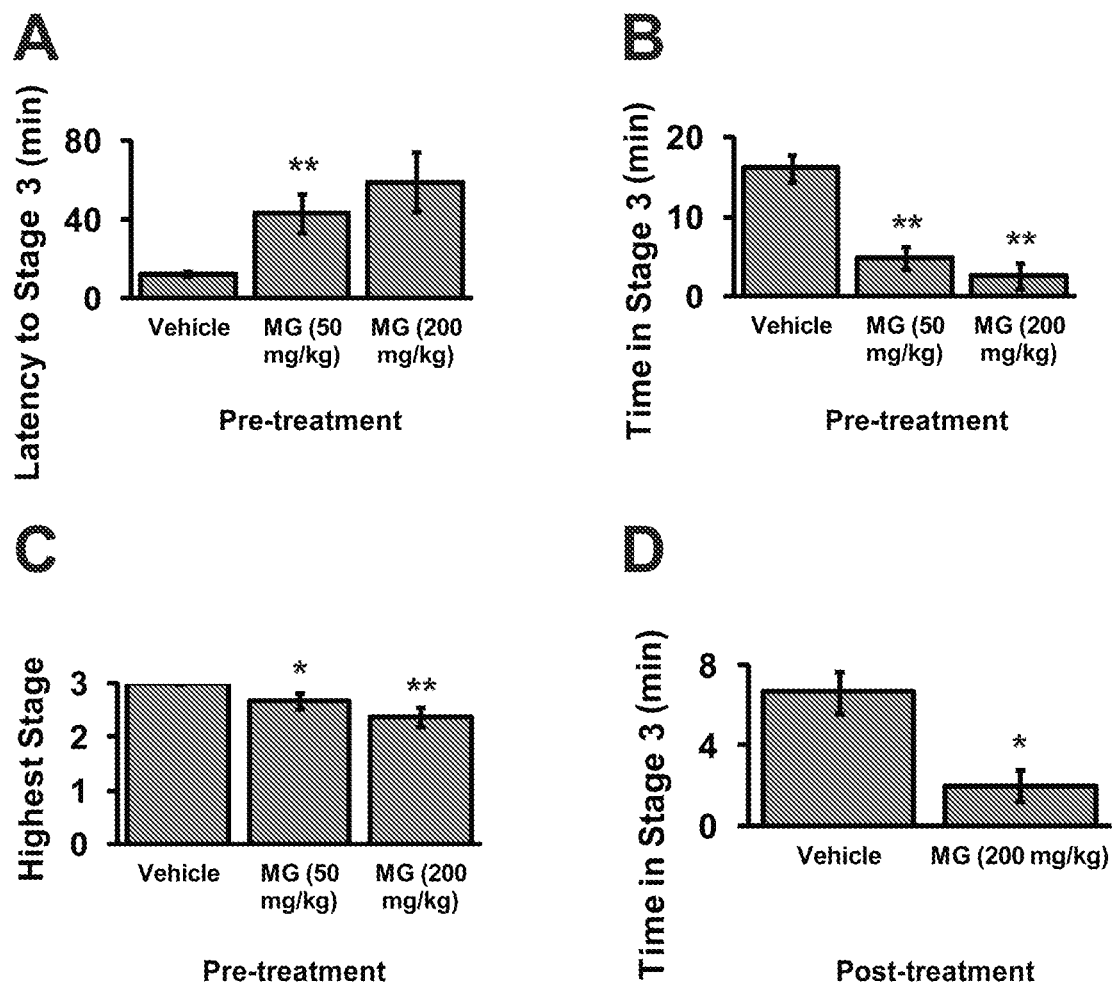

FIGS. 30A-30D: Methylglyoxal pre-treatment attenuates pilocarpine-induced seizures. A-C, Mice were pre-treated with vehicle or MG (50 and 200 mg/kg) prior to seizure induction with pilocarpine (250 mg/kg). n=19 vehicle, 12 MG (50 mg/kg), 8 MG (200 mg/kg). FIG. 30A, MG pre-treatment increased the latency to reach stage 3. P=0.0033 by Kruskal-Wallis test. FIG. 30B, MG pre-treatment reduced the time spent in stage 3. P<0.0001 by Kruskal-Wallis test. FIG. 30C, MG pre-treatment reduced the highest seizure stage reached. P=0.0015 by Kruskal-Wallis test. FIG. 30D, Seizures were induced with pilocarpine (250 mg/kg); 10 minutes later, mice were treated with vehicle or MG (200 mg/kg). MG treatment reduced time spent in stage 3. n=6 per group. Data are mean±SEM. *P<0.05, **P<0.005 versus vehicle-treated group by Mann-Whitney U tests.

Figure 31:
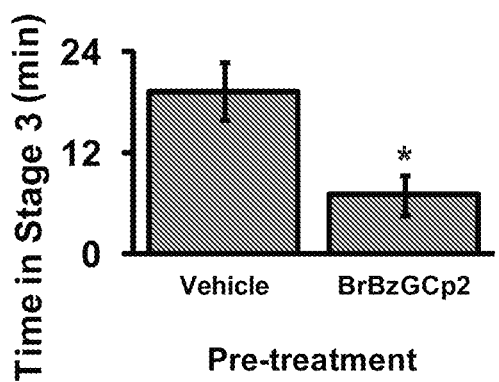

FIG. 31: GLO1 inhibition attenuates seizures. Mice were treated with vehicle or BrBzGCp2 (50 mg/kg). Two hours later, seizures were induced with pilocarpine (250 mg/kg). Pre-treatment with BrBzGCp2 reduced time spent in stage 3. Data are mean±SEM. n=12 vehicle, 8 BrBzGCp2. *P<0.05 by Mann-Whitney U test.

Figure 32A:
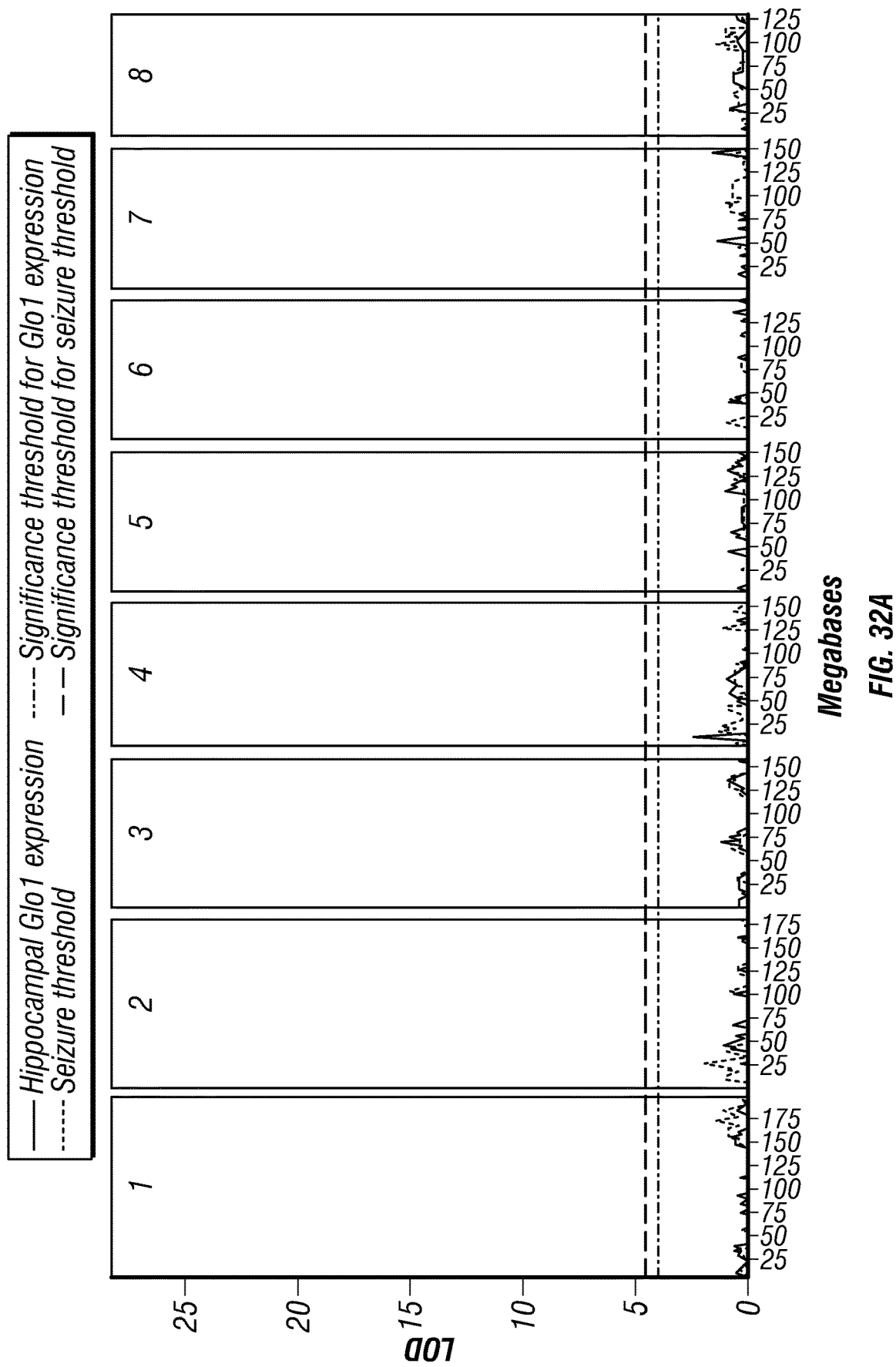

FIGS. 32A-32D: Glo1 expression is negatively correlated with seizure threshold in BXD recombinant inbred lines. FIG. 32A, The position along the mouse genome is on the x-axis, and the logarithm of odds (LOD) score is on the y-axis. Pink and blue horizontal lines indicate genome-wide significance thresholds for Glo1 expression and seizure threshold, respectively. Hippocampal Glo1 mRNA expression was assessed by microarray (record ID 1424109_a_at). Seizure threshold data were obtained using record ID 10388. The figure was generated by www.genenetwork.org. FIG. 32B, The data from A are replotted to show only chromosome 17. FIG. 32C, Association between Glo1 expression in the hippocampus (record ID 1424109_a_at) and seizure threshold (record ID 10388). Pearson correlation: $r^2=0.59$, $P=5.42 \times 10^{-5}$. FIG. 32D, BXD RI lines were classified as duplicated or non-duplicated based on their genotype at SNP rs3145545. Those with the Glo1 duplication displayed reduced seizure threshold than those without the duplication (record ID 10388). n=11 non-duplicated, 12 duplicated. P=0.0003 by two-tailed t-test. Data were obtained from www.genenetwork.org using the indicated record IDs. For Glo1 expression, each unit represents a two-fold difference in expression level. For seizure threshold, units represent the pressure (atm) at which animals seized. For B and C, black symbols represent BXD RI lines harboring the B6 Glo1 allele, and gray symbols represent BXD RI lines harboring the D2 Glo1 allele based on their genotype at SNP rs3145545.

Figures 33A, 33B, 33C, 33D:
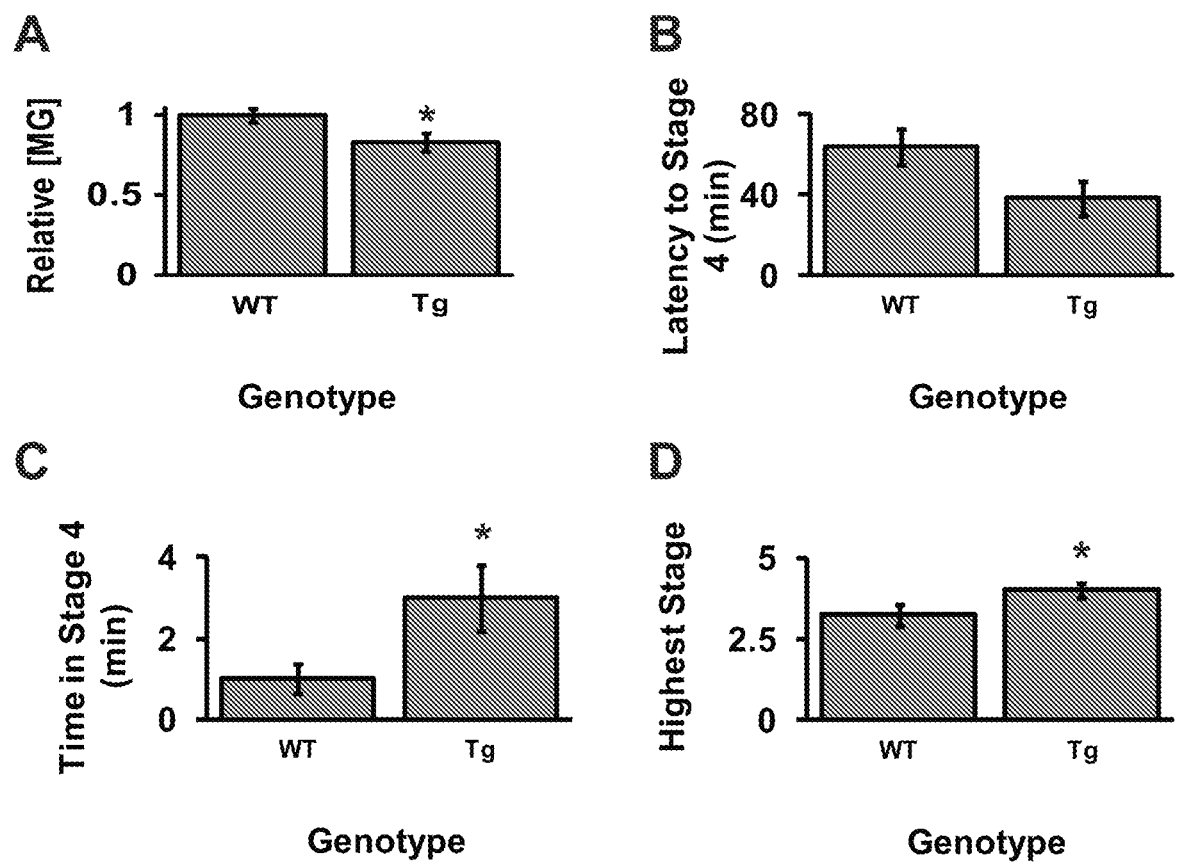

FIGS. 33A-33D: Glo1 overexpression exacerbates seizures. FIG. 33A, MG concentration was measured by HPLC in the brains of FVB WT and Tg mice. n=7 WT, 7 Tg. FIGS. 33B-33D, Seizures were induced in FVB WT and Tg mice with pilocarpine (300 mg/kg). n=13 WT, 8 Tg. There was a trend for Tg mice to reach stage 4 seizures sooner than WT mice (FIG. 33B). Tg mice spent significantly more time in stage 4 (FIG. 33C) and had more severe seizures (FIG. 33D) than WT mice. Data are mean±SEM. *P<0.05 by Mann-Whitney U tests.

Figure 34:
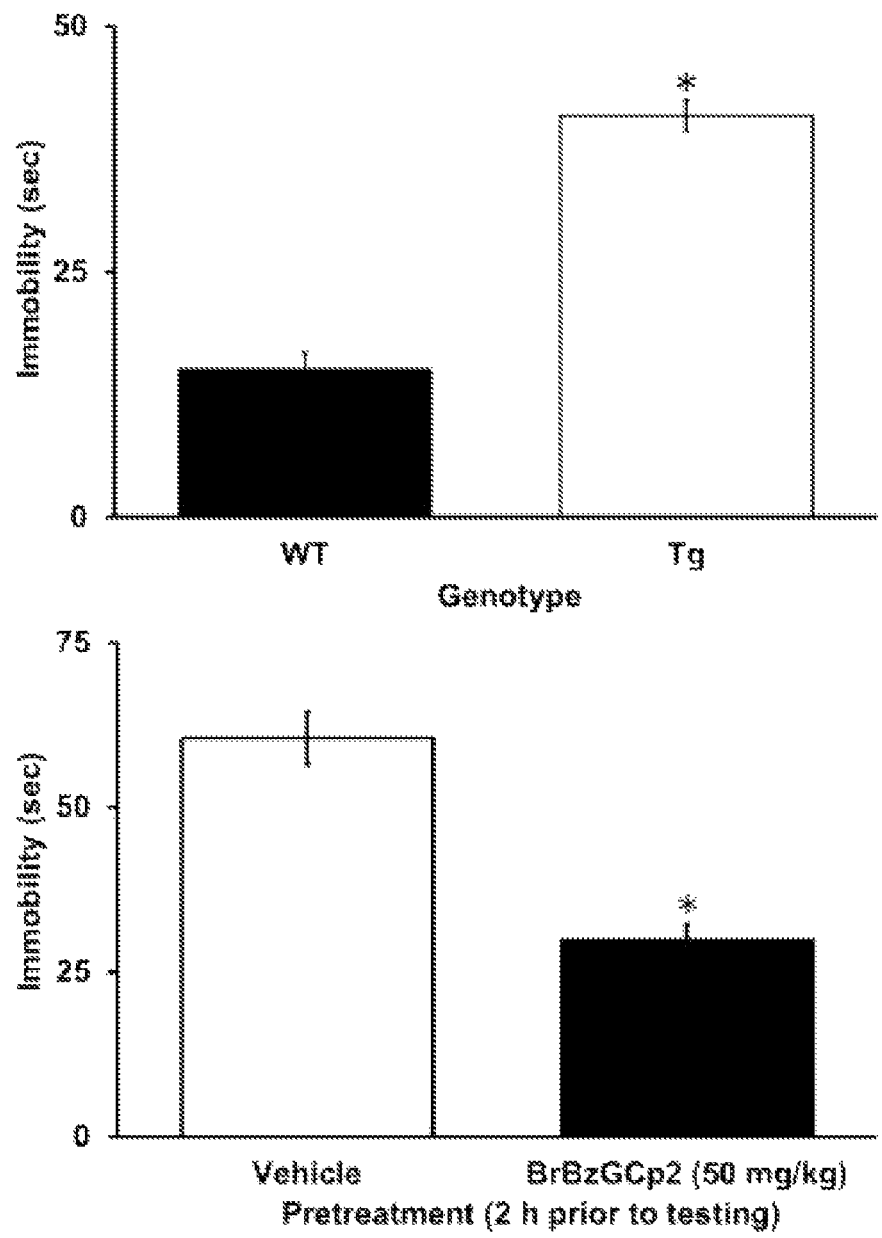

FIG. 34. In order to determine if the reported correlation with Glo1 was causal the inventors examined TST behavior in the inventors' Glo1 Tg mice, which are on an isogenic background, and thus provide more definitive results than the panel of inbred strains used by Benton et al (2011). As shown in the upper panel of FIG. 34, Tg mice showed greater immobility on the TST, which is opposite to the effects obtained when an antidepressant is administered. The inventors then used separate cohort of mice to examine the effects of the inventors' small molecule inhibitor of GLO1. As shown in the lower panel of FIG. 34, the GLO1 inhibitor produced antidepressant-like effects.

Figure 35:
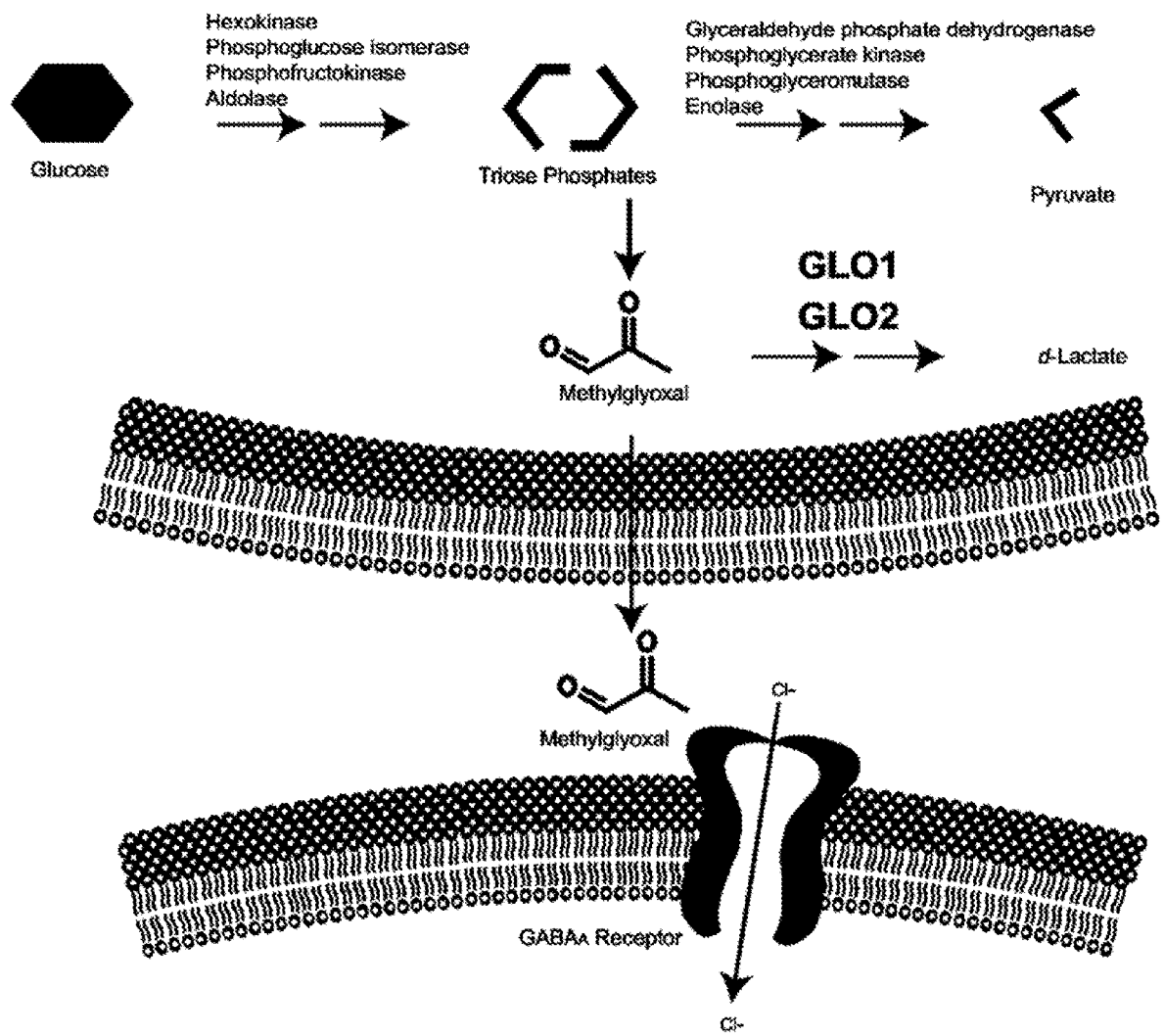

FIG. 35: A model of the glyoxalase system's role in GABAergic signaling. During glycolysis, triose phosphate intermediates can be converted to MG by non-enzymatic fragmentation. Excess MG is catabolized by the glyoxalase system (GLO1 and GLO2) to form d-lactate. MG that is not catabolized can cross the plasma membrane, where it accesses $GABA_A$ receptors. MG binding causes $GABA_A$ receptor activation, inward $Cl^-$ current, and membrane hyperpolarization. This enhances neuronal inhibitory tone, which mediates downstream behaviors, including anxiety, depression, and seizure susceptibility.

Figures 36A, 36B, 36C:
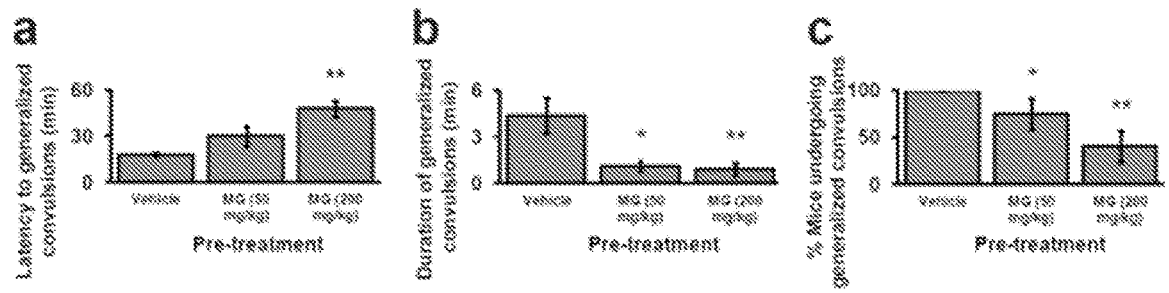

FIGS. 36A-36C: Exogenous MG attenuates picrotoxin-induced seizures at the behavioral level. B6 mice were pre-treated with vehicle or MG (50 and 200 mg/kg) prior to seizure induction with picrotoxin (5 mg/kg). FIG. 36A, MG pre-treatment increased the latency to first generalized convulsion. P=0.0002 by Kruskal-Wallis test. FIG. 36B, MG pre-treatment reduced the duration of generalized convulsions. P=0.0025 by Kruskal-Wallis test. FIG. 36C, MG pre-treatment reduced the percentage of animals undergoing generalized convulsions. P=0.0033 by Kruskal-Wallis test. Data are mean±SEM. n=16 vehicle, 8 MG (50 mg/kg), 10 MG (200 mg/kg). *P<0.05, **P<0.005 versus vehicle-treated group as determined by Mann-Whitney U tests.

Figures 37A, 37B, 37C, 37D:
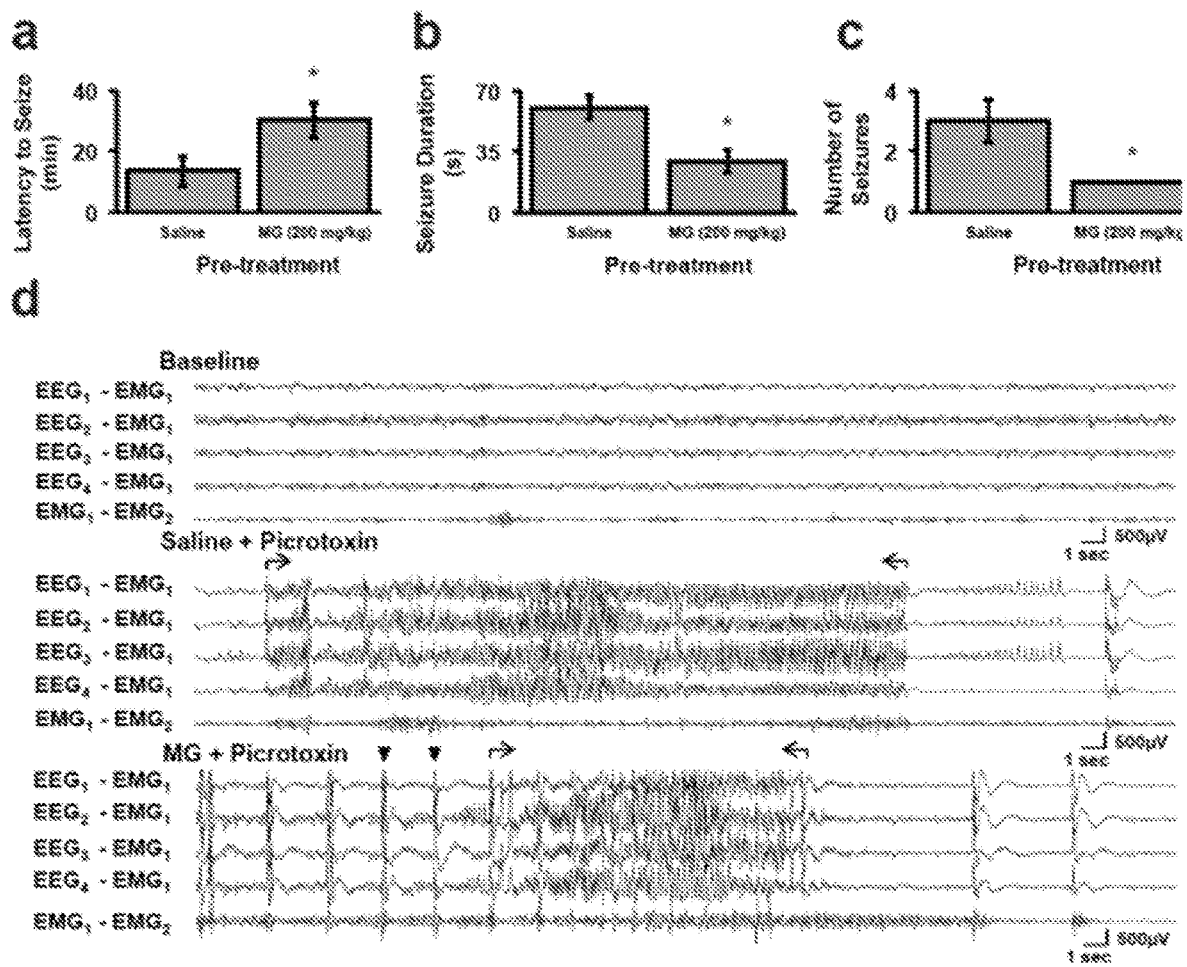

FIGS. 37A-37D: Exogenous MG attenuates picrotoxin-induced seizures as assessed by EEG. B6 mice were pre-treated with vehicle or MG (200 mg/kg) prior to seizure induction with picrotoxin (7 mg/kg). FIG. 37A, MG pre-treatment increased the latency to first EEG-confirmed seizure. P=0.036 by Mann-Whitney U test. FIG. 37B, MG pre-treatment reduced the duration of EEG-confirmed seizures. P=0.014 by Mann-Whitney U test. c, MG pre-treatment reduced the number of EEG-confirmed seizures. P=0.028 by Mann-Whitney U test. B6 mice were pre-treated with vehicle or MG (200 mg/kg) prior to seizure induction with picrotoxin (7 mg/kg). a, MG pre-treatment increased the latency to first EEG-confirmed seizure. P=0.036 by Mann-Whitney U test. FIG. 37B, MG pre-treatment reduced the duration of EEG-confirmed seizures. P=0.014 by Mann-Whitney U test. FIG. 37C, MG pre-treatment reduced the number of EEG-confirmed seizures. P=0.028 by Mann-Whitney U test. FIG. 37D, Representative EEG recordings of a mouse during baseline period (prior to any injections), after acute saline and picrotoxin (7 mg/kg) injections, or after acute MG (200 mg/kg) and picrotoxin (7 mg/kg) injections. As shown in 2b, MG pre-treatment reduced the duration of EEG-confirmed generalized seizures (high amplitude and high frequency spike discharges located between arrows). Seizures are associated with high muscle activity, as indicated by the electromyography (EMG) trace. Note: animals from both groups (MG and saline) showed myoclonic jerks associated with high amplitude single spikes (▼). EEG traces correspond to four differential recordings from each of four subdural electrodes (EEG1 and EEG2 (right cortical hemisphere), EEG3 and EEG4 (left cortical hemisphere)). EMG activity was recorded using two fine wires placed into the neck muscle. Calibration mark: 500 µV/mm and 1 second. Data are mean±SEM. n=4 vehicle, 5 MG (200 mg/kg). *P<0.05 versus vehicle-treated group as determined by Mann-Whitney U tests.

Figures 38A, 38B, 38C, 38D:
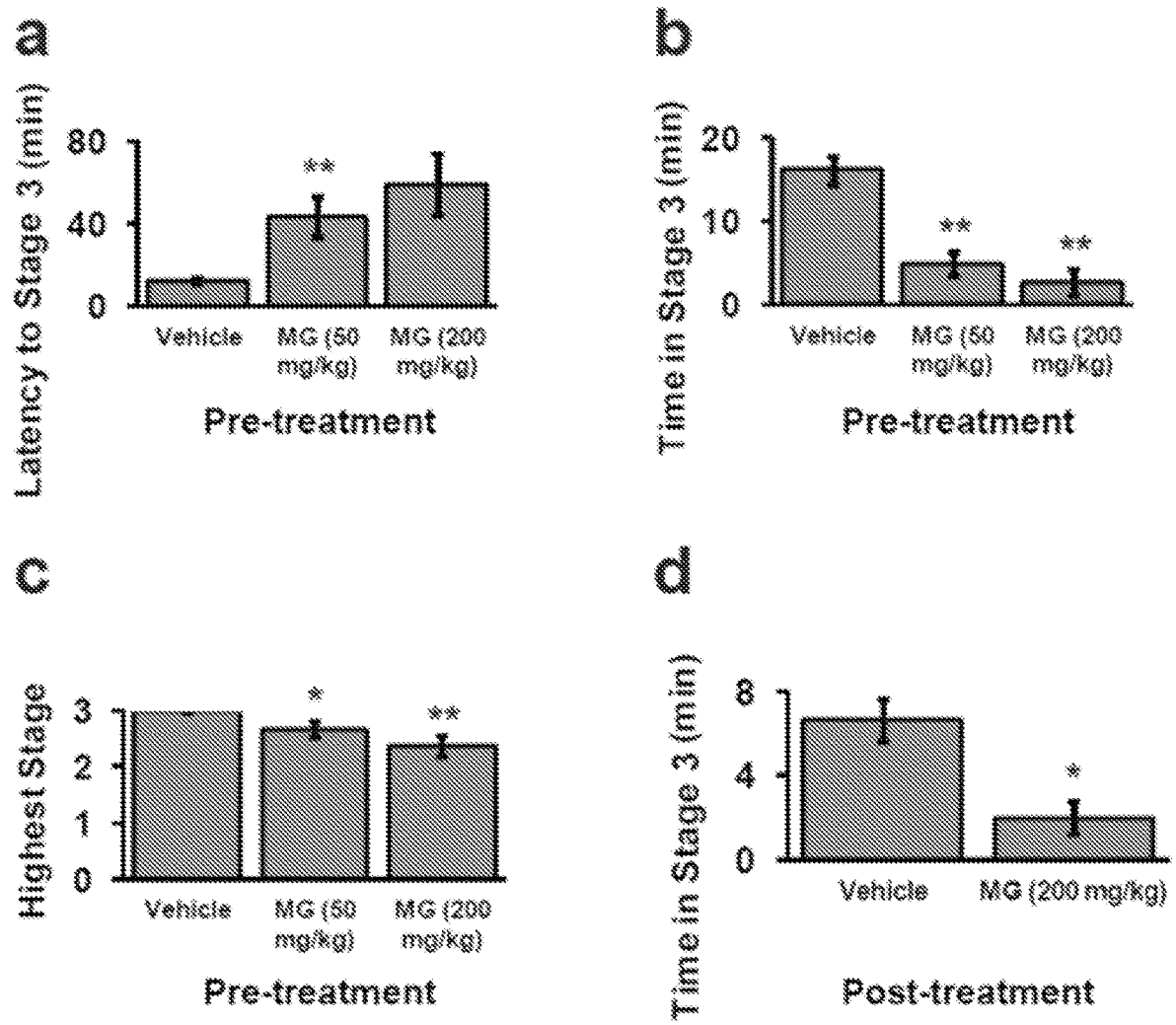

FIGS. 38A-38D: Exogenous MG attenuates pilocarpine-induced seizures. FIGS. 38A-38C, B6 mice were pre-treated with vehicle or MG (50 and 200 mg/kg) prior to seizure induction with pilocarpine (250 mg/kg). n=19 vehicle, 12 MG (50 mg/kg), 8 MG (200 mg/kg). FIG. 38A, MG pre-treatment increased the latency to reach stage 3. P=0.0033 by Kruskal-Wallis test. FIG. 38B, MG pre-treatment reduced the time spent in stage 3. P<0.0001 by Kruskal-Wallis test. FIG. 38C, MG pre-treatment reduced the highest seizure stage reached. P=0.0015 by Kruskal-Wallis test. FIG. 38AD, Seizures were induced in B6 mice with pilocarpine (250 mg/kg); 10 minutes later, mice were treated with vehicle or MG (200 mg/kg). MG treatment reduced time spent in stage 3. n=6 per group. Data are mean±SEM. *P<0.05, **P<0.005 versus vehicle-treated group as determined by Mann-Whitney U tests.

Figure 39:
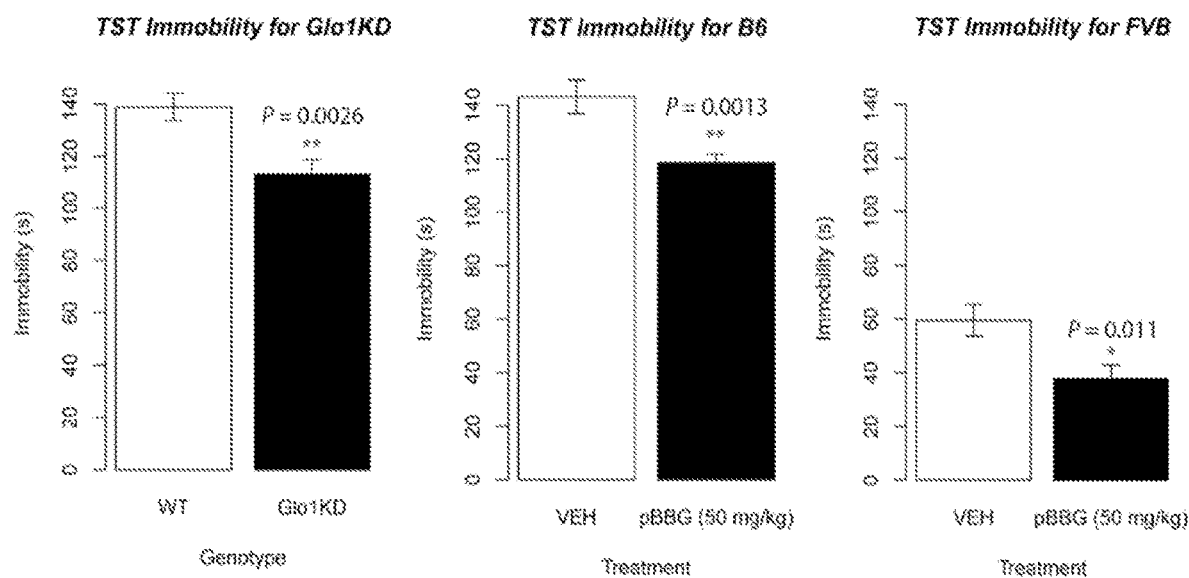

FIG. 39: GLO1 inhibition reduce immobility on the tail suspension test (TST). Both knockdown of Glo1 and pharmacological inhibition of GLO1 with pBBG reduce immobility on the tail suspension test (TST), indicating antideprssant activity. The effects of pBBG were observed in two inbred mouse strains (B6 and FBV).

Figure 40:
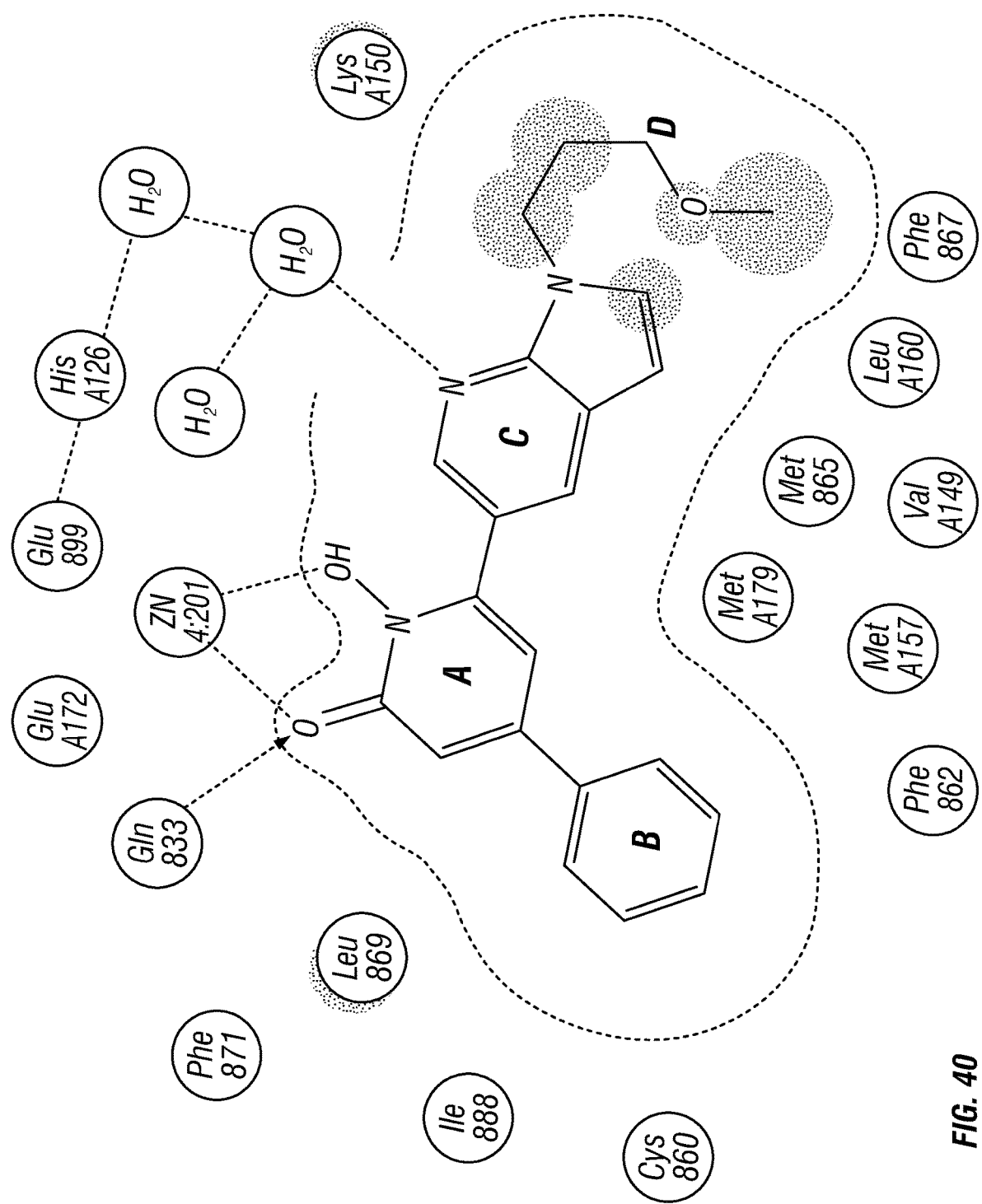

FIG. 40: Crystal structure of GLO1 and 3d. A-D are moieties of diversity

Figures 41A, 41B:
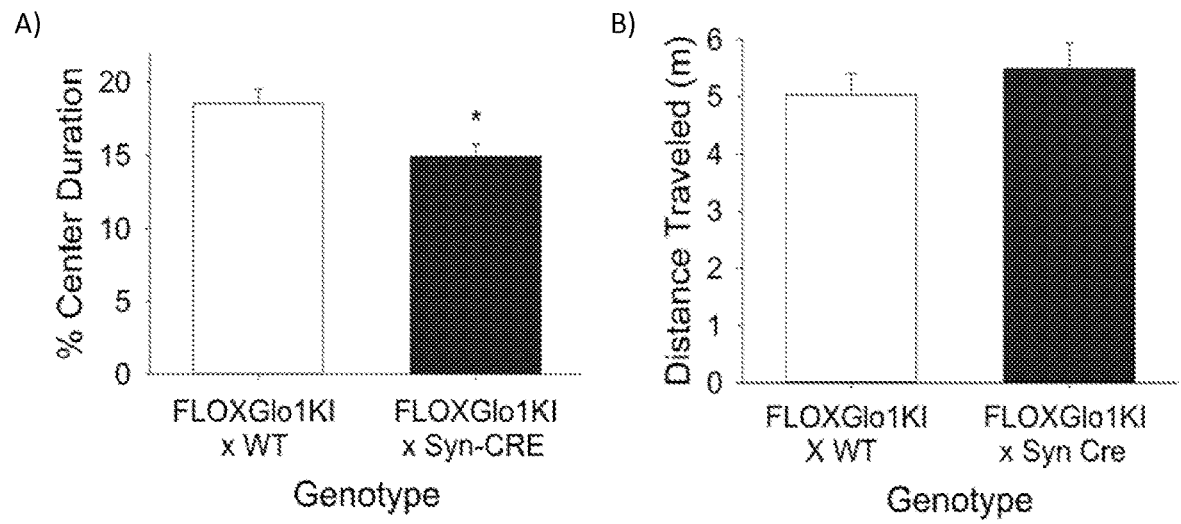

FIG. 41A-41B: Neuron specific overexpression of Glo1 increases anxiety-like behavior in the open field test (OFT). Neuron specific overexpression of Glo1 was achieved by crossing FloxGlo1 mice (hGlo1 with a floxed STOP knocked-in to ROSA26 locus, C57BL6/J background) to mice hemizygous for Syn-Cre (Jackson Labs #003966, synapsin1 promotor). Mice were 8-13 weeks old for behavioral testing (male, n=19-22). Mice overexpressing Glo1 in neurons show (A) reduced center duration in the OFT, indicating increased anxiety-like behavior. (B) Mice did not differ in total distance traveled. Data are mean±SEM. *p<0.05 by two tailed t-Test. These data indicate that the effects of Glo1 on anxiety are centrally mediated.

Figures 42A, 42B:
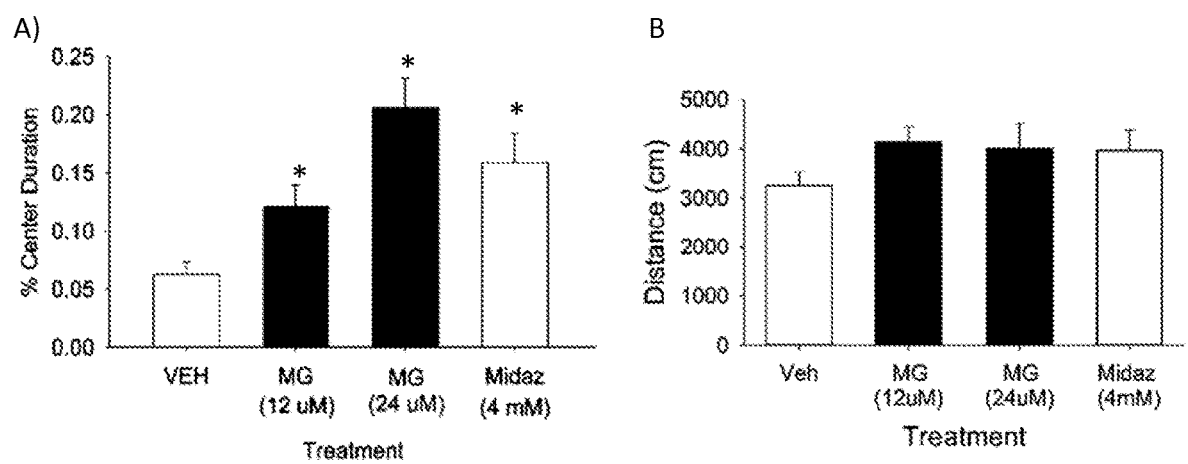

FIG. 42A-42B: Bilateral microinjection of methylglyoxal into the basolateral-amygdala (BLA) reduces anxiety-like behavior in the OFT. C57BL6/J mice (7-9 weeks old; Jackson Labs; n=9-15) were bilaterally implanted with cannula targeting the BLA (AP—1.4, ML±3.2, DV 5.1). Animals were allowed to recover 5-6 days. On test day, cannulated animals received bilateral microinjections (0.5 ul over 2 min, additional 2 min allowed for diffusion) of vehicle (0.9% saline), 12 uM MG, 24 uM MG or 4 mM midazolam (positive control) and were placed directly into the OFT. Direct injection of MG (12 uM or 24 uM) or Midazolam (Midaz, 4 mM) to the BLA increased center duration in the OFT over 30 m, indicating reduced anxiety-like behavior. Data are mean±SEM. *p<0.05 by One-way ANOVA. These data indicate that the amygdala is a key target for MG and that we can obtain better control of anxiety using MG as compared to a prototypic benzodiazepine. We beelive this may be due to MG acting as a competative partial agonist at GABA-A receptors. These data establish that MG, either by direct administration or, by extension, accumulating due to Glo1 inhibition, may improve upon the current standard of care.

Figures 43A, 43B, 43C:
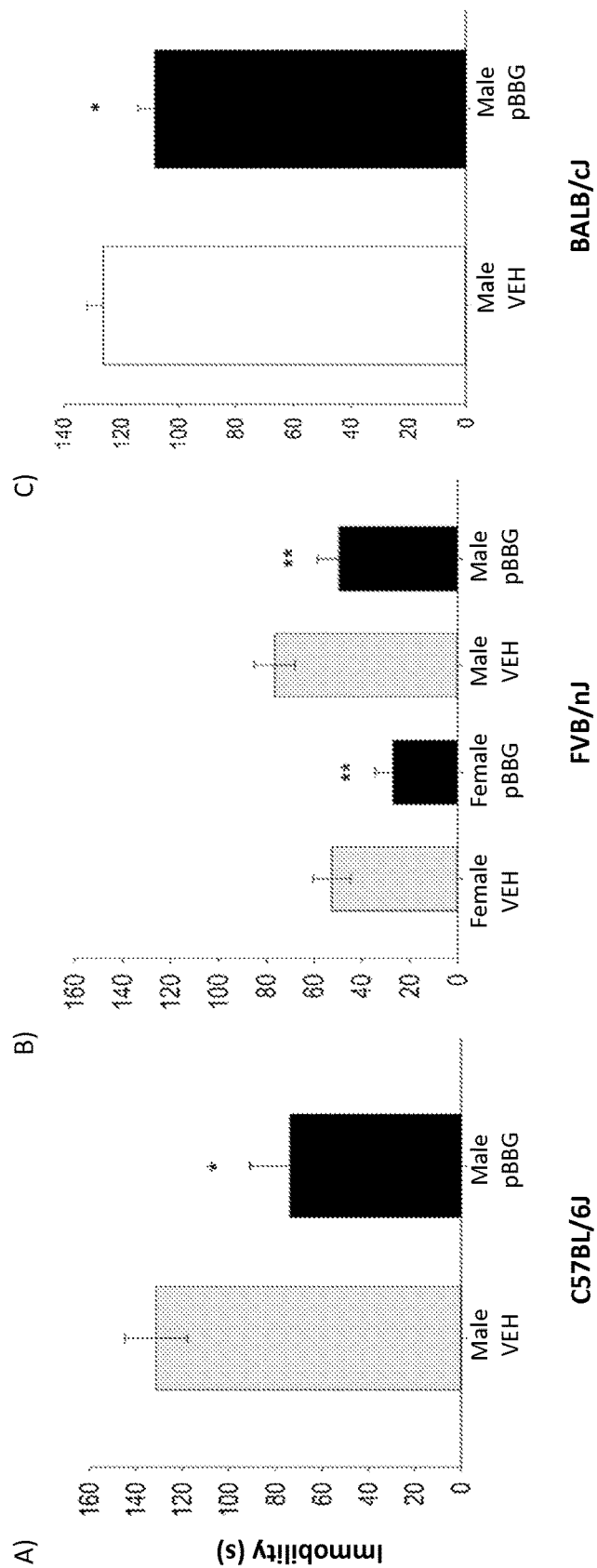

FIG. 43A-43C: GLO1 inhibition reduces depression-like behavior in multiple mouse strains in the forced swim test (FST). Three different strains of mice A) C57BL/6J, B) FVB/nJ, and C) BALB/cJ showed reduced immobility in the FST 2 hours after 50 mg/kg i.p. administration of GLO1 inhibitor, pBBG. These data suggest that GLO1 inhibitors can be effective antidepressants. Data are mean±SEM. *p<0.05 by two tailed t-Test. **p<0.01 by two-way ANOVA.

Figures 44A, 44B:
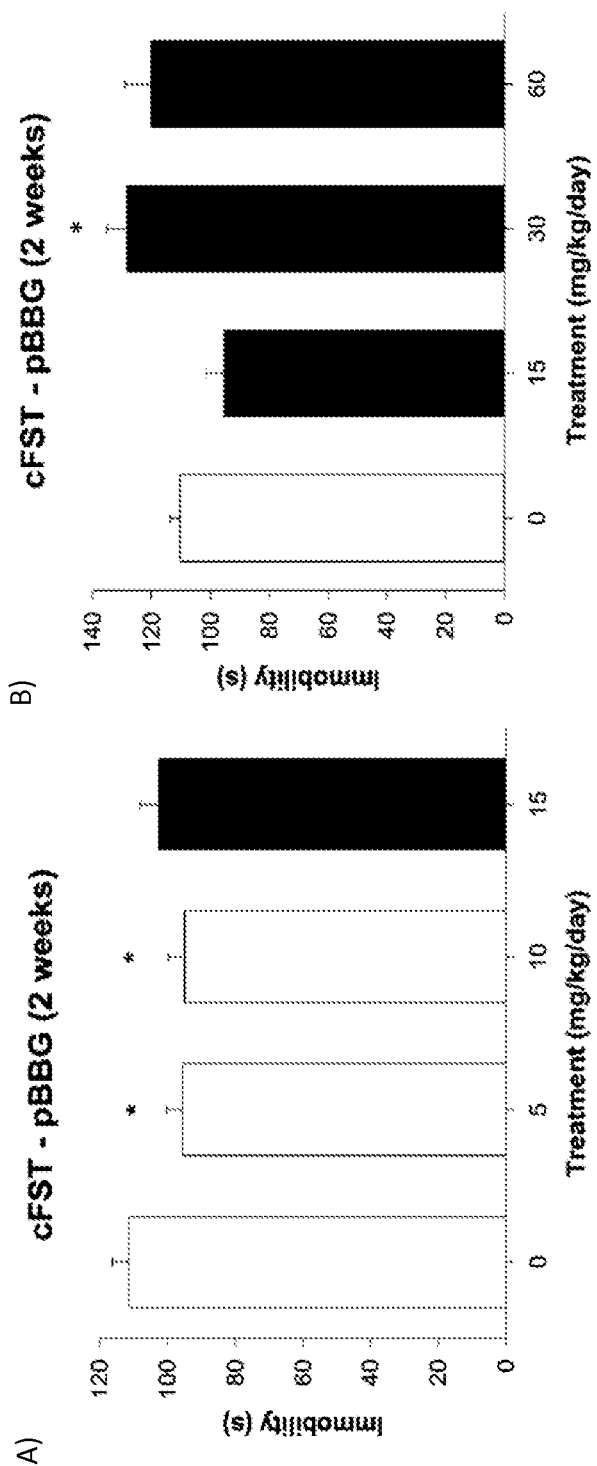

FIG. 44A-44B: Chronic treatment with GLO1 inhibitor pBBG reduces depression-like behavior in the forced swim test (cFST). (A) Chronic (14 day) treatment by osmotic minipump with 5 or 10 mg/kg/day pBBG reduced immobility in the FST, establishing that chronic administration has antidepressant effects. (B) Higher doses (30, 60 mg/kg/day) increased immobility in the FST, perhaps reflecting an inverted U shaped dose-response function and also indicating that abuse potential may be limited by aversive effects, which would constitute a unique advantage of existing anxiolytic drugs Data are mean±SEM. *p<0.05 by One-way ANOVA. Note that mice were also assessed for signs of toxicity following chronic administration of pBBG and none were observed, suggesting that chronic/behaviorally relevant inhibition of GLO1 is well tolerated.

Figure 45:
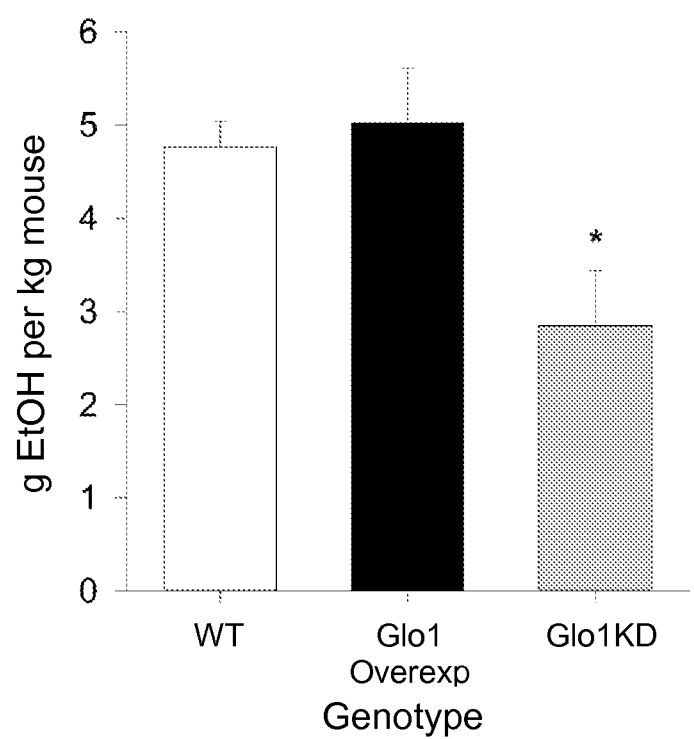

FIG. 45: Glo1 expression regulates consumption of 20% Ethanol over 4 hours during drinking in the dark. Wild-type (WT), Glo1 overexpressing (Glo1 Overexp) or Glo1-Knockdown (Glo1KD) mice were given access to 20% Ethanol in water for 2 hours on the first day and 4 hours on the second day. These data represent the total amount in grams of ethanol consumed by mouse weight over the 4 hr access on the second day. Glo1KD mice drank significantly less ethanol than WT or Glo1Overexp mice. Data are mean±SEM. *p<0.05 by One-way ANOVA. These data indicate that inhibition of Glo1, presumably via its ability to increase MG concentrations, can dramatically reduce alcohol consumption. It has been contemplated this may be due to its amplification of ethanol's effects, or due to a decreased drive to seek those effects. These effects could extend to other drugs of abuse including nicotine, stimulants, and opiates.

Figure 46A:
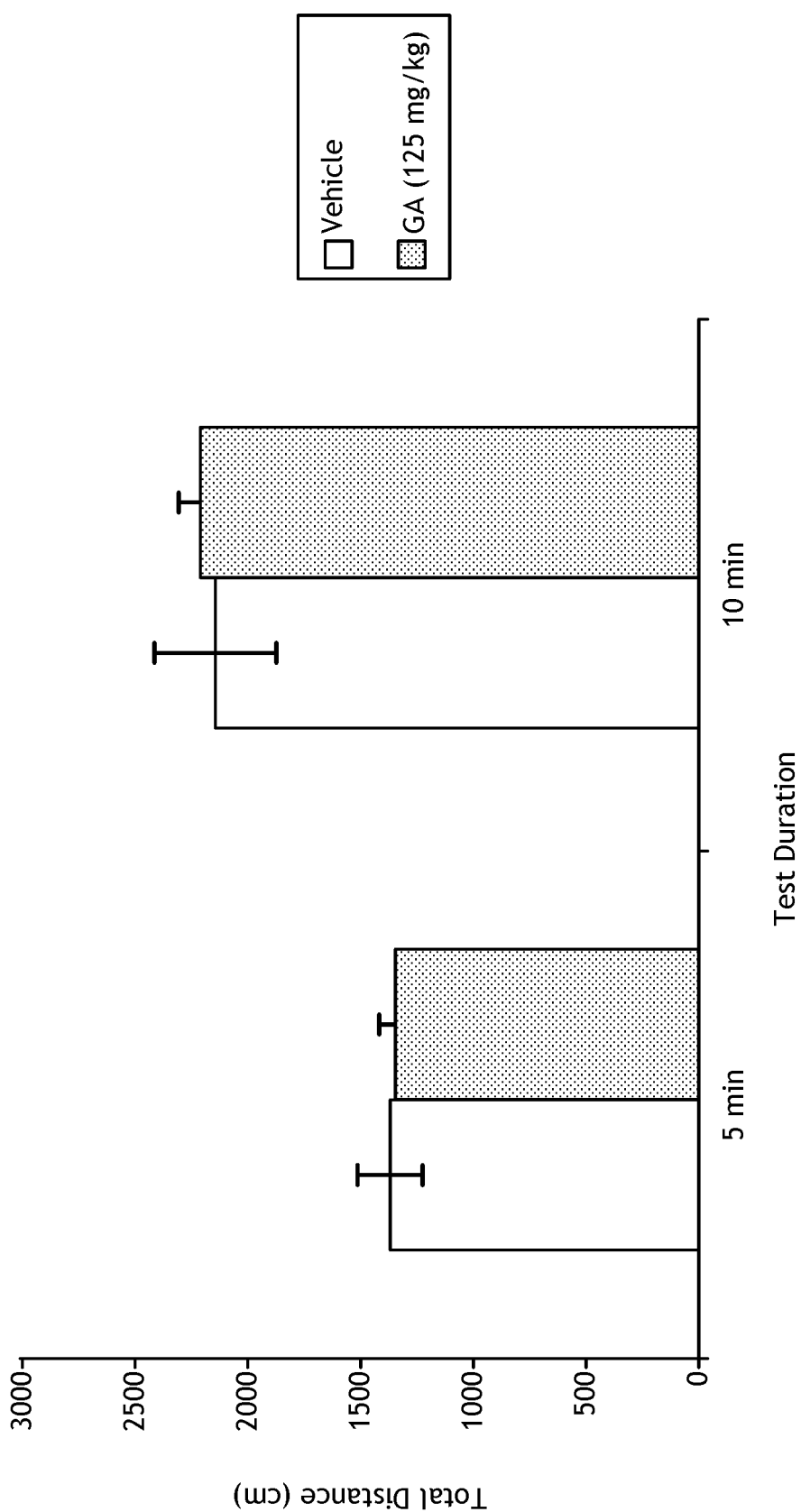
Figure 46B:
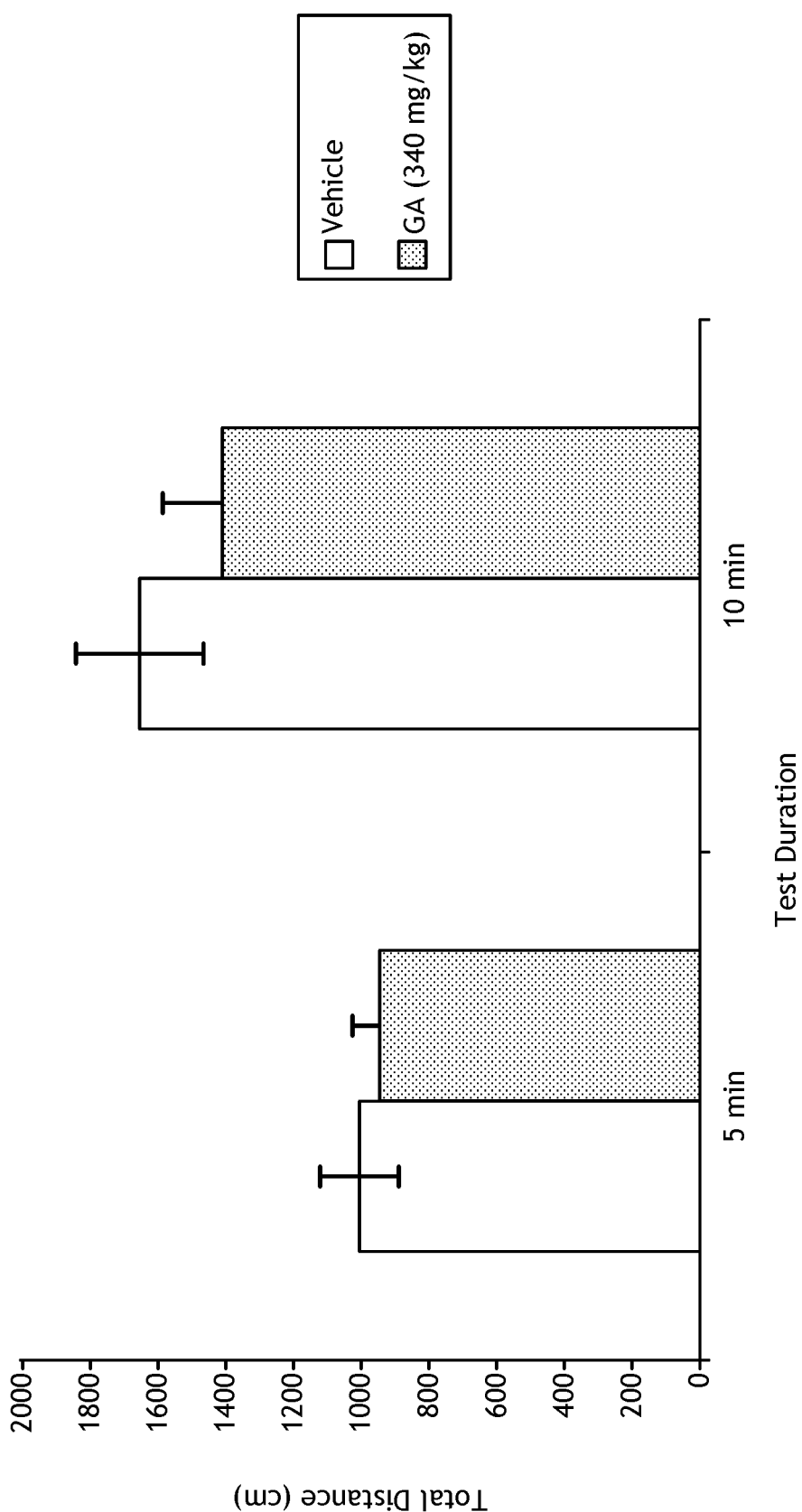
Figure 46C:
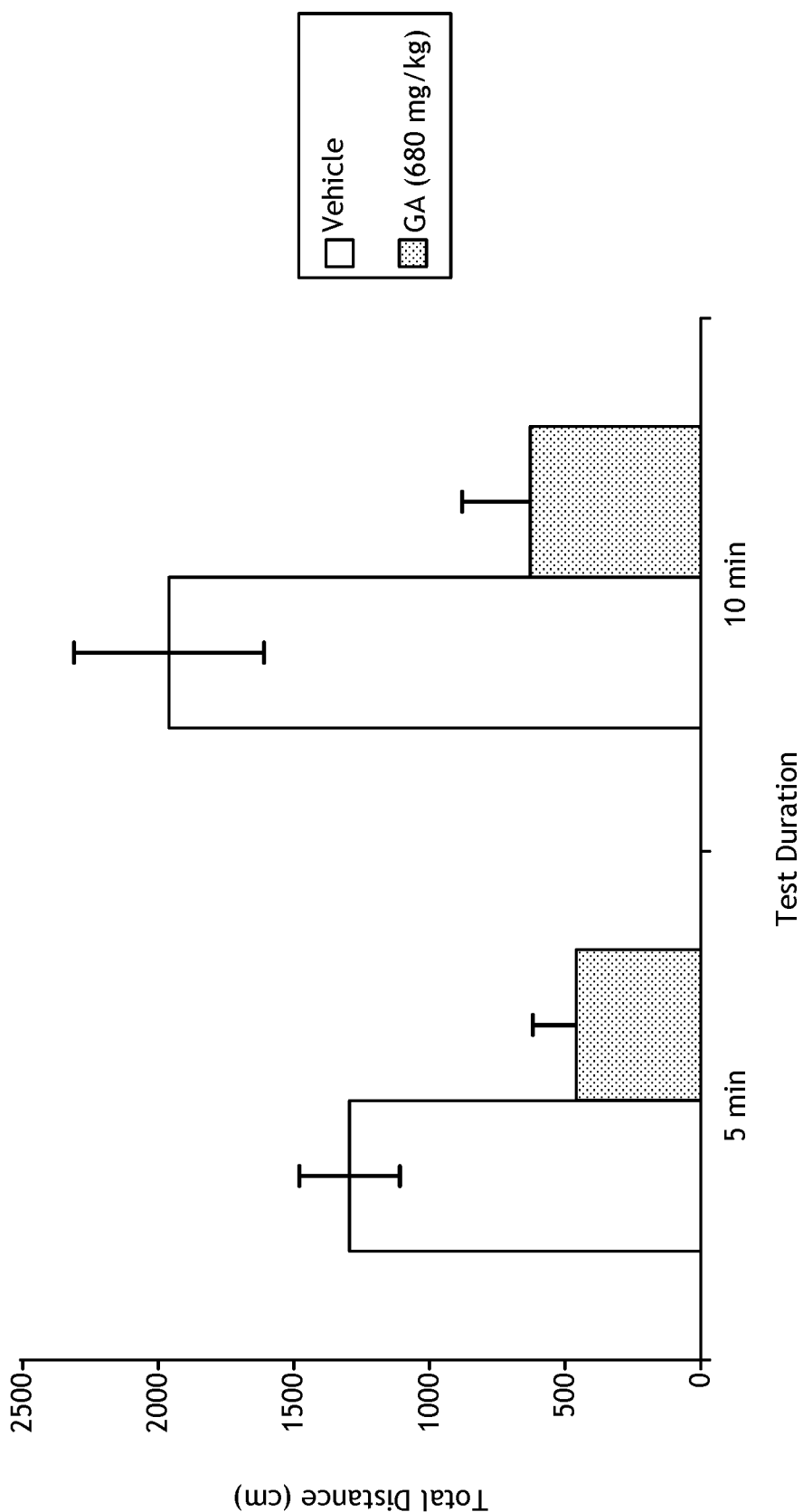

FIG. 46A-46C: The MG precursor glyceraldehyde (GA) has locomotor depressant effects. GA is rapidly converted into MG. Cd-1 mice (Charles River, Portage Mich.) were treated i.p. With vehicle (0.9% NaCl) or GA at the indicated doses. Ten minutes after injection, mice were tested in the open field (OF) test (locomotor chambers). Behavioral data were collected at 5 and 10 minutes. Because vehicle-treated mice differed in total distance traveled between the testing days, the data were not combined into a single analysis. Statistical analyses included repeated-measures anova for the factor treatment. The repeated measures were total distance (at 5 and 10 min) and % center time (at 5 and 10 min). For comparison of vehicle and GA at individual time points, a t-test was used. These data support the idea that GA or some similar pro-drug/precursor could be used to influence the Glo1/MG system. This would be an additional means of obtaining desirable clinical effects, including anxiolytic, antidepressant, anti-epileptic, and induction of sleep.

Figure 47:
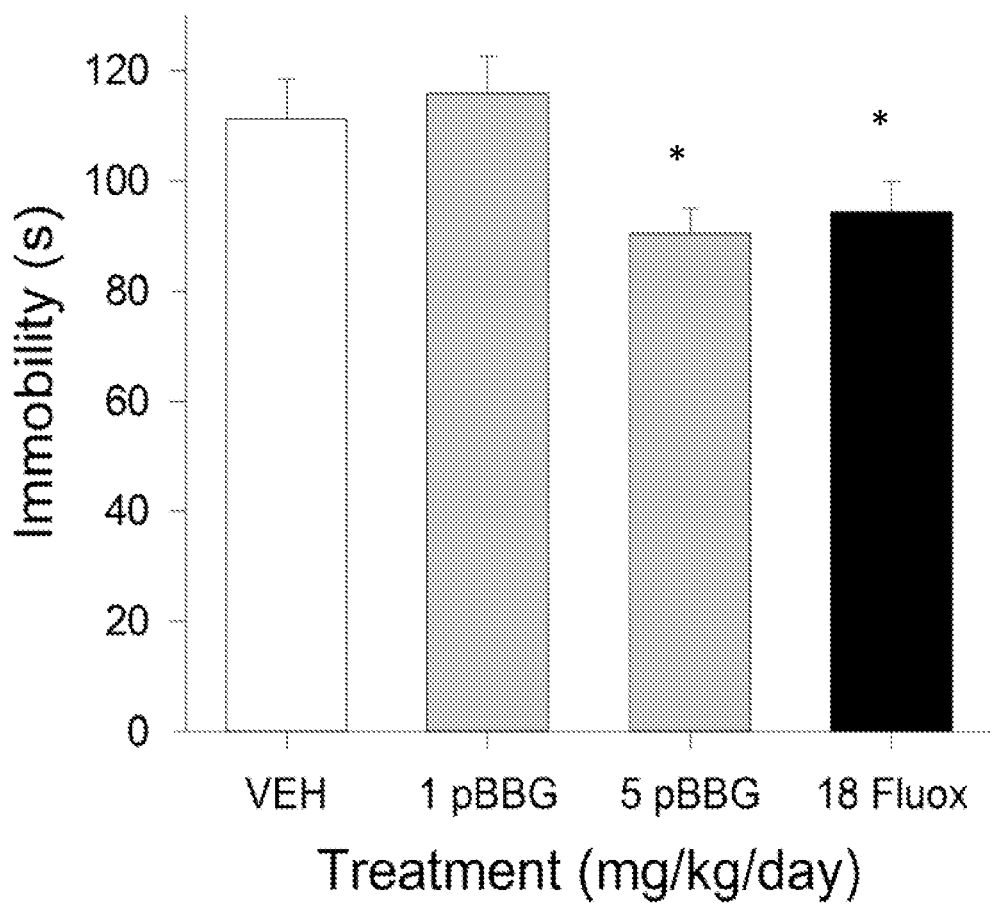

FIG. 47: Chronic treatment with GLO1 inhibitor, pBBG, or a prototypical SSRI, fluoxetine, reduces depression-like behavior in the forced swim test (cFST). Chronic (14 day) treatment by osmotic minipump with 5 mg/kg/day pBBG reduced immobility in the FST to a similar extent as a selective serotonin reuptake inhibitor (SSRI) commonly used in the treatment of depression, fluoxetine (18 mg/kg/day). Data are mean±SEM. *p<0.05 by One-way ANOVA. These data show that Glo1 inhibition has antidepressant effects when administered chronically to mice. These effects are at least as strong as prototypical anti-depressants such as fluoxetine.

Figures 48A, 48B:
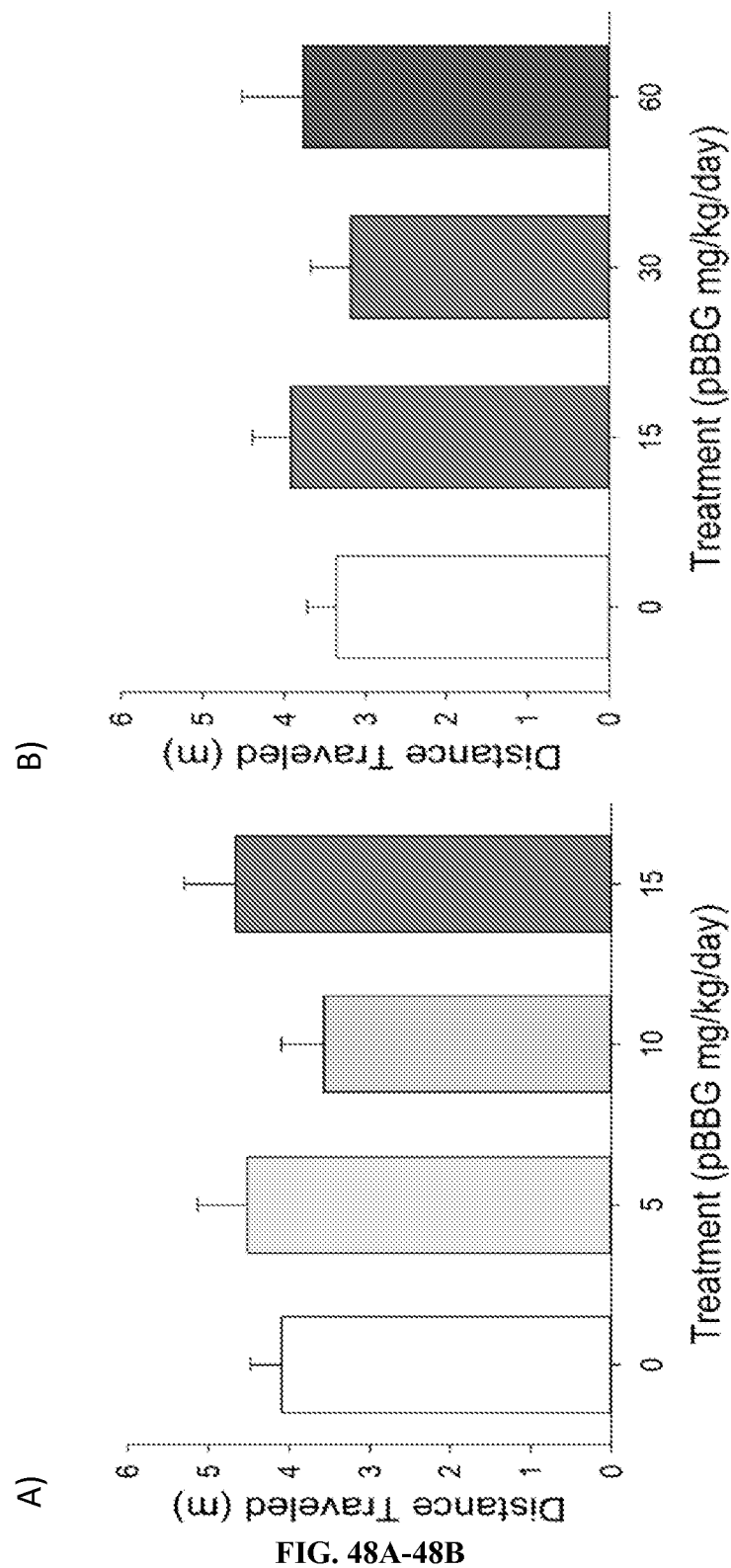

FIG. 48A-48B: Chronic treatment with GLO1 inhibitor pBBG does not show sedative effects in the open field test (OFT) at doses that are effective at producing anti-depressant effects. (A) Chronic (14 days) treatment with 5, 10, or 15 mg/kg/day pBBG had no effect on total distance traveled in the OFT. (B) Chronic (14 days) treatment with pBBG at higher doses and (15, 30 or 60 mg/kg/day) also had no effect on total distance traveled. These data indicate chronic treatment with pBBG in mice does not affect locomotor behavior, suggesting chronic GLO1 inhibition may reduce anxiety and depression-like behavior (see earlier figures) without sedative effects common to currently used anxiolytics such as benzodiazepines. Data are mean±SEM. p>0.7 by One-way ANOVA

DETAILED DESCRIPTION OF THE INVENTION

Certain embodiments are directed to compositions and methods relating to use of GLO1 inhibitors or MG or its prodrug or precursor for therapeutic applications, particularly those methods and compositions related to preventing or treating neurological conditions or diseases.

I. GLO1 (GLYOXALASE 1)

In enzymology, a lactoylglutathione lyase (EC 4.4.1.5) (also known as glyoxalase I) is an enzyme that catalyzes the isomerization of hemithioacetal adducts, which are formed in a spontaneous reaction between a glutathionyl group and aldehydes such as methylglyoxal.

glutathione+methylglyoxal ⇌ hemithioacetal adduct
⇌ (R)—S-lactoylglutathione

Glyoxalase I derives its name from its catalysis of the first step in the glyoxalase system, a critical two-step detoxification system for methylglyoxal. Methylglyoxal is produced naturally as a byproduct of normal biochemistry, but may be toxic, due to its chemical reactions with proteins, nucleic acids, and other cellular components. The second detoxification step, in which (R)—S-lactoylglutathione is split into glutathione and D-lactate, is carried out by glyoxalase II, a hydrolase. Unusually, these reactions carried out by the glyoxalase system does not oxidize glutathione, which usually acts as a redox coenzyme. Although aldose reductase can also detoxify methylgloxal, the glyoxalase system is more efficient and seems to be the most important of these pathways. Glyoxalase I is an attractive target for the development of drugs to treat infections by some parasitic protozoa, and cancer. Several inhibitors of glyoxalase I have been identified, such as S—(N-hydroxy-N-methylcarbamoyl)glutathione.

Glyoxalase I is classified as a carbon-sulfur lyase although, strictly speaking, the enzyme does not form or break a carbon-sulfur bond. Rather, the enzyme shifts two hydrogen atoms from one carbon atom of the methylglyoxal to the adjacent carbon atom. In effect, the reaction is an intramolecular redox reaction; one carbon is oxidized whereas the other is reduced. The mechanism proceeds by subtracting and then adding protons, forming an enediolate intermediate, rather than by transferring hydrides. Unusually for a metalloprotein, this enzyme shows activity with several different metals.

Glyoxalase I is also unusual in that it is stereospecific in the second half of its mechanism, but not in the first half Structurally, the enzyme is a domain-swapped dimer in many species, although the two subunits have merged into a monomer in yeast, through gene duplication.

Due to their roles in AGE formation and cytotoxicity, GLO1 and MG have been shown to influence diseases where these effects are relevant to pathogenesis, such as diabetic complications, aging, and cancer (Brownlee 2001; Ahmed 2007; Fleming 2010; Morcos 2008; Thornalley 2003; Thornalley 2011).

GLO1 has also been implicated in degenerative changes associated with aging. During the aging process, GLO1 activity declines, while MG and AGEs accumulate (Xue 2011). AGE accumulation has been associated with age-related diseases, such as Alzheimer's disease, diabetic complications, and atherosclerosis (Brownlee 2001; Krautwald 2010). Further, in *C. elegans*, overexpression of the Glo1 homolog increased lifespan, while its knockdown reduced lifespan (Morcos 2008).

GLO1's cytoprotective effects paradoxically promote disease in patients with cancer, where malignant cells utilize GLO1 to increase survival and resist chemotherapy. For example, in patients with malignant melanoma, cancer cells were found to significantly overexpress GLO1 compared to cells from healthy controls (Bair 2010). Knockdown of GLO1 in cancer cells increased their susceptibility to MG-induced cyotoxicity (Bair 2010). Similarly, GLO1 inhibitors have been shown to prevented tumor growth in vitro and in vivo (Creighton 2003).

In contrast to GLO1's well-characterized roles in the pathogenesis of these diseases, its mechanistic role in neurological disorders such as anxiety disorders is not established. In fact, none of GLO1's established cellular effects has been mechanistically linked to anxiety.

II. TREATMENT METHODS AND COMPOSITIONS

Method and compositions include treatments for a disease or condition responsive to GLO1 inhibition or GABA-A agonists. A GLO1 inhibitor can be given to prevent or treat a subject having a neurological disease or disorder or suspected of having a neurological disease or disorder or at risk of having a neurological disease or disorder. Methods may be employed with respect to individuals who have been tested for having a neurological disease or disorder or who are deemed to be at risk for having a neurological disease or disorder.

In particular, there are methods of treatment for a neurological disease or disorder, particularly sleep disorders, mood disorders such as depression or bipolar disorders, epilepsy, anxiety disorders, or alcohol withdrawal syndrome. Moreover, methods concern treating any condition or disease that is caused by, perpetuated by, or promoted by reduced GABA-A signaling activity.

III. DISEASE OR DISORDER TO BE TREATED

Method and compositions involving Glo1 inhibitors may be provided to treat diseases or disorders such as any neurological diseases or disorders, including, but not limited to, anxiety disorders, depressive disorders, epilepsy, sleep disorders, mood disorders, substance abuse or dependence, substance withdrawal symptoms.

A. Anxiety Disorders

GABAA receptors are critical in regulating neuronal inhibitory tone throughout the CNS (Kalueff 2007); as such, they contribute to the pathogenesis of several neurological disorders. Through their effect on GABAA receptors, GLO1 and MG are likely to contribute to a broad range of CNS conditions in addition to anxiety.

Anxiety disorders are the most common psychiatric conditions in the United States, affecting 40 million adults each year (NIMH 2009). However, current anxiolytic therapies are not effective in all patients and can have undesirable side effects (Pollack 2009). Therefore, investigating novel molecular pathways that contribute to anxiety may identify new therapeutic targets.

Although Glo1 has been associated with anxiety, the underlying mechanism was unknown. In fact, Glo1 is an unlikely candidate for regulating anxiety. Despite its high expression in the brain, Glo1 is not brain-specific, but rather is ubiquitously expressed (Thornalley 1993). Further, GLO1's cellular function is not typical of a mediator of anxiety. GLO1 is an enzyme in the glyoxalase system, a metabolic pathway that detoxifies methylglyoxal (MG) by converting it into d-lactate (Thornalley 2003). MG is formed from the non-enzymatic fragmentation of the glycolytic intermediates dihydroxyacetone phosphate and glyceraldehyde-3-phosphate (Thornalley 1993). GLO1 is the major cellular enzyme regulating MG; as such, changes in GLO1 activity and Glo1 expression directly affect MG levels. In vitro, inhibition of GLO1 increased MG accumulation (Kuhla 2006), and overexpression of Glo1 prevented MG accumulation (Shinohara 1998). When MG accumulates to high levels, it induces cytotoxic effects, including protein modification (Brownlee 2001), reactive oxygen species (ROS) generation (Schleicher 2007), and apoptosis (Kuhla 2006; Loh 2006; Di Loreto 2008). MG forms adducts on proteins and nucleotides, termed advanced glycation end-products (AGEs). The effects of AGEs are twofold: first, AGE formation causes dysfunction of affected proteins (Brownlee 2001). Second, AGEs ligate the receptor for AGEs (RAGE), which triggers the production of ROS (Schleicher 2007) and leads to apoptosis (Loh 2006). Glo1 expression and GLO1 activity mediate MG-induced cytotoxicity; for instance, GLO1 inhibition results in reduced cellular viability (Kuhla 2006).

GLO1 had no obvious mechanistic relationship to anxiety. Rather, GLO1 was best characterized for detoxifying MG, a cytotoxic byproduct of glycolysis (Thornalley 1993; Thornalley 2003). In the present work, the inventors demonstrated that GLO1 increases anxiety by reducing MG concentration. Glo1 overexpression reduced MG concentration in the brain (FIGS. 7B and 33A), and MG administration reduced anxiety-like behavior (FIGS. 8-12). Together, these data suggest that MG is anxiolytic. The inventors next characterized MG as an endogenous partial agonist at GABAA receptors, which are well-established mediators of anxiety (Kalueff 2007). MG elicited electrophysiological effects characteristic of GABAA receptor activation in CGN and FIN (FIGS. 21 and 26). MG-evoked currents were approximately one-third the magnitude of those elicited by GABA (FIGS. 21B and 26A), and co-application with MG reduced the magnitude of GABA-evoked currents (FIGS. 24 and 26A). These data identify MG as a competitive partial agonist at GABAA receptors. Although MG competed with GABA for GABAA receptor activation, the two molecules are not structurally similar, suggesting that they do not share a binding site. Rather, MG binding likely hinders GABA binding. In the future, structural studies will be important for identifying MG's exact binding site. Specifically, GABAA receptor point mutants could be assessed for MG binding and/or activation.

GABAA receptors are comprised of various combinations of subunits, and different receptor compositions mediate different GABAergic effects, such as anxiety and sedation (Rudolph 2011). Therefore, MG's activity at different receptor subtypes may contribute to its endogenous role in the CNS. While the inventors did not identify the specific GABAA receptor subtypes activated by MG, potent activation of currents in CGN suggests that MG operates receptors containing α6 subunits, which are prevalent in CGN (Nusser 1999). Further, MG-evoked currents were enhanced by co-application of diazepam, midazolam, and zolpidem (FIG. 26B). Diazepam and midazolam operate GABAA receptors that contain α1, 2, 3, and 5 subunits, while zolpidem targets receptors with α1 and γ2 subunits. The present data suggest that MG acts at a broad range of GABAA receptors on neurons throughout the CNS.

MG is generated intracellularly by both neurons and glia and then crosses the plasma membrane (FIG. 25) to activate GABAA receptors in a paracrine manner. The inventors speculate that MG activates synaptic GABAA receptors, which regulate phasic inhibitory signaling, as well as extrasynaptic GABAA receptors, which contribute to tonic inhibitory signaling (Hablitz 2009). Tonic inhibition via extra-synaptic GABAA receptors decreases cellular input resistance, which diminishes the propagation of excitatory currents and decreases the probability that an action potential will be initiated by excitatory inputs (Kullmann 2005). MG's actions at extra-synaptic GABAA receptors likely contributes to tonic inhibitory tone (Hablitz 2009) and anxiety (Maguire 2005). Consistent with this hypothesis, midazolam, which increases tonic conductance (Teung 2003), enhanced MG-evoked currents (FIG. 26). Future studies must directly measure the effect of MG on extra-synaptic receptors in order to determine the relative contribution of MG to phasic and tonic inhibitory activity in the CNS. In particular, recording inhibitory postsynaptic currents in slice preparations may further elucidate MG's role in neural physiology.

Based on the results, a mechanism has been contemplated in certain aspects of the invention whereby GLO1 reduces endogenous MG concentration, thus reducing neuronal inhibitory tone and increasing anxiety-like behavior. MG is generated intracellularly from triose phosphates during glycolysis (Thornalley 1993; Thornalley 2003) and is then metabolized by GLO1 and GLO2 (Thornalley 1993; Thornalley 2003). MG that is not catabolized crosses the plasma membrane to activate GABAA receptors and regulate downstream behaviors, including anxiety. This mechanism is summarized in FIG. 35.

B. Depression

Interestingly, while antidepressant drugs are also effective for some anxiety symptoms, anxiolytic drugs that act via GABAergic mechanisms do not have antidepressant effects (Birkenhager 1995; Johnson 1985; Barbui 2011). While there are many effective pharmacotherapies for both disorders, there is an urgent need for better drugs. Major limitations of existing anxiolytic drugs include sedating side effects and abuse liability. For antidepressant drugs limitations include side effects and a slow onset of therapeutic effects. In addition, a significant fraction of patients fail to respond to existing drugs. Thus, the available treatments leave significant room for improvement.

The inventors demonstrated that Glo1 overexpression increased depression-like behavior in mice (FIG. 28A and FIG. 39). This supports results from a previous study, where increased levels of GLO1 protein were associated with increased depression-like behavior among inbred mice (Benton 2011). This is consistent with a common genetic basis for anxiety and depression. The inventors hypothesize that GLO1 increases depression by reducing MG concentrations in vivo. Although acute MG administration did not have antidepressant effects in the TST (FIG. 28B), chronic administration of MG might. This is likely, because Hambsch et al. found that chronic intracerebroventricular administration of MG had antidepressant effects in the TST (Hambsch 2010). Indeed, the GABAergic mechanisms that contribute to depression are longer-term effects (Luscher 2011). If chronic MG administration affects behavior in the TST, it would be interesting to measure these long-term effects, including hippocampal neurogenesis and function of the hypothalamic-pituitary-adrenal axis (Luscher 2011). Similarly, making these measurements in WT and Tg mice could provide additional insight into the mechanism through which GLO1 and MG affect depression.

C. Epilepsy

It was demonstrated that exogenous administration of MG reduced the duration and severity of both picrotoxin- and pilocarpine-induced seizures (FIGS. 29 and 30). This is consistent with MG's role in the CNS as an agonist at GABAA receptors, which are responsible for mediating neuronal inhibitory tone (MacDonald 2010). Pre-treatment with MG affected three important measures of seizure susceptibility: latency to seize, seizure duration, and seizure severity. This suggests that MG is a powerful anti-seizure agent. MG's efficacy in two seizure models demonstrates its broad anti-seizure effects across mechanistically distinct seizure models. This key finding has important implications. First, it demonstrates that MG protects against seizures. Second, it suggests that endogenous levels of MG may mediate seizure phenotypes in vivo. Third, it enables further investigation of MG's therapeutic potential in the treatment of epilepsy.

An important caveat is that these studies utilized a crude MG preparation to investigate seizure phenotypes. As such, it remains possible that contaminants in the preparation could have affected the results. This is unlikely, because pure and crude MG were found to have similar effects in vivo (e.g., anxiolysis, locomotor depression, ataxia, and hypothermia) and in vitro (FIG. 27). Nevertheless, future studies must investigate the anti-seizure effects of pure MG to rule out this possibility.

GLO1 inhibition with BrBzGCp2 decreased seizure duration (FIG. 31), demonstrating that increasing endogenous MG also attenuates seizures. Importantly, this finding argues against the possibility that the anti-seizure effects of crude MG resulted from contaminants. The inventors note that BrBzGCp2 administration did not affect seizure stage, suggesting that GLO1 inhibition was less effective than administration of exogenous MG. One possible explanation is that administration of exogenous MG increased MG concentration to a higher degree than is possible with GLO1 inhibition. However, the inventors do not know whether BrBzGCp2 completely ablated GLO1 activity in vivo. Therefore, it is possible that higher doses of BrBzGCp2 could have stronger anti-seizure effects. Alternatively, endogenously generated MG might have different effects than exogenous MG due to brain region-specific differences in MG concentration.

Figure 32A:
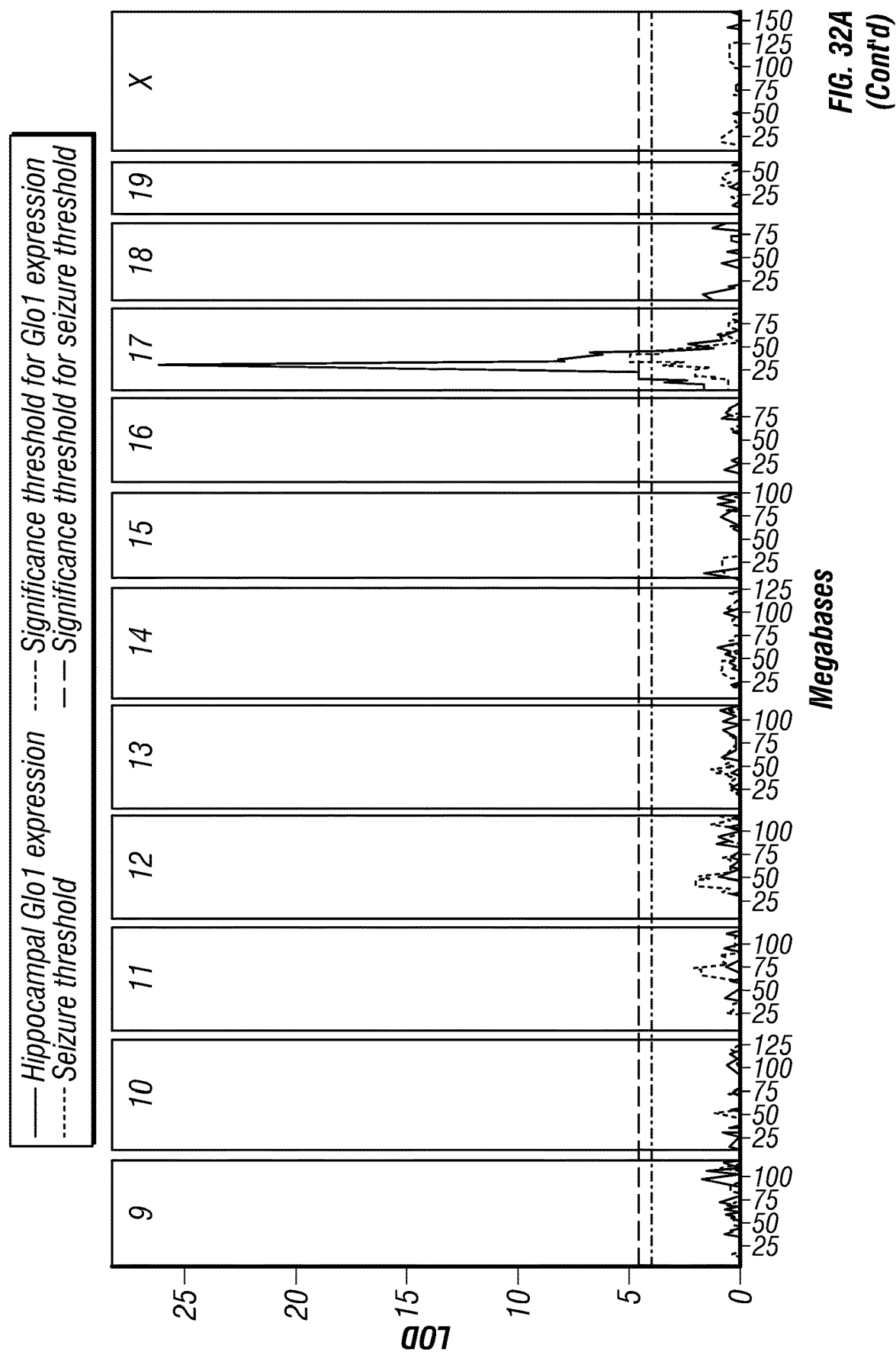

Finally, the inventors examined the effect of differential Glo1 expression on seizures. The inventors found that differential expression of Glo1 in BXD RI lines was associated with seizure susceptibility FIG. 32). The inventors then used Tg mice overexpressing Glo1 to establish a causal role for Glo1 in increasing seizure susceptibility and severity. Tg mice had reduced MG concentration in the brain and increased susceptibility to seizures (FIG. 33). Therefore, it has been contemplated in certain aspects that genetic variants in Glo1 may contribute to epilepsy.

These studies emphasize the importance of GLO1 and MG in neuronal physiology through regulating neuronal inhibitory tone as well as associated pathophysiological conditions, including anxiety, depression, and epilepsy. Moreover, these results may provide insight into the high comorbidity between epilepsy and anxiety disorders (Titlic 2009; Schmidt 2009; LaFrance 2008; Beyenburg 2005). There is a 25-50% prevalence of anxiety disorders among patients with epilepsy, which is twice the prevalence among the general population (LaFrance 2008). The prevalence of comorbid anxiety disorders is especially high in epileptic patients who do not respond to AEDs (Schmidt 2009; LaFrance 2008). This could suggest a convergent pathologic mechanism that is not targeted by current AEDs. Polymorphisms in Glo1 and related changes in MG concentration may contribute to both anxiety and epilepsy, providing a common underlying pathway.

In addition to the behavioral manifestations of seizures, there remain additional features of epilepsy that the present study did not investigate, particularly neuronal cell death resulting from status epilepticus (Naegele 2007; Henshall 2008; Rakhade 2009; Willmore 2005; Pitkanen 2003). Mechanisms underlying this type of neuronal cell death are largely excitotoxic, whereby increased activation of NMDA receptors causes excessive cellular Ca2+ influx, organelle swelling, initiation of the caspase cascade, activation of degradative enzymes (proteases, lipases, etc.), ROS generation, and apoptosis (Naegele 2007; Henshall 2008). The long-term sequelae of seizure-related neuronal cell death include reduced brain volume (Henshall 2008) and epileptogenesis, an increased predilection toward future seizures (Henshall 2008; Rakhade 2009). Therefore, protection against neuronal cell death is an important goal in the treatment of epilepsy. Unfortunately, experimental studies of anti-apoptotic agents have not demonstrated their anti-seizure or anti-epileptogenic effects (Naegele 2007; Henshall 2008). More promisingly, several AEDs, such as lamotrigine, levetiracetam, and topiramate, have been shown to be neuroprotective after status epilepticus (Willmore 2005; Pitkanen 2002). Therefore, it is possible that MG could have neuroprotective effects in addition to its anti-seizure effects. This possibility would add a layer of complexity to MG's physiological role, as it has previously been characterized as cytotoxic. Importantly, the inventors found no evidence of cytotoxicity at the doses of MG used in this study. If MG were neuroprotective, this would indicate that MG has a dichotomous cellular action, with cytoprotective effects at physiological concentrations and cytotoxic effects at supraphysiological concentrations.

D. Alcohol Withdrawal Syndrome

Methods and compositions can be also provided for preventing or treating an alcohol withdrawal syndrome. Alcohol withdrawal syndrome is the set of symptoms seen when an individual reduces or stops alcohol consumption after prolonged periods of excessive alcohol intake. Excessive use of alcohol leads to tolerance, physical dependence, and an alcohol withdrawal syndrome. The withdrawal syndrome is largely due to the central nervous system being in a hyper-excitable state. The withdrawal syndrome can include seizures and delirium tremens and may lead to excito-neurotoxicity.

Sedative-hypnotics, such as alcohol, are well known for their propensity to induce physiological dependence. Alcohol withdrawal occurs as a result of neuro-adaptation resulting from chronic exposure to alcohol. A withdrawal syndrome occurs upon declining blood levels of alcohol which can be alleviated by reintroduction of alcohol or a cross-tolerant agent. Alcohol withdrawal is characterized by neuropsychiatric excitability and autonomic disturbances similar to other sedative-hypnotic drugs. Dependence on other sedative-hypnotics increases the severity of the withdrawal syndrome.

E. Addictive Agents and Substance Abuse/Dependence Disorders

The term "addiction" is used to describe a recurring compulsion by an individual to engage in some specific activity, despite harmful consequences to the individual's health, mental state or social life. The term is often reserved for drug addictions, but it is applied to other compulsions, such as problem gambling, and binge eating. Factors that have been suggested as causes of addiction include genetic, biological/pharmacological and social factors.

The medical community now makes a careful theoretical distinction between physical or physiological dependence (characterized by symptoms of withdrawal) and psychological dependence (sometimes referred to simply as addiction). Addiction is now narrowly defined as "uncontrolled, compulsive use." If there is no harm being suffered by, or damage done to, the patient or another party, then clinically it may be considered compulsive, but to the definition of some it is not categorized as "addiction". In practice, the two kinds of addiction (physiological dependence and psychological dependence) are not always easy to distinguish. Addictions often have both physical and psychological components.

"Physical dependence" (or "drug dependence") refers to a state resulting from habitual use of a drug, where negative physical withdrawal symptoms result from abrupt discontinuation. Examples of addictive agents for which a user may develop a physical dependence include nicotine, opioids, barbiturates, benzodiazepines, alcohol, i.e., ethyl alcohol, GHB, and methaqualone.

Commonly abused stimulants such as cocaine or amphetamine class drugs are not believed to cause significant physical dependence. However, their potential for extreme psychological addiction can compel the user to consume amounts which become physically damaging, but life-threatening withdrawal effects have not been observed.

As used herein, "addictive agent(s)" includes any and all agents to which a subject can become addicted, either physically or psychologically, or both. As noted above, addiction includes addiction to chemical entities, such as drugs, as well as addiction to behaviors, as in impulse control disorders.

Addictive agents include addictive recreational drugs, as well as addictive medications. Examples of addictive agents include, but are not limited to, alcohol, e.g., ethyl alcohol, gamma hydroxybutyrate (GHB), caffeine, nicotine, *cannabis* (marijuana) and *cannabis* derivatives, opiates and other morphine-like opioid agonists such as heroin, phencyclidine and phencyclidine-like compounds, sedative hypnotics such as benzodiazepines, methaqualone, mecloqualone, etaqualone and barbiturates and psychostimulants such as cocaine, amphetamines and amphetamine-related drugs such as dextroamphetamine and methylamphetamine. Other examples include LSD, psilocybin, ecstasy and other hallucinogens. Examples of addictive medications include, e.g., benzodiazepines, barbiturates, and pain medications including alfentanil, allylprodine, alphaprodine, anileridine benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofenitanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, OXYCONTIN®, oxymorphone, papaveretum, pentazocine, phenadoxone, phenomorphan, phenazocine, phenoperidine, piminodine, piritramide, proheptazine, promedol, properidine, propiram, propoxyphene sufentanil, tramadol, tilidine, salts thereof, mixtures of any of the foregoing, mixed µ-agonists/antagonists, and the like.

In certain embodiments, a subject may be addicted to an opioid agonist. The terms "opioid agonist," "opioid" and "opiate" are used interchangably herein and are used to designate a group of drugs that are, to varying degrees, opium- or morphine-like in their properties. Their main use is for pain relief. These agents work by binding to opioid receptors, which are found principally in the central nervous system and the gastrointestinal tract. Opiates are also addictive agents. Opiates include alfentanil, allylprodine, alphaprodine, anileridine, apomorphine, benzylmorphine, beta-hydroxy 3-methylfentanyl, bezitramide, carfentanil, clonitazene, codeine, desomorphine, dextromoramide, diacetylmorphine (heroin), diampromide, dihydro codeine, dihydroetorphine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene, etorphine, fentanyl, hydrocodone, hydromorphone, hydroxypethidine, isomethadone, ketobemidone, LMM, levorphanol, levophenacylmorphan, lofentanil, meperidine, metapon, metazocine, methadone, methadyl acetate, metopon, morphine, myrophine, narceine, nicomorphine, norlevorphanol, normethadone, normorphine, norpipanone, opium, oxycodone, oxymorphone, papaverine, phenadoxone, phenomorphan, phenoperidine, piminodine, piritramide, propheptazine, promedol, properidine, propoxyphene, remifentanil, sufentanil, thebaine, tildine, and tramadol.

Naturally occurring opiates include codeine, morphine, noscapine, papaverine, and thebaine. Semi-synthetic opioids include diacetylmorphine, hydrocodone, hydromorphone, levorphanol, metapon, nalorphine, naloxone, naltrexone, oxycodone, oxymorphone, and tramadol. Synthetic opioids include ethoheptazine, fentanyl, levorphanol, meperidine, methadone, phenazocine, propoxyphene and sufentanil.

Three broad classifications of opiates are phenanthrenes, phenylheptylamines, and phenylpiperidines. Examples of phenanthrenes include codeine, etorpine, hydrocodone, hydromorphone, morphine, oxycodone, and oxymorphone. Examples of phenylheptylamines include dimeheptanol, dimenoxadol, dipipanone, isomethadone, methadone, methadyl acetate, and propoxyphene. Examples of phenylpiperidines include alfentanyl, alphaprodine, beta-promedol, carfentanyl, fentanyl, lofentanil, meperidine, properidine, and sufentanil.

Specific psychostimulants include, by way of example, amphetamine, cocaine, dextroamphetamine, methamphetamine, pemoline, Ritalin, Adderall and methylenedioxymethamphetamine.

As noted above, addiction includes addiction to behaviors, e.g., food addiction, binge eating disorder, pathological gambling, pathological use of electronic devices, e.g., BlackBerry®, pathological use of electronic video games, pathological use of electronic communication devices, pathological use of cellular telephones, addiction to pornography, sex addiction, obsessive-compulsive disorder, compulsive spending, intermittent explosive disorder, kleptomania, pyromania, trichotillomania, compulsive over-exercising, and compulsive overworking.

In one aspect, a subject suffers from food addiction or binge eating disorder, often with secondary health problems such as obesity due to excessive consumption of food and/or malnutrition due to excessive consumption of foods that are high in fat and/or sugar and low in vitamins and minerals.

As used herein "binge eating disorder" or "binge eating" includes at least one of the following episodic symptoms: eating large amounts of food, eating even when full, rapid eating, feeling that eating behavior is out of control, eating substantial amounts of food when not hungry, frequent dieting possibly without weight loss, eating alone, feeling depressed or disgusted about eating habits, eating in response to stress. Binge eating disorder is distinguished from other types of eating disorders, including food addiction, bulimia and binge-purge syndromes. Unlike bulimia and binge-purge syndromes, a subject suffering from binge eating disorder and food addiction-like behavior is that subjects suffering from binge eating disorder and food addiction-like behavior do not undertake compensatory behavior to attenuate excessive calorie consumption.

A body of scientific literature is building to support the characterization of certain types of problematic eating behaviors as addictions, given that binge eating and chronic excess eating share many characteristics with addictive behaviors (e.g., diminished control, continued use despite negative consequences). Despite similarities, binge eating disorder and food addiction may represent unique yet overlapping conditions. Gearhardt, A. N., et al., Binge Eating Disorder and Food Addiction, Curr. Drug Abuse Rev, 4:201-207 (2011).

As used herein, the term "food addiction" refers to a regular, persistent and habitual pattern of overeating characterized by craving and seeking high caloric foods, overeating in response to stimuli other than hunger, diminished control over food consumption, continued consumption despite negative consequences and diminished ability to cut down and abstain from consumption of an excess of food. Food addiction is a chronic relapsing disorder that typically follows a course of over-eating, tolerance, withdrawal, high caloric food seeking behavior and relapse (initiation of overeating after a period of abstinence).

A natural preference for highly palatable foods rich in fat and carbohydrate has developed for evolutionary reasons due to the high caloric support associated with such foods. Although it is indisputable that feeding behavior is regulated by homeostatic mechanisms, eating and overeating are also regulated by emotional, affective and learning processes. Polivy, et al., "Food restriction and binge eating: a study of a former prisoner of war," J Abnorm Psychol 103:409-411 (1994). In this respect several commonalities exist between excessive eating and drug abuse (reward, reinforcement, effects on mood, external cue-control of appetite, stress-induced motivation). Evidence is accumulating that excessive intake of certain foods under specific conditions produces behaviors and changes in the brain that resemble an addiction-like state. Gold, et al., "Overeating, binge eating, and eating disorders as addictions," Psychiatr Ann 33:112-116 (2003); Kenny, et al., "Common cellular and molecular mechanisms in obesity and drug addiction," Nat Rev Neurosci 12:638-651 (2011); Pelchat, et al., "Images of desire: food-craving activation during fMRI," Neuroimage 23:1486-1493 (2004); Avena, et al., "Evidence for sugar addiction: behavioral and neurochemical effects of intermittent, excessive sugar intake," Neurosci Biobehav Rev 32:20-39 (2008); Ifland, et al., "Refined food addiction: a classic substance use disorder," Med Hypotheses 72:518-526 (2009); Gearhardt, et al., "Food addiction: an examination of the diagnostic criteria for dependence," J Addict Med 3:1-7 (2011).

Drug addiction can be characterized by progressive escalation in drug use, tolerance development, abstinence following abrupt cessation of their use and recurrent relapse, and similar phenomena have been described for high sucrose high fat food. For example, rats fed with highly palatable sucrose solution experience opiate-like withdrawal symptoms following sucrose removal. Cross sensitization between sucrose and drugs of abuse has also been described. Avena, et al., "Evidence for sugar addiction: behavioral and neurochemical effects of intermittent, excessive sugar intake," Neurosci Biobehav Rev 32:20-39 (2008); Avena, et al., "Dysregulation of brain reward systems in eating disorders: Neurochemical information from animal models of binge eating, bulimia nervosa, and anorexia nervosa," Neuropharmacology (Epub ahead of print) (Nov. 27, 2011). Moreover, it has been well documented that psychological stress and dysphoric mood states play a major role in facilitating overeating as well as excessive drug use, and contribute to the high rate of recidivism typical of both disorders. Corwin, et al., "Feeling and reward: perspective from three rat models of binge eating," Physiol Behav 104:87-97 (2011); Ghitza, et al., "The anxiogenic drug yohimbine reinstates palatable food seeking in a rat relapse model: a role of CRF1 receptors," Neuropsychopharmacology 31(10):2188-2196 (2006); Mizes, et al., "Bulimia: A review of its symptomatology and treatment," Adv. Behav. Res. Ther. 7:91-142 (1985); Crowther, et al., "The role of daily hassles in binge eating," Int J Eat Disord 29:449-454 (2001); Herman, et al., "Anxiety, restraint, and eating behaviour," J Abnorm Psychol 84:66-72 (1975).

Exposure to environmental conditioning stimuli has also been shown to play a critical role in eliciting drug craving in addicted individuals as well as food craving in obese patients meeting the criteria for food addiction. Gearhardt, et al., "Food addiction: an examination of the diagnostic criteria for dependence," J Addict Med 3:1-7 (2011). Consistent with studies in humans, in laboratory animals it has been shown that exposure to environmental conditioning factors and exposure to stress (i.e., yohimbine) are similarly effective in eliciting reinstatement behaviors for drugs of abuse and for highly palatable food. Cifani, et al., "Preclinical model of binge-eating elicited by yo-yo dieting and stressful exposure to food: effect of sibutramine, fluoxetine, topiramate and midazolam," Psychopharmacology 204:113-25 (2009); Cifani, et al., "Pre-exposure to environmental cues predictive of food availability elicits hypothalamic-pituitary-adrenal axis activation and increases operant responding for food in female rats," Addict Biol. 14(4):397-407 (September 2009); Pickens, et al., "Effect of fenfluramine on reinstatement of food seeking in female and male rats: implications for the predictive validity of the reinstatement model," Psychopharmacology (Berl) 221(2):341-353 (May 2012). Neural systems that motivate and reinforce drug abuse have also been proposed to underlie behaviors associated with compulsive food seeking and excessive food intake. Johnson, et al., "Dopamine D2 receptors in addiction-like reward dysfunction and compulsive eating in obese rats," Nat Neurosci 13:635-641 (2010); Hoebel, et al., "Brain neurotransmitters in food and drug reward," Am J Clin Nutr 42(5 Suppl):1133-1150 (1985); Volkow, et al., "How can drug addiction help us understand obesity?" Nat Neurosci 8:555-560 (2005); Corwin, et al., "Feeling and reward: perspective from three rat models of binge eating," Physiol Behav 104:87-97 (2011); Gearhardt, et al., "Neural correlates of food addiction," Arch Gen Psychiatry 68:808-816 (2011); Wang, et al., "Enhanced striatal dopamine release during food stimulation during binge eating disorder," Obesity 19(8):1601-1608 (August 2011). For example, studies suggest that like in drug addicts, an altered regulation of striatal dopamine (DA) may exist in patients with bulimia nervosa.

Interest in the concept of food addiction has recently received greater attention, in large part due to the similarities between the behavioral indicators of addiction and binge eating disorder (BED). Episodes of binge eating in humans are characterized by compulsive, non-homeostatic consumption of an unusually large quantity of highly palatable food in a short period of time. Even though they are not hungry, subjects eat more rapidly than normal until feeling uncomfortably full. As described by the DMS-IV-TR (American Psychiatric Association, "Diagnostic and statistic manual of mental disorders," Washington, D.C. (2000)), these episodes are accompanied by a subjective sense of loss of control over eating, and are associated with feeling of distress, disgust, depression, being guilty about overeating, and eating alone because of embarrassment.

BED, described for the first time by Stunkard, "Eating patterns and obesity," Psychiatry Q 33:284-295 (1959), is probably the most prevalent eating disorder. Hudson, et al., "The prevalence and correlates of eating disorders in the National Comorbidity Survey Replication," Biol Psychiatry 61:348-58 (2007). It is characterized by repeated episodes of binge eating in the absence of compensatory behaviors to avoid weight gain. The diagnostic criteria for BED in the DSM-IV-TR include that binge eating episodes should occur at least 2 days per week for six months. BED is associated with significant medical and psychiatric co-morbidity. Javaras, et al., "Co-occurrence of binge eating disorder with psychiatric and medical disorders," J Clin Psychiatry 269: 266-273 (2008); Grucza, et al., "Prevalence and correlates of binge eating disorder in a community sample," Compr Psychiatry 48:124-131 (2007). It is estimated that binge eating afflicts approximately 5% of the US adult population at some time during their lives (Foulds, et al., "The biology of binge eating," Appetite 52:545-553 (2009)) and that it contributes to aggravate obesity and associated pathologies. Hudson, et al., "The prevalence and correlates of eating disorders in the National Comorbidity Survey Replication," Biol Psychiatry 61:348-58 (2007); Yanovski, "Binge eating disorder and obesity in 2003: could treating an eating disorder have a positive effect on the obesity epidemic?" Int J Eat Disord 34 Suppl: S117-S1120 (2003).

A large body of evidence suggests that dieting, stress and negative affective states represent important triggers of binge eating in patients suffering from BED or bulimia nervosa. Wardle, et al., "Stress, dietary restraint and food intake," J Psychosom Res 48:195-202 (2000); Freeman, et al., "Daily stress, coping, and dietary restraint in binge eating," Int J Eat Disord 36: 204-212 (2004). Indeed, dieting periods are common in the histories of binge eaters, although hunger itself does not appear to be enough to induce bing eating in the absence of stress and negative affective state. Polivy, et al., "Food restriction and binge eating: a study of former prisoner of war," J Abnorm Psychol 103:409-411 (1994); Waters, et al., "Internal and external antecedents of binge eating episodes in a group of women with bulimia nervosa," Int J Eat Disord 29:17-22 (2001). Considerable evidence suggests that binge eating may be caused by a unique interaction between dieting and stress; thus, environmental stress and a history of cyclic food restrictions may be responsible for its precipitation and maintenance. Stice, et al. "Subtyping binge eating-disordered women along dieting and negative affect dimensions," Int J Eat Disord 30:11-27 (2001); Crowther, et al., "The role of daily hassles in binge eating," Int J Eat Disord 29:449-454 (2001). Accordingly, recurring food restrictions are consistently the strongest predictor of overeating in response to stress. Wardle, et al., "Stress, dietary restraint and food intake," J Psychosom Res 48:195-202 (2000).

While a subject may be addicted to a single addictive agent or behavior, frequently subject is addicted to two or more addictive agents or behaviors. Addiction to two or more addictive agents or addictive behaviors is referred to as polyaddiction.

F. GLO1 in Other Neurological Diseases

Methods and compositions can be also provided for preventing or treating other neurological diseases, such as autism and Alzheimer's disease. Previous studies have also suggested associations between GLO1 and other diseases of the CNS, including autism and Alzheimer's disease (Junaid 2004; Sacco 2007; Chen 2004). The present study may provide mechanistic insight into GLO1's role in these diseases.

1. Autism

Autism is a disorder characterized by abnormal development in social interaction and communication as well as restricted interests (Habig 1974). As described above, Junaid et al. reported that the 419A GLO1 allele was more 1.5 times more common among autistic patients than controls (Junaid 2004). However, this study was limited by its small sample size (71 autistic subjects and 49 controls) and its use of a candidate gene approach. Candidate gene studies can suffer from biases and confounding variables (e.g., population stratification) (Tabor 2002). Indeed, subsequent studies have not replicated the association between the GLO1 419 SNP and autism (Wu 2008; Rehnstrom 2008; Sacco 2007). Although this could have resulted from differences in design or population between the studies (Tabor 2002), several human GWAS have also failed to identify associations between GLO1 polymorphisms and autism. This suggests that the findings of Junaid et al. were spurious or that they overestimated the effect size of GLO1's contribution to autism.

Nevertheless, Junaid et al. suggested that the 419A GLO1 allele was associated with a functional change in GLO1 enzymatic activity. Specifically, they reported that post-mortem brain tissue from autistic patients had reduced GLO1 enzymatic activity and increased AGE content compared to that from control patients (Junaid 2004). In a later study, they reported a correlation between the 111E GLO1 isoform and reduced enzymatic activity (Barua 2011).

However, the inventors' data do not indicate reduced enzymatic activity of the 111E GLO1 isoform. Instead, the 111E GLO1 isoform had 20-30% greater enzymatic activity than the 111A isoform. In addition, the inventors' behavioral data suggest that the 111A/E isoforms are not likely to significantly affect MG concentration or behavior. Glo1 KD mice, which had a similar 25% reduction in enzymatic activity, displayed no change in MG concentration or anxiety-like behavior (FIG. 26). Barua et al. reported that the GLO1 111E isoform was correlated with a 57% increase in MG concentration; however, the inventors' data suggest that this is not likely a causal relationship. In Glo1 KD mice, a similar 20-30% change in enzymatic activity did not affect MG concentration (FIG. 17B), and in Tg mice, a five-fold increase in GLO1 enzymatic activity reduced MG concentration by only 10% (FIG. 7). Therefore, the present examples argue against a functional role for the GLO1 419A/C polymorphism in autism.

Nevertheless, the association between autism and high levels of MG and AGEs may indicate a functional role for GLO1 in the pathogenesis of autism (Junaid 2004). Few studies have examined whether AGEs contribute to autism (Boso 2006); therefore, the mechanism underlying this association is unclear. Alternatively, it is possible that GLO1's role in GABAergic signaling could contribute to autism, since disruptions in GABAergic signaling are thought to underlie autism (Rubenstein 2011; DiCristo 2007). However, the GABAergic dysfunction observed in autism likely arises from aberrant development of GABAergic circuits and aberrant cortical plasticity of GABAergic neurons (Rubenstein 2011; Di Cristo 2007).

2. Alzheimer's Disease

Alzheimer's disease is a neurodegenerative disease prevalent among the elderly that results in cognitive impairment. The hallmark neuropathological features of Alzheimer's disease are aggregated protein depositions, specifically amyloid-β plaques and tau-containing neurofibrillary tangles (Ittner 2011). Previous reports have suggested an association between GLO1 and Alzheimer's disease. In mice with a transgenic mutant tau protein, which increases neurofibrillary tangles and thus models some aspects of Alzheimer's disease (Gotz 2001), there was a 1.8-fold increase in GLO1 protein in the brain compared to WT mice (Chen 2004). This finding was supported by studies in humans: post-mortem brains of patients with Alzheimer's disease displayed increased GLO1 protein compared to those of healthy controls (Chen 2004; Kuhla 2005). In contrast, there was an increased level of MG in the cerebrospinal fluid (Kuhla 2005) and increased AGEs in the brains of patients with Alzheimer's disease (Grillo 2008). As such, it was suggested that increased Glo1 expression is a compensatory mechanism to combat the toxic effects of AGEs.

Despite this correlation between Glo1 expression and Alzheimer's disease, Chen et al. did not identify a genetic association between the 419A/C SNP and Alzheimer's disease (Chen 2004). An earlier study also failed to identify associations between GLO1 alleles and Alzheimer's disease (Nerk 1984), and GAWS for Alzheimer's disease have not identified polymorphisms in GLO1. The strength of the mouse data is also questionable. Specifically, differential Glo1 expression could have been an artifact of differential fixation of the Glo1 CNV. The mutant tau transgenic mice were generated on a B6/D2 F1 background and were then intercrossed with B6 mice (Gotz 2001). The D2 background contains the Glo1 duplication, while the B6 background does not (Vince 1971). Since the mice were not backcrossed, it is possible that the transgene was linked to the Glo1 locus. This could result in differential Glo1 expression due to the CNV rather than a functional role of GLO1 in Alzheimer's disease. In order to rule out this possibility, these mice should be genotyped for the presence of the Glo1 duplication (Vince 1971).

Although AGEs have been identified in the amyloid-β and neurofibrillary tangles characteristic of Alzheimer's disease (Grillo 2008), it is unclear whether slight differences in Glo1 expression are sufficient to regulate this. Instead, it is possible that the aggregated proteins become glycated spontaneously, since AGEs form non-specifically. AGEs are not unique to Alzheimer's disease and are thought to accumulate with age (Xue 2011; Semba 2010). In summary, it is unclear whether GLO1 contributes to the pathogenesis of Alzheimer's disease. Future studies must experimentally manipulate Glo1 expression to assess its effect on disease progression, including development of senile plaque and neurofibrillary tangles, neurotoxicity, and cognitive deficits. If GLO1 modulates disease pathogenesis, a potential mechanism can then be pursued. Due to the prevalence of AGEs in the brains of patients with Alzheimer's disease, as well as the known role of cytotoxicity in disease progression, GLO1 is more likely to influence Alzheimer's disease through its role in AGE formation than its role in GABAergic signaling, which is not a well-established mechanism in Alzheimer's disease.

G. Other CNS Diseases Such as Sleep Disorders

Compositions and methods in certain aspects can be used to treat other CNS diseases, such as schizophrenia, or other diseases responsive to modulation of GABAA receptor signaling, such as sleep disorders.

GLO1 may contribute to other CNS disorders as well. For instance, recent studies have suggested a role for GLO1 in schizophrenia (Arai 2010; Toyosima 2011). In particular, a frameshift mutation in GLO1 was identified in a schizophrenic patient and was correlated with reduced GLO1 enzymatic activity (Toyosima 2011). Further, schizophrenic patients were found to have increased AGE accumulation compared to control subjects (Arai 2010). Nevertheless, small sample sizes and confounding variables make this association preliminary.

Human GWAS have also identified an association between restless legs syndrome (RLS) and a haplotype containing GLO1 (Kemlink 2009; Stefansson 2007). Because GABAA receptor agonists are used to treat RLS (Trenkwalder 2010), GLO1's role in GABAergic signaling could underlie its association with RLS.

Finally, it is possible that GLO1 and MG affect other diseases where GABAA receptor signaling is important to pathogenesis, including sleep disorders (Winsky-Sommerer 2009).

IV. GLO1 AS A TARGET FOR THERAPEUTIC AGENTS

Certain aspects demonstrated that GLO1 inhibition increased MG concentration in vivo (FIG. 14B), reduced anxiety-like behavior (FIG. 14C, 14E), and attenuated seizures (FIG. 31). This suggests that GLO1 may be a novel therapeutic target in the treatment of GABA-related disorders.

Similarly, there may be provided methods and compositions for increasing MG concentration as a novel therapeutic approach for treating epilepsy. MG levels increase under conditions of high metabolic load, such as diabetes (Shinohara 1998; Brownlee 2001; Masterjohn 2011), positioning MG as an intermediate between metabolic state and neuronal inhibitory tone. Therefore, metabolic interventions that raise endogenous MG levels could be a promising intervention for epilepsy without the adverse side effects of AEDs (Brodie 2011; Perucca 2011; Rossetti 2011).

For instance, the ketogenic diet is a high-fat, low-carbohydrate diet that is administered to patients with epilepsy who do not respond to AEDs (Rosetti 2011; Payne 2011). The mechanism by which the ketogenic diet controls seizures is unknown, but it has been hypothesized that the ketogenic diet increases MG levels (Beisswenger 2005; Hartman 2007; Kalapos 2007; Gasior 2007). When the inventors administered the ketogenic diet ad libitum to mice for one month, however, there was no increase in MG concentration in the brain (data not shown). The inventors did not investigate whether the ketogenic diet reduced seizures in the inventors' mice, so it was unclear that it was effectively administered. Therefore, it remains possible that the ketogenic diet acts by increasing MG levels. Furthermore, other interventions that increase MG should be investigated as novel methods for controlling seizures.

GLO1 inhibition would represent a novel mechanism of action among anxiolytic drugs and AEDs. Most current anxiolytic therapies target neurotransmitter systems, including the serotonin and GABA systems (Pollack 2009). Similarly, most AEDs target ion channels, including GABAA receptors (Brodie 2011; Perucca 2011; Rossetti 2011). GLO1 inhibitors would increase the production of an endogenous GABAergic agent. This could have a milder side effect profile than agents that directly activate GABAA receptors or other ion channels. For instance, endogenously generated MG might have brain-region specificity, thus preventing off-target effects. Similarly, GLO1 inhibition may not increase MG levels sufficiently to cause sedation or have abuse potential, which are common concerns of current GABAA receptor agonists. Indeed, in the inventors' experience, mice treated with BrBzGCp2 did not display sedation or gross deficits. However, the inventors have not thoroughly characterized its side effect profile, and this remains an important direction for future studies.

Studies of the adverse effects of GLO1 inhibition in vivo must also pay particular attention to cytotoxicity. In vitro studies have demonstrated that GLO1 inhibition can cause cell death (Kuhla 2006). This is unlikely to occur in vivo over a short period of time, since GLO1 inhibition increased MG levels by only 20% (FIG. 22B), which is well below the level required to induce cell death. Nevertheless, chronic GLO1 inhibition may increase MG to more toxic levels, causing AGE formation or cell death.

Certain examples involve the investigation of GLO1's effect on anxiety and elucidated the underlying molecular mechanism. In doing so, uncovered novel physiological roles were unconverted for GLO1 and its substrate, MG, as modulators of GABAA receptors. This finding was extended to identify a role for GLO1 and MG in other CNS disorders, including depression and epilepsy. Finally, it was established the therapeutic potential of GLO1 inhibition in the treatment of anxiety and epilepsy.

V. COMBINATION TREATMENTS

In some embodiments, the treatment is administered in conjunction with a second treatment for such a neurological disease or disorder. Furthermore, in some examples, treatment comprises administration of other agents commonly used against such a neurological disease or disorder. The compositions and related methods, particularly administration of a GLO1 inhibitor or a compound that inhibits GLO1, may also be used in combination with the administration of traditional therapies for sleep disorders, mood disorders, epilepsy, alcohol withdrawal syndrome or anxiety disorders.

A. Combination Treatment for Mood and/or Anxiety Disorders

In order to increase the effectiveness of the treatment method provided in certain aspects, it may be desirable to combine the treatment methods with secondary treatments to treat the mood disorders such as bipolar disorders or depressive disorders and/or anxiety diseases, disorders or conditions, such as chemical stimulation or the use of stimulating drugs (e.g., antidepressants), psychotherapy, and the use of devices including electroconvulsive therapy, vagus nerve stimulation, repetitive transcranial magnetic stimulation, and cranial electrotherapy stimulation.

Herein, stimulating drugs may comprise medications, anesthetic agents, synthetic or natural peptides or hormones, neurotransmitters, cytokines and other intracellular and intercellular chemical signals and messengers, and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein includes stimulation of cell bodies and axons in the area.

Similarly, excitatory neurotransmitter agonists (e.g., norepinephrine, epinephrine, glutamate, acetylcholine, serotonin, dopamine), agonists thereof, and agents that act to increase levels of an excitatory neurotransmitter(s) (e.g., edrophonium; Mestinon; trazodone; SSRIs (e.g., flouxetine, paroxetine, sertraline, citalopram and fluvoxamine); tricyclic antidepressants (e.g., imipramine, amitriptyline, doxepin, desipramine, trimipramine and nortriptyline), monoamine oxidase inhibitors (e.g., phenelzine, tranylcypromine, isocarboxasid)), generally have an excitatory effect on neural tissue, while inhibitory neurotransmitters (e.g., dopamine, glycine, and gamma-aminobutyric acid (GABA)), agonists thereof, and agents that act to increase levels of an inhibitory neurotransmitter(s) generally have an inhibitory effect. (Dopamine acts as an excitatory neurotransmitter in some locations and circumstances, and as an inhibitory neurotransmitter in other locations and circumstances.) However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g., prazosin, and metoprolol) and agents that decrease levels of excitatory neurotransmitters may inhibit neural activity.

Exemplary second treatments of anxiety disorders include, but are not limited to therapy such as cognitive-behavioral therapy (CBT), exposure therapy, acceptance and commitment therapy (ACT), dialectical behavioral therapy (DBT), interpersonal therapy (IPT) or eye movement desensitization and reprocessing (EMDR) or medications such as SSRIs, SNRIs, Benzodiazepines or tricyclic antidepressants.

Selective Serotonin Reuptake Inhibitors (SSRIs). SSRIs relieve symptoms by blocking the reabsorption, or reuptake, of serotonin by certain nerve cells in the brain. This leaves more serotonin available, which improves mood. SSRIs (citalopram, escitalopram, fluoxetine, paroxetine, and sertraline) generally produced fewer side effects when compared with tricyclic antidepressants. However, common side effects include insomnia or sleepiness, sexual dysfunction, and weight gain. They are considered an effective treatment for all anxiety disorders, although the treatment of obsessive-compulsive disorder, or OCD, typically requires higher doses.

Serotonin-Norepinephrine Reuptake Inhibitors (SNRIs).

The serotonin-norepinephrine reuptake inhibitor, or SNRI, class (venlafaxine and duloxetine) is notable for a dual mechanism of action: increasing the levels of the neurotransmitters serotonin and norepinephrine by inhibiting their reabsorption into cells in the brain. As with other medications, side effects may occur, including stomach upset, insomnia, headache, sexual dysfunction, and minor increase in blood pressure. These medications are considered as effective as SSRIs, so they are also considered a first-line treatment, particularly for the treatment of generalized anxiety disorder.

Benzodiazepines.

This class of drugs is frequently used for short-term management of anxiety. Benzodiazepines (alprazolam, clonazepam, diazepam, and lorazepam) are highly effective in promoting relaxation and reducing muscular tension and other physical symptoms of anxiety. Long-term use may require increased doses to achieve the same effect, which may lead to problems related to tolerance and dependence.

Tricyclic Antidepressants.

Concerns about long-term use of the benzodiazepines led many doctors to favor tricyclic antidepressants (amitriptyline, imipramine, and nortriptyline). Although effective in the treatment of anxiety, they can cause significant side effects, including orthostatic hypotension (drop in blood pressure on standing), constipation, urinary retention, dry mouth, and blurry vision.

There may be different types of treatments available for mood disorders, such as therapy and medications. Major depressive disorder medications usually include antidepressants, while bipolar disorder medications can consist of antipsychotics, mood stabilizers and/or lithium. Exemplary second treatments of depressive disorders include, but are not limited to medications including stimulating drugs (e.g., antidepressants), psychotherapy, and the use of devices including electroconvulsive therapy, vagus nerve stimulation, repetitive transcranial magnetic stimulation, and cranial electrotherapy stimulation. Non-limiting anti-depressants include SSRIs, SNRIs, Norepinephrine reuptake inhibitors (NRIs), Norepinephrine-dopamine reuptake inhibitors (NDRIs), Norepinephrine-dopamine releasing agents (NDRAs), Tricyclic antidepressants (TCAs), Tetracyclic antidepressants (TeCAs), Monoamine oxidase inhibitors (MAOIs), 5-HT1A Receptor Partial Agonists, 5-HT2 Receptor Partial Agonists, 5-HT7 Receptor Antagonists, D2 Receptor Partial Agonists, D2 Receptor Antagonists, D3 Receptor Antagonists, D4 Receptor Antagonists, α-adrenergic Receptor Antagonists, mACh Receptor Antagonists, Serotonin Reuptake Inhibitors (SRIs), Norepinephrine Reuptake Inhibitors (NRIs), Selective Serotonin Reuptake Enhancers (SSREs), Sigma Receptor Agonists and Mood Stabilizers.

B. Combination Treatment for Epilepsy

The treatment methods provided in certain aspects can be combined with other treatment of epilepsy such as anticonvulsant medications. For example, drugs for treatment of epileptic seizures include, but are not limited to, carbamazepine (common US brand name Tegretol), clorazepate (Tranxene), clonazepam (Klonopin), ethosuximide (Zarontin), felbamate (Felbatol), fosphenytoin (Cerebyx), gabapentin (Neurontin), lacosamide (Vimpat), lamotrigine (Lamictal), levetiracetam (Keppra), oxcarbazepine (Trileptal), phenobarbital (Luminal), phenytoin (Dilantin), pregabalin (Lyrica), primidone (Mysoline), tiagabine (Gabitril), topiramate (Topamax), valproate semisodium (Depakote), valproic acid (Depakene), zonisamide (Zonegran), clobazam (Frisium), vigabatrin (Sabril), retigabine, brivaracetam, and seletracetam.

Other drugs are commonly used to abort an active seizure or interrupt a seizure flurry; these include diazepam (Valium, Diastat) and lorazepam (Ativan). Drugs used only in the treatment of refractory status epilepticus include paraldehyde (Paral), midazolam (Versed), and pentobarbital (Nembutal).

Some anticonvulsant medications do not have primary FDA-approved uses in epilepsy but are used in limited trials, remain in rare use in difficult cases, have limited "grandfather" status, are bound to particular severe epilepsies, or are under current investigation. These include acetazolamide (Diamox), progesterone, adrenocorticotropic hormone (ACTH, Acthar), various corticotropic steroid hormones (prednisone), or bromide.

The goal for individual patients is no seizures and minimal side-effects, and the job of the physician is to aid the patient to find the best balance between the two during the prescribing of anticonvulsants. Some patients can achieve this balance best with monotherapy, the use of a single anticonvulsant medication. Some patients, however, require polypharmacy, the use of two or more anticonvulsants.

If a person's epilepsy cannot be brought under control after adequate trials of two or three (experts vary here) different drugs, that person's epilepsy is generally said to be medically refractory. A study of patients with previously untreated epilepsy demonstrated that 47% achieved control of seizures with the use of their first single drug. 14% became seizure free during treatment with a second or third drug. An additional 3% became seizure-free with the use of two drugs simultaneously.

Other treatments such as the treatment comprising GLO1 inhibitors, in addition to or instead of, anticonvulsant medications may be considered by those people with continuing seizures.

Epilepsy surgery is also an option for people with focal seizures that remain resistant to treatment. The goal for these procedures is total control of epileptic seizures, although anticonvulsant medications may still be required. The evaluation for epilepsy surgery is designed to locate the "epileptic focus" (the location of the epileptic abnormality) and to determine if resective surgery will affect normal brain function. Physicians will also confirm the diagnosis of epilepsy to make sure that spells arise from epilepsy (as opposed to non-epileptic seizures). The evaluation typically includes neurological examination, routine EEG, Long-term video-EEG monitoring, neuropsychological evaluation, and neuroimaging such as MRI, Single photon emission computed tomography (SPECT), positron emission tomography (PET). Some epilepsy centers use intracarotid sodium amobarbital test (Wada test), functional MRI or Magnetoencephalography (MEG) as supplementary tests.

Certain lesions require Long-term video-EEG monitoring with the use of intracranial electrodes if noninvasive testing was inadequate to identify the epileptic focus or distinguish the surgical target from normal brain tissue and function. Brain mapping by the technique of cortical electrical stimulation or Electrocorticography are other procedures used in the process of invasive testing in some patients.

The most common surgeries are the resection of lesions like tumors or arteriovenous malformations, which, in the process of treating the underlying lesion, often result in control of epileptic seizures caused by these lesions.

Other lesions are more subtle and feature epilepsy as the main or sole symptom. The most common form of intractable epilepsy in these disorders in adults is temporal lobe epilepsy with hippocampal sclerosis, and the most common type of epilepsy surgery is the anterior temporal lobectomy, or the removal of the front portion of the temporal lobe including the amygdala and hippocampus. Some neurosurgeons recommend selective amygdalahippocampectomy because of possible benefits in postoperative memory or language function. Surgery for temporal lobe epilepsy is effective, durable, and results in decreased health care costs. Despite the efficacy of epilepsy surgery, some patients decide not to undergo surgery owing to fear or the uncertainty of having a brain operation.

Palliative surgery for epilepsy is intended to reduce the frequency or severity of seizures. Examples are callosotomy or commissurotomy to prevent seizures from generalizing (spreading to involve the entire brain), which results in a loss of consciousness. This procedure can therefore prevent injury due to the person falling to the ground after losing consciousness. It is performed only when the seizures cannot be controlled by other means. Multiple subpial transection can also be used to decrease the spread of seizures across the cortex especially when the epileptic focus is located near important functional areas of the cortex. Resective surgery can be considered palliative if it is undertaken with the expectation that it will reduce but not eliminate seizures.

Hemispherectomy involves removal or a functional disconnection of most or all of one half of the cerebrum. It is reserved for people suffering from the most catastrophic epilepsies, such as those due to Rasmussen syndrome. If the surgery is performed on very young patients (2-5 years old), the remaining hemisphere may acquire some rudimentary motor control of the ipsilateral body; in older patients, paralysis results on the side of the body opposite to the part of the brain that was removed. Because of these and other side-effects, it is usually reserved for patients having exhausted other treatment options.

Other treatements may include:

A ketogenic diet (high-fat, low-carbohydrate) was first tested in the 1920s, but became less used with the advent of effective anticonvulsants. In the 1990s specialized diets again gained traction within the medical community. The mechanism of action is unknown. It is used mainly in the treatment of children with severe, medically intractable epilepsies, and the New York Times reported that use is supported by peer-reviewed research that found that the diet reduced seizures among drug-resistant epileptics by >50% in 38% of patients and by >90% in 7% of patients.

While far from a cure, operant-based biofeedback based on conditioning of EEG waves has some experimental support (see Professional practice of behavior analysis). Overall, the support is based on a handful of studies reviewed by Barry Sterman. These studies report a 30% reduction in weekly seizures.

Electrical stimulation methods of anticonvulsant treatment are both currently approved for treatment and investigational uses. A currently approved device is vagus nerve stimulation (VNS). Investigational devices include the responsive neurostimulation system (RNS) and deep brain stimulation (DBS).

Vagus nerve stimulation (US manufacturer Cyberonics) consists of a computerized electrical device similar in size, shape and implant location to a heart pacemaker that connects to the vagus nerve in the neck. The device stimulates the vagus nerve at preset intervals and intensities of current. Efficacy has been tested in patients with localization-related epilepsies, demonstrating 50% of patients experience a 50% improvement in seizure rate. Case series have demonstrated similar efficacies in certain generalized epilepsies, such as Lennox-Gastaut syndrome. Although success rates are not usually equal to that of epilepsy surgery, it is a reasonable alternative when the patient is reluctant to proceed with any required invasive monitoring, when appropriate presurgical evaluation fails to uncover the location of epileptic foci, or when there are multiple epileptic foci.

Responsive neurostimulator system (US manufacturer Neuropace) consists of a computerized electrical device implanted in the skull, with electrodes implanted in presumed epileptic foci within the brain. The brain electrodes send EEG signals to the device, which contains seizure-detection software. When certain EEG seizure criteria are met, the device delivers a small electrical charge to other electrodes near the epileptic focus, which disrupt the seizure. The efficacy of the RNS is under current investigation with the goal of FDA approval.

Deep brain stimulation (U.S. manufacturer Medtronic) consists of a computerized electrical device implanted in the chest in a manner similar to the VNS, but electrical stimulation is delivered to deep brain structures through depth electrodes implanted through the skull. In epilepsy, the electrode target is the anterior nucleus of the thalamus. The efficacy of the DBS in localization-related epilepsies is currently under investigation.

Noninvasive surgery using the gamma knife or other devices used in radiosurgery is currently being investigated as an alternative to traditional open surgery in patients who would otherwise qualify for anterior temporal lobectomy.

Avoidance therapy consists of minimizing or eliminating triggers in patients whose seizures are particularly susceptible to seizure precipitants (see above). For example, sunglasses that counter exposure to particular light wavelengths can improve seizure control in certain photosensitive epilepsies.

Canine warning system is where a seizure response dog, a form of service dog, is trained to summon help or ensure personal safety when a seizure occurs. These are not suitable for everybody, and not all dogs can be so trained. Rarely, a dog may develop the ability to sense a seizure before it occurs. Development of electronic forms of seizure detection systems are currently under investigation.

Seizure prediction-based devices using long-term EEG recordings is presently being evaluated as a new way to stop epileptic seizures before they appear clinically.

Alternative or complementary medicine, including acupuncture, psychological interventions, vitamins and yoga, was evaluated in a number of systematic reviews by the Cochrane Collaboration into treatments for epilepsy, and found there is no reliable evidence to support the use of these as treatments for epilepsy. Exercise or other physical activity have also been proposed as efficacious strategies for preventing or treating epilepsy.

C. Combination Treatments for Sleep Disorders

Sleep disorders can generally be divided into 3 large groups: (1) those producing insomnia (complaints of difficulty falling asleep, staying asleep, or nonrestorative sleep), (2) those with a primary complaint of daytime sleepiness, and (3) those associated with disruptive behaviors during sleep—the disorders of arousal.

Additional sleep disorder treatments that may be used in combination treatments may include, but are not limited to, amitriptyline (Elavil and others), amoxapine (Asendin and others), bupropion (Wellbutrin), buspirone (BuSpar), carbidopa-levodopa (Sinemet and others), citalopram (Celexa), clonazepam (Klonopin and others), clorazepate (Tranxene and others), desipramine (Norpramin and others), desmopressin (DDAVP and others), dextroamphetamine (Dexedrine and others), diazepam (Valium and others), doxepin (Sinequan and others), estazolam (ProSom and others), fluoxetine (Prozac), flurazepam (Dalmane and others), fluvoxamine (Luvox), medroxyprogesterone (Provera and others), methylphenidate (Ritalin and others), mirtazapine (Remeron), modafinil (Provigil), nefazodone (Serzone), nortriptyline (Pamelor and others), paroxetine (Paxil), pemoline (Cylert), pergolide (Permax), phenelzine (Nardil), phenobarbital (Donnatal and others), pramipexole (Mirapex), protriptyline (Vivactil), ropinirole (Requip), selegiline (Eldepryl), sertraline (Zoloft), temazepam (Restoril and others), tranylcypromine (Parnate), trazodone (Desyrel and others), triazolam (Halcion and others), trimipramine (Surmontil), venlafaxine (Effexor), zaleplon (Sonata), zolpidem (Ambien). Particular examples are described in Pagel et al., 2001.

D. Combination Treatments for Alcohol Withdrawal Syndrome

Second treatment of alcohol withdrawal syndrome can be managed with various pharmaceutical medications including barbiturates and clonidine. Certain vitamins are also an important part of the management of alcohol withdrawal syndrome.

Benzodiazepines, such as diazepam or lorazepam, are the most commonly used drug for the treatment of alcohol withdrawal and are generally safe and effective in suppressing alcohol withdrawal signs. Chlordiazepoxide and diazepam are the benzodiazepines most commonly used in alcohol detoxification.

Antipsychotic agents, such as haloperidol, are sometimes used for alcohol withdrawal as an add-on to first-line measures such as benzodiazepines to control agitation or psychosis. Antipsychotics may potentially worsen alcohol withdrawal effects (or other CNS depressant withdrawal states) as they lower the seizure threshold and can worsen withdrawal effects. Clozapine, olanzapine or low potency phenothiazines (e.g. chlorpromazine) are particularly risky; if used, extreme caution is required. There is also concern for this class of drugs prolonging the QT interval, sometimes leading to fatal heart dysrhthmias.

Some evidence indicates that topiramate carbamazepine and other anticonvulsants are effective in the treatment of alcohol withdrawal.

Baclofen has been shown to be as effective as diazepam in uncomplicated alcohol withdrawal syndrome.

Barbiturates are superior to diazepam in the treatment of severe alcohol withdrawal syndromes such as delirium tremens but equally effective in milder cases of alcohol withdrawal.

Clomethiazole (Heminevrin) is a non-benzodiazepine sedative-hypnotic with anticonvulsant effects which is active on the barbiturate site of the GABA-A receptor. Clomethiazole also inhibits the enzyme alcohol dehydrogenase, which is responsible for breaking down alcohol in the body. This slows the rate of elimination of alcohol from the body, which helps to relieve the sudden effects of alcohol withdrawal in alcoholics.

Clonidine has demonstrated superior clinical effects in the suppression of alcohol withdrawal symptoms in a head to head comparison study with the benzodiazepine drug chlordiazepoxide.

Alcohol (ethanol) itself at low doses, but only when given intravenously by medical personnel, has been found to be superior to chlordiazepoxide in the detoxification of alcohol dependent patients.

Flumazenil, which has shown some promise in the management of the benzodiazepine withdrawal syndrome has also demonstrated benefit in a research study in reducing anxiety withdrawal related symptomatology during alcohol withdrawal.

Trazodone has demonstrated efficacy in the treatment of the alcohol withdrawal syndrome. It may have particular use in withdrawal symptoms, especially insomnia, persisting beyond the acute withdrawal phase.

Magnesium appears to be effective in the treatment of alcohol withdrawal related cardiac arrhythmias. It is ineffective in controlling other symptoms of alcohol withdrawal.

Nitrous oxide has been shown to be an effective and safe treatment for alcohol withdrawal.

E. Combination Treatments for Substance Abuse/Dedence/Withdrawal

The additional therapeutic agent provided in combination with a Glo1 inhibitor may be any therapeutic agent that contributes to an aspect of the effective treatment or prevention of the addiction. For example, the additional therapeutic agent may be a drug used to treat an addiction or a drug used to alleviate side-effects associated with physiological withdrawal from an addictive agent. In addition, the additional therapeutic agent may be any drug that affects brain serotonin neurotransmission, such as selective serotonin reuptake inhibitors (SSRIs), and tricyclic and tetracyclic serotonin and norepinephrine reuptake inhibitors (SNRIs) as described below, and serotonin agonists such as sumatriptan, ergonovine, dihydroergotamine and buspirone. In certain embodiments, the additional therapeutic agent is an opioid antagonist, including mixed opioid partial agonist/antagonists, an antidepressant, an antiepileptic, an antiemetic, a dopaminergic agent such as a dopamine D1 receptor agonist, a corticotrophin-releasing factor-1 (CRF-1) receptor antagonist, a selective serotonin-3 (5-HT3) antagonist, a 5-HT2A/2C antagonist such as mianserin, mirtazapine and ketanserin, or a cannabinoid-1 (CB1) receptor antagonist, including but not limited to those therapeutic agents specifically described herein.

1. Opioid Antagonists

An opioid antagonist acts on one or more opioid receptors. At least three types of opioid receptors, mu, kappa, and delta opioid receptors, have been reported, and opioid antagonists are generally classified by their effects on the opioid receptors. Opioid antagonists may antagonize central receptors, peripheral receptors or both. Naloxone and naltrexone are commonly used opioid antagonist drugs that are competitive in that they bind to the opioid receptors with higher affinity than agonists, but do not activate the receptors. This effectively blocks the receptor, preventing the body from responding to opiates and endorphins.

Many opioid antagonists are not pure antagonists but also produce some weak opioid partial agonist effects, and can produce analgesic effects when administered in high doses to opioid-naive individuals. Examples of such compounds include nalorphine, and levallorphan. However, the analgesic effects from these drugs are limited and tend to be accompanied by dysphoria, most likely due to action at the kappa opioid receptor. Since they induce opioid withdrawal effects in people who are taking, or have previously used, opioid full agonists, these drugs are considered to be antagonists.

Naloxone is one example of an opioid antagonist that has no partial agonist effects. Instead, it is a weak inverse agonist at mu opioid receptors, and is used for treating opioid overdose.

Specific examples of opioid antagonists that may be used include alvimopan, binaltorphimine, buprenorphine, cyclazocine, cyclorphan, cypridime, dinicotinate, beta-funaltrexamine, levallorphan, methylnaltrexone, nalbuphine, nalide, nalmefene, nalmexone, nalorphine, nalorphine dinicotinate, naloxone, naloxonazine, naltrendol, naltrexone, naltrindole, oxilorphan, and pentazocine.

2. Antidepressents

Antidepressents are drugs used to treat depression. The three neurotransmitters believed to be involved in depression are serotonin, dopamine, and norepinephrine. Certain types of antidepressants increase the levels of one or more of these neurotransmitters in the brain by blocking their reabsorption.

Several different classes of antidepressants have been identified, including selective serotonin reuptake inhibitors (SSRIs), tricyclic and tetracyclic serotonin and norepinephrine reuptake inhibitors (SNRIs), norepinephrine reuptake inhibitors (NRIs), norepinephrine and dopamine reuptake inhibitors (NDRIs), azaspirones, monoamine oxidase inhibitors (MAOIs), and atypical antidepressants.

SSRIs include, e.g., cericlamine, citalopram, clomipramine, cyanodothiepin, dapoxetine, duloxetine, escitalopram, femoxetine, fluoxetine, fluvoxamine, ifoxetine, imipramine, indalpine, indeloxazine, litoxetine, lofepramine, mianserine, milnacipran, mirtazapine, nefazadone, nortriptyline, paroxetine, sertraline, sibutramine, tomoxetine, trazodone, venlafaxine, and zimeldine.

Amitriptyline, amoxapine, butriptyline, clomipramine, demexiptiline, desipramine, dibenzepin, dimetacrine, dothiepin, doxepin, imipramine, iprindole, lofepramine, maprotiline, melitracen, metapramine, mianserin, mirtazpine, nortriptyline, propizepine, protriptyline, quinupramine, setiptiline, tianeptine, and trimipramine are all tricyclic and tetracyclic antidepressants.

SNRIs include, e.g., amoxapine, atomoxetine, bicifadine, desipramine, desvenlafaxine, duloxetine, maprotiline, milnacipran, nefazodone, reboxetine, sibutramine, and venlafaxine.

Nisoxetine, nortriptyline, reboxetine, talsupram, and tomoxetine are all examples of NRIs.

NDRIs include, e.g., bupropion, hydroxybupropion, and tesofensine.

Azaspirones include, e.g., buspirone, gepirone, ipsapirone, tandospirone, and tiaspirone. Buspirone is an anxiolytic (partial agonist at 5-HT1 autoreceptors) that may be provided with an anti-depressant such as an SSRI.

Specific MAOIs include, e.g., amiflamine, brofaromine, clorgyline, alpha-ethyltryptamine, iproclozide, iproniazid, isocarboxazid, mebanazine, moclobemide, nialamide, pargyline, phenelzine, pheniprazine, pirlindole, safrazine, selegiline, toloxatone, and tranlcypromine.

Atypical antidepressants include, e.g., amesergide, amineptine, benactyzine, bupropion, clozapine, fezolamine, levoprotiline, lithium, medifoxamine, mianserin, minaprine, olanzapine, oxaflozane, oxitriptan, rolipram, teniloxazine, tofenacin, trazodone, tryptophan, and viloxazine.

3. Antiepileptics

The anticonvulsants, also called anti-epileptic drugs (AEDs) are a diverse group of drugs used in prevention of the occurrence of epileptic seizures and bipolar disorders. AEDs suppress the rapid and excessive firing of neurons that begins a seizure and/or prevents the spread of the seizure within the brain and offer protection against possible excitotoxic effects that may result in brain damage. Many anticonvulsants block sodium channels, calcium channels, AMPA receptors, or NMDA receptors.

Anti-epileptic agents include, but are not limited to, benzodiazepines, barbituates, valproates, GABA agents, iminostilibenes, hydantoins, NMDA antagonists, sodium channel blockers and succinamides.

Benzodiazepines include, e.g., alprazolam, chlordiazepoxide, cholrazepate, clobazam, clonazepam, diazepam, halazapam, lorazepam, oxazepam, and prazepam.

Barbiturates used as anti-epileptics include, e.g., amobarbital, mepobarbital, methylphenobarbital, pentobarbital, phenobarbital, and primidone.

Valproates used as anti-epileptics include, e.g., sodium valporate, valproic acid, valproate semisodium, and valpromide.

Anti-epileptic GABA agents include, e.g., gabapentin, losigamone, pregabalin, retigabine, rufinamide, and vigabatrin.

Carbamazepine and oxcarbazepine are examples of iminostilbenes.

Hydantoins include, e.g., fosphenyloin sodium, mephenyloin, and phenyloin sodium.

NMDA antagonists such as harkoseramide are used as anti-epileptics.

Sodium channel blockers such as lamotrigine are also anti-epileptic agents.

Succinimides include, e.g., ethosuximide, methsuximide, and phensuximide.

Other anti-epileptic drugs include acetazolamide, briveracetam, CBD cannabis derivative, clomthiazole edisilate, divalproex sodium, felbamate, isovaleramide, lacosamide, lamotrigine, levetiracetam, methanesulphonamide, talampanel, tiagabine, topiramate, safinamide, seletracetam, soretolide, stiripentol, sultiam, valrocemide, and zonisamide.

4. Antiemetics

Antiemetics are drugs effective against vomiting and nausea. Antiemetics are typically used to treat motion sickness and the side effects of opioid analgesics, general anaesthetics, and chemotherapy.

Classifications of antiemetics include, e.g., 5-hydroxytryptamine 3 (5-HT3) receptor antagonists, histamine receptor antagonists, dopamine receptor antagonists, muscarinic receptor antagonists, acetyl choline receptor antagonists, cannabinoid receptor antagonists, limbic system inhibitors, NK-1 receptor antagonists, corticosteroids, tachykinin antagonists, GABA agonists, cannabinoids, benzodiazepines, anticholinergics, and substance P inhibitors.

5-HT3 receptor antagonists include, e.g., alosetron, azasetron, bemesetron, cilansetron, dolasetron, granisetron, indisetron, itasetron, ondansetron, palonosetron, propisetron, ramosetron, renzapride, tropisetron, and zatosetron.

Coritcosteroid antiemetics include dexamethasone and methylprednisolone.

Lymbic system inhibitors include alprazolam, lorazepam, and midazolam.

Dopamine receptor antagonists include diphenhydramine, dronabinol, haloperidol, metoclopramide, and prochlorperazine.

NK-1 receptor antagonists used as an antiemetic include aprepitant and morpholine, and an example of a GABA agonist is propofol.

Thiethylperazine is a type of histamine receptor antagonist.

Cannabinoid receptor antagonists or agonists used as antiemetics include dronabinol, nabilone, rimonabant, tanarabout, and tetrahydrocannabinol.

Examples of other antiemetics include acetylleucine, monoethanolamine, alizapride, benzquinamide, bietanautine, bromopride, buclizine, chlorpromazine, clebopride, cyclizine, dimenhydrinate, dipheniodol, domperidone, dranisetron, meclizine, methalltal, metopimazine, oxypendyl, pipamazine, piprinhydrinate, scopolamine, thioproperzaine, and trimethobenzamide.

5. Cannabinoid Receptor Antagonists

The cannabinoid receptors are a class of the G-protein coupled receptor superfamily. Their ligands are known as cannabinoids. There are currently two known subtypes, CB1 which is expressed mainly in the brain, but also in the lungs, liver, and kidney, and CB2, which is mainly expressed in the immune system and in hematopoietic cells. It is also believed that there are novel cannabinoid receptors that is, non-CB1 and non-CB2, which are expressed in endothelial cells and in the CNS. Cannabinoid receptor antagonists may be selective for either the CB1 or CB2 receptor. For example, either or both CB1 and CB2 receptor antagonists can be used.

Addictive agents (e.g., alcohol, opiates, Delta(9)-tetrahydrocannabinol (Delta(9)-THC) and psychostimulants, including nicotine) elicit a variety of chronically relapsing disorders by interacting with endogenous neural pathways in the brain. In particular, they share the common property of activating mesolimbic dopamine brain reward systems, and virtually all abused drugs elevate dopamine levels in the nucleus accumbens. Cannabinoid-1 (CB1) receptors are expressed in this brain reward circuit and modulate the dopamine-releasing effects of Delta(9)-THC and nicotine.

Rimonabant (SR141716), a CB1 receptor antagonist, blocks both the dopamine-releasing and the discriminative and rewarding effects of Delta(9)-THC in animals. Although CB1 receptor blockade is generally ineffective in reducing the self-administration of cocaine in rodents and primates, it reduces the reinstatement of extinguished cocaine-seeking behavior produced by cocaine-associated conditioned stimuli and cocaine priming injections. Similarly, CB1 receptor blockade is effective in reducing nicotine-seeking behavior induced by re-exposure to nicotine-associated stimuli. In human clinical trials, rimonabant was shown to block the subjective effects of Delta(9)-THC in humans and prevents relapse to smoking in ex-smokers.

Other examples of cannabinoid receptor CB1 antagonists include SR141716A (rimonabant), rosanabant, taranabant and CP-945598.

6. Dopaminergic Agents

Drug addiction is a chronic, relapsing disease characterized by a loss of control over drug use, compulsive drug seeking and craving for a substance, use that persists despite negative consequences, and physical and/or psychological dependence on the substance. A fundamental role in the pathogenesis of addiction has been attributed to dopamine. Dopamine, in fact, has permeated the natural history of drug addiction at all levels, from its involvement in shaping individual response to vulnerability factors (i.e., genetics, environmental and stress) to its role in the mechanism of action of the drugs of abuse.

The mesocorticolimbic dopamine system originates in the ventral tegmental area (VTA), which prominently projects to the nucleus accumbens (NAc) and the prefrontal cortex (PPC). It is a defining commonality of all addictive drugs that at least initially they stimulate dopamine transmission in the terminal areas of the mesolimbic system and in particular in the nucleus NAc shell. Nestler, E. J., "is there a common molecular pathway for addiction?" *Nat Neurosci* 8:1445-1449 (2005); Pierce, R. C., et al., "The mesolimbic dopamine system: The final common pathway for the reinforcing effect of drugs of abuse?" *Neurosci Biobehav Rev* 30:215-238 (2006). Brain imaging studies have extended these observations to humans. Drevets, W. C., et al., "Amphetamine-induced dopamine release in human ventral striatum correlates with euphoria," *Biol Psychiatry* 49:81-96 (2001); Brody A. L., et al., "Smoking-induced ventral striatum dopamine release," *Am J Psychiatry* 161:1211-1218 (2004). The release of dopamine from these projections is thought to play an important role in mediating drug reward, reinforcement and in the induction of compulsive addictive behaviour. Although dopamine is involved in the predisposition and in the initial stages of the development of drug addiction, this condition, once established, is associated with long-lasting changes related to the chronic exposure to the drugs themselves.

These changes are collectively indicated as "neuroadaptive" and are thought to be the substrate of behavioural sensitization, a long-lasting increase in the sensitivity to the behavioural stimulant properties of drugs and of changes in the baseline of hedonic state (hedonic allostasis). Berridge K. C., et at, "What is the role of dopamine in reward: Hedonic impact, reward learning, or incentive salience?" Brain Res Rev 28:309-369 (1998); Koob, G. F., et al., "Neurobiological mechanisms for opponent motivational processes in addiction," *Philos Trans R Soc. Lond B Biol Sci.* 363:3113-3123 (2008). Neuroadaptations occurs also at the level of the dopamine system, where a relative reduction in the basal level of activity of dopamine transmission in ventral striatal areas and a reduction in dopamine D2-receptor levels has been documented. Volkow, N. D., et al., "Dopamine in drug abuse and addiction: results from imaging studies and treatment implications," *Mol Psychiatry* 9:557-569 (2004); Volkow, N. D., et al., "Dopamine in drug abuse and addiction: results from imaging studies and treatment implications," *Arch Neurol* 64:1575-1579 (2007); Fehr, C. et al., "Association of low striatal dopamine d2 receptor availability with nicotine dependence similar to that seen with other drugs of abuse," *Am Psychiatry* 165:507-514 (2008).

The most common mechanism through which drugs of abuse result in dopamine neurotransmission is through modulation of VTA presynaptic γ-aminobutyric acid (GABA) activity. Lüscher, C., et al., "The mechanistic classification of addictive drugs," *PLoS Med* 3:e437 (2006). In the VTA, GABA neurons act as local inhibitory interneurons playing a tonic control on corticomesolimbic dopamine cells. Reduction in GABA neurotransmission leads to a net disinhibition of dopamine neurons and increased dopamine release in terminal areas such as the NAc and in the PFC.

A prototypical example of this mechanism is offered by opiates that following activation of μ opioid receptors located onto presynaptic GABA cells lead to a marked inhibition of GABAergic neurotransmission resulting in disinhibition of VTA dopaminergic cells. Johnson, S. W., et al., "Opioids excite dopamine neurons by hyperpolarization of local interneurons," J Neurosci 12:483-488 (1992). *Cannabis* derivatives appear to increase VIA dopamine firing rate with a similar mechanism but through selective activation of cannabinoid receptor 1 (CB1R) located on presynaptic GABA neurons. Also nicotine, increases dopamine neurotransmission but through a complex interplay of actions of nicotinic receptors on GABA and on glutamatergic inputs to dopamine neurons. Lüscher C, et al., The mechanistic classification of addictive drugs., PLoS Med. 3(11):e437 (2006). In fact, nicotine through β2-containing nAChRs decreases presynaptic GABA release leading to a prolonged disinhibition of dopamine, at the same time acting on homomeric α7-containing nAChRs, which are mainly expressed on synaptic terminals of excitatory glutamatergic afferents on dopamine neurons in the VTA, facilitating glutamate release. This effect may also contribute to nicotine-evoked dopamine release. Furthermore, recent evidence suggests that nicotine directly modulates dopamine release in the NAc. Ethanol and benzodiazepines also appear to stimulate VTA dopamine neurotransmission through inhibition of presynaptic GABA activity via modulation of specific GABA-A receptors subunits.

Psychostimulants like amphetamine derivatives and cocaine, comprise a class of addictive drugs that act directly on dopaminergic terminals by inhibiting dopamine reuptake mechanisms or by facilitating dopamine release from synapses. Through these mechanisms they increase extracellular dopamine levels in terminal areas (i.e., NAc and MPF) of the brain dopamine system. Most notably, however, dopamine terminals are also present in the VTA where D1- and D2-like receptors are expressed on dopaminergic cell bodies (autoreceptors) as well as on glutamatergic and GABAergic presynaptic neurons. Direct application of cocaine in the VIA results in a reduction or to an increase (depending on the dose) of dopamine firing rate, an effect that could be potentially mediated by D1 receptors located onto presynaptic GABA and glutamate cells, respectively. Hence presynaptic modulation of VTA DA activity may play a role also in the regulation of the addictive properties of psychostimulants. Brodie, M. S., et al., "Cocaine effects in the ventral tegmental area. Evidence for an indirect dopaminergic mechanism of action" *Naunym Schmiedebergs Arch Pharmacol* 342:660-665 (1990); Bonci, A., et al., "Increased probability of GABA release during withdrawal from morphine," *J Neurosci* 17:796-803 (1997).

Accordingly, in one embodiment the additional therapeutic agent administered in combination, concurrently or sequentially with a Glo1 inhibitor is a dopaminergic agent to treat a patient suffering from an addiction or compulsive disorder. In another embodiment, the Glo1 inhibitor is administered in combination, concurrently or sequentially with a dopamine receptor agonist to treat a patient suffering from an addiction or impulse control disorder. In another embodiment, the Glo1 inhibitor is administered in combination, concurrently or sequentially with a dopamine D1 receptor agonist (i.e., a dopamine subtype D1 receptor agonist) to treat a patient suffering from an addiction or impulse control disorder.

Exemplary dopaminergic agents suitable for administration in conjunction with Glo1 inhibitors include, for example, levodopa (also referred to as "L-dopa"), carbidopa, and dopamine receptor agonists and precursors such as bromocriptine, pergolide, pramipexole, ropinirole, cabergoline, apomorphine, lisuride, rotigotine and quinagolide, as well as fenoldopam, which is selective for dopamine receptor D1.

Suitable dosages of D1 receptor agonists for administration in conjunction with a Glo1 inhibitor may be determined by medical practitioners but may be, for example, in the range of 0.1 mg to 1,000 mg per day or biweekly, or 0.25 mg to 100 mg per day or biweekly.

VI. REGIMES OF COMBINATION TREATMENTS

In one aspect, it is contemplated that a GLO1 inhibitor therapy is used in conjunction with other treatment. Alternatively, the therapy may precede or follow the other agent treatment by intervals ranging from minutes to weeks. In embodiments where the other agents and/or a proteins or polynucleotides are administered separately, one would generally ensure that a significant period of time did not expire between the time of each delivery, such that the agent and antigenic composition would still be able to exert an advantageously combined effect on the subject. In such instances, it is contemplated that one may administer both modalities within about 12-24 h of each other or within about 6-12 h of each other. In some situations, it may be desirable to extend the time period for administration significantly, where several days (2, 3, 4, 5, 6 or 7) to several weeks (1, 2, 3, 4, 5, 6, 7 or 8) lapse between the respective administrations.

Various combinations may be employed, for example antibiotic therapy is "A" and the Glo1 inhibitor is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the compositions of certain aspects to a patient/subject will follow general protocols for the administration of such compounds, taking into account the toxicity, if any, of the composition, or other compositions described herein. It is expected that the treatment cycles would be repeated as necessary. It also is contemplated that various standard therapies, such as hydration, may be applied in combination with the described therapy.

VII. GLO1 INHIBITORS

Certain aspects provide compounds useful as GLO1 inhibitors for preventing or treating neurological diseases or disorders. The GLO1 inhibitors may be inhibitory nucleic acids, antibodies or small molecules.

In particular aspects, the GLO1 inhibitor may be a small molecule. For example, the GLO1 inhibitor may have a glutathione group, such as an S-substituted glutathione or an S-substituted glutathione prodrug, particularly S-bromobenzylglutathione cyclopentyl diester (BrBzGCp2). In certain aspects, the GLO1 inhibitor may not have a glutathione group.

Other known GLO1 inhibitor may be a 1-hydroxy-6,7-diphenylpyridin-2-one derivative, a flavonoid, a curcumin, a benzothiazole derivative, or a 4-(7-azaindole)-substituted 6-phenyl-N-hydroxypyridones, or 4,6-diphenyl-N-hydroxypyridon (Chiba 2012, which is hereby incorporated by reference). For example, the GLO1 inhibitor may be called 3d and has an $IC_{50}$ value of 11 nM. FIG. 40 shows 3d cocrystallized with GLO1 (Chiba 2012, which is hereby incorporated by reference). 3d is derived from 1-hydroxy-6,7-diphenylpyridin-2-one, which is patented as a radiation-sensitive recording material (EP0510440; EP 0510443; U.S. Pat. Nos. 5,229,254; 5,230,985; each of which is hereby incorporated by reference), a reducer of hair growth (U.S. Pat. Nos. 5,230,985; 6,060,471; WO/1999/037277; each of which is hereby incorporated by reference), and a hair cosmetic (U.S. Pat. Nos. 4,185,106; 4,552,754; 4,711,775; each of which is hereby incorporated by reference). The application of 1-hydroxy-6,7-diphenylpyridin-2-one as a hair cosmetic is based on its antimicrobial activity mediated by the ability to chelate metals ions (Lohaus 1981, which is hereby incorporated by reference). The same mode of action has been observed for 3d and its remote structural drug analogs ciclopirox-olamine and metipirox (Csonga 1996, which is hereby incorporated by reference). Because of 3d's excellent GLO1 binding and unexplored IP in regard to anxiety and depression, 3d may be a particular example of GLO1 inhibitors in certain aspects. Other non-peptidic GLO1 inhibitors also have been developed (Chiba 2012; Santel 2008; Takasawa 2008; Takasawa 2011; each of which is hereby incorporated by reference).

For example, the GLO1 inhibitors may be S-substituted glutathiones or corresponding prodrugs. The inventors have shown that the GLO1 inhibitor pBBG (i.e., S-bromobenzyl-glutathione cyclopentyl diester (BrBzGCp2)) (Vince 1971, which is hereby incorporated by reference) has anti-anxiety effects in behavioral mouse models, is non-sedating, and increases the concentration of MG in the brain (Distler 2012, which is hereby incorporated by reference). pBBG, like other GLO1 inhibitors (Vince 1971; Al-Timari 1986; Lo 1992; Hamilton 1992; Murthy 1994; More 2009; each of which is hereby incorporated by reference), is based on the GSH scaffold and has been patented for a variety of disorders (Creighton 2000; U.S. Pat. Nos. 3,984,569; 5,616,563; 5,969,174; WO/1998/009986; WO/1999/035128; each of which is hereby incorporated by reference). Numerous S-substituted glutathione GLO1 inhibitors are known, such as, for example, the reversible competitive inhibitors including: S—(N-p-chlorophenyl-N-hydroxycarbamoyl)glutathione, S—(N-p-bromophenyl-N-hydroxycarbamoyl)glutathione, S—(N-p-iodophenyl-N-hydroxycarbamoyl)glutathione, S—(N-phenyl-N-hydroxycarbamoyl)glutathione, S-p-bromobenzyl-glutathione, and S—(N-alkyl-N-hydroxycarbamoyl)glutathione (where alkyl is methyl, ethyl, n-propyl, n-butyl, n-pentyl and n-hexyl. Particularly examples are S—(N-aryl/alkyl-N-hydroxycarbamoyl)glutathiones.

Other S-substituted glutathiones or S-substituted glutathione prodrug(s) include irreversible inactivators. Irreversible inactivators of certain aspects may be compounds of the formula S—($CH_2C(O)ORO$ $C(O)CH_2X$) glutathione, wherein R is selected from the group consisting of alkylene ($C_1$-$C_{20}$), (poly)ethylene glycol ($CH_2CH_2O)_{1-20}$, (poly)ethylene amine ($CH_2CH_2N)_{1-20}$, and arylene ($C_6$-$C_{20}$), and wherein X is a halogen. According to certain aspects, irreversible inactivators may be employed as monovalent GLO1 inactivators, or alternatively, employed as bivalent inhibitors in combination with other inhibitors such as irreversible inactivators or reversible competitive inhibitors.

Particular examples of irreversible inactivators are compounds of the formula $CH_2C(O)O(CH_2)_nOC(O)CH_2X$ glutathione, wherein n is 2 through 6 and wherein X is a halogen. Particularly examples of irreversible inactivators are S-(bromoacetoxy butyl acetoxy)glutathione and S-(bromoacetoxy propyl acetoxy)glutathione. Computational docking of these compounds into the X-ray crystal structure of GLO1 indicates that the S-substituents are ideally positioned to alkylate the sulfhydryl group of Cys60 in the active site, which is located about 12 to 13 Angstroms from the sulfur atom of the bound inactivators. Other irreversible inactivators are accommodated by the GLO1 active site, especially where the S-substituent is able to assume a "bowed" conformation in the active site, allowing the haloacetyl function to be positioned near Cys60.

Exemplary irreversible inactivators may have bromoacetoxy, chloroacetoxy, acryloyl and crotonyl groups. Particular examples are irreversible inactivators having a bromoacetoxy group. For example, U.S. Pat. No. 5,616,563, which is hereby incorporated by reference, describes methods of synthesis for S—(N-hydroxycarbamoyl)glutathione derivatives including: S—(N-p-chlorophenyl-N-hydroxycarbamoyl)glutathione, S—(N-p-bromophenyl-N-hydroxycarbamoyl)glutathione, S—(N-p-iodophenyl-N-hydroxycarbamoyl)glutathione, S—(N-phenyl-N-hydroxycarbamoyl)glutathione. Moreover, the synthesis of the S—(N-aryl/alkyl-N-hydroxycarbamoyl)glutathiones is described by Kalsi, et al, *J. Med. Chem.* 2000, 43, 3981-3986, which is hereby incorporated by reference.

As used herein, the term "S-substituted glutathione prodrug" refers to any [glycyl, glutamyl] dialkyl, diaryl or diarylalkyl ester or [glycyl] or [glutamyl] mono-alkyl, mono-aryl or mono-arylalkyl esters of an S-substituted glutathione. Exemplary embodiments include mono- or diethyl esters, mono- or di-n-propyl or mono- or diisopropyl esters, and mono- or di-cyclopentyl esters. The rates of cellular accumulation of the prodrugs described above are believed to increase with increasing hydrophobicity of the ester functions, as accumulation involves simple passive diffusion across the cell membrane (Kavarana 1999).

According to certain aspects, any GLO1 inhibitors (for example as described in U.S. Pat. No. 7,700,560, which is hereby incorporated by reference) may be linked together to increase binding affinity for the enzyme over the monovalent form of the inhibitor. Particularly example may be the linking of a relatively high affinity reversible competitive inhibitor, such as CHG, to a lower affinity irreversible inactivator, such as S-(bromoacetoxy butyl acetoxy)glutathione and S-(bromoacetoxy propyl acetoxy)glutathione.

While any S-substituted glutathione may be employed according to certain aspects, one skilled in the art understands that the hydrophobicity of the S-substituent correlates with a higher affinity for the human GLO1 active site. Moreover, the S—(N-aryl-N-hydroxycarbamoyl)-glutathione derivatives bind especially tightly to the active site of GLO1, as these compounds mimic the stereoelectronic features of the tightly bound transition state formed along the reaction coordinate of the enzyme during normal catalysis. In certain embodiments, one or more of the GLO1 inhibitors discussed herein may not be used, or may be excluded, in methods or compositions.

In other aspects, GLO1 inhibitors may be inhibitory nucleic acids. Examples of an inhibitory nucleic acid include but are not limited to siRNA (small interfering RNA), short hairpin RNA (shRNA), double-stranded RNA, an antisense oligonucleotide, a ribozyme and a nucleic acid encoding thereof. An inhibitory nucleic acid may inhibit the transcription of a gene or prevent the translation of a gene transcript in a cell. An inhibitory nucleic acid may be from 16 to 1000 nucleotides long, and in certain embodiments from 18 to 100 nucleotides long. In certain embodiments, the inhibitory nucleic acid is an isolated nucleic acid that binds or hybridizes to a GLO1 nucleotide sequence and inhibits the expression of a gene that encodes GLO1.

In some embodiments, GLO1 inhibitors may be antibodies, such as a monoclonal antibody or a polyclonal antibody. In further embodiments, the antibody is selected from the group consisting of a chimeric antibody, an affinity matured antibody, a humanized antibody, and a human antibody. In some embodiments, the antibody is an antibody fragment. In some embodiments, the antibody is a Fab, Fab', Fab'-SH, F(ab')$_2$, or scFv.

In one embodiment, the antibody is a chimeric antibody, for example, an antibody comprising antigen binding sequences from a non-human donor grafted to a heterologous non-human, human or humanized sequence (e.g., framework and/or constant domain sequences). In one embodiment, the non-human donor is a mouse. In one embodiment, an antigen binding sequence is synthetic, e.g., obtained by mutagenesis (e.g., phage display screening, etc.). In one embodiment, a chimeric antibody may have murine V regions and human C region. In one embodiment, the murine light chain V region is fused to a human kappa light chain or a human IgG1 C region.

Examples of binding include, without limitation: (i) the Fab fragment, consisting of VL, VH, CL and CH1 domains; (ii) the "Fd" fragment consisting of the VH and CH1 domains; (iii) the "Fv" fragment consisting of the VL and VH domains of a single antibody; (iv) the "dAb" fragment, which consists of a VH domain; (v) isolated CDR regions; (vi) F(ab')2 fragments, a bivalent fragment comprising two linked Fab fragments; (vii) single chain Fv molecules ("scFv"), wherein a VH domain and a VL domain are linked by a peptide linker which allows the two domains to associate to form a binding domain; (viii) bi-specific single chain Fv dimers (see U.S. Pat. No. 5,091,513, which is hereby incorporated by reference) and (ix) diabodies, multivalent or multispecific fragments constructed by gene fusion (US Patent Pub. 2005/0214860, which is hereby incorporated by reference). Fv, scFv or diabody molecules may be stabilized by the incorporation of disulphide bridges linking the VH and VL domains. Minibodies comprising a scFv joined to a CH3 domain may also be made (Hu et al, 1996, which is hereby incorporated by reference).

VIII. PHARMACEUTICAL FORMULATIONS AND MODES OF ADMINISTRATION

Pharmaceutical compositions in accordance with certain embodiments comprise an effective amount of one or more GLO1 inhibitors or additional active ingredient dissolved or dispersed in a pharmaceutically acceptable carrier.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent.

The pharmaceutical composition can be introduced to a subject by any method known to those of ordinary skill in the art. Examples may include, but not be limited to administration intravenously, intradermally, intrathecally, intraarterially, intraperitoneally, intramuscularly, subcutaneously; orally, intrarectally, mucosally (intranasal, intravaginal, etc.), topically (e.g. transdermally), locally, via inhalation (e.g., aerosol inhalation), via injection, via infusion, via continuous infusion, via localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The pharmaceutical composition may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may include isotonic agents, such as, for example, sugars, sodium chloride or combinations thereof.

The GLO1 inhibitors described herein can be formulated for parenteral administration, e.g., formulated for injection via the intravenous, intramuscular, sub-cutaneous, or even intraperitoneal routes. The preparation of an aqueous composition that contains GLO1 inhibitors will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified. In addition to the compounds formulated for parenteral administration, other pharmaceutically acceptable forms include, e.g., aerosolizable, inhalable, or instillable formulations; tablets or other solids for oral administration; time release capsules; creams; lotions; mouthwashes; and the like. The preparation of such formulations will be known to those of skill in the art in light of the present disclosure.

The pharmaceutical forms suitable for injectable use may include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi. In certain embodiments the active ingredient is combined with a liquid for intravenous administration.

The carrier also can be a solvent or dispersion medium containing, e.g., water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it may include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in the required amount in the appropriate solvent with various of the other ingredients enumerated above, as required, followed by filtered sterilization. Dispersions may be prepared by incorporating the various sterilized active ingredients into a sterile vehicle that contains the basic dispersion medium and the required other ingredients from those enumerated above. In the case of sterile powders for the preparation of sterile injectable solutions, methods of preparation are, e.g., vacuum-drying and freeze-drying techniques, which yield a powder of the active ingredient, plus any additional desired ingredient from a previously sterile-filtered solution thereof.

The actual dosage amount of a composition in accordance with certain embodiments administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a particular dosage and/or an effective amount may vary according to the response of the subject. The practitioner responsible for administration will, in any event, determine the concentration of active ingredient(s) in a composition and appropriate dose(s) for the individual subject.

Some variation in dosage will necessarily occur depending on the condition of the subject. The person responsible for administration will, in any event, determine the appropriate dose for the individual subject. An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the effects desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

Typically, for a human adult (weighing approximately 70 kilograms), from about 0.1 mg to about 3000 mg (including all values and ranges there between), or from about 5 mg to about 1000 mg (including all values and ranges there between), or from about 10 mg to about 100 mg (including all values and ranges there between), of a compound are administered. It is understood that these dosage ranges are by way of example only, and that administration can be adjusted depending on the factors known to the skilled artisan.

IX. DEFINITIONS

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

As used herein, the term "IC$_{50}$" refers to an inhibitory dose which is 50% of the maximum response obtained.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002).

"Prevention" or "preventing" includes: (1) inhibiting the onset of a neurological disease, disorder, or condition in a subject or patient which may be at risk and/or predisposed to the disease, disorder or condition but does not yet experience or display any or all of the pathology or symptomatology of such, and/or (2) slowing the onset of the pathology or symptomatology of a neurological disease, disorder, condition in a subject or patient which may be at risk and/or predisposed to the neurological disease, disorder, condition but does not yet experience or display any or all it the pathology or symptomatology.

"Prodrug" means a compound that is convertible in vivo metabolically into an inhibitor according to embodiments discussed herein. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

"Therapeutically effective amount" or "pharmaceutically effective amount" means that amount which, when administered to a subject or patient for treating the neurological disease or disorder, is sufficient to effect such treatment.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of a nucleic acid that inhibits GLO1 for the purposes of minimizing the symptoms of a neurological disease or disorder. "Treatment" or "treating" includes (1) inhibiting neurological disease or disorder in a subject or patient experiencing or displaying the pathology or symptomatology of the neurological disease, disorder, or condition (e.g., arresting further development of the pathology and/or symptomatology), (2) ameliorating the neurological disease, disorder or condition in a subject or patient that is experiencing or displaying the pathology or symptomatology of the disease (e.g., reversing the pathology and/or symptomatology), and/or (3) effecting any measurable decrease in the disease, disorder or condition in a subject or patient that is experiencing or displaying the relevant pathology or symptomatology.

As used herein, the term "water soluble" means that the compound dissolves in water at least to the extent of 0.010 mole/liter or is classified as soluble according to literature precedence.

As used herein, the term "mood disorder" refers to a group of diagnoses in the Diagnostic and Statistical Manual of Mental Disorders (DSM IV TR) classification system where a disturbance in the person's mood is hypothesized to be the main underlying feature. The classification is known as mood (affective) disorders in ICD 10. Examples of mood disorders include depression or bipolar disorders.

As used herein, the term "depression" refers to a mental disorder typically characterized by a lasting sad mood and/or lost of interest or pleasure in most activities. Examples of depression disorders which may be treated using an effective amount of a named compound or pharmaceutically acceptable salt thereof include, but are not limited to: major depressive disorder also known as major depression, unipolar disorder, or clinical depression; major depressive episode; atypical depression; depression (mood); melancholic depression; psychotic depression; and postpartum depression.

As used herein, the term "anxiety" refers to an anxiety disorder. Examples of anxiety disorders which may be treated using an effective amount of a named compound or pharmaceutically acceptable salt thereof include, but are not limited to: panic attack; agoraphobia; acute stress disorder; specific phobia; panic disorder; psychoactive substance anxiety disorder; organic anxiety disorder; obsessive-compulsive anxiety disorder; posttraumatic stress disorder; generalized anxiety disorder; and anxiety disorder NOS.

As used herein, the term "sleep disorder" refers to a disruptive pattern of sleep arising from many causes. Examples of sleep disorders which may be treated using an effective amount of a named compound or pharmaceutically acceptable salt thereof include, but are not limited to: insomnia (e.g., transient, short-term, and chronic), delayed sleep phase syndrome, hypnotic-dependent sleep disorder, and stimulant-dependent sleep disorder; disorders associated with difficulties in staying awake such as sleep apnea, narcolepsy, restless leg syndrome, obstructive sleep apnea, central sleep apnea, idiopathic hypersomnia, respiratory muscle weakness-associated sleep disorder; disorders associated with difficulties in adhering to a regular sleep schedule such as sleep state misperception, shift work sleep disorder, chronic time zone change syndrome, and irregular sleep-wake syndrome; disorders associated with abnormal behaviors such as sleep terror disorder (e.g., parasomnia) and sleepwalking (e.g., somnambulism); and other disorders such as sleep bruxism, fibromyalgia, and nightmares.

As used herein, the term "epilepsy" refers to a disorder of brain function characterized by recurrent unprovoked seizures.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

X. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of certain embodiments, are provided as an example, and are not intended as limitations on the scope of the invention. Changes therein and other uses which are encompassed within the spirit of the invention as defined by the scope of the claims will occur to those skilled in the art.

Example 1

Glo1 Copy Number Regulates Glo1 Expression and Anxiety-Like Behavior

A/J Mice Segregate a CNV Including Glo1

Previous work identified a CNV in mice that caused a duplication of four genes including Glo1 and was positively correlated with Glo1 expression and anxiety-like behavior (Williams 2009). A previous survey of CNVs across the mouse genome suggested different Glo1 copy numbers among A/J mice (Egan 2007). Therefore, the inventors investigated whether A/J mice segregated the Glo1 CNV and whether this affected Glo1 expression and anxiety-like behavior. In contrast to previous studies of the Glo1 CNV, the present experiment investigated the effect of the CNV on a near-isogenic background.

The inventors obtained 50 A/J mice from Jackson Laboratories (JAX) and used quantitative real-time PCR (qPCR) to measure Glo1 copy number relative to C57Bl/6J (B6) mice, which do not carry the duplication. qPCR results revealed Glo1 copy numbers ranging from 2.17 to 4.46 (Table 1). In a pilot study of the Glo1 copy number assay, DBA/2J (D2) mice, which carry the Glo1 duplication, showed an average qPCR value of 2.03 (average minimum, 1.8; average maximum, 2.3). The inventors concluded that the qPCR values were accurate to approximately ±0.25 copies. The inventors used this criterion to assign whole and half Glo1 copy numbers to each animal. For instance, mice with qPCR values between 1.75 and 2.25 were classified as having 2 copies, while those with values between 2.25 and 2.75 were classified as having 2.5 copies. Using these criteria, A/J mice from JAX were classified as having 2-4.5 copies of Glo1 (Table 1).

TABLE 1

Glo1 copy number in A/J mice obtained from JAX (Glo1 copy number was measured by qPCR, and copy numbers were assigned based on the following criteria: 2 copies, ≤2.25; 2.5 copies, 2.26-2.75; 3 copies, ≥2.76.)

| Animal ID | qPCR Results | Initial copy number assignment | Revised copy number assignment |
|---|---|---|---|
| 24426 | 3.08 | 3 | 3 |
| 24427 | 3.14 | 3 | 3 |
| 24428 | 2.88 | 3 | 3 |
| 24429 | 3.04 | 3 | 3 |
| 24430 | 3.05 | 3 | 3 |
| 24431 | 3.03 | 3 | 3 |
| 24432 | 3.40 | 3.5 | 3 |
| 24433 | 3.50 | 3.5 | 3 |
| 24434 | 3.65 | 3.5 | 3 |
| 24435 | 3.01 | 3 | 3 |
| 24436 | 2.70 | 2.5 | 2.5 |
| 24437 | 3.07 | 3 | 3 |
| 24438 | 3.17 | 3 | 3 |
| 24439 | 3.33 | 3.5 | 3 |
| 24440 | 2.86 | 3 | 3 |
| 24441 | 3.66 | 3.5 | 3 |
| 24442 | 3.59 | 3.5 | 3 |
| 24443 | 3.47 | 3.5 | 3 |
| 24444 | 3.14 | 3 | 3 |
| 24445 | 3.02 | 3 | 3 |
| 24446 | 2.63 | 2.5 | 2.5 |
| 24447 | 3.32 | 3.5 | 3 |
| 24448 | 2.81 | 3 | 3 |
| 24449 | 3.83 | 4 | 3 |
| 24450 | 4.46 | 4.5 | 3 |
| 24451 | 3.51 | 3.5 | 3 |
| 24452 | 3.74 | 3.5 | 3 |
| 24453 | 2.89 | 3 | 3 |
| 24454 | 2.77 | 3 | 3 |
| 24455 | 2.69 | 2.5 | 2.5 |
| 24456 | 2.43 | 2.5 | 2.5 |
| 24457 | 3.11 | 3 | 3 |
| 24458 | 3.31 | 3.5 | 3 |
| 24459 | 3.01 | 3 | 3 |
| 24460 | 2.62 | 2.5 | 2.5 |
| 24461 | 3.32 | 3.5 | 3 |
| 24462 | 3.22 | 3 | 3 |
| 24463 | 2.17 | 2 | 3 |
| 24464 | 2.88 | 3 | 3 |
| 24465 | 3.02 | 3 | 3 |
| 24466 | 2.95 | 3 | 3 |
| 24467 | 3.36 | 3.5 | 3 |
| 24468 | 2.90 | 3 | 3 |
| 24469 | 3.15 | 3 | 3 |
| 24470 | 2.80 | 3 | 3 |

TABLE 1-continued

Glo1 copy number in A/J mice obtained from JAX (Glo1 copy number was measured by qPCR, and copy numbers were assigned based on the following criteria: 2 copies, ≤2.25; 2.5 copies, 2.26-2.75; 3 copies, ≥2.76.)

| Animal ID | qPCR Results | Initial copy number assignment | Revised copy number assignment |
|---|---|---|---|
| 24471 | 2.68 | 2.5 | 2.5 |
| 24472 | 2.89 | 3 | 3 |
| 24473 | 2.70 | 2.5 | 2.5 |
| 24474 | 3.42 | 3.5 | 3 |
| 24475 | 2.71 | 2.5 | 2.5 |

Figures 1A, 1B, 1C:
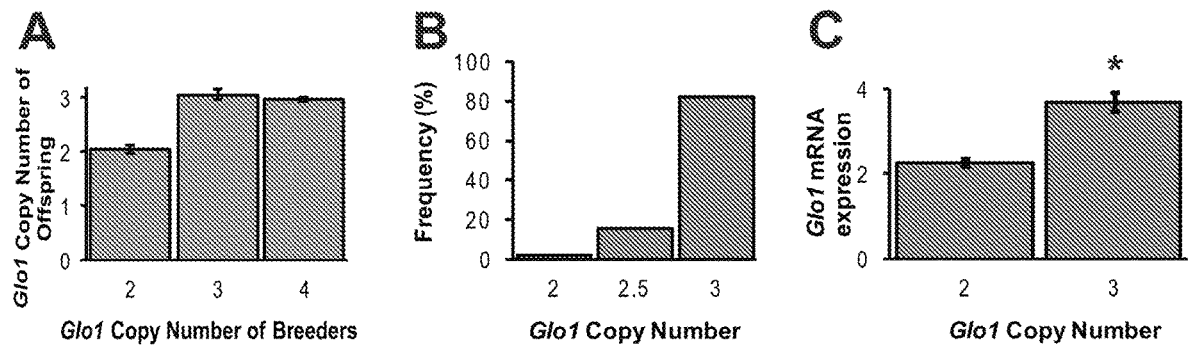
FIGS. 1A-1C: A/J mice segregate a Glo1 copy number variant that regulates Glo1 expression.

Next, the inventors investigated whether the different copy numbers bred true by forming breeder pairs homozygous for whole Glo1 copy numbers (2, 3, and 4). Because only one A/J mouse obtained from JAX had 2 copies of Glo1, the inventors used an intermediate breeding step. The mouse with 2 copies of Glo1 was bred with a mouse with 2.5 copies, and the resulting 2-copy offspring formed a homozygous breeder pair. Breeders homozygous for 2 copies produced offspring with 2 copies of Glo1, and those homozygous for 3 copies produced offspring with 3 copies of Glo1 (FIG. 1A). However, those with 4 copies also produced offspring with 3 copies of Glo1 (FIG. 1A), suggesting that qPCR values above 3.25 were spurious and that there was no 4-copy Glo1 allele. Based on these data, the inventors conclude that A/J mice from JAX segregate a Glo1 CNV with homozygotes having 2 and 3 copies and heterozygotes having 2.5 copies (Table 1). The allelic frequencies were 0.1 for 2 copies and 0.9 for 3 copies (FIG. 1B).

The inventors then used qPCR to measure Glo1 mRNA expression in the brains of mice homozygous for 2 and 3 copies of Glo1. Similar to the inventors' previous findings (Williams 2009), increased Glo1 copy number was positively correlated with increased Glo1 expression (FIG. 1C).

Figures 2A, 2B:
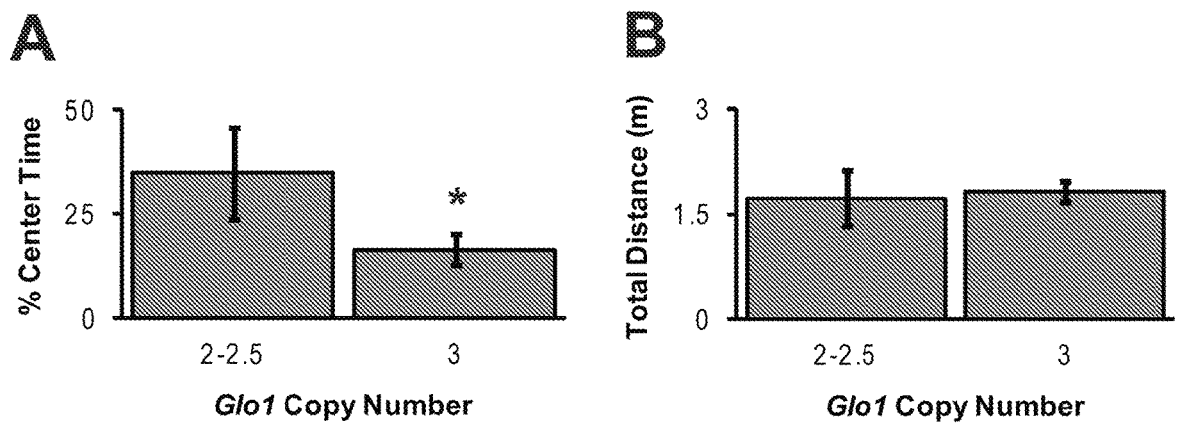
FIGS. 2A-2B: Glo1 copy number regulates anxiety-like behavior in A/J mice. A/J mice obtained from JAX were tested in the OF. Mice with 2 and 2.5 copies of Glo1 were combined into a single group, because there was only one animal with 2 copies of Glo1.

Next, the inventors used the OF test to assess anxiety-like behavior in A/J mice obtained from JAX. Mice with high Glo1 copy numbers spent less time in the center of the OF compared to mice with low Glo1 copy numbers (FIG. 2A) and did not differ in total distance traveled (FIG. 2B). This suggests that Glo1 increases anxiety-like behavior in A/J mice without changing locomotor activity. However, when this experiment was repeated in mice homozygously bred for 2 and 3 copies of Glo1, the behavioral results were inconclusive (data not shown). Specifically, numerous mice with high and low copies of Glo1 displayed low levels of locomotion and few transitions between the center and periphery, which are characteristic behaviors of A/J mice (Milner 2008). Accordingly, their center time in the OF was confounded by their low locomotion, making the data difficult to interpret. Importantly, these results demonstrate that A/J mice are suboptimal for investigating behaviors that rely on locomotor activity.

Based on these data, the inventors conclude that a Glo1 CNV segregates among A/J mice and regulates Glo1 expression. Although there was some evidence suggesting that increased copies of Glo1 increased anxiety-like behavior in A/J mice, the data were inconclusive. This highlights the need for additional studies of Glo1's effect on anxiety using different genetic backgrounds.

Generation of BAC Transgenic Mice

In order to investigate GLO1's role in anxiety and overcome limitations of previous experiments, the inventors generated mice with a transgenic bacterial artificial chromosome (BAC) containing the Glo1 gene and its cis-regulatory elements. BAC transgenic (Tg) mice are widely used in neuroscience research (Heintz 2001). Traditional transgenes are susceptible to positional effects: their expression can be affected by insertion site, resulting in variegated, ectopic, uncontrolled, or silenced expression (Giraldo 2003). BACs, on the other hand, are large enough to contain the cis-regulatory elements necessary for accurate transgene expression (Yang 2005). This partially protects BACs from positional effects, allowing for copy number-dependent transgene expression (Heintz 2001; Yang 2005; Chandler 2007). Nevertheless, multiple lines of Tg mice should be tested in order to establish the transgene's true effect and to control for remaining positional effects.

The use of BAC Tg mice for investigating Glo1's effect on anxiety had several advantages over previous studies. First, Glo1 was expressed under its endogenous promoter elements, which accurately reflected its physiological effects. This was superior to studies using viral vectors, which overexpressed Glo1 in only one brain region during adulthood (Hovatta 2005). Second, the inventors ablated the transcriptional start sites of the genes in the BAC flanking Glo1 by inserting ampicillin and kanamycin cassettes into the first exons of each gene, respectively (FIG. 3A). Therefore, BAC Tg mice overexpressed only Glo1. This overcame limitations of previous genetic studies investigating the CNV, which could not distinguish the effects of Glo1 from those of the three other genes in the duplicated region (Williams 2009). Third, BAC Tg mice allowed for investigating Glo1's effect on an isogenic background, in contrast to previous genetic studies, which could only investigate a correlation between Glo1 and anxiety-like behavior (Kromer 2004; Williams 2009). Finally, the inventors generated BAC transgenic mice in strains optimal for behavioral research. This overcame the limitations of using A/J mice, whose low level of locomotor activity interfered with the interpretation of anxiety-like behavior.

The inventors generated three lines of BAC Tg mice on a B6 background. The inventors measured BAC copy number in each line using qPCR: Tg lines had 2, 8, and 10 copies of the BAC (FIG. 3B). Tg animals were fertile, healthy, and did not display any grossly discernible physical or behavioral abnormalities (Table 2). The inventors also measured the proportion of Tg mice produced from each line. The expected proportion was 0.5; deviation from the expected rate was assessed by a Chi-square test. Although the Tg proportion deviated from the expectation in some lines, Tg proportion was not at all correlated with BAC copy number. Therefore, the inventors concluded that Glo1 overexpression did not decrease fitness. The decreased Tg proportion in some lines was more likely due to integration effects rather than an effect of Glo1 copy number. Wild-type (WT) and Tg mice were scored for body position, neurological reflexes (righting, toe pinch, ear twitch, whisker orienting, eye blink, and whisker placing reflexes), vision (visual placing response), and motor coordination (using the balance beam test). WT and Tg mice did not significantly differ in any of these parameters, indicating that Tg mice did not have deficits that would interfere with the interpretation of behavioral tests of anxiety.

Gene Expression in Tg Mice

TABLE 2

General health and behaviors of wild-type and transgenic mice

|  | Line | BAC Copy Number | Proportion of Tg Offspring | Tg Proportion higher or lower vs. expected | Body Position | Righting reflex | Toe pinch reflex | Ear twitch reflex | Whisker placing response | Whisker orienting reflex | Eye blink reflex | Visual placing response[†] | Balance beam |
|---|---|---|---|---|---|---|---|---|---|---|---|---|---|
| B6 | WT | 0 | | | 6 | 6/6 | 6/6 | 6/6 | 6/6 | 6/6 | 6/6 | 6/6 | 0.333 |
| | Line 1 | 2 | 0.398* | Lower | 6 | 3/3 | 3/3 | 3/3 | 3/3 | 3/3 | 3/3 | 3/3 | 0.333 |
| | Line 2 | 8 | 0.458 | — | 6 | 3/3 | 2/3 | 3/3 | 3/3 | 3/3 | 3/3 | 3/3 | 0.333 |
| | Line 3 | 10 | 0.363* | Lower | 6 | 4/4 | 4/4 | 4/4 | 4/4 | 4/4 | 4/4 | 4/4 | 0.25 |
| FVB | WT | 0 | | | 6 | 6/6 | 6/6 | 6/6 | 6/6 | 6/6 | 6/6 | | 0.333 |
| | Line 1 | 2 | 0.418* | Lower | | | | | | | | | |
| | Line 2 | 7 | 0.500 | — | 6 | 4/4 | 4/4 | 4/4 | 4/4 | 4/4 | 4/4 | | 0.5 |
| | Line 3 | 28 | 0.636* | Higher | 6 | 1/1 | 1/1 | 1/1 | 1/1 | 1/1 | 1/1 | | 0 |
| | Line 4 | 35 | 0.356* | Lower | 6 | 2/2 | 2/2 | 2/2 | 2/2 | 2/2 | 2/2 | | 0 |
| | Line 5 | 50 | 0.478 | — | 6 | 2/2 | 2/2 | 2/2 | 2/2 | 2/2 | 2/2 | | 0 |

The proportion of Tg mice produced from each line was measured. The expected proportion was 0.5; deviation from the expected rate was assessed by a Chi-square test. Tg proportions that significantly differed from expected are indicated by an asterisk (*). All together, 4 lines had lower, 1 line had higher, and 3 lines had the expected Tg proportion. WT and Tg mice from B6 and FVB lines were tested for body position, neurological reflexes, vision, and motor coordination. Body position was scored on a scale of 1-8 (223) and is reported as mean. Presence (1) or absence (0) of reflexes was measured; data are reported as fraction of mice with the reflex present. The balance beam test was used to assess motor coordination; data are reported as mean footslips.
[†]The visual placing reflex was not measured in FVB mice, because they are homozygous for the $Pde6b^{rd1}$ allele, which results in early onset retinal degeneration (http://jaxmice.jax.org/strain/001800.html).

In order to investigate the relationship between Glo1 copy number and expression, the inventors measured Glo1 mRNA using qPCR. Tg mice showed a copy number-dependent increase in Glo1 mRNA in the brain (FIG. 4A), including the hippocampus and amygdala (FIGS. 4B-C), as well as peripheral tissues (FIGS. 4D-F). Similarly, Tg mice displayed a copy number-dependent increase in GLO1 protein in the brain as measured by immunoblot (FIGS. 4G-H). Thus, the BAC dose-dependently increased Glo1 mRNA and protein levels.

Next, the inventors used a microarray to investigate differential gene expression in the brains of WT and Tg mice from B6 line 3. Importantly, the inventors confirmed that Tg mice did not overexpress the ablated genes in the BAC, Dnahc8 and Btbd9 (Table 3). This indicates that Tg mice should suitably model Glo1's effect on anxiety without the confounding effect of other genes in the CNV.

Anxiety-Like Behavior in Tg Mice

The inventors used male Tg mice to investigate the effect of Glo1 overexpression on anxiety-like behavior in the OF test, which was sensitive to differential Glo1 expression in previous studies (Hovatta 2005; Williams 2005).

Tg mice displayed a significant, copy number-dependent decrease in center time compared to WT mice (FIG. 5A), reflecting increased anxiety-like behavior (Bourin 2007). WT and Tg mice did not significantly differ in total distance traveled during the test (FIG. 5B), ruling out a potential confound in the interpretation of center time differences (Bouwknecht 2008). These data provide direct evidence that Glo1 increases anxiety-like behavior.

Generation and Characterization of FVB BAC Tg Mice

Because previous studies of GLO1's role in anxiety-like behavior have yielded conflicting results (Hovatta 2005; Kromer 2005; Williams 2009), it was suggested that GLO1's effect could be mouse strain-specific (Thornalley 2006). Therefore, the inventors generated five additional lines of Tg mice on a FVB/NJ (FVB) background to assess the generalizability of GLO1's anxiogenic effect. FVB Tg mice showed increased Glo1 copy number by qPCR with 2, 7, 28, 36, and 49 copies (FIG. 6A). Compared to WT mice, FVB Tg mice had a copy-number dependent increase in Glo1 mRNA expression in the brain (FIG. 6B). In the OF test, FVB Tg mice displayed decreased center time compared to WT mice (FIG. 6C). This indicates an increase in anxiety-like behavior. However, there was a significant effect of genotype on locomotor activity (FIG. 6D), a potential confound in the interpretation of center time differences. Specifically, decreased locomotor activity can con-

TABLE 3

Microarray data of brain mRNA expression in wild-type and transgenic mice

| Probe set ID | Gene symbol | mRNA accession | Genomic location | Fold change (Tg v. WT) | q-value | Validated by qPCR in Tg line 3? | Validated by qPCR in all Tg lines? |
|---|---|---|---|---|---|---|---|
| 10536444 | Foxp2 | NM_053242 | chr6: 15135506-15391977 | 0.64 | 0.0029* | Yes | No |
| 10449644 | Glo1 | NM_025374 | chr17: 30729807-30749604 | 2.81 | 0.0029* | Yes | Yes |
| 10543145 | Thsd7a | NM_001164805 | chr6: 12261608-12699253 | 0.63 | 0.0029* | Yes | No |
| 10471675 | Glo1 | NM_025374 | chr17: 30729807-30749604 | 2.85 | 0.0099* | Yes | Yes |
| 10534407 | Phf14 | NM_029404 | chr6: 11875881-12031198 | 0.53 | 0.022* | Yes | No |
| 10543134 | Ndufa4 | NM_010886 | chr6: 11850373-11857446 | 0.58 | 0.027* | Yes | No |
| 10449631 | Btbd9 | NM_027060 | chr17: 30352469-30713232 | 1.19 | 0.99 | | |
| 10443598 | Dnahc8 | NM_013811 | chr17: 30940008-30950175 | 1.11 | 0.99 | | |
| 10449652 | Dnahc8 | NM_013811 | chr17: 30940008-30950175 | 0.99 | — | | |

Whole-brain mRNA was purified from WT and Tg littermates from B6 line 3. P-values were converted to q-values, and q-values < 0.05 were considered statistically significant (indicated by an asterisk). Only genes that were significantly differentially expressed between WT and Tg were measured by qPCR. qPCR data for Glo1 are presented in FIG. 4. qPCR data for Foxp2, Thsd7a, Phf14, and Ndufa4 are not shown.
n = 5 WT, 5 Tg from B6 Line 3.

found the interpretation of decreased center time in the OF test (Bouwknecht 2008). Only FVB Tg line 1 had a reduction in total distance traveled, and this line did not significantly differ from WT in center time. In contrast, FVB Tg line 3 displayed an increase in total distance traveled, while the remaining FVB Tg lines did not significantly differ from WT mice. As such, it is unlikely that the difference in center time between WT and Tg mice was confounded by locomotor activity. Therefore, the inventors conclude that FVB Tg mice displayed increased anxiety-like behavior in the OF test. These results replicate the findings from B6 Tg mice and demonstrate that Glo1 increases anxiety-like behavior across multiple genetic backgrounds.

Effect of Glo1 Overexpression on Anxiety-Like Behavior in Additional Tests

In order to more thoroughly assess GLO1's role in anxiety, the inventors tested WT and Tg mice in two additional tests, the LD box test and the EPM. In the LD box test, Tg mice spent significantly less time in the light compartment compared to WT mice (Table 4). WT and Tg mice did not significantly differ in the number of transitions between the compartments, which indicates normal locomotor activity (Bourin 2003; Bouwknecht 2008). In the EPM, Tg mice made fewer entries into the open arms compared to WT mice (Table 5). WT and Tg mice did not differ in the number of total arm entries, again indicating normal locomotor activity. Together, these behavioral data corroborate findings from the OF test and demonstrate that Glo1 overexpression increases anxiety-like behavior.

TABLE 4

Glo1 overexpression increases anxiety-like behavior in the light-dark box test

| Genotype | n | % Time in Light | P-value |
|---|---|---|---|
| B6 WT | 10 | 40.5 ± 3.3 | 0.028 |
| B6 Tg | 12 | 31.6 ± 2.1 | |
| FVB WT | 11 | 37.5 ± 4.3 | 0.041 |
| FVB Tg | 10 | 26 ± 2.8 | |

TABLE 5

Glo1 overexpression increases anxiety-like behavior in the elevated plus maze (WT and Tg littermates from FVB line 4 were tested in the EPM. Tg mice made significantly fewer entries into the open arms compared to WT mice, indicating increased anxiety-like behavior. WT and Tg mice did not differ in total number of arm entries. Data are mean ± SEM. P-values were determined by two-tailed t-tests.)

| Genotype | n | % Open Arm Entries | P-value | Total Entries | P-value |
|---|---|---|---|---|---|
| FVB WT | 8 | 35.2 ± 3.7 | 0.044 | 19.6 ± 1.5 | 0.20 |
| FVB Tg | 10 | 22.8 ± 4.1 | | 15.9 ± 2.2 | |

The inventors also measured fear learning in WT and Tg mice using a FC paradigm. WT and Tg mice did not significantly differ in fear learning (data not shown). This contrasts with the results from the OF, LD box, and EPM tests. While fear learning and innate anxiety share similar neural substrates (Ponder 2007; Lissek 2005), they are distinct phenotypes. Previous work in the inventors' lab also demonstrated that the Glo1 duplication did not affect fear learning in outbred CD-1 mice, which segregate the Glo1 CNV (unpublished data).

Conclusions

In BAC Tg mice, Glo1 copy number regulated Glo1 expression and anxiety-like behavior. This corroborates previous findings suggesting that a CNV underlies differential Glo1 expression and anxiety-like behavior among inbred mouse strains. Furthermore, this finding helps resolve the previous discrepancy in the literature and demonstrates that Glo1 overexpression increases anxiety-like behavior.

Example 2

Glo1 Increases Anxiety by Reducing Methylglyoxal Concentration in the Brain

MG Clearance and Concentration in Tg Mice

The inventors explored the molecular mechanism underlying GLO1's anxiogenic effect using the B6 line with the highest copy number (B6 Tg line 3). Given GLO1's known role in clearing MG (Thornalley 2003), the inventors hypothesized that GLO1 increases anxiety by regulating MG concentration. First, the inventors measured MG metabolism in WT and Tg mice using a GLO1 enzymatic activity assay. Brain tissue from Tg mice metabolized a hemithioacetal substrate, formed from MG and glutathione, more rapidly than brain tissue from WT mice (FIG. 7A). This reflects an increased capacity for clearing MG. Next, the inventors measured MG concentration in the brains of WT and Tg mice by high-performance liquid chromatography (HPLC). B6 Tg mice had an approximately 10% reduction in MG concentration in the brain compared to WT mice (FIG. 7B).

The concentration of MG measured in the brain (~5 µM, Table 6) was within the previously reported range: 1.5 to 175 µM (Hambsch 2010; Kurz 2011). Using the same detection method, the inventors found that the MG concentration in the plasma was 720 nM (±150 nM, n=3). Again, this was within the range previously reported for blood, plasma, and serum: 50 nM to 4.5 µM (Jia 2007; Wang 2008; Dhar 2009; Randella 2005; Lu 2011). Interestingly, the concentration of MG in the brain was higher than that in blood, suggesting that MG concentration in the brain could regulate anxiety-like behavior.

MG is Anxiolytic

Glo1 overexpression reduced MG concentration in the brain and increased anxiety-like behavior. Therefore, the inventors hypothesized that MG is anxiolytic and that GLO1 increases anxiety by reducing endogenous MG concentration. To test this hypothesis, the inventors administered MG intra-peritoneally (i.p.) to male WT mice. First, the inventors confirmed that MG treatment dose-dependently increased MG concentrations in the brain (FIG. 8A and Table 6). The inventors then treated mice with MG (50 mg/kg) and tested them in the OF ten minutes later. MG treatment increased center time by approximately 30% (FIG. 8B) without affecting distance traveled (FIG. 8C). This indicates that MG is anxiolytic and suggests that GLO1 could increase anxiety-like behavior by decreasing MG concentration.

TABLE 6

Methylglyoxal concentration in the brain with and without exogenous methylglyoxal administration

| Treatment | MG concentration (nmol/g tissue) | Relative MG concentration (%) | Estimated MG concentration (µM)† |
|---|---|---|---|
| Vehicle | 4.89 ± 0.43 | 100.00 | 5.13 |
| MG (50 mg/kg) | 5.66 ± 0.36 | 115.75 | 5.94 |
| MG (100 mg/kg) | 6.23 ± 0.26 | 127.40 | 6.54 |
| MG (300 mg/kg) | 7.87 ± 0.56 | 160.94 | 8.26 |

The inventors then used a three-pronged approach to establish the validity and robustness of MG's anxiolytic effect. First, the inventors performed six replication studies to independently confirm MG's anxiolytic effect in the OF test. A meta-analysis of the replication studies demonstrated that MG treatment had a large effect on anxiety-like behavior (Cohen's d=0.78; meta-analysis z-score=5.0) that was highly significant ($P<10^{-5}$) (FIG. 9 and Table 7). Second, the inventors demonstrated that MG's anxiolytic effect was not strain-specific by treating CD-1 mice with MG (50 mg/kg) and testing them in the OF. Again, MG treatment increased center time in the OF (FIG. 10A) without affecting distance traveled (FIG. 10B). Third, the inventors treated B6 mice with MG (50 mg/kg) and tested them in the LD box. MG treatment increased time spent in the light compartment (FIG. 11A) without affecting the number of transitions (FIG. 11B). This bolstered the inventors' initial finding and demonstrated that MG was anxiolytic across different behavioral tests of anxiety. Together, these results provide robust evidence that MG is acutely anxiolytic and suggest that MG levels could mediate GLO1's effect on anxiety.

TABLE 7

Meta-analysis of methylglyoxal's anxiolytic effect in the open field test (A meta-analysis was performed on a total of seven individual experiments (the first demonstration plus six replication studies) using a fixed-effect model. Total n = 181. The meta-analysis revealed that MG had a large effect on anxiety-like behavior (Cohen's d = 0.78). The result was statistically significant (P < 0.0001). There was no significant heterogeneity among the studies.)

| Meta-analysis | |
|---|---|
| Cohen's d | 0.7798 |
| 95% CI lower limit | 0.4747 |
| 95% CI upper limit | 1.0848 |
| Meta-analysis z-score | 5.0096 |
| P-value | <0.0001 |
| Heterogeneity | |
| Q | 4.0687 |
| P-value | 0.6674 |
| H | 1 |
| 95% CI lower limit | 1 |
| 95% CI upper limit | 1.8509 |
| $I^2$ | 0% |
| 95% CI lower limit | 0% |
| 95% CI upper limit | 70.81% |
| $t^2$ | 0 |
| Q-index | 0% |

Increasing MG Levels Reverses GLO1's Anxiogenic Effect

The inventors then investigated whether increasing MG concentration could reverse GLO1's anxiogenic effect. In CD-1 mice, which segregate a Glo1 CNV, the Glo1 duplication increased anxiety-like behavior (Williams 2009) (FIG. 12). Treatment with exogenous MG reduced anxiety-like behavior in mice with the Glo1 duplication (FIG. 12). These results support the inventors' hypothesis that GLO1 increases anxiety by reducing MG concentration in the brain.

MG is Anxiolytic when Acutely and Chronically Administered

The inventors performed time course experiments to further characterize MG's effects. First, the inventors administered an anxiolytic dose of MG (50 mg/kg) to separate cohorts of mice and tested them at different intervals after injection. The inventors found that MG's anxiolytic effect persisted until 20 minutes after injection and diminished thereafter (FIG. 13A), indicating a short duration of action when administered acutely.

Next, the inventors investigated MG's chronic anxiolytic effect. The inventors administered a low dose of MG (4 mg/kg) twice daily for five days and tested mice in the OF on the sixth day. Mice chronically treated with MG displayed a significant reduction in anxiety-like behavior compared to vehicle-treated mice (FIG. 13B). These data are consistent with those of a previous study, where intracerebroventricular administration of MG for six days reduced anxiety-like behavior in the EPM (Hambsch 2010). the inventors' data demonstrate that chronic MG treatment reduces anxiety-like behavior and further support the inventors' hypothesis that long-term differences in MG concentration underlie the difference in anxiety-like behavior between WT and Tg mice.

Conclusions

Tg mice had an increased capacity for clearing MG and a corresponding reduction in MG concentration. Further, administration of exogenous MG was anxiolytic. MG's acute and short-acting effects suggest that changes in MG concentration are linked to rapid behavioral effects. MG's anxiolytic effect upon chronic administration suggests that long-term differences in MG concentration between WT and Tg mice could account for their differential anxiety-like behavior.

Example 3

Glo1 Inhibition Increases Methylglyoxal Concentration and Reduces Anxiety-Like Behavior The inventors hypothesized that a reduction in GLO1 activity would have an opposite effect from Glo1 overexpression on anxiety-like behavior. To test this hypothesis, the inventors obtained S-bromobenzylglutathione cyclopentyl diester (BrBzGCp2), a previously described GLO1 inhibitor (Vince 1971; Thornalley 1996), and confirmed its ability to inhibit GLO1 enzymatic activity in vitro (FIG. 14A). Then, the inventors administered BrBzGCp2 at 30 mg/kg by i.p. injection to WT B6 mice and allowed MG levels to increase for 2 hours (Kuhla 2006) (FIG. 14B). GLO1 inhibition by BrBzGCp2 increased center time in the OF test (FIG. 14C) without changing distance traveled (FIG. 14D), suggesting that GLO1 inhibition reduced anxiety-like behavior. Similarly, CD-1 mice treated with BrBzGCp2 showed increased center time in the OF, again reflecting reduced anxiety-like behavior (FIGS. 14E-F). The inventors then investigated whether treatment with BrBzGCp2 could reverse GLO1's anxiogenic effect. CD-1 mice with the Glo1 duplication displayed increased anxiety-like behavior compared to those without the duplication (Williams 2009), and treatment with BrBzGCp2 reversed this effect (FIG. 15). Therefore, the inventors concluded that a reduction in GLO1 activity increased MG concentration, which reduced anxiety-like behavior. These results complement those from Tg mice, where Glo1 overexpression reduced MG concentration and increased anxiety-like behavior. Furthermore, this result indicates that GLO1 inhibition may be a novel therapeutic approach for the treatment of anxiety disorders.

Genetic Reduction in Glo1 Expression

Glo1 Knockout Mice are not Viable

These results indicate that Glo1 overexpression increases anxiety-like behavior and that pharmacological inhibition of GLO1 reduces anxiety-like behavior. Therefore, the inventors hypothesized that a genetic reduction in Glo1 expression would reduce anxiety-like behavior in mice.

To test this, the inventors first attempted to generate Glo1 knockout mice. The inventors obtained embryonic stem (ES) cells with gene-trapped Glo1 alleles from Texas A&M Institute for Genomic Medicine (TIGM). Gene trapping is a technique that allows a gene-trap vector, which contains a splice acceptor followed by a stop codon and polyadenylation sequence, to prematurely terminate the transcribed portion of a gene (Hansen 2008). The inventors obtained four ES cell lines from TIGM with gene-trap vectors inserted between the first and second exons of Glo1. The ES cells were injected into mouse blastocysts and implanted into pseudo-pregnant females by the Transgenic Core Facility at the University of Chicago. Unfortunately, Glo1 gene-trapped mice were not successfully generated. There were few gene-trap positive founders: only three positive males were produced from four rounds of injection with each of the four ES cell lines. The founders were poor breeders and produced no gene-trap positive offspring. Therefore, the inventors concluded that generation of Glo1 knockout mice was difficult, if not impossible, due to reduced viability even in heterozygous mice.

Characterization of Glo1 Knockdown Mice

Because the inventors were unable to generate Glo1 knockout mice, the inventors utilized mice with a transgenic siRNA targeting Glo1, termed Glo1 knockdown (KD) mice. These mice were previously reported to have reduced GLO1 enzymatic activity (Queisser 2010). The inventors used qPCR to measure Glo1 mRNA expression in the brain and peripheral tissues of KD mice. KD mice had reduced Glo1 mRNA expression in all tissues assayed, although the level of knockdown varied by tissue type. In the eye, KD mice exhibited a 70% knockdown of Glo1 expression compared to WT mice (FIG. 16A). In the liver, KD mice exhibited a 50% knockdown in Glo1 expression compared to WT mice (FIG. 16B). In the brain, however, KD mice exhibited only a 30% knockdown in Glo1 expression compared to WT mice (FIG. 16C). These data demonstrate that siRNA targeting Glo1 knocked down Glo1 expression to a variable degree in different tissues. The variability between tissues is likely due to tissue-specific properties, such as rate of RNA production and turnover. It is also possible that different tissues have different mechanisms for regulating Glo1 synthesis in the face of siRNA-mediated RNA degradation.

Next, the inventors investigated whether KD mice had altered MG handling. In the brain, KD mice had a 25% reduction in GLO1 enzymatic activity compared to WT mice (FIG. 17A), indicating a reduced capacity for clearing MG. The inventors then measured MG concentration in the brain. The inventors found no significant differences in MG concentration between KD and WT mice (FIG. 17B). This indicates that although KD mice had a slight reduction in Glo1 expression and GLO1 enzymatic activity, the residual Glo1 was sufficient to maintain normal levels of MG.

The inventors then measured anxiety-like behavior in Glo1 KD mice using the OF test. Glo1 KD mice did not significantly differ from WT mice in time spent exploring the center of the OF (FIG. 18A) or in total distance traveled (FIG. 18B), indicating no difference in anxiety-like behavior. The inventors propose that this lack of an anxiety-like phenotype resulted from an insufficient level of Glo1 knockdown. This result supports the inventors' hypothesis that Glo1 mediates anxiety-like behavior through regulating MG levels. The 25% reduction in Glo1 enzymatic activity did not change MG concentration in the brain, resulting in normal anxiety-like behavior in Glo1 KD mice.

Conclusions

Glo1 overexpression increased anxiety-like behavior, and GLO1 inhibition reduced anxiety-like behavior. However, in Glo1 KD mice, which exhibited a 25% reduction in GLO1 enzymatic activity, there was no change in MG concentration or anxiety-like behavior. This suggests that an increase in MG concentration requires a dramatic reduction in GLO1 activity.

Example 4

Methylglyoxal is an Endogenous Partial Agonist at $GABA_A$ Receptors

MG does not Exert its Anxiolytic Effect Through Inducing Cytotoxicity

The inventors next explored the molecular mechanism underlying MG's anxiolytic effect. MG is best characterized as a cytotoxic agent that induces AGEs and apoptosis, although neither process has a known mechanistic role in anxiety. Nevertheless, a previous study reported that intracerebroventricular administration of MG reduced anxiety-like behavior coincident with AGE formation (Hambsch 2010). This group utilized a high dose of MG that exceeded the anxiolytic concentration of approximately 6 μM (Table 6). Specifically, they administered 7 μmol of MG into the cerebrospinal fluid (CSF) via the third ventricle. This corresponds to a concentration of 17.5 mM throughout the CSF, assuming a CSF volume of 0.04 mL (Johanson 2008), and an average concentration of 1.6 mM throughout the brain, assuming a brain volume of 0.45 mL (www.mbl.org). Administration of this excessive dose over a prolonged time course could have induced AGEs independent of MG's anxiolytic effect. In contrast, the inventors found that a low dose of MG was anxiolytic within minutes of administration; this time course is inconsistent with AGE formation, which requires hours to days (Lo 1994). As such, the inventors considered AGE formation to be an unlikely candidate in mediating MG's effect on anxiety.

Similarly, MG's apoptotic effect is not relevant to its effect on anxiety. In vitro, MG concentrations of 100-1,000 μM induce neuronal cell death (Di Loreto 2008; Di Loreto 2004; Li 2010). On the other hand, an anxiolytic dose of MG increased the concentration of MG in the brain to approximately 6 μM (Table 6), a concentration well below that leading to neuronal apoptosis. In addition, MG requires hours to days to induce apoptosis (Di Loreto 2008), which is inconsistent with MG's acute behavioral effects. The inventors further ruled out apoptosis as the mechanism underlying MG's anxiolytic effect by using in situ TUNEL staining to quantify apoptosis in the brains of mice twenty-four hours after treatment with MG (FIG. 19). The inventors found no evidence of increased apoptosis in mice treated with an anxiolytic dose of MG (50 mg/kg). Notably, 300 mg/kg MG non-significantly increased apoptosis; however, this dose was near the lethal dose in 50% of animals ($LD_{50}$~400 mg/kg, determined experimentally) and was not relevant to anxiety. Given the disparity in time course and the lack of apoptosis in brains of mice treated with 50 mg/kg MG, the inventors conclude that MG's anxiolytic effect is independent of cytotoxicity. These results suggest that MG has a previously uncharacterized cellular function underlying its effect on anxiety.

MG has GABAergic Properties In Vivo

To gain insight into MG's mechanism of action in the brain, the inventors examined its pharmacological properties at higher doses in WT B6 mice. At 100 mg/kg, MG caused decreased locomotion in the OF (FIG. 20A). At 300 mg/kg, MG caused sedation (data not shown), hypothermia (FIG. 20B), and ataxia (FIGS. 20C-D). Specifically, on a balance beam, mice treated with 300 mg/kg MG made more footslips than vehicle-treated mice (FIG. 20C). Similarly, CD-1 mice treated with 300 mg/kg MG fell from an accelerating rotarod at slower speeds than vehicle-treated mice (FIG. 20D). This pharmacodynamic profile is similar to those of known $GABA_A$ receptor agonists, such as ethanol, barbiturates, and benzodiazepines (Carter 2009; Kumar 2009; Rudolph 2004). Therefore, the inventors hypothesized that MG is an endogenous $GABA_A$ receptor agonist.

MG Activates $GABA_A$ Receptors

To test the hypothesis that MG activates $GABA_A$ receptors, the inventors studied MG's electrophysiological effects on primary cerebellar granule neurons (CGN) using current-clamp recording to assess neuronal membrane potential ($V_m$) and voltage-clamp recording to measure ionic currents. In whole-cell current-clamp mode, extracellular application of MG rapidly depolarized CGN in a concentration-dependent manner (FIG. 21A). Initial, rapid depolarization was followed by repolarization of the $V_m$. In whole-cell voltage-clamp mode, application of MG produced inward currents at negative membrane potentials, characteristic of chloride channel activation under the inventors' recording conditions (FIG. 21B). The MG-evoked current diminished rapidly, consistent with activation and desensitization of ligand-gated ion channels. These electrophysiological effects were similar to those elicited by application of GABA (FIGS. 21A-B). Current density was concentration-dependent and similar in character to that evoked by GABA, while the relative amplitude was approximately one-third that of GABA. To establish that MG acts at $GABA_A$ receptors, responses were studied in the presence of the selective $GABA_A$ receptor antagonist SR-95531 (SR). SR inhibited >95% of the $V_m$ (FIG. 21C) and current-density changes (FIG. 21D) induced by both MG and GABA.

The inventors next established that MG's electrophysiological effects were specific to $GABA_A$ receptor activation. MG did not affect the major sodium currents (FIG. 22A) or potassium currents (FIGS. 22B, D-F) in CGN. Moreover, MG did not activate $GABA_B$ receptors (FIG. 22C), glycine receptors (FIG. 22G), or glutamate receptors (FIGS. 22H-I). Together, these results demonstrate that activation of $GABA_A$ receptors is both necessary and sufficient for MG's electrophysiological activity.

The inventors also compared the baseline electrophysiological properties of CGN cultured from WT and Tg mice. Neurons from Tg mice were more excitable, displaying a diminished potassium leak current (IKso), a depolarized $V_m$, and increased cellular input resistance (FIGS. 23A-E).

MG is a Competitive Partial Agonist at $GABA_A$ Receptors

After establishing that MG activates $GABA_A$ receptors, the inventors investigated whether MG acts competitively or non-competitively with GABA. To do this, the inventors co-applied MG and GABA to CGN at 100 µM, concentrations that saturate the $GABA_A$ receptor response, indicating that binding sites are maximally occupied. Consistent with FIG. 21B, the current elicited by 100 µM MG was approximately one-third the magnitude of that elicited by 100 µM GABA. In contrast, co-application of 100 µM MG and 100 µM GABA activated a current approximately 60% the magnitude of that elicited by 100 µM GABA alone (FIG. 24). The fraction of maximal current evoked by co-application of MG and GABA increased as the concentration of MG was reduced (FIG. 24). These findings suggest that MG is a partial agonist at $GABA_A$ receptors and acts competitively with GABA.

MG Diffuses Across the Plasma Membrane to Activate $GABA_A$ Receptors

Endogenous MG is generated intracellularly; therefore, the inventors investigated MG's intracellular effects on $GABA_A$ receptors using macropatches of plasma membrane. When applied to the intracellular face, MG elicited an inward current following a latency of approximately 40 seconds; this current was inhibited when SR was applied to the extracellular face, suggesting that MG crosses the plasma membrane by diffusion to activate $GABA_A$ receptors (FIG. 25). In contrast, GABA, which is unable to cross the plasma membrane, did not elicit a current when applied to the intracellular face of the macropatch (FIG. 25). These data suggest that endogenously produced MG accesses $GABA_A$ receptors by diffusing across the plasma membrane.

MG Activates Multiple $GABA_A$ Receptor Subtypes Across Different Neuronal Types The inventors next investigated MG's GABAergic effects in different neuronal types and at different $GABA_A$ receptor subtypes. First, the inventors demonstrated that MG's electrophysiological effects in CGN were similar in primary cultures of hippocampal neurons (FIN) (FIG. 26A), a cell type relevant to anxiety (Crestani 1999; Canteras 2010). Specifically, MG dose-dependently evoked inward currents in FIN with peak responses approximately one-third of those evoked by GABA. Co-application of 100 µM MG and 100 µM GABA activated a current approximately 60% of the magnitude elicited by 100 µM GABA alone; the proportion of the maximal current evoked by co-application increased as the concentration of MG was reduced (FIG. 26A). These data implicate MG as a partial $GABA_A$ receptor in FIN as well as CGN. More importantly, they suggest that MG activates $GABA_A$ receptors to a similar degree in different neuronal types, including those relevant to anxiety.

The inventors next investigated MG's specificity for $GABA_A$ receptor subtypes. $GABA_A$ receptors are pentamers comprised of various combinations of at least 16 possible subunits: α1-6, β1-3, γ1-3, δ, ε, θ, and π (Bollan 2003). Different subunits and subunit compositions are thought to mediate different GABAergic effects. For instance α2 subunits are thought to mediate the anxiolytic effects of benzodiazepines, while α5 subunits largely mediate their sedative effects (Rudolph 2011). Investigating MG's receptor subunit selectivity may elucidate its endogenous role in the CNS. Therefore, the inventors co-applied 10 µM MG to FIN with different subtype-selective positive modulators of GABA currents. Similar to GABA-evoked currents, MG-evoked currents were increased by co-application of diazepam, midazolam, and zolpidem (FIG. 26B). Diazepam, which acts at $GABA_A$ receptors containing α1, 2, 3, or 5 subunits, increased MG-evoked currents by approximately 60% and GABA-evoked currents by approximately 45%. Midazolam also modulates $GABA_A$ receptors containing α, 2, 3, or 5 subunits in addition to γ2 subunits. Co-application of 500 nM midazolam increased MG-evoked currents by approximately 40% and GABA-evoked currents by approximately 27%. Zolpidem selectively modulates $GABA_A$ receptors containing α1 and γ2 subunits. Co-application of 500 nM zolpidem increased MG-evoked currents by approximately 15% and GABA-evoked currents by approximately 17% (FIG. 26B). Further, CGN have a diverse receptor population containing high levels of α1, α6, β2, β3, γ2, and δ subunits (Sieghart 2002), suggesting that MG acts at receptors containing these subunits as well. Together, these data demonstrate that MG is not subtype-specific, but rather operates a broad range of $GABA_A$ receptor subtypes, similar to GABA. MG's activity at $GABA_A$ receptors with different subunit compositions across different neuronal cell types could highlight an important role for MG in mediating various GABAergic effects throughout the CNS.

Conclusions

In vivo, MG has a pharmacodynamic profile characteristic of $GABA_A$ receptor agonists, including anxiolysis, locomotor depression, hypothermia, and sedation. MG activates $GABA_A$ receptors in vitro and is a partial competitive agonist across a range of $GABA_A$ receptor subtypes and neuronal cell types. Together, these data demonstrate an important physiological role for MG as a $GABA_A$ receptor agonist.

Behavioral and Electrophysiological Effects of Pure Methylglyoxal

The behavioral experiments described above utilized a crude MG preparation obtained from Sigma-Aldrich. Crude preparations of MG have been reported to contain contaminants, such as formaldehyde and methanol (Pourmotabbed 1986; McLellen 1992). Although the exact concentrations of these contaminants in the inventors' MG preparation are unknown, they could have had biological effects in vivo and in vitro. Therefore, the inventors obtained MG free of impurities, as verified by nuclear magnetic resonance spectroscopy. The inventors investigated the effects of pure MG in vivo, including behavior in the OF test, locomotor depression, ataxia, and hypothermia. Pure MG had similar pharmacological effects as crude MG. At a low dose, pure MG was anxiolytic in the OF test (FIG. 27A), and at a high dose, it caused locomotor depression (FIG. 27B), ataxia (FIG. 27C), and hypothermia (FIG. 27D). Notably, the doses of pure MG required for sedation, locomotor depression, ataxia, and hypothermia were similar to the doses of crude MG. In contrast, pure MG elicited an anxiolytic effect at a lower dose (5 mg/kg) than crude MG (50 mg/kg, FIG. 8B). This surprising finding indicates that pure MG is more potent than crude MG at low doses but not at high doses. Possible explanations could include an effect of the impurities on MG's bioavailability or on anxiety-like behavior directly. Nevertheless, the inventors' data demonstrate that crude MG and pure MG have similar effects in vivo.

MG's electrophysiological effects described above were studied using pure MG. However, the inventors also confirmed that pure MG and crude MG had identical electrophysiological effects in CGN (FIG. 27E), including an identical dose-response curve. Together, these data confirm MG's GABAergic effects in vivo and rule out the possibility that the inventors' results were an artifact of impurities in the crude MG preparation.

Example 5

Glo1's Role in Depression

Background

The inventors have established that GLO1 mediates anxiety-like behavior by regulating endogenous levels of MG, a $GABA_A$ receptor agonist. The inventors predicted that this pathway is applicable to neurological phenotypes in addition to anxiety. Therefore, the inventors investigated the roles of MG and GLO1 in other disorders with a known GABAergic component, including depression and epilepsy. The inventors also recognized the utility of the inventors' Tg mouse model for assessing non-behavioral phenotypes associated with Glo1 overexpression. In particular, the inventors investigated metabolic phenotypes in Tg mice given the well-established association between GLO1 and diabetes.

Affective disorders are common psychiatric conditions that are divided into depressive and bipolar disorders. Depressive disorders are characterized by depressive episodes and depressed mood; bipolar disorders are characterized by manic episodes, often with depressive episodes as well (American Psychiatric Association 2000). There is strong evidence for a shared genetic vulnerability to anxiety and depression (Cerda 2010). Benton et al. found a positive correlation between GLO1 protein levels and baseline depression-like behavior as well as anxiety-like behavior across a panel of inbred mice (Benton 2011). This suggests that Glo1 contributes to the common genetic etiology of anxiety and depression.

Deficits in the GABA system are thought to contribute to depression (Luscher 2011; Hasler 2011). Depressed patients have reduced GABA levels in the plasma and cerebrospinal fluid (Petty 1981; Petty 1984; Gerner 1981) and altered expression of $GABA_A$receptor-encoding genes (Luscher 2011). Furthermore, mice heterozygous for the null allele of the γ2 $GABA_A$ receptor subunit show increased anxiety-like and depression-like behavior (Crestani 1999; Shen 2010; Earnheart 2007). Therefore, the inventors hypothesized that GLO1 regulates both anxiety and depression through modulating GABAergic tone. Accordingly, the inventors investigated the effects of Glo1 overexpression and MG administration in the tail-suspension test (TST), a mouse model of depression (O'Leary 2009). In this model, mice are suspended by their tails for several minutes, representing an inescapable stressor (O'Leary 2009). Initially, mice display escape behaviors, including running, jerking, and writhing. Eventually, mice exhibit "behavioral despair" and display immobility, the duration of which reflects depression-like behavior (O'Leary 2009). The inventors utilized the TST, because it has excellent predictive validity, and several studies have suggested that it is sensitive to genetic factors underlying depression (O'Leary 2009). Further, Benton et al. used the TST to establish a positive correlation between GLO1 and depression-like behavior (Benton 2011).

Glo1 Overexpression Increases Depression-Like Behavior

First, the inventors tested WT and Tg mice from FVB Tg line 3 in the TST. Tg mice had a longer duration of immobility than WT mice (FIG. 28A), suggesting increased depression-like behavior. The inventors hypothesized that GLO1 increased depression by reducing MG concentration, similar to its action in anxiety. To test this, the inventors treated mice with MG (50 mg/kg) or vehicle and assayed depression-like behavior in the TST ten minutes later. Surprisingly, acute MG administration did not affect the duration of immobility (FIG. 28B). This conflicts with MG's acute anxiolytic effect in the OF test and LD box test. This result could suggest that GLO1 affects depression through a different mechanism than it affects anxiety. Alternatively, MG concentration may regulate depression, but its acute administration may not adequately model the underlying mechanism. Specifically, many GABAergic mechanisms of depression include adaptive and long-term processes, such as regulation of hippocampal neurogenesis and modulation of the hypothalamic-pituitary-adrenal axis (Luscher 2011). Acute administration of MG may not be sufficient to affect these processes. Similarly, acute administration of known $GABA_A$ receptor agonists does not have antidepressant effects in the TST (Porsolt 1987; Stem 1987; Stem 1985; van der Heyden 1987; Guardiola-Lernaitre 1992; Liu 2003). Therefore, chronic administration of MG may more accurately model MG's effect on depression. Indeed, Hambsch et al. found that intracerebroventricular administration of MG for six days reduced immobility in the TST, suggesting an antidepressant effect (Hambsch 2010).

Glo1 overexpression increases both anxiety-like behavior and depression-like behavior. Given the role of GABAergic signaling in depression, it is possible that GLO1 increases depression by reducing MG concentration. Although acute administration of MG did not affect depression-like behavior in mice, further experiments are required to investigate this possibility.

Example 6

Methylglyoxal Levels Modulate Seizure Susceptibility and Severity

Background

Epileptic seizures are transient interruptions of brain function due to abnormal (e.g., excessive or synchronous) neuronal activity (Fischer 2005). Epilepsy is a neurological disorder characterized by a predisposition toward epileptic seizures (Fischer 2005). It is not a single disease, but rather a group of disorders that share seizures as a common manifestation (Noe 2011). Epilepsy is a complex trait with multiple genetic, non-genetic, and interacting causes (Mulley 2005). In the majority of patients with epilepsy, there is no known genetic cause (Rees 2010). Unfortunately, current anti-epileptic drugs (AEDs) have adverse side effects and are not effective in all patients (Brodie 2011; Perucca 2011; Rossetti 2011). Therefore, identifying novel genes and biological pathways underlying epilepsy will provide valuable insight into its pathogenesis as well as therapeutic targets.

Abundant clinical and experimental evidence has demonstrated that mutations in $GABA_A$ receptor-encoding genes perturb $GABA_A$ receptor signaling and cause epileptic seizures (Briggs 2011; Galanopoulou 2010). Furthermore, several well-established AEDs activate or potentiate $GABA_A$ receptors, including carbamazepine, phenobarbital, and valproate (Perucca 2011). Given the prominent role of $GABA_A$ receptors in epilepsy and MG's action at $GABA_A$ receptors, the inventors hypothesized that MG would protect against epileptic seizures. This would represent an endogenous pathway whereby a metabolic byproduct could influence inhibitory tone via $GABA_A$ receptors and affect downstream seizure phenotypes.

MG Treatment Reduces Seizure Severity and Duration

The inventors investigated whether MG could prevent or attenuate seizures by administering exogenous MG (50 and 200 mg/kg) to mice before seizure induction. After pre-treatment with MG, the inventors induced seizures using picrotoxin. Picrotoxin is a GABAA receptor antagonist that induces generalized convulsions in mice (Fisher 1989). Pre-treatment with MG dose-dependently attenuated generalized convulsions. Specifically, MG treatment delayed seizure onset (FIG. 29A), reduced seizure duration (FIG. 29B), and reduced the percentage of mice undergoing generalized convulsions (FIG. 29C).

Next, the inventors induced seizures using a second pharmacological agent, pilocarpine, which is a muscarinic cholinergic agonist that induces severe, continuous limbic seizures (Curia 2008). The inventors scored pilocarpine-induced seizures on a five-stage scale that reflects seizure severity (Winawer 2011). The inventors pre-treated mice with MG (50 and 200 mg/kg) and then induced seizures with 250 mg/kg pilocarpine. This dose of pilocarpine induced partial status epilepticus (stage 3 seizures) but not generalized status epilepticus. MG pre-treatment dose-dependently delayed seizure onset (FIG. 30A), reduced seizure duration (FIG. 30B), and reduced seizure stage (FIG. 30C). The inventors then investigated whether MG could stop or reduce the severity of ongoing seizures. The inventors induced seizures with pilocarpine and then administered MG (200 mg/kg) ten minutes after seizure induction. The inventors selected this time point, because control mice first reach stage 3 seizures approximately ten minutes after pilocarpine administration (FIG. 30A). The inventors found that MG treatment reduced seizure duration in mice undergoing pilocarpine-induced seizures (FIG. 30D). These results suggest that MG is an endogenous anti-seizure agent.

GLO1 Inhibition Reduces Seizure Severity

To explore the therapeutic potential of increasing endogenous levels of MG, the inventors treated mice with BrBzGCp2, which increased MG concentration in the brain by approximately 20% when administered at 30 mg/kg (FIG. 14B). Mice pre-treated with BrBzGCp2 two hours before administration of pilocarpine displayed reduced seizure durations compared to those treated with vehicle (FIG. 31). However, GLO1 inhibition did not significantly affect seizure latency or seizure stage (data not shown). These data demonstrate that increasing endogenous levels of MG reduces seizure duration. Further, they indicate that GLO1 inhibition is a potential therapeutic intervention for seizures. Other factors that increase endogenous MG, such as reduced Glo1 expression or increased metabolic load (Shinohara 1998; Brownlee 2001; Masterjohn 2011), may also affect seizure susceptibility and severity.

Differential Glo1 Overexpression Affects Seizure Susceptibility and Severity

Finally, the inventors explored whether genetic changes that affect MG concentration affect epileptic seizures. This may provide a link between the complex genetic architecture underlying epilepsy and MG, a novel mediator of seizures in mice. Specifically, the inventors focused on Glo1. The inventors hypothesized that mice with increased Glo1 expression would display increased seizure susceptibility and severity.

The inventors first utilized data from BXD recombinant inbred (RI) lines (Shifman 2006; Peirce 2004; Williams 2001), which are derived from intercrosses between B6 and D2 inbred strains. The D2 strain carries a genomic duplication of Glo1, while the B6 strain does not (Williams 2009). The inventors assessed the correlation between the Glo1 duplication and published seizure phenotypes in these lines, specifically their susceptibility to high pressure-induced seizures. In this seizure model, mice exposed to increasing pressure in a helium-oxygen atmosphere suffer from progressive convulsive seizures (McCall 1981; Mansfield 1980; Lever 1971). This model is clinically relevant, because patients with epilepsy have an increased susceptibility to seizures at high atmospheric pressure (Doherty 2007). Previous studies identified a locus on chromosome 17 associated with seizure susceptibility at high atmospheric pressure among BXD RI lines (McCall 1981; Plomin 1991). The inventors used tools at Gene Network (www.genenetwork.org) to demonstrate that the locus for seizure susceptibility co-localized with that of Glo1 expression, which the inventors previously attributed to the Glo1 duplication (FIGS. 32A-B) (Williams 2009). Indeed, BXD RI lines with the Glo1 duplication displayed a significant reduction in seizure threshold compared to those without the duplication (FIG. 32C). Further, there was a significant inverse correlation between Glo1 expression and seizure threshold (FIG. 32D). This is consistent with the inventors' hypothesis that increased Glo1 expression increases seizure susceptibility. Thus, naturally occurring differences in Glo1 expression may regulate MG concentration and seizure sensitivity in mice.

BXD RI lines are a convenient population for investigating the effects of differential Glo1 expression on seizure susceptibility. However, there are numerous genetic differences between the lines, making it impossible to establish a causal relationship with a particular variant. Furthermore, genes in linkage disequilibrium with a particular variant could contribute to the phenotype of interest, leading to spurious associations. In order to more directly test Glo1's effect on seizures, the inventors employed FVB Tg mice overexpressing Glo1. FVB Tg mice had approximately 20% less MG in the brain than WT mice (FIG. 33A). The inventors administered pilocarpine (300 mg/kg) to WT and Tg mice and measured seizure severity. Tg mice displayed a trend toward reduced seizure latency (FIG. 33B) and significantly increased seizure duration and severity compared to WT mice (FIGS. 33C-D). This demonstrates that reducing endogenous MG concentration increases seizure susceptibility. Further, it suggests that differences in Glo1 expression or activity may influence seizure phenotypes. Thus, Glo1 polymorphisms may contribute to the genetic underpinnings of epilepsy.

Conclusions

The present results demonstrate an important physiological role for MG in reducing seizure susceptibility and severity. Increasing endogenous MG by GLO1 inhibition had a similar effect and may be a useful therapeutic strategy. Finally, polymorphisms in Glo1 that regulate MG concentration may contribute to the genetic underpinnings of epilepsy.

Example 7

The Use of Glo1 Inhibitors as a Treatment for Depression

This Example focuses on GLO1's potential as an anti-depressant. An independent group found that Glo1 overexpression increased immobility on the tail-suspension test (TST; Benton et al 2011) and another group found that administration of MG decreased immobility on the TST (Hambsch et al 2010), which is a behavioral assay for anti-depressant drugs. This was surprising because the inventors' data showed that MG acts at GABA-A receptors and all other known GABA-A agonists (e.g. benzodiazepines and barbiturates) do not decrease immobility on the TST (Cryan et al 2005). Indeed, because GABA-A agonists cause locomotor-depression at higher doses, they tend to increase rather than decrease immobility in the TST.

In order to determine if the reported correlation with Glo1 was causal the inventors examined TST behavior in the inventors' Glo1 Tg mice, which are on an isogenic background, and thus provide more definitive results than the panel of inbred strains used by Benton et al (2011). As shown in the upper panel of FIG. 34, Tg mice showed greater immobility on the TST, which is opposite to the effects obtained when an antidepressant is administered. The inventors then used separate cohort of mice to examine the effects of the inventors' small molecule inhibitor of GLO1. As shown in the lower panel of FIG. 34, the GLO1 inhibitor produced antidepressant-like effects.

The inventors present preliminary data showing that GLO1 inhibitors have both anxiolytic and antidepressant effects and provide an example of the qualitatively different effects obtained via GLO1 inhibition compared to conventional $GABA_A$ agonists. Whereas there is extremely strong genetic evidence of comorbidity between anxiety and depression, GABAergic anxiolytic drugs have consistently failed to show activity in preclinical models of antidepressant drug action (Cryan 2005), a conclusion supported by clinical experience (Birkenhager 1995; Johnson 1985; Barbui 2011). In contrast, the inventors present preliminary data suggesting that inhibition of Glo1 expression or GLO1 activity produces antidepressant-like effects in a preclinical model. The inventors contemplate that this is due to the novel mechanism by which chances in GLO1 activity alter GABAergic signaling.

Whereas the inventors had focused on Glo1's role in anxiety-like behavior, an independent group found that Glo1 expression was correlated with immobility on the tail-suspension test (TST) (Benton 2012), which is among the most reliable and heavily used screens for antidepressant drug activity. All major classes of antidepressant drugs decrease immobility of the TST (Cryan 2005). Consistent with this observation, another group reported that chronic administration of MG decreased immobility on the TST (Hambsch 2010). This was surprising because these data showed that MG acts at $GABA_AR$ and all other known $GABA_AR$ agonists (e.g. benzodiazepines and barbiturates) do not decrease immobility on the TST (Cryan 2005).

To determine if the reported correlation with Glo1 expression and effects of MG administration were causal, the inventors examined TST behavior in Glo1 knockdown (Glo1KD) mice, which express less Glo1 than wild type mice and can thus be thought of as a genetic model of GLO1 inhibition. As predicted, the Glo1KD mice showed decreased immobility on the TST (FIG. 39). Based on those results the inventors tested the effects of pretreatment with pBBG on behavior in the TST. The inventors found that pBBG decreased immobility on the TST in both C57BL/6J (B6) and FVB/NJ (FBV) mice (FIG. 39). Importantly, these data are not confounded by locomotor depression, which would increase rather than decrease immobility. Taken together these data suggest that pBBG may be an antidepressant. This is in contrast to all other $GABA_AR$ acting drugs that do not show antidepressant-like activity in the TST (Cryan 2005). These data reflect the different and potentially useful impact of alteration of GABAergic signaling by GLO1 inhibition compared to positive allosteric modulation of $GABA_AR$.

Because GLO1 inhibition alters an endogenous negative feedback system that links glycolysis to GABAergic inhibitory tone, GLO1 inhibition may offer advantages over existing anti-depressants, such as fewer side-effects, faster efficacy, efficacy for comorbid anxiety disorders or efficacy in treatment refractory individuals. The short-term goal of this application is to obtain better pre-clinical evidence of the efficacy of GLO1 inhibitors and to further elucidate the mechanisms of GLO1 inhibition.

Experimental Plan

The inventors will examine the following behavioral assays of anti-depressant activity: chronic forced swim test (cFST; Hollick et al 2008), Novelty induced hypophagia (NIH; Dulawa et al 2005) and the chronic mild stress paradigm (CMS; Jiao et al 2012). The inventors will use three manipulations of Glo1: constitutive Glo1 over-expressing mice, conditional Glo1 over-expressing mice, and chronic pharmacological inhibition of GLO1.

The inventors will explore the effects of Glo1 overexpression on cFST, NIH and CMS using constitutive BAC Tg mice (Distler et al 2012). Since the inventors' prior studies have shown consistent effects across multiple founder lines, the inventors will use only one founder line for these studies. Groups of 12 mice per genotype per sex (48 per test) will be used for initial studies, however the inventors may add additional subjects if needed to obtain significant results. The inventors anticipate there may be interactions with sex since prior results have shown the anxiolytic effects more clearly in Tg males than females. For behavioral tests that yield significant results the inventors will run follow-up studies with conditional Tg mice (the inventors have already obtained these mice from a collaborator). These Tg mice have a floxed stop codon inserted prior to the first coding exon of Glo1 (Tg-floxed-stop-Glo1). When Tg-floxed-stop-Glo1 mice are crossed to a CRE driver line, Glo1 will be overexpressed only in tissues where CRE is expressed. The inventors will use these mice in conjunction with the B6.Cg-Tg(Camk2a-cre)T29-1Stl/J driver line in an effort to narrow down the minimally sufficient brain region for Glo1 overexpression to alter behavioral assays for antidepressant-like behavior. While the inventors assume that Glo1 expression in the limbic system is critical, Glo1 is expressed at high levels in all cells in the body, so the inventors have yet to define its neuroanatomy. Using this conditional system will allow us to begin to define the anatomical specificity of Glo1's behavioral effects.

In a parallel set of studies, the inventors will examine the effects of the GLO1 inhibitor BrBzGCp2 on cFST, NIH and CMS. These studies will require chronic administration of BrBzGCp2, which will be accomplished using Alzet osmotic pumps. The inventors will determine appropriate doses by measuring GLO1 activity in brain homogenates using an in vitro assay, as previously described (Distler et al 2012). While the inventors anticipate the osmotic pumps will be effective, the inventors could revert to chronic injections if needed. Once the inventors identify a doses that produce robust inhibition of GLO1, the inventors will perform studies using 2-3 doses for each behavioral paradigm and a positive control dose of fluoxetine (18 mg/kg/day). Since the inventors are actively working to develop more drug-like (more selective, orally available, etc) compounds, the inventors may be able to substitute such compounds rather than using BrBzGCp2 (e.g. Chiba et al 2012). As with the TG studies, the inventors anticipate using 12 mice per dose and sex for each test but will increase the number of animals or doses as needed based on preliminary results. The goal of these studies would be to determine whether inhibition of GLO1 acts like an antidepressant drug in these chronic behavioral paradigms.

The preliminary data suggests that manipulation of the Glo1/MG system can alter antidepressant behavior. Manipulation of the Glo1/MG system is fundamentally different from benzodiazepines and barbiturates and will therefore have distinct and useful pharmacologic effects. The approach will be to examine the acute forced swim test (aFST), the chronic forced swim test (cFST) (Holick 2008), novelty induced hypophagia (NIH) (Dulawa 2005) and the chronic mild stress paradigm (CMS) (Jiao 2012), all of which are validated behavioral measures that are sensitive to the effects of antidepressant drugs. The inventors will examine transgenic (Tg) Glo1 overexpressing and Glo1 knockdown (Glo1KD) mice and pBBG in these assays. The rationale for these studies is that Tg, Glo1KD and pBBG treatment have all shown antidepressant-like activity on the TST, but the inventors have not yet examined other tests that are sensitive to antidepressants. The inventors also plan to test a subset of the novel GLO1 inhibitors using these same tests.

In clinical practice it is common to treat depressed patients with a combination of serotonin specific reuptake inhibitors (SSRI) and GABAergic drugs because patients commonly present with both depression and anxiety. While SSRIs can treat symptoms of both depression and anxiety, benzodiazepines are not considered to be a useful treatment for depression (Birkenhager 1994; Johnson 1985; Barbui 2011). Similarly, $GABA_AR$ acting drugs have consistently been found not to influence rodent screens for antidepressant drug activity (Cryan 2005). Indeed there are few indications that co-administration of SSRIs and GABAergic drugs act synergistically on behavioral assays of antidepressant activity (Christensen 2012), and in many cases apparently synergistic effects of GABAergic drugs are inconsistent (DaRocha 1997). The introduction of a novel drug that acted via a GABAergic mechanism and treated both depression and anxiety-like disorders could provide an extremely valuable option either as a primary treatment for both disorders or as an adjunctive therapy. Before GLO1 inhibitors can be examined for antidepressant effects in humans additional preclinical testing is required to better establish the likelihood of success. In addition, a critical limitation of current antidepressant drugs is their slow onset. Therefore the inventors will also examine whether GLO1 inhibition produces antidepressant effects faster than a conventional antidepressants.

All studies using Tg or Glo1KD mice will use littermate wild-type controls; both lines are maintained on pure B6 backgrounds. Since the inventors's prior studies have shown consistent effects across multiple founder lines, they will use only one founder line for these studies. Pharmacological studies will use B6 mice obtained from JAX. Group sizes will be 12 per group per sex. The inventors will use male and female mice for all studies because of known sex differences the Glo1/MG system (Distler 2012) and because of well documented sexual dimorphism in depression and anxiety disorders in humans (Kendler 2007). Mice will be young adults (60-90 days old) when tested.

The inventors will test a single cohort of Tg and Glo1KD mice and the corresponding wild-type controls in the NIH (Dulawa 2005), aFST (Holick 2008), and CMS (Jiao 2012) paradigms. Because these mice have been genetically manipulated the inventors do not need to consider dose or time course, so a single cohort is sufficient.

In addition, the inventors will perform similar studies using pBBG. The inventors will deliver pBBG using Alzet osmotic minipumps, which are capable continuously delivering drug over up to 28 days; this avoids the confounding stressful effects of daily injections. The inventors will consider several doses with the goal of obtaining steady state plasma concentrations across the relevant range of inhibitory doses. For the aFST and cFST the inventors will test mice at 5 and 14 days after minipumps implantation; the 5 day time point is considered acute. The inventors will also examine the response to an acute injection of pBBG. SSRIs (e.g. citalopram) and tricyclic (e.g. desipramine) antidepressants do not increase swimming until the 14 day time point under these conditions. For the NIH the inventors will use a between groups design, with separate cohorts of mice being tested at 5 and 21 days. SSRIs and tricyclic antidepressants do not ameliorate hypophagia until the 21 day time point under these conditions. CMS involves a challenge day once per week during which anhedonia is assessed by monitoring sucrose drinking SSRIs and tricyclic antidepressants do not reduce stress-induced anhedonia until 14 or 21 days of chronic treatment. The inventors will also evaluate novel GLO1 inhibitor small molecule compounds in this same manner.

The above study addresses two critical questions. First, it uses a battery of well-validated and mechanistically distinct behavioral paradigms to examine the antidepressant-like effects of GLO1 inhibitors. This is a key question because further development of GLO1 inhibitors as antidepressants is only justified if they are effective in multiple different behavioral tests. The second key question is whether or not GLO1 inhibitors may have faster onset than conventional SSRIs. If GLO1 inhibitors are active at these time points it will suggest that GLO1 inhibitors may be fast acting antidepressants, which would be a major clinical advantage over existing drugs.

Example 8

Glyoxalase 1 and its Substrate Methylglyoxal are Novel Regulators of Seizure Susceptibility MG Treatment Reduces the Severity and Duration of Picrotoxin-Induced Seizures:

First, the inventors investigated whether MG could prevent or attenuate seizures by administering exogenous MG (50 and 200 mg/kg) or vehicle to mice before seizure induction. The inventors previously demonstrated that this treatment dose-dependently increases MG concentration in the brain (Distler et al., 2012). Treatment with 50 mg/kg and 200 mg/kg MG is expected to increase the concentration of MG in the brain by approximately 16% and 43%, respectively, and does not cause cytotoxicity (Distler et al., 2012). After pre-treatment with MG, the inventors induced seizures using picrotoxin. Picrotoxin is a $GABA_A$ receptor antagonist, which the inventors selected based on its ability to induce seizures in mice (Fisher, 1989) and MG's role as a $GABA_A$ receptor agonist (Distler et al., 2012). Pre-treatment with MG dose-dependently attenuated generalized convulsions induced by 5 mg/kg picrotoxin. Specifically, MG treatment delayed seizure onset (FIG. 36A), reduced seizure duration (FIG. 36B), and reduced the percentage of animals undergoing generalized convulsions (FIG. 36C) at the behavioral level.

In order to validate these behavioral data, the inventors assessed seizure activity by EEG analysis of mice treated with 7 mg/kg picrotoxin. Again, pre-treatment with 200 mg/kg MG delayed seizure onset (FIG. 37A), reduced seizure duration (FIG. 37B), and reduced the number of seizures (FIG. 37C) as measured by EEG. Representative EEG traces are shown in FIG. 37D. Thus, MG attenuates seizures induced by $GABA_A$ receptor blockade at both the behavioral and EEG level.

MG Treatment Reduces the Severity and Duration of Pilocarpine-Induced Seizures:

The inventors next investigated MG's anti-seizure effects in a mechanistically distinct seizure model. The inventors induced seizures using pilocarpine, a muscarinic cholinergic agonist that induces severe, continuous limbic seizures after acute administration (Curia et al., 2008). The inventors pre-treated mice with MG (50 mg/kg and 200 mg/kg) or vehicle and then induced seizures with 250 mg/kg pilocarpine. This dose of pilocarpine induced partial status epilepticus (stage 3 seizures), but not generalized status epilepticus, in vehicle- and MG-treated mice. Pre-treatment with MG (50 and 200 mg/kg) dose-dependently delayed acute seizure onset (FIG. 38A), reduced seizure duration (FIG. 38B), and reduced the highest seizure stage reached (FIG. 38C) in response to pilocarpine.

The inventors then investigated whether MG could stop or reduce the severity of ongoing seizures. The inventors induced seizures with pilocarpine and then administered MG (200 mg/kg) 10 minutes after seizure induction. The inventors selected this time point, because vehicle-treated mice first reach stage 3 seizures approximately 10 minutes after pilocarpine administration (FIG. 38A). MG treatment reduced seizure duration in mice undergoing pilocarpine-induced seizures (FIG. 38D). Neither vehicle-nor MG-treated mice returned to normal behavior during the observation period. Therefore, the inventors conclude that this dose of MG reduced time spent in partial status epilepticus but did not eliminate seizure activity altogether. The inventors did not explore higher doses of MG, because their potential cytotoxic effects could confound the interpretation of the results.

Example 9

Methods

Animals:

A/J mice: A/J mice were obtained from JAX. Mice homozygous for 2 and 3 copies of Glo1 were maintained as breeders.

B6 mice: WT B6 mice were obtained from JAX and were used for pharmacological studies and as breeders for Tg mice.

FVB mice: WT FVB mice were obtained from JAX and were used as breeders for Tg mice.

BAC Tg mice: The mouse BAC RP23-247F19 was obtained from CHORI and modified by RED/ET recombination (Copeland 2001). To prevent expression of alternatively spliced variants of Btbd9 and Dnahc8, their first exons were replaced with ampicillin and kanamycin cassettes, respectively. Primers for recombineering and screening the modified BAC are reported in Table 8. The modified BAC was purified and injected into B6 or FVB pronuclei by the University of Chicago's Transgenic Core Facility. Positive founders that transmitted the BAC to their offspring were maintained as founder lines and were bred to WT mice.

CD-1 mice: CD-1 mice were obtained from Charles River and were used for pharmacological studies.

Glo1 knockout mice: Gene trap ES cell lines were obtained from TIGM. ES cells were injected into blastocysts, which were implanted into pseudopregnant B6 female mice. Offspring were genotyped for the presence of the gene-trap vector, and positive mice were bred with WT mice. None of the founders generated offspring positive for the gene-trapped allele.

Glo1 KD mice: Glo1 KD mice were obtained from Dr. Michael Brownlee at Albert Einstein College of Medicine, Bronx, N.Y. (Queisser 2010).

For all studies, mutant mice were tested in parallel with their WT littermates. WT mice from each Tg line did not significantly differ and were pooled. All animal procedures were approved by the University of Chicago's IACUC.

TABLE 8

Primers used for recombineering and screening the modified BAC

| | |
|---|---|
| AMP cassette with 50 bp overhangs homologous to Btbd9 | F: GGTGGCTGATAGAATGTGTGGTTT TGTGCGCATGCTCCTCTTGCTCACTA-GTGGCACTTTTCGGGGAAATGTGC (SEQ ID NO. 1)<br>R: CTGCTTCCCACATGACTTAAATAT AAGTAATAATAAGAATAACCATTATT-CTCGAGGCTAGCTCTAGAAGTCCAGC (SEQ ID NO. 2) |

TABLE 8-continued

Primers used for recombineering and screening the modified BAC

| | |
|---|---|
| KAN cassette with 50 bp overhangs homologous to Dnahc8 | F: GATAAGGCATCACTGGGAGAAATA AAAACACCCAATGGTCAAGTTATTTG-GGCCTGGTGATGATGGCGGGATCG (SEQ ID NO. 3)<br>R: ACACTCGTACACACCCCAAAACAA AGGGGAAAACAAATACGGGCACGACT-TCAGAAGAACTCGTCAAGAAGGCG (SEQ ID NO. 4) |
| Sreening for Btbd9 modification | F: GTCTGTCCCAGACAGCCTTC (SEQ ID NO. 5)<br>R: AGCCCTCCCGTATCGTAGTT (SEQ ID NO. 6) |
| Screening for Dnahc8 modification | F: TCCTCAGTTGAGATCCCCTCTA (SEQ ID NO.7)<br>R: GCCGAAAAGGTGTCAAGAAA (SEQ ID NO. 8) |

These primers were used for generating the AMP cassette with 50-bp ends homologous to the region of Btbd9 to be excised and the KAN cassette with 50-bp ends homologous to the region of Dnahc8 to be excised. The 50 by homology ends are underlined. Primer sequences used for screening correctly modified BACs are also included. All sequences are reported from 5' to 3'.

Glo1 Copy Number:

Genomic DNA was used as a template in qPCR with SYBR reagents (Applied biosystems). Primers targeted Glo1 and a region of Btbd9 outside the BAC (Glo1 Forward: 5'-CTG CTG AGG ATA CCA GGT TTG TT-3' [SEQ ID NO. 9]; Glo1 Reverse: 5'-AGC ATC CTG ACG GCA GAT TTA-3' [SEQ ID NO. 10]; Btbd9 Forward: 5'-TGC CAG TGT GAT TGA AGG AG-3' [SEQ ID NO. 11]; Btbd9 Reverse: 5'-GTG CCA GCT GAA CCA CAA T-3' [SEQ ID NO. 12]). Glo1 copy number was determined using the $\Delta\Delta C_T$ method (Schmittgen 2008). For A/J mice, copy number was compared to WT B6 mice. For Tg mice, BAC copy number was calculated as (Fold change v. WT×2)−2, because WT B6 and FVB mice have 2 genomic copies of Glo1 (Williams 2009).

General Health and Reflexes:

Body position and righting, toe pinch, ear twitch, whisker orienting, and eye blink reflexes were scored as previously described (Crawley 2007). The whisker placing and visual placing responses were scored as previously described (Fox 1965). The balance beam test was performed as previously described (Crabbe 2003). The balance beam was 97 cm×9.5 mm and elevated to 46 cm. Mice were tested on the balance beam, and missteps were counted.

mRNA Expression:

qPCR: Tissue was dissected, flash frozen on dry ice, and then stored at −80° C. until use. RNA was extracted using the RNeasy kit with DNase digestion (Qiagen). cDNA was generated by reverse transcription (MultiScribe, Applied Biosystems) using oligo dT primers (Invitrogen). cDNA was used as a template in qPCR using SYBR reagents (Applied Biosystems). Primers targeted genes of interest and a housekeeping gene, β-actin. Gene expression was normalized to β-actin and reported as fold change versus WT using the $2^{-\Delta\Delta C_T}$ method (Schmittgen 2008). Primer sequences are listed in Table 9.

Microarray: Microarrays were Mouse Gene 1.0 ST Arrays (Affymetrix). Whole brains were dissected, snap frozen, and stored at −80° C. until use. RNA was extracted using TRIzol (Invitrogen) and was cleaned using the RNeasy kit (Qiagen). RNA samples were transferred on dry ice to Precision Biomarker Resources, who processed the samples and performed all procedures, including data analysis. Statistical analyses were performed by converting P-values into q-values using Q-value software (Storey 2003).

TABLE 9 qPCR primers for measuring mRNA expression

| mRNA Target | Sequences | | SEQ ID NO. |
|---|---|---|---|
| β-actin | F: | CCA CAG CTG AGA GGG AAA TC | 13 |
| | R: | TCT CCA GGG AGG AAG AGG AT | 14 |
| Glo1 | F: | ACT GGC GTT CAT TCA AGA CC | 15 |
| | R: | CCC ATA CCT CAA AGG CAC AT | 16 |
| Thsd7a | F: | GCC AGC TTT CTG ACT GGT CT | 17 |
| | R: | CTT GAA AGG GCT GGG TTA CA | 18 |
| Pfh14 | F: | ATG CCG AGA AAG ACG AAA AA | 19 |
| | R: | GCC ATC TCT GCT TCC ATG TC | 20 |
| Ndufa4 | F: | ACT GTA TGT GAT GCG CTT GG | 21 |
| | R: | CCA GTT TGT TCC ATG GCT CT | 22 |
| Foxp2 | F: | AGC AGC AAG CTG TGA TGT TG | 23 |
| | R: | TGC AAA AGC TGA AGA TGT AAC TG | 24 |

The primers used for gene amplification by qPCR are listed. All sequences are reported from 5' to 3'.

Immunoblot:

Tissue was homogenized in RIPA buffer. Twenty μg of protein was separated by SDS-PAGE and transferred to a PVDF membrane. Membranes were probed with primary antibodies against GLO1 (1:15,000, gift from Dr. Iiris Hovatta at University of Helsinki, Helsinki, Finland) and GAPDH (1:5,000, Cell Signaling Technology). Peroxidase-conjugated secondary antibodies were used (1:100,000, Jackson ImmunoResearch). Blots were developed with ECL plus (Thermo Scientific), digitized, and band intensity was measured by densitometry using NIH ImageJ software. GLO1 band intensity was normalized to GAPDH.

Tests of Anxiety-Like Behavior:

OF test: Mice were placed into the center of the OF, and activity was monitored for five to ten minutes. The apparatus was illuminated to approximately 40 lux. Data were collected and processed using the manufacturer's software (AccuScan Instruments).

LD box test: Mice were placed in the light compartment, and activity was monitored for 4 minutes. The light compartment was illuminated to approximately 1,000 lux, and the dark compartment was illuminated to approximately 5 lux. Behavior was recorded and automatically scored by the Noldus Ethovision System.

EPM: The elevated plus maze (Stoelting) consisted of four arms measuring 5 cm×35 cm; the two closed arms had 15-cm-high walls. The apparatus was raised 40 cm above the ground and was illuminated to approximately 15 lux. Mice were placed into the center of the apparatus, and behavior was scored for 5 minutes.

Enzymatic Activity:

GLO1 activity was assayed by measuring the rate of formation of S-d-lactoylglutathione (Allen 1993).

Brain: Brain tissue was homogenized in 0.1 M sodium phosphate buffer (pH 7.5), 1 mM EDTA, and proteinase inhibitors. Brain homogenate (10-50 μg protein) was added to a hemithioacetal substrate (2 mM MG and 2 mM GSH, Sigma-Aldrich), and the absorbance at 240 nm was measured every 30 seconds for 4 minutes.

Purified protein: 100 ng of purified protein was added to a hemithioacetal substrate, and enzymatic activity was measure as described above.

MG Quantification by HPLC:

MG concentration was measured by HPLC as previously described with modifications (Dhar 2009). Tissue was homogenized in 50 mM sodium phosphate buffer (pH 6.6) and 0.8N perchloric acid. It was then incubated on ice for 10 minutes and centrifuged. The supernatant was filtered, and MG was derivatized with 10 mM o-phenylenediamine to form 2-methylquinoxaline (2-MQ). 5-methylquinoxaline (5-MQ, 15 µM) was spiked into each sample as an internal standard. 2-MQ was quantified using an HP 1100 HPLC system (Agilent) with a Nova-Pak C18 column (Waters Corporation). Column effluent was monitored at 315 nm. 2-MQ concentration was determined by comparison to 2-MQ standards of known mass. Quantification of 2-MQ was corrected for losses by comparison with 5-MQ. MG concentration was calculated as 2-MQ/tissue weight.

Methylglyoxal Pharmacology In Vivo:

Treatment: Unless otherwise noted, crude MG was used for all behavioral experiments. MG was obtained from Sigma-Aldrich, filter-sterilized (0.22 µm filter, Millipore), diluted in vehicle (0.9% NaCl), and adjusted to pH 7.4. Mice were injected i.p. with 10 ml/kg MG or vehicle.

HPLC: Ten minutes post-injection, mice were sacrificed, and brains were rapidly dissected and flash-frozen on dry ice. MG concentration was measured as described above.

OF test: Ten minutes post-injection, mice were placed into the center of the OF. The apparatus was illuminated to approximately 40 lux. Behavior was measured as described above.

OF test replication studies: Ten to twenty minutes post-injection, mice were tested in the OF for five to ten minutes. In some experiments, behavior was scored as described above. In other experiments, mice were tested in the OF, and behavior was automatically scored by the Noldus Ethovision System. For mice tested in the Noldus system, the apparatus was illuminated to approximately 1,000 lux.

LD box test: Ten minutes post-injection, mice were placed in the light compartment, and activity was monitored for three minutes. The light compartment was illuminated to approximately 1,000 lux, and the dark compartment was illuminated to approximately 5 lux. Behavior was recorded and automatically scored by the Noldus Ethovision System.

Hypothermia: Thirty minutes post-injection, rectal temperature was measured with a digital thermometer.

Balance beam: The balance beam test was performed as described above. Ten minutes post-injection, mice were tested on the balance beam, and missteps were recorded. Data were analyzed using non-parametric statistics, because vehicle-treated mice generally did not make errors.

Rotarod: CD-1 mice were tested on the rotarod with the following settings: acceleration from 4 revolutions per minute (rpm) to 60 rpm at 0.125 rpm/sec. On day 1, mice were trained on the rotarod for five consecutive trials. On day 2, mice were treated with vehicle or MG and were tested once on the rotarod ten minutes after treatment. The latency to fall and the rotarod speed at the time of the fall were recorded.

Chronic MG administration: For five days, mice were injected twice daily with vehicle or MG (4 mg/kg). Twelve hours after the final injection, mice were tested in the OF as described above.

Pure MG: Pure MG was obtained from Dr. John Termini at the City of Hope, Duarte, Calif. It was administered at the indicated doses by i.p. injection. Mice were tested as described above.

TUNEL Staining:

WT B6 male mice were treated i.p. with vehicle or MG (50 or 300 mg/kg). Twenty-four hours post-injection, mice were anesthetized with ketamine (100 mg/kg) and xylazine (10 mg/kg) and were then transcardially perfused with PBS (pH 7.4). Brains were dissected and post-fixed for 48 hours in 4% paraformaldehyde (pH 7.4). Fixed brains were washed in PBS and placed in 70% ethanol until processing. Brains were submitted to the University of Chicago's Human Tissue Resource Center for processing. Brains were embedded in paraffin, sectioned to 5 µm, TUNEL stained using the ApopTag Plus Peroxidase In Situ Apoptosis Detection Kit (Millipore) according to the manufacturer's instructions, and counterstained with hematoxylin. Slides were digitally scanned with ScanScope XT (Aperio Technologies). Images were analyzed using Spectrum Plus software (Aperio Technologies) to count TUNEL-positive cells and total cells in each section. % TUNEL positive values were calculated as: (TUNEL positive cells/total cells)×100%. A positive control (female rodent mammary gland 3-5 days post-weaning, provided in the kit) was stained and analyzed in parallel with the experimental samples.

BrBzGCp2 (GLO1 Inhibitor):

Synthesis: BrBzGCp2 was a gift from Dr. John Termini at the City of Hope, Duarte, Calif. and was prepared on a multi-gram scale in two steps from reduced glutathione as previously described with modifications (Vince 1971; Thornalley 1996). Reduced glutathione was reacted with 4-bromobenzylbromide and sodium hydroxide in ethanol for ten days followed by acidification with HI to pH 3.5 and filtration to give bromobenzylglutathione (Thornalley 1996) as a bright white solid (Vince 1971). This was then esterified with excess acidified cyclopentanol to give crude BrBzGCp (Thornalley 1996) as a mixture of mono- and diesters. The desired diester was moderately soluble in diethyl ether, whereas the monoester was virtually insoluble. Repeated suspension of the crude product in diethyl ether, followed by filtration and evaporation of the filtrate, gave the desired BrBzGCp2 in >95% purity as assessed by NMR.

Enzymatic activity: Vehicle (DMSO) or 100 µM BrBzGCp2 was added to 10 ng of purified human GLO1. Enzymatic activity was measured as described above.

Treatment: BrBzGCp2 was dissolved in vehicle (8% DMSO and 18% Tween-80). Mice were treated i.p. with 10 ml/kg BrBzGCp2 or vehicle.

HPLC: 2 hours post-injection, mice were sacrificed, and brains were rapidly dissected and flash-frozen on dry ice. MG concentration was measured as described above.

OF test: Two hours post-injection, mice were tested in the OF test as described above. The center size was 10×10 cm. The apparatus was illuminated to approximately 40 lux.

Glo1 Duplication Genotyping:

CD-1 mice were genotyped for the presence or absence of the Glo1 duplication using PCR as previously reported (Williams 2009).

Electrophysiology:

Reagents: All reagents were obtained from Sigma-Aldrich. Pure MG was provided by Dr. John Termini at the City of Hope, Duarte, Calif.; electrophysiological results were identical between pure MG and MG obtained from Sigma-Aldrich. MG, GABA, glycine, 1-glutamate, SR, strychnine, CNQX, AP-5, diazepam, midazolam, and zolpidem were applied with a computer controlled MPS-2 multichannel perfusion system (WPI).

Culture of rat CGN: CGN were cultured from mixed-sex Sprague-Dawley rats. Tissue was dissected from 6- to 8-day-old rats. Cells were suspended in minimal essential medium supplemented with 10% fetal calf serum, 26 mM glucose, 19 mM KCl, 2 mM 1-glutamine, and penicillin/streptomycin (50 IU/ml and 50 μg/ml). Cells were seeded on poly-1-lysine-coated coverslips and incubated in a humidified atmosphere containing 5% $CO_2$ at 37° C. After 48 hours, the culture medium was replaced with minimal essential medium supplemented with 10% horse serum, 26 mM glucose, 19 mM KCl, 2 mM 1-glutamine, penicillin/streptomycin (50 IU/ml and 50 μg/ml), and 80 μM 1-fluorodeoxyuridine. Culture medium was exchanged every three days. All recordings were made from cells between days 6 to 9 in culture.

Culture of rat HN: HN were prepared from E17 Sprague-Dawley rats as previously described (Plant 2011) and seeded on poly-1-lysine coated glass coverslips. Neurons were maintained in neurobasal medium with B27 supplement and glutamax in a humidified atmosphere with 5% $CO_2$ at 37° C.

Whole-cell patch clamp: Whole-cell patch-clamp was performed as previously described (Plant 2006) using an Axopatch 200B amplifier and pCLAMP software (Molecular Devices). Filter and sampling frequencies were 5 and 25 kHz, respectively, for voltage-clamp experiments and 1 and 10 kHz, respectively, for current-clamp recording. Experiments were performed at 32° C. using a feedback-controlled heated perfusion system (Warner Instruments). $V_m$, ligand-gated currents, and potassium channel currents were studied in a bath solution containing 1 mM $CaCl_2$, 1 mM $MgCl_2$, 4 mM KCl, 140 mM NaCl, 5 mM glucose, and 10 mM HEPES (pH 7.4). Electrodes were fabricated from borosilicate glass (Clark) and had a resistance of 4-5 MΩ when filled with a solution containing 136 mM KCl, 1 mM $MgCl_2$, 2 mM $K_2ATP$, 5 mM EGTA, and 10 mM HEPES (pH 7.2). Electrodes were coated with Sigmacote (Sigma) prior to use.

Macropatch recording: Macropatch recording was performed with 1.5-2 MΩ electrodes filled with bath solution. The inside of excised patches was perfused with electrode solution containing the indicated reagents. SR was added to the electrode where indicated.

Potassium currents: Voltage-gated potassium channel currents were evoked using a previously reported protocol with modifications (Plant 2006). The whole voltage-gated potassium current, $I_{K+}$, and the delayed rectifier current, $I_{DR}$ were isolated with two voltage protocols. First, $I_{K+}$ was evoked by 250 ms test pulses to between −80 and 90 mV from −80 mV following a 250 ms pre-pulse to −140 mV. Then, the protocol was repeated using a −50 mV pre-pulse to inactivate $I_{K+}$ and isolate $I_{DR}$. The inactivating component of the current, $I_{KA}$, was isolated by subtracting $I_{DR}$ from $I_{K+}$ recorded in the same cells. The standing outward potassium leak current, IKso, and the inwardly rectifying potassium current, $I_{KIR}$, were studied as previously reported with modifications (Plant 2002). Cells were held at −20 mV, and the membrane potential was ramped to −120 mV over a period of 100 ms before returning to −20 mV. Ramp hyperpolarizations were repeated every 20 seconds.

Sodium currents: Sodium currents were studied as previously described (Plant 2006) using a bath solution containing 130 mM NaCl, 5 mM CsCl, 2 mM $CaCl_2$, 1.2 mM $MgCl_2$, 5 mM glucose, and 10 mM HEPES adjusted to pH 7.4 with NaOH. 500 nM tetrodotoxin (Sigma) was included in the bath to block voltage-gated sodium currents. The electrode solution contained 60 mM CsCl, 80 mM CsF, 10 mM EGTA, 1 mM $CaCl_2$, 1 mM $MgCl_2$, 5 mM $Na_2ATP$, and 10 mM HEPES adjusted to pH 7.4 with CsOH. All voltage-gated currents were studied following a P/5 leak subtraction protocol, and voltage-clamp errors were minimized with 80% series resistance compensation.

Ligand-gated currents: Ligand-gated currents were studied in voltage-clamp mode by application of reagents to cells held at −50 mV. GABAergic and glycinergic currents were activated by application of GABA and glycine and antagonized by application of SR and strychnine, respectively (Kaneda 1995). Glutamatergic currents were activated by 1-glutamate and antagonized by CNQX and AP-5 (Wyllie 1994).

TST:

Mice were suspended by their tails using adhesive tape attached to a bar elevated approximately 46 cm above a table. The apparatus was illuminated to approximately 1,000 lux. Mice were tested individually, and time spent immobile was scored manually for six minutes. For MG studies, mice were treated with vehicle (0.9% saline) or crude MG (Sigma-Aldrich, 50 mg/kg) by i.p. injection ten minutes before the test. Behavior was scored for five minutes.

Seizure Testing:

Drug administration: All experiments with MG utilized crude MG obtained from Sigma-Aldrich. For pre-treatment, MG (50 or 200 mg/kg) or vehicle (0.9% saline) was administered by i.p. injection 10 minutes before the seizure-inducing agent. For treatment after seizure onset, MG (200 mg/kg) or vehicle (0.9% saline) was administered by i.p. injection ten minutes after seizure onset. For GLO1 inhibition, BrBzGCp2 (50 mg/kg) or vehicle (8% DMSO and 18% Tween-80) was administered by i.p. injection two hours before seizure induction.

Seizure induction: For picrotoxin-induced seizures, 5 mg/kg of picrotoxin in 0.9% saline was administered by i.p. injection. Seizures were scored for one hour after picrotoxin administration. For pilocarpine-induced seizures, mice were pre-treated with atropine (5 mg/kg in 0.9% saline) by i.p. injection in order to reduce the peripheral effects of pilocarpine. Thirty minutes after atropine administration, pilocarpine was administered by i.p. injection. B6 mice were treated with 250 mg/kg pilocarpine in 0.9% saline, and FVB mice (WT and Tg) were treated with 300 mg/kg pilocarpine in 0.9% saline. Seizures were scored for 90 minutes after pilocarpine administration.

Seizure scoring: Picrotoxin-induced seizures were scored as the presence of generalized convulsions as well as the latency to and duration of generalized convulsions.

Pilocarpine-induced seizures were scored as previously reported (Winawer 2011):

Stage 1: Immobility/Lying Low

Stage 2: Partial (limbic) seizures. Non-continuous twitching/tremor/shaking of tail/head/body/limbs, forelimb and/or tail extension, rigid posture, repetitive movements, head bobbing Stage 3: Partial status epilepticus. Continuous tremor/clonic seizures of body and tail while retaining posture Stage 4: Generalized seizures. Rearing/hyperexcitability/running/falling, tonic extension/clonic seizures with loss of posture Stage 5: Generalized status epilepticus (continuous stage 4 seizures) resulting in death Gene Network:

Data on seizure susceptibility and Glo1 expression in BXD RI lines were obtained from and analyzed using WebQTL at world wide web via www.genenetwork.org (Wang 2003). The record ID for hippocampal Glo1 expression was 1424109_a_at from the Hippocampus Consortium M430v2 (June 6) PDNN database. The record ID for seizure susceptibility was 10388, representing data reported by McCall and Frierson (McCall 1981). Data were retrieved on Jan. 28, 2012.

Metabolic Cages:

WT and Tg littermates from FVB line 3 were individually housed in metabolic cages (TSE Systems) for one week. Mice were allowed to acclimate for five days, and measurements from the sixth and seventh days were used for analysis.

Glucose Homeostasis:

WT and Tg mice from FVB Tg lines 3, 4, and 5 were fasted overnight. Baseline blood glucose concentration was made using a Contour glucometer (Bayer). Then, mice were given an i.p. injection of 10% glucose (10 ml/kg body weight), and subsequent blood glucose measurements were made 30, 60, and 120 minutes later.

Human GLO1:

Human GLO1 cDNA (419A) was obtained from Open Biosystems (clone ID 4182593) in a pCMV-SPORT6 vector. The 419C variant was generated by site-directed mutagenesis using a Quik-Change kit (Stratagene) according to the manufacturer's protocol. Sequences for the mutagenic primers were: 5'-GGC ACT GAA GAT GAT GCG ACC CAG AGT TAC CAC-3' (sense) [SEQ ID NO. 25] and 5'-GTG GTA ACT CTG GGT CGC ATC ATC TTC AGT GCC-3' (anti-sense) [SEQ ID NO. 26]. After mutagenesis, the sequence was verified using PCR-based sequencing by the University of Chicago DNA Sequencing Facility. The 419A and 419C cDNA sequences were subcloned into pTrcHis expression vectors (Invitrogen) to add a 6x-Histidine tag to the N-terminus of the translated protein. To do so, the cDNA sequence was amplified by PCR using the following primers: 5'-ATA CTG CAG CCA TGC AGA ACC-3' (forward) [SEQ ID NO. 27] and 5'-TGA ATC GGG ACA GTG ATC CA-3' (reverse) [SEQ ID NO. 28]. The amplicon was gel-extracted and digested with PstI and EcoRI and inserted into the pTrcHis vector. The construct's sequence was verified using PCR-based sequencing at the University of Chicago's DNA Sequencing Facility. JM109 competent *E. coli* were transformed with the plasmids. The recombinant His-tagged 111A and 111E GLO1 proteins were purified under native conditions using a Ni-NTA protein purification kit (Qiagen) according to the manufacturer's protocol. Enzymatic activity of the purified proteins was performed as described above.

Statistical Analyses:

All statistical analyses were carried out using StatView for Windows (SAS Institute, Inc.) unless otherwise noted. Normally distributed data were analyzed by t-tests or analyses of variance (ANOVA) as appropriate. Post-hoc tests were used to determine significant differences between groups when the ANOVA yielded a significant result. For data that were not normally distributed, Mann-Whitney U tests were used for two-group comparisons; Kruskal-Wallis tests were used for three-group comparisons, and post-hoc comparisons were made using Mann-Whitney U tests. For statistical analysis of the microarray data, P-values were converted to q-values using Q-value software (Storey 2003). For the meta-analysis of MG's anxiolytic effect, results from individual experiments were compiled and analyzed with MIX 1.7 software using a fixed-effect model (Bax 2006). The relationship between Glo1 expression and seizure phenotypes in BXD RI lines was assessed using Pearson correlations. $P<0.05$ was considered statistically significant. The figure legends indicate the specific tests used and their respective P-values.

Example 10

The Use of Glo1 Inhibitors/Mg as Treatment for an Anxiety Disorder

Many studies indicate amygdala-prefrontal cortex circuitry in both normal and disease states of anxiety as well as, in depression (Earnheart et al. 2007; Luscher, Shen & Sahir 2011). As Glo1 and MG are expressed throughout the brain and MG activates $GABA_A$ receptors that are highly expressed within amygdala-prefrontal cortex circuitry, we predicted that the Glo1/MG pathway exerts control over anxiety-like behavior through this circuitry. The studies performed here aimed to determine whether the effects of Glo1/MG on anxiety-like behavior are peripherally or centrally mediated and if central, to elucidate the neuroanatomical systems responsible for regulating the effects of MG on anxiety-like behavior. To test this, mice that have a human copy of Glo1 with a floxed stop codon on a B6 background (FloxGlo1) that results in overexpression of Glo1 only in tissue expressing CRE were used. These FloxGlo1 mice were bred to mice expressing CRE recombinase under the direction of the synapsin promoter to limit overexpression of Glo1 to all neurons. Indeed, limiting overexpression of Glo1 to neurons was sufficient to induce anxiety-like behavior in the OFT (FIG. 41A).

While many nuclei of the amygdala contribute to anxiety-like behavior, direct injection of a benzodiazepine (in this case midazolam) to the basolateral amygdala (BLA) has been shown to elicit greater anxiolytic effects than other nuclei in the amygdala and is required for the consolidation of anxiety in behavioral models of anxiety-like behavior (Vyas & Chattarji 2004; Heldt & Ressler 2006). As MG is a $GABA_A$ receptor agonist, it was contemplated that direct injection of MG into the BLA would reduce anxiety-like behavior in the OFT to a similar extent as a positive modulator of $GABA_A$ receptors, midazolam. Indeed, a dose dependent increase was observed in center duration after direct injection of MG into the BLA that was comparable to that of midazolam. These data suggest the GLO1/MG pathway modulates anxiety-like behavior through typical circuitry. MG is cell permeable, and as such, it is possible that MG preferentially acts at extrasynaptic GABAA receptors where concentrations of GABA are low. Extrasynaptic receptors are believed to mediate inhibitory tone, reducing the probability of a neuron firing an action potential. Insufficient inhibition in amygdala-prefrontal cortex circuitry could explain Glo1/MG control over anxiety-like behavior and may suggest a role for Glo1/MG in normal mediation of behaviors associated with anxiety. The extraysnatic effects of MG may be a key benefit of targeting the MG/Glo1, for example by using a GLO1 inhibitor.

While many $GABA_A$ receptor-acting anxiolytic drugs are already is use, they are predominately positive allosteric modulators. GLO1 inhibition/MG accumulation is fundamentally different because MG is an endogenously produced competitive partial agonist and accumulation of MG is dictated by local MG production. Therefore, the neuroanatomical distribution of MG production will influence the effects of GLO1 inhibition. This might account for the better anxiolytic effects observed in FIG. 42A.

Example 11

The Use of Glo1 Inhibitors/MG as Treatment for Depression

The forced swim test (FST) is a highly reliable screen used to predict antidepressant efficacy after acute antidepressant treatments (Petit-Demouliere, Chenu & Bourin 2005). The FST relies on the phenomenon that relative to no treatment, mice receiving treatment with antidepressants will spend more time performing escape-oriented behaviors than immobile postures. Though similar, intra-strain and interstrain comparisons suggest different biological substrates underlie the observed behavior in this test and convergent data on potential antidepressants can bolster claims of antidepressant activity (Petit-Demouliere, Chenu & Bourin 2005). Mice on three genetic backgrounds (C57BL/6J, FVB/nJ and BALB/cJ) were treated with 50 mg/kg pBBG (i.p.) and assessed depression-like behavior in the FST two hours later. Treatment with pBBG reduced immobility in all strains, suggesting a therapeutic potential of GLO1 inhibition for the treatment of depression (FIG. 43).

To fully assess the therapeutic potential of GLO1 inhibitors, it is necessary to utilize behavioral models sensitive to chronic administration. These models are highly informative as the therapeutic onset of antidepressant action mimics clinical onset in humans. pBBG was administered by osmotic minipumps (Alzet) for 14 days at various doses (0, 5, 10, 15, 30 and 60 mg/kg/day) to establish a dose response curve. Osmotic minipumps are ideal for chronic treatment as they release a constant volume at a very slow rate minimizing the stress of multiple injections. These studies indicate low doses (5 or 10 mg/kg/day) of the GLO1 inhibitor pBBG reduce immobility in the FST after chronic treatment for 14 days. These data suggest that inhibition of GLO1 acts as both an antidepressant and anxiolytic drug, without inducing locomotor depression reflecting the different and potentially useful impact of alteration of GABAergic signaling by GLO1 inhibition compared to positive allosteric modulators of $GABA_A$ receptors.

Example 12

The Use of Glo1 Inhibitors/MG in Treatment of Alcohol and Other Substance Abuse/Dependence According to the National Institute on Alcohol Abuse and Alcoholism, about 18 million people have alcohol use disorders. Binge drinking is drinking enough alcohol within about 2 hours for blood alcohol concentration (BAC) levels to reach 0.08 g/dL. Binge drinking and drinking to intoxication are associated with higher risk for developing AUDs (Courtney & Polich, 2009). The drinking in the dark (DID) paradigm in mice emulates binge drinking in humans as it limits mouse exposure to ethanol to a portion of their dark cycle when their natural consummatory behaviors are greatest. B6 mice are known to consume pharmacologically significant amounts of ethanol in this paradigm. Water bottles are replaced with 20% ethanol 3 hours into the dark phase of the light cycle. The ethanol bottle is removed after 2 hours on the first day of access and after 4 hours on the second day. This results in mice achieving BACs high enough to induce behavioral intoxication on the second day (Barkley-Levenson & Crabbe, 2013). Expression of Glo1 was found to alter ethanol consumption in the DID paradigm (FIG. 45). Glo1 knockdown mice drank significantly less ethanol than wild-type or Glo1 overexpressing mice. These data suggest inhibition of Glo1 reduces ethanol consumption and may thereby be a viable treatment for alcohol abuse disorders.

REFERENCES

The following references, to the extent that they provide exemplary procedural or other details supplementary to those set forth herein, are specifically incorporated herein by reference.

2000. *The Amygdala: A Functional Analysis.* New York: Oxford Press.
Ahmed & Thornalley, *Diabetes Obes Metabl.* 9:233-45, 2007.
Aldinger, et al., *PLoS One.* 4:e4729, 2009.
Allen, et al., *J Protein Chem.* 12:111-9, 1993.
Al-Timari & Douglas, *Biochim Biophys Acta.* 870:219-25, 1986.
American Psychiatric Association. Diagnostic and Statistical Manual of Mental Disorders. Washington, D.C.: American Psychiatric Association. 2000.
Anderson, et al., *Int J Psychiatry Med.* 32:235-47, 2002.
Arai, et al., *Arch Gen Psychiatry.* 67:589-97, 2010.
Aronsson, et al., *Biochem J.* 197:67-75, 1981.
Association, A. P. 2000. Diagnostic and Statistical Manual of Mental Disorders. Washington, D.C.: American Psychiatric Association.
Baguley & Walton, *Angewandte Chemie-International Edition.* 37:3073-3082, 1998.
Bair, et al., *Melanoma Res.* 20:85-96, 2010.
Barbui, et al., *Br J Psychiatry.* 198:11-6, sup 1, 2011.
Barnard, E. A. The Molecular Architecture of GABA-A Receptors in In Mohler (Ed): *Handbook of experimental pharmacology: Pharmacology of GABA and Glycine Neurotransmission.* 150:79-100, 2001.
Barnard, et al., *Pharmacol Rev.* 50:291-313, 1998.
Banos & Deitmer, *Brain Res Rev.* 63:149-59, 2010.
Barton, et al., *J Chem Soc Chem Commun.* 939-941, 1983.
Barua, et al., *Autism Res.* 4:262-70, 2011.
Bax, et al., *BMC Med Res Method.* 6, 2006.
Beg & Jorgensen, *Nat NeuroSci.* 6:1145-51, 2003.
Beisswenger, et al., *Ann NY Acad Sci.* 1043:201-10, 2005.
Beisswenger, et al., *Ann N Y Acad Sci.* 1043:201-210, 2005.
Belzung & Griebel, *Behav Brain Res.* 125:141-49, 2001.
Benton, et al., *Psychopharmacology (Berl).* 221(2):297-315, 2012.
Berner, et al., *Diabetologia.* 55:845-854, 2012.
Beyenburg, et al., *Epilepsy Behav.* 7:161-171, 2005.
Birkenhager, et al., *Int Clin Psychopharmacol.* 10:181-95, 1995.
Bollan, et al., *Biochem Soc Trans.* 31:875-879, 2003.
Boso, et al., *Neurosci Lett.* 410:169-173, 2006.
Bouche & Fromm, *Trends Plant Sci* 9:110-115, 2004.
Bouffard, et al., *Org Lett.* 10:37-40, 2008.
Bourin, M., and Hascoet, M. 2003. The mouse light/dark box test. Eur J Pharmacol 463:55-65.
Bourin, et al., *Fundam Clin Pharmacol.* 21:567-574, 2007.
Bouwknecht, et al., *Behav Pharmacol.* 19:385-402, 2008.
Briggs & Galanopoulou, *Neural Plast.* 2011:527605, 2011.
Brodie, et al., *Epilepsy Behav.* 21:331-341, 2011.
Brouwers, et al., *J Biol Chem.* 286:1374-1380, 2010.
Brownlee, *Nature* 414:813-820, 2001.
Bryant, et al., *J Neurogenet.* 22:315-31, 2008.
Bunck, et al., *PLoS One.* 4:e5129, 2009.
Cameron, et al., *Biochemistry.* 38:13480-13490, 1999.
Cameron, et al., *EMBO Journal.* 16:3386-3395, 1997.

Canteras, et al., *Curr Top Behav Neurosci.* 2:77-96, 2010.
Carter, et al., *Pharmacol Ther.* 121:100-114, 2009.
Caspi & Moffitt, *Nat Rev Neurosci.* 7:583-590, 2006.
Castagne, et al., Behavioral Assessment of Antidepressant Activity in Rodents. in *Methods of Behavior Analysis in Neuroscience,* 2009.
Castagne, et al., *Curr Protoc Neurosci.* Chapter 8, Unit 8 10A (2011).
Cerda, et al., *J Affect Disord.* 126:14-38, 2010.
Chandler, *Drug Discov Today.* 18:202-6, 2013).
Chandler, et al., *Mamm Genome* 18:693-708, 2007.
Chang, et al., *Heterocycles.* 12:903-907, 1979.
Chang, et al., *J Org Chem.* 46:4188-4193, 1981.
Chatterjee, et al., *Biosens Bioelectron.* 42:349-54, 2013.
Chen, et al., *Assay Drug Dev Technol.* 10:325-35, 2012.
Chen, et al., *Chem Soc Rev.* 39:2120-35, 2010.
Chen, et al., *Proc Natl Acad Sci USA* 101:7687-7692, 2004.
Chiba, et al., *Bioorg Med Chem Lett.* 22(24):7486-9, 2012.
Christensen, et al., *Eur Neuropsychopharmacol.* 22:751-60, 2012.
Churchill, et al., *Nat Genet.* 36:1133-7, 2004.
Clayton, et al., *Curr Med Chem.* 14:2755-2775, 2007.
Conn & Roth, *Neuropsychopharmacology.* 33:2048-60, 2008.
Cooper, et al., *Annu Rev Microbiol* 38:49-68, 1984.
Copeland, et al., *Nat Rev Genet* 2:769-779, 2001.
Crabbe, et al., *J Appl Physiol* 95:1338-1351, 2003.
Crawley, *Brain Res* 835:18-26, 1999.
Crawley, Wiley-Liss, 2007.
Crawley, *Neuron* 57:809-818, 2008.
Creighton, *Biochem Soc Trans* 31:1378-1382, 2003.
Crestani, et al., *Proc Natl Acad Sci USA.* 99:8980-5, 2002.
Crestani, et al., *Nat Neurosci* 2:833-839, 1999.
Cryan, et al., *Neurosci Biobehav Rev.* 29(4-5):571-625, 2005.
Csonga, et al., *FEBS Lett.* 380:209-14, 1996.
Curia, et al., *J Neurosci Methods.* 172:143-157, 2008.
Czibere, et al., *PLoS One* 6:e23604, 2011.
Da-Rocha, et al., *J Psychopharmacol.* 11:211-8, 1997.
Davies, et al., *Arch Toxicol Suppl* 9:46-50, 1986.
Davis, *Annu Rev Neurosci* 15:353-375, 1992.
Dawson, et al., *Trends Pharmacol Sci* 16:33-36, 1995.
Dhar, et al., *J Chromatogr B Analyt Technol Biomed Life Sci* 877:1093-1100, 2009.
Di Cristo, *Clin Genet* 72:1-8, 2007.
Di Lio, et al., *Neuropharmacology.* 60:626-32, 2011.
Di Loreto, et al., *Brain Res* 1006:157-167, 2004.
Di Loreto, et al., *Int J Biochem Cell Biol* 40:245-257, 2008.
Dias, et al., *J Neurosci.* 25:10682-8, 2005.
Dina, et al., *Nat Genet* 39:724-726, 2007.
Distler & Palmer. *Front Genet.* 3:250. doi: 10.3389/fgene.2012.00250, 2012 Distler, et al., *Epilepsia* (2013). PMC Journal—In Process
Distler, et al., *J Clin Invest.* 122:2306-2315, 2012.
Distler, et al., *PLoS One* 7:e51235, 2012.
U.S. Pat. No. 4,711,775
U.S. Pat. No. 4,185,106
Ditzen, et al., *Mol Cell Proteomics* 5:1914-1920, 2006.
Ditzen, et al., *Mol Psychiatry* 15:702-711, 2010.
Doherty, et al., *Epilepsia.* 48:1764-1767, 2007.
WO1998009986
Dulawa & Hen, *Neurosci Biobehav Rev.* 29(4-5):771-83, 2005.
Dutton, et al., *Neurobiol Dis.* 25:49C:211-220, 2012.
Earnheart, et al., *J Neurosci* 27:3845-3854, 2007.
Edwankar, et al., *Org Lett.* 13:5216-5219, 2011.
Egan, et al., *Nat Genet* 39:1384-1389, 2007.
EP0510440 A1
EP0510443 A1
EP1049444 B1
European Patent 1051396 (A1)
Farrant, et al., *Nat Rev Neurosci* 6:215-229, 2005.
Filiou, et al., *Biol Psychiatry.* 70(11):1074-82, 2011.
Finn, et al., *Neurogenetics.* 4:109-35, 2003.
Fischer, et al., *Neuropharmacology.* 59:612-618, 2010.
Fisher, *Brain Res Brain Res Rev.* 14:245-278, 1989.
Fisher, et al., *Epilepsia.* 46:470-472, 2005.
Fleming, et al., *Gerontology.* 57(5):435-43, 2011.
Flint, *Methods* 53:163-174, 2010.
Foldvary-Schaefer, et al., *Cleve Clin J Med.* 71 Suppl 2:S11-18, 2004.
Fox, *Anim Behav* 13:234-241, 1965.
Frayling, et al., *Science* 316:889-894, 2007.
Fujimoto, et al., *Neurosci Lett* 438:196-199, 2008.
Galanopoulou, *Pflugers Arch.* 460:505-523, 2010.
Garakani, et al., *Mt Sinai J Med* 73:941-949, 2006.
Gasior, et al., *Epilepsia.* 48:793-800, 2007.
Gerner & Hare *Am J Psychiatry* 138:1098-1101, 1981.
Gill, et al., *Neuropsychopharmacology.* 36:1903-1911, 2011.
Giraldo, et al., *Transgenic Res* 12:751-755, 2003.
Gisselmann, et al., *Br J Pharmacol* 142:409-413, 2004.
Golden, et al., *Assay Drug Dev Technol.* 9:608-19, 2011.
Gotz, et al., *Science* 293:1491-1495, 2001.
Grant, et al., *Nat Genet* 38:320-323, 2006.
Green & Marsden, *ACS Chem Neurosci.* 4:9-12, 2013.
Gregory, et al., *Eur Arch Psychiatry Clin Neurosci* 258:69-75, 2008.
Grillo & Colomobatto *Amino Acids* 35:29-36, 2008.
Guardiola-Lemaitre, et al., *Pharmacol Biochem Behav* 41:405-408, 1992.
Guthrie, et al., *Proc Natl Acad Sci USA* 86:7378-7381, 1989.
Habig, et al., *Proc Natl Acad Sci USA.* 71:3879-82, 1974
Hablitz, et al., *Neuroscientist* 15:218-224, 2009.
Hamann, *Neuroscientist* 11:288-293, 2005.
Hambsch, et al., *J Neurochem.* 113(5):1240-51, 2010.
Hamilton, et al., *J Biol Chem.* 267:24933-6, 1992.
Hansen, et al., *Genome Res* 18:1670-1679, 2008.
Hart, et al., *Methods Mol Biol* 602:299-321, 2010.
Hartman, et al., *Pediatr Neurol.* 36:281-292, 2007.
Hasler & Northoff. *Mol Psychiatry* 16:604-619, 2011.
Haza, L. *Acta Chimica Hungarica* 117, 99-116 (1984).
He, et al., *Drug Des Discov.* 17:131-71, 2000.
Heintz, *Nat Rev Neurosci* 2:861-870, 2001.
Henshall & Murphy *Curr Opin Pharmacol* 8:75-81, 2008.
Hohoff, *J Neural Transm* 116:679-687, 2009.
Holick, et al., *Neuropsychopharmacology.* 33(2):406-17, 2008.
Hovatta, et al., *Nature.* 438(7068):662-6, 2005.
Hovatta & Barlow, *Ann Med* 40:92-109, 2008.
Huang, et al., *J Med Chem.* 43: 71-95, 2000.
Inglese, et al., *Proc Natl Acad Sci USA.* 103:11473-8, 2006.
Inoue, et al., *Semin Cell Dev Riot* 22:278-284, 2011.
Irwin, *Psychopharmacologia.* 13:222-57, 1968.
Ittner & Gottz, *Nat Rev Neurosci* 12:65-72, 2011.
Jacquier, et al., *Nutr Rev* 70:118-131, 2012.
Jia & Wu, *Mol Cell Biochem* 306:133-139, 2007.
Jiao, et al., *Mol Psychiatry.* doi: 10.1038/mp.2012.136. [Epub ahead of print], 2012
Johansen, et al., *Cell* 147:509-524, 2011.
Johanson, et al., *Cerebrospinal Fluid Res* 5:10, 2008.
Johnson, *Br J Clin Pharmacol.* 19 Suppl 1:31S-35S, 1985
Junaid, et al., *Am J Med Genet A* 131:11-17, 2004.
Kabir, et al., *J Org Chem.* 75:3626-3643, 2010.
Kalapos, *Med Hypotheses* 68:1382-1388, 2007.

Kalueff & Nutt, *Depress Anxiety* 24:495-517, 2007.
Kaneda, et al., *J Physiol* 485 (Pt 2):419-435, 1995.
Kavarana et al *J. Med. Chem.* 42:221-228, 1999.
Kemlink, et al., *J Med Genet.* 46:315-8, 2009.
Kendler, et al., *Psychol Med.* 37:453-62, 2007.
Kent, et al., *Biol Psychiatry* 52:1008-1030, 2002.
Khattab, S. *Ind. J. CHem.* 15B: 432-5, 1977.
Kim, et al., *J Biochem* 117:359-361, 1995.
Kirik & Bjorklund, *Trends Neurosci* 26:386-392, 2003.
Kitamura, et al., *J Am Chem Soc.* 124:6649-6667, 2002.
Kompf, et al., *Humangenetik* 27:141-143, 1975.
Krautwald, et al., *Exp Gerontol* 45:744-751, 2010.
Kromer, et al., *J Neurosci* 25:4375-4384, 2005.
Kuhla, et al., *Ann N Y Acad Sci* 1043:211-216, 2005.
Kuhla, et al., *J Neurosci Res.* 83:1591-600, 2006.
Kullmann, et al., *Prog Biophys Mol Biol* 87:33-46, 2005.
Kumar & Punekar *Mycological Research* 101:403-409, 2007.
Kumar, et al., *Psychopharmacology* (Berl) 205:529-564, 2009.
Kurz, et al., *Cellular and Molecular Life Sciences* 68:721-733, 2011.
LaFrance, et al., *Int Rev Neurobiol.* 83:347-383, 2008.
Landgraf, et al., *Neurosci Biobehav Rev.* 31:89-102, 2007.
LeDoux, *Curr Biol* 17:R868-874, 2007.
LeDoux, *Annu Rev Neurosci* 23:155-184, 2000.
Leonardo, et al., *Annu Rev Psychol.* 57:117-137, 2006.
Lever, et al., *Nature.* 231:368-371, 1971.
Li, et al., *Cell Biochem Funct.* 29(1):30-5, 2011.
Lissek, et al., *Behav Res Ther.* 43:1391-1424, 2005.
Liu, et al., *J Psychiatr Res.* 37:249-259, 2003.
Lo & Thornalley, *Biochem Pharmacol* 44: 2357-63, 1992.
Lo, et al., *J Biol Chem.* 269:32299-32305, 1994.
Loh, et al., *Curr Alzheimer Res.* 3:327-337, 2006.
Lohaus & Dittmar, *Arzneimittelforschung* 31:1311-6, 1981.
Loos, et al., *Genes Brain Behav.* 8:817-828, 2009.
Low, et al., *Science* 290: 131-4, 2000.
Lu, et al., *Clin Biochem.* 44:307-311, 2011.
Luscher, et al., *Mol Psychiatry.* 16:383-406, 2011.
Ma, et al., *J Org Chem.* 74:264-273, 2009.
Macdonald, et al., *J Physiol.* 588:1861-1869, 2010.
Maguire, et al., *Nat Neurosci.* 8:797-804, 2005.
Maitra, A. The Endocrine System. In Robbins and Cotran Pathologic Basis of Disease. V. Kumar, A. Abbas, N. Fausto, and J. Aster, editors. Philadelphia: Elsevier, 2010.
Mansfield, et al., *J Appl Physiol.* 49:390-397, 1980.
Manto, M. *Cerebellum.* 7:505-516, 2008.
Markou, et al., *Neuropsychopharmacology.* 34:74-89, 2009.
Martin, et al., *Hum Mol Genet.* 16:2892-2899, 2007.
Martin, et al., *J Biol Chem.* 285:9823-9834, 2010.
Masterjohn, et al., *J Nutr Biochem.* 23(3):292-8, 2012.
McCall & Frierson D, *Genetics* 99:285-307, 1981.
McCallum, et al. *J Biomol Screen* (2013).
McKenney & Short, *Surg Clin North Am.* 91:1139-1148, vii, 2011.
McKernan, et al., *Nat Neurosci.* 3:587-92, 2000.
McLean & Anderson, *Clin Psychol Rev* 29:496-505, 2009.
McLellan & Thornalley, *Analytica Chimica Acta.* 263:137-142, 1992.
Mehta, et al., *Curr Psychiatry Rep.* 12:135-144, 2010.
Miller, *Science.* 329:502-4, 2010.
Milner & Crabbe, *Genes Brain Behav* 7:496-505, 2002.
Morcos, et al., *Aging Cell.* 7:260-269, 2008.
More & Vince, *J Med Chem.* 52:4650-6, 2009.
Moser, et al., *J Pharmacol Exp Ther.* 336:588-95, 2011.
Movassaghi & Schmidt, *Abstracts of Papers of the American Chemical Society.* 234, 2007.
Mulley, et al., *Hum Mol Genet.* 14 Spec No. 2:R243-249, 2005.
Murthy, et al., *J Med Chem.* 37:2161-6, 1994.
Naegele, *Epilepsia* 48 Suppl 2:107-117, 2007.
Namjoshi, et al., *J Org Chem.* 76(11):4721-4727, 2011
Nandhikonda, et al., *J Med Chem* 55:4640-51, 2012
Nerl, et al., *Neurology.* 34:310-314, 1984.
Nillni, et al. *Clin psychol Rev.* 31:1183-1191, 2011.
NIMH, Anxiety Disorders. Bethesda: National Institutes of Health, 2009.
Noe, *Semin Neurol.* 31:54-64, 2011.
Nusser, et al., *J Neurosci.* 18:1693-703, 1998.
Nusser, et al., *Eur J Neurosci.* 11:1685-1697, 1999.
O'Leary, O. F., and Cryan, J. F. The Tail-Suspension Test: A Model for Characterizing Antidepressant Activity in Mice. In Mood and Anxiety Related Phenotypes in Mice. T. D. Gould, editor. New York: Humana Press. 119-137, 2009.
Oehldrich, et al., *J Org Chem.* 42:889-894, 1977.
Ohmori & Iwamoto, *J Chromatogr.* 431:239-47, 1988.
Okumoto, et al., *Annu Rev Plant Biol.* 63:663-706, 2012
Overall, et al., *Front Neurosci* 3:55, 2009.
Pagel & Parnes, *Prim Care Companion J Clin Psychiatry.* 3(3):118-125, 2001.
Palanza, *Neurosci Biobehav Rev.* 25:219-233, 2001.
Palmer & Dulawa, *Front Neurosci.* 4:177, 2010
Palmer, et al., *Brain Res.* 1237:62-74, 2008
Papale, et al., *J Biol Chem.* 285:16553-16561, 2010.
Pare, et al., *J Neurophysiol.* 92:1-9, 2004.
Parker & Palmer, *Front Genet* 2:32, 2011
Parker, et al., *Behav Genet.* 42:437-48, 2012.
Payne, et al., *Epilepsia.* 52:1941-1948, 2011.
Payne, et al., *Hum Hered.* 32:404-407, 1982.
Peirce, et al., *BMC Genet.* 5:7, 2004.
Peng, et al., *Sensors (Basel)* 12:15907-46, 2012
Perucca, et al., *Lancet Neurol.* 10:446-456, 2011.
Petty & Schlesser, *J Affect Disord.* 3:339-343, 1981.
Petty & Sherman, *J Affect Disord.* 6:131-138, 1984.
Philip, et al., *Genome Res.* 21:1223-38, 2011.
Pitkanen, *Epilepsy Res.* 50:141-160, 2002.
Plant, et al., *J Clin Invest.* 116:430-435, 2006.
Plant, et al., *J Gen Physiol.* 137:441-454, 2011.
Plant, et al., *Stroke.* 33:2324-2328, 2002.
Plant, et al., *Neurobiol Aging.* 27:1673-1683, 2006.
Plomin, et al., *Behav Genet.* 21:99-116, 1991.
Politi, et al., *Neurosci Lett.* 396:163-166, 2006.
Pollack, *J Clin Psychiatry.* 70 Suppl 2:32-38, 2009.
Ponder, et al., *Behav Genet.* 38:277-91, 2008.
Ponder, et al., *Genes Brain Behav.* 6:736-49, 2007.
Ponder, et al., *Mamm Genome.* 18: 221-8, 2007.
Porsolt, et al., *Arch Int Pharmacodyn Ther.* 288:11-30, 1987.
Pourmotabbed & Creighton, *J Biol Chem.* 261:14240-14244, 1986.
Queisser, et al., *Diabetes.* 59:670-678, 2010.
Racker, *J Biol Chem.* 190:685-96, 1951.
Rader & Pure, *Circ Res.* 86:1013-1015, 2000.
Rakhade & Jense, *Nat Rev Neurol.* S5:380-391, 2009.
Randella, et al., *J Pharmacol Toxicol Meth.* 51:153-157, 2005.
Rauh, et al., *Trends Pharmacol Sci.* 11:325-329, 1990.
Rees, M. I. 2010. The genetics of epilepsy—the past, the present and future. *Seizure* 19:680-683.
Rehnstrom, et al., *Am J Med Genet B Neuropsychiatr Genet.* 147B:124-127, 2008.
Reiner-Benaim, et al., *Bioinformatics.* 23:2239-2246, 2007.
Ridderstrom, et al., *J Biol Chem.* 271:319-23, 1996.
Ridderstrom, et al., *J. Biol. Chem.* 273:21623-21628, 1998.

Rivas, et al., *J Med Chem.* 52:1795-8, 2009
Rossetti & Lowenstein, *Lancet Neurol.* 10:922-930, 2011.
Roux, et al., *Curr Protoc Pharmacol.* Chapter 10, Unit 10 10, 2005.
Rubenstein, *J Child Psychol Psychiatry.* 52:339-355, 2011.
Rudolph, et al., *Nature.* 401:796-800, 1999.
Rudolph & Knoflach, *Nat Rev Drug Discov.* 10:685-697, 2011.
Rudolph & Mohler, *Annu Rev Pharmacol Toxicol.* 44:475-98, 2004.
Sacco, et al., *BMC Med Genet.* 8:11, 2007.
Sah, et al., *Physiol Rev.* 83:803-834, 2003.
Sakamoto, et al., *Clin Cancer Res.* 7:2513-8, 2001.
Samocha, et al., *Genes Brain Behav.* 9:759-67, 2010.
Santel, et al., *PLoS One* 3:e3508, 2008
Saraiva, et al., *Tetrahedron.* 65:3563-3572, 2009
Savic, et al., *Neuropsychopharmacology* 33:332-339, 2008
Savic, et al., *PLoS One.* 6:e26897, 2011
Scharfman, et al., *Epilepsia.* 48 Suppl 2:33-41, 2007.
Schauwecker, *Epilepsy Res.* 97:1-11, 2011.
Schauwecker, *Neurobiol Dis.* 45:297-304, 2012.
Schleicher & Friess, *Kidney Int. Suppl*:S17-26, 2007.
Schmidt, *Epilepsy Behav.* 15:56-65, 2009.
Schmidt, et al., *Neuropsychopharmacology.* 35(12): 2378-2391, 2010.
Schmittgen & Livak, *Nat Protoc.* 3:1101-1108, 2008.
Schumacher, et al., *J Med Genet.* 48:361-368, 2011.
Semba, et al., *J Gerontol A Biol Sci Med Sci.* 65:963-975, 2010.
Shen, et al., *Biol Psychiatry.* 68:512-520, 2010.
Shifman, et al., *PLoS Biol.* 4:e395, 2006.
Shin, et al., *Neuropsychopharmacology.* 35:169-191, 2010.
Shinohara, et al., *J Clin Invest.* 101:1142-7, 1998
Shulman, et al., *Trends Neurosci.* 27:489-495, 2004.
Sieghart & Sperk, *Curr Top Med Chem.* 2:795-816, 2002.
Smoller, et al., *Depress Anxiety.* 26:965-975, 2009.
Snow, et al., *Tetrahedron Lett.* 17:4447-4450, 1976.
Sokoloff, et al., *Genes Brain Behav.* 10:604-14, 2011.
Solomon & Herman, *Physiol Behav.* 97:250-258, 2009.
Stefansson, et al., *N Engl J Med.* 357:639-47, 2007.
Stein, *J Clin Psychiatry.* 70 Suppl 2:15-19, 2009.
Stern, et al., *Psychopharmacology* (Berl) 85:367-370, 1985.
Stern, et al., *Prog Neuropyschopharmacol Biol Psychiatry.* 11:659-671, 1987.
Stevens, et al., *Trends Mod Med.* 13:512-519, 2007.
Storey & Tibshirani, *Proc Natl Acad Sci USA.* 100:9440-9445, 2003.
Tabor, et al., *Nat Rev Genet.* 3:391-397, 2002.
Taft, et al., *Trends Genet.* 22:649-653, 2006.
Takasawa, et al., *Bioorg Med Chem Lett.* 21:4337-42, 2011
Takasawa, et al., *Bioorg Med Chem.* 16:3969-75, 2008
Tarantino, et al., *The Origins of Schizophrenia*, (Columbia University Press, N Y, 2011).
Tasan, et al., *Neuroscience.* 183:71-80, 2011.
Thornalley, et al., *J Med Chem* 39:3409-3411, 1996.
Thornalley, *Mol Aspects Med* 14, 287-371, 1993.
Thornalley, *Heredity (Edinb).* 67 (Pt 2):139-142, 1991.
Thornalley, *Biochem Soc Trans.* 31:1343-1348, 2003.
Thornalley, *Biochem Soc Trans.* 31:1372-7, 2003.
Thornalley, *Trends Mol Med.* 12:195-9, 2006.
Thornalley, et al., *Semin Cell Dev Biol.* 22:318-325, 2011.
Titlic, et al., *Bratisl Lek Listy.* 110:105-109, 2009.
Toyosima, et al., *Br J Psychiatry.* 199:345-6, 2011.
Trenkwalder, et al., *Nat Rev Neurol.* 6:337-46, 2010. C.,
Ulrich-Lai, et al., *Proc Natl Acad Sci USA.* 107:20529-34, 2010.
U.S. Pat. No. 3,984,569
U.S. Pat. No. 4,552,754
U.S. Pat. No. 5,229,254
U.S. Pat. No. 5,230,985
U.S. Pat. No. 5,616,563
U.S. Pat. No. 5,969,174
U.S. Pat. No. 6,060,471
U.S. Pat. No. 7,235,656
U.S. Pat. No. 7,700,560
U.S. Pat. No. 8,268,854 B2
US Patent Publication 2010/0261711 A1
US Patent Publication 2012/0220596 A1
van der Heyden, et al., *Psychopharmacology (Berl).* 92:127-30, 1987.
Vanin, et al., *Anxiety Disorders: A Pocket Guide for Primary Care.* NJ: Humana Press, 2008.
Velez, et al., *Behav Genet.* 40:201-10, 2010
Veliskova, *Neuroscientist.* 13:77-88, 2007.
Vince, et al., *Biochem Biophys Res Commun.* 35:593-8, 1969.
Vince, et al., *J Med Chem.* 14:402-4, 1971.
Vithlani, et al., *Physiol Rev.* 91:1009-22, 2010.
Wang, et al., *Neuroinformatics.* 1:299-308, 2003.
Wang, et al., *J Hypertension.* 26:765-72, 2008.
Whitham, *Comphrehensive Organic Chemistry* 1:129, 1979.
Wieland, et al., *J Biol Chem.* 267:1426-9, 1992.
Williams, et al., *Genome Biol.* 2:RESEARCH0046, 2001.
Williams, et al., *PLoS One.* 4:e4649, 2009.
Willmore, *Epilepsy Behav.* 7 Supp 3: S25-8, 2005.
Winawer, et al., *Epilepsia.* 52:2076-2083, 2011.
Winkelmann, et al., *Nat Genet.* 39:1000-6, 2007.
Winsky-Sommerer, *Eur J Neurosci.* 29:1779-94, 2009.
Wittchen, et al. *Eur Neuropsychopharmacol.* 21:655-79, 2011.
WO/1999/035128
WO/1999/037277
Wu, et al., *Prog Neuropsychopharmacol Biol Psychiatry.* 32:1740-4, 2008.
Wyllie & Cull-Candy, *J Physiol.* 475:95-114, 1994.
Xue, et al., *Semin Cell Dev Biol.* 22:293-301, 2011.
Yadav, et al., *Drug Metabol Drug Interact.* 23:51-68, 2008.
Yang, et al., *Curr Protoc Neurosci.* 5(5):20, 2005.
Yeung, et al., *Mol Pharmacol.* 63:2-8, 2003.
Yin, et al., *Bioorg and Med. Chem.* 21:7548-7564, 2010.
Zhang, et al., *Mol Cell Proteomics.* 10(12):M111.008110, 2011.

The invention claimed is:

1. A method of treating a condition in a human subject, comprising treating the condition by administering to the human subject a therapeutically effective amount of a composition comprising a Glo1 inhibitor; wherein the condition is a depressive disorder, wherein the Glo1 inhibitor is an antibody, an inhibitory nucleic acid, a molecule having a glutathione structure, a 1-hydroxy-6,7-diphenylpyridin-2-one derivative (3d), a flavonoid, a curcumin, a benzothiazole derivative, a 4-(7-azaindole)-substituted 6-phenyl-N-hydroxypyridones or 4,6-diphenyl-N-hydroxypyridone.

2. The method of claim 1, further comprising administering a second treatment for the depressive disorder.

3. The method of claim 2, wherein the second treatment is an antidepressant, a psychotherapy, electroconvulsive therapy, vagus nerve stimulation, repetitive transcranial magnetic stimulation, or cranial electrotherapy stimulation.

4. The method of claim 1, wherein the Glo1 inhibitor is an antibody[H] or an inhibitory nucleic acid.

5. The method of claim 1, wherein the Glo1 inhibitor is a molecule having a glutathione structure, a 1-hydroxy-6,7-diphenylpyridin-2-one derivative (3d), a flavonoid, a curcumin, a benzothiazole derivative, a 4-(7-azaindole)-substituted 6-phenyl-N-hydroxypyridones, or 4,6-diphenyl-N-hydroxypyridon.

6. The method of claim 1, wherein the composition is administered orally, topically, nasally, intravascularly, intraperiotoneally, intrathecally, intratracheally, by inhalation or instillation.

7. The method of claim 1, wherein the human subject has been determined to have a depressive disorder.

8. The method of claim 1, further comprising identifying the human subject as having a depressive disorder.

9. The method of claim 1, further comprising testing the human subject for a depressive disorder.

10. The method of claim 1, wherein the human subject is administered the composition within 1 week of being determined to have a depressive disorder.

11. The method of claim 1, wherein the human subject is at risk of a depressive disorder.

12. The method of claim 1, further comprising monitoring the human subject for the depressive disorder within a week of first administering the composition.

* * * * *

UNITED STATES PATENT AND TRADEMARK OFFICE
CERTIFICATE OF CORRECTION

| | | |
|---|---|---|
| PATENT NO. | : 11,235,020 B2 | Page 1 of 1 |
| APPLICATION NO. | : 14/774886 | |
| DATED | : February 1, 2022 | |
| INVENTOR(S) | : Palmer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 114 days.

Signed and Sealed this
Twentieth Day of December, 2022

Katherine Kelly Vidal
*Director of the United States Patent and Trademark Office*

SEQUENCE LISTING

<160> NUMBER OF SEQ ID NOS: 28

<210> SEQ ID NO 1
<211> LENGTH: 74
<212> TYPE: DNA
<213> ORGANISM: Artificial Sequence
<220> FEATURE:

<223> OTHER INFORMATION: Synthetic Primer

<400> SEQUENCE: 1
ggtggctgat agaatgtgtg gttttgtgcg catgctcctc ttgctcacta gtggcacttt    60
tcggggaaat gtgc    74

<210> SEQ ID NO 2
<211> LENGTH: 76
<212> TYPE: DNA
<213> ORGANISM: Artificial Sequence
<220> FEATURE:
<223> OTHER INFORMATION: Synthetic Primer

<400> SEQUENCE: 2
ctgcttccca catgacttaa atataagtaa taataagaat aaccattatt ctcgaggcta    60
gctctagaag tccagc    76

<210> SEQ ID NO 3
<211> LENGTH: 74
<212> TYPE: DNA
<213> ORGANISM: Artificial Sequence
<220> FEATURE:
<223> OTHER INFORMATION: Synthetic Primer

<400> SEQUENCE: 3
gataaggcat cactgggaga aataaaaaca cccaatggtc aagttatttg ggcctggtga    60
tgatggcggg atcg    74

<210> SEQ ID NO 4
<211> LENGTH: 74
<212> TYPE: DNA
<213> ORGANISM: Artificial Sequence
<220> FEATURE:
<223> OTHER INFORMATION: Synthetic Primer

<400> SEQUENCE: 4
acactcgtac acaccccaaa acaaagggga aaacaaatac gggcacgact tcagaagaac    60
tcgtcaagaa ggcg    74

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
gtctgtccca gacagccttc    20

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
agccctcccg tatcgtagtt    20

<210> SEQ ID NO 7
<211> LENGTH: 22
<212> TYPE: DNA
<213> ORGANISM: Artificial Sequence
<220> FEATURE:
<223> OTHER INFORMATION: Synthetic Primer

<400> SEQUENCE: 7
tcctcagttg agatccctc ta                                           22

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
gccgaaaagg tgtcaagaaa                                             20

<210> SEQ ID NO 9
<211> LENGTH: 23
<212> TYPE: DNA
<213> ORGANISM: Artificial Sequence
<220> FEATURE:
<223> OTHER INFORMATION: Synthetic Primer

<400> SEQUENCE: 9
ctgctgagga taccaggttt gtt                                         23

<210> SEQ ID NO 10
<211> LENGTH: 21
<212> TYPE: DNA
<213> ORGANISM: Artificial Sequence
<220> FEATURE:
<223> OTHER INFORMATION: Synthetic Primer

<400> SEQUENCE: 10
agcatcctga cggcagattt a                                           21

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11
tgccagtgtg attgaaggag                                             20

<210> SEQ ID NO 12
<211> LENGTH: 19
<212> TYPE: DNA
<213> ORGANISM: Artificial Sequence
<220> FEATURE:
<223> OTHER INFORMATION: Synthetic Primer

<400> SEQUENCE: 12
gtgccagctg aaccacaat                                              19

<210> SEQ ID NO 13
<211> LENGTH: 20
<212> TYPE: DNA
<213> ORGANISM: Artificial Sequence
<220> FEATURE:
<223> OTHER INFORMATION: Synthetic Primer

<400> SEQUENCE: 13
ccacagctga gagggaaatc                                             20

```
<210> SEQ ID NO 14
<211> LENGTH: 20
<212> TYPE: DNA
<213> ORGANISM: Artificial Sequence
<220> FEATURE:
<223> OTHER INFORMATION: Synthetic Primer

<400> SEQUENCE: 14
tctccaggga ggaagaggat                                                    20

<210> SEQ ID NO 15
<211> LENGTH: 20
<212> TYPE: DNA
<213> ORGANISM: Artificial Sequence
<220> FEATURE:
<223> OTHER INFORMATION: Synthetic Primer

<400> SEQUENCE: 15
actggcgttc attcaagacc                                                    20

<210> SEQ ID NO 16
<211> LENGTH: 20
<212> TYPE: DNA
<213> ORGANISM: Artificial Sequence
<220> FEATURE:
<223> OTHER INFORMATION: Synthetic Primer

<400> SEQUENCE: 16
cccatacctc aaaggcacat                                                    20

<210> SEQ ID NO 17
<211> LENGTH: 20
<212> TYPE: DNA
<213> ORGANISM: Artificial Sequence
<220> FEATURE:
<223> OTHER INFORMATION: Synthetic Primer

<400> SEQUENCE: 17
gccagctttc tgactggtct                                                    20

<210> SEQ ID NO 18
<211> LENGTH: 20
<212> TYPE: DNA
<213> ORGANISM: Artificial Sequence
<220> FEATURE:
<223> OTHER INFORMATION: Synthetic Primer

<400> SEQUENCE: 18
cttgaaaggg ctgggttaca                                                    20

<210> SEQ ID NO 19
<211> LENGTH: 20
<212> TYPE: DNA
<213> ORGANISM: Artificial Sequence
<220> FEATURE:
<223> OTHER INFORMATION: Synthetic Primer

<400> SEQUENCE: 19
atgccgagaa agacgaaaaa                                                    20

<210> SEQ ID NO 20
<211> LENGTH: 20
<212> TYPE: DNA
<213> ORGANISM: Artificial Sequence
<220> FEATURE:
<223> OTHER INFORMATION: Synthetic Primer
```

```
<400> SEQUENCE: 20
gccatctctg cttccatgtc                                          20

<210> SEQ ID NO 21
<211> LENGTH: 20
<212> TYPE: DNA
<213> ORGANISM: Artificial Sequence
<220> FEATURE:
<223> OTHER INFORMATION: Synthetic Primer

<400> SEQUENCE: 21
actgtatgtg atgcgcttgg                                          20

<210> SEQ ID NO 22
<211> LENGTH: 20
<212> TYPE: DNA
<213> ORGANISM: Artificial Sequence
<220> FEATURE:
<223> OTHER INFORMATION: Synthetic Primer

<400> SEQUENCE: 22
ccagtttgtt ccatggctct                                          20

<210> SEQ ID NO 23
<211> LENGTH: 20
<212> TYPE: DNA
<213> ORGANISM: Artificial Sequence
<220> FEATURE:
<223> OTHER INFORMATION: Synthetic Primer

<400> SEQUENCE: 23
agcagcaagc tgtgatgttg                                          20

<210> SEQ ID NO 24
<211> LENGTH: 23
<212> TYPE: DNA
<213> ORGANISM: Artificial Sequence
<220> FEATURE:
<223> OTHER INFORMATION: Synthetic Primer

<400> SEQUENCE: 24
tgcaaaagct gaagatgtaa ctg                                      23

<210> SEQ ID NO 25
<211> LENGTH: 33
<212> TYPE: DNA
<213> ORGANISM: Artificial Sequence
<220> FEATURE:
<223> OTHER INFORMATION: Synthetic Primer

<400> SEQUENCE: 25
ggcactgaag atgatgcgac ccagagttac cac                           33

<210> SEQ ID NO 26
<211> LENGTH: 33
<212> TYPE: DNA
<213> ORGANISM: Artificial Sequence
<220> FEATURE:
<223> OTHER INFORMATION: Synthetic Primer

<400> SEQUENCE: 26
gtggtaactc tgggtcgcat catcttcagt gcc                           33

<210> SEQ ID NO 27
```

```
<211> LENGTH: 21
<212> TYPE: DNA
<213> ORGANISM: Artificial Sequence
<220> FEATURE:
<223> OTHER INFORMATION: Synthetic Primer

<400> SEQUENCE: 27
atactgcagc catgcagaac c                                             21

<210> SEQ ID NO 28
<211> LENGTH: 20
<212> TYPE: DNA
<213> ORGANISM: Artificial Sequence
<220> FEATURE:
<223> OTHER INFORMATION: Synthetic Primer

<400> SEQUENCE: 28
tgaatcggga cagtgatcca                                                20
```